United States Patent
Zhang et al.

(10) Patent No.: US 10,766,912 B2
(45) Date of Patent: Sep. 8, 2020

(54) SILICON-CONTAINING COMPOUND FOR RESISTANCE TO HEPATITIS C VIRUS INFECTION

(71) Applicant: CHIA TAI TIANQING PHARMACEUTICAL GROUP CO., LTD., Lianyungang, Jiangsu Province (CN)

(72) Inventors: Yinsheng Zhang, Lianyungang (CN); Baomin Liu, Lianyungang (CN); Yu Huang, Lianyungang (CN); Zhengbang Chen, Lianyungang (CN); Kuo Gai, Lianyungang (CN); Xushi Liu, Lianyungang (CN); Xiaojin Wang, Lianyungang (CN); Hongjiang Xu, Lianyungang (CN)

(73) Assignee: Chia Tai Tianqing Pharmaceutical Group Co., Ltd., Lianyungang, Jiangsu Province (CN)

( * ) Notice: Subject to any disclaimer, the term of this patent is extended or adjusted under 35 U.S.C. 154(b) by 0 days.

(21) Appl. No.: 16/494,604

(22) PCT Filed: Mar. 22, 2018

(86) PCT No.: PCT/CN2018/079965
§ 371 (c)(1),
(2) Date: Sep. 16, 2019

(87) PCT Pub. No.: WO2018/171660
PCT Pub. Date: Sep. 27, 2018

(65) Prior Publication Data
US 2020/0017532 A1    Jan. 16, 2020

(30) Foreign Application Priority Data

Mar. 22, 2017 (CN) .......................... 2017 1 0172925
Sep. 19, 2017 (CN) .......................... 2017 1 0845367

(51) Int. Cl.
*C07F 7/08*     (2006.01)
*A61P 31/14*    (2006.01)

(52) U.S. Cl.
CPC ............ *C07F 7/0816* (2013.01); *A61P 31/14* (2018.01)

(58) Field of Classification Search
CPC .................................................. C07F 7/0816
See application file for complete search history.

(56) References Cited

U.S. PATENT DOCUMENTS

2014/0252318 A1* 9/2014 Boudreault ......... H01L 51/0094
257/40

FOREIGN PATENT DOCUMENTS

| CN | 101558059 A | 10/2009 |
| CN | 103819459 A | 5/2014 |
| CN | 104193729 A | 12/2014 |
| WO | 2008/021927 A2 | 2/2008 |
| WO | 2010/144646 A2 | 12/2010 |
| WO | 2012/051361 A1 | 4/2012 |

OTHER PUBLICATIONS

International Search Report in PCT/CN2018/079965, dated Jun. 22, 2018.

* cited by examiner

*Primary Examiner* — Shawquia Jackson
(74) *Attorney, Agent, or Firm* — Kilpatrick Townsend & Stockton LLP

(57) ABSTRACT

The present invention provides a silicon-containing compound for resistance to hepatitis c virus infection, and in particular provides a compound represented by formula I, or a pharmaceutically acceptable salt, or a tautomer, or a stereoisomer, or a deuterated compound thereof and mixture among them, a preparation process therefor, and a pharmaceutical composition comprising the same. The present application also provides a use of the compound, or a pharmaceutically acceptable salt, or a tautomer, or a stereoisomer, or a deuterated compound thereof and mixture among them, and a pharmaceutical composition comprising the same in treatment of hepatitis c virus infection.

Formula I

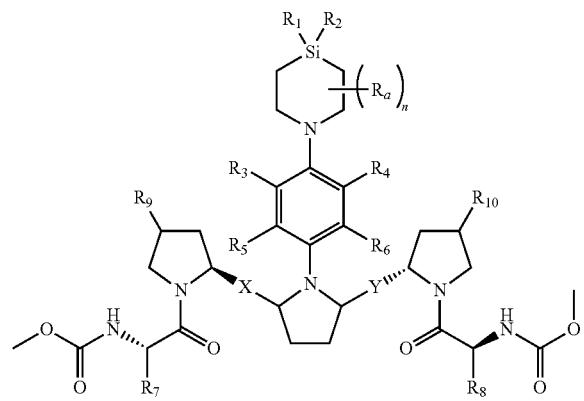

20 Claims, No Drawings

SILICON-CONTAINING COMPOUND FOR RESISTANCE TO HEPATITIS C VIRUS INFECTION

CROSS REFERENCE TO RELATED APPLICATIONS

The present application is a U.S. National Stage Application of PCT/CN2018/079965, International Filling Date Mar. 22, 2018, which claims the priorities to and benefits of the Chinese patent application No. 201710172925.8 filed with the China National Intellectual Property Administration on Mar. 22, 2017 and the Chinese patent application No. 201710845367.7 filed with the China National Intellectual Property Administration on Sep. 19, 2017, the disclosures of which are incorporated herein by reference in their entireties.

TECHNICAL FIELD

The present application belongs to the field of pharmaceutical chemistry, and specifically relates to silicon-containing compounds resistant to hepatitis C virus infection, preparation processes thereof, and pharmaceutical compositions comprising the same. The present application also relates to the use of these compounds and pharmaceutical compositions in the treatment of hepatitis C virus (HCV) infection.

BACKGROUND

HCV is a positive-strand RNA virus and belongs to the genus Hepacivirus of the Flaviviridae family, and it has been identified to have at least six major genotypes and comprises more than 50 subtypes. The single strand HCV RNA genome is approximately 9500 nucleotides in length and has a single open reading frame (ORF) encoding a single large polyprotein of approximately 3000 amino acids. In infected cells, this polyprotein is cleaved by cellular and viral proteases at multiple sites, resulting in structural and non-structural (NS) proteins. In the case of HCV, the formation of mature non-structural proteins (NS2, NS3, NS4A, NS4B, NS5A and NS5B) is achieved by two viral proteases.

A treatment regimen for chronic HCV infection comprises: peginterferon-α in combination with ribavirin for treating HCV-infected patients and patients with cirrhotic. If the treatment fails, the treatment regimen including interferon is used again, and the sustained virological response rate will be as low as 14%. In addition, the treatment regimen including interferon has increased toxic side effects in patients with cirrhotic.

With the development of HCV NS3/4A protease inhibitors, NS5A inhibitors and NS5B polymerase inhibitors, as new therapies, the use of interferon and ribavirin is not required, which not only reduces toxicity but also shortens treatment duration. These new classes of inhibitors include ABT-267 (WO2010144646), ABT-530 (WO2012051361), etc.

SUMMARY OF THE INVENTION

In one aspect, the present application provides a compound of Formula I, a pharmaceutically acceptable salt, a tautomer, a stereoisomer or a deuteride thereof, or a mixture thereof:

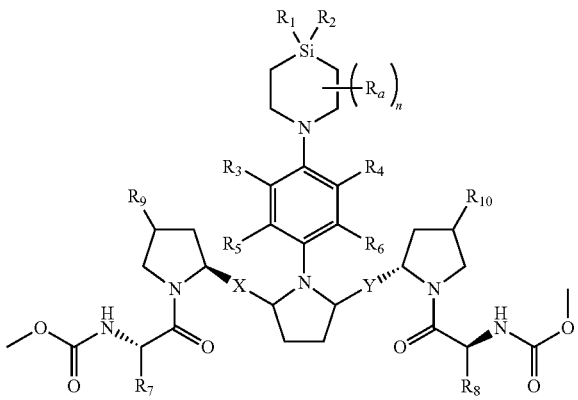

Formula I wherein:

$R_1$ and $R_2$ are each independently selected from the group consisting of hydroxyl, alkyl, alkoxy and aryl, or $R_1$ and $R_2$ are joined to form a silicon-containing saturated aliphatic ring containing 1, 2 or 3 silicon atoms;

$R_3$, $R_4$, $R_5$ and $R_6$ are each independently selected from the group consisting of hydrogen and halogen;

X is selected from the group consisting of the following groups:

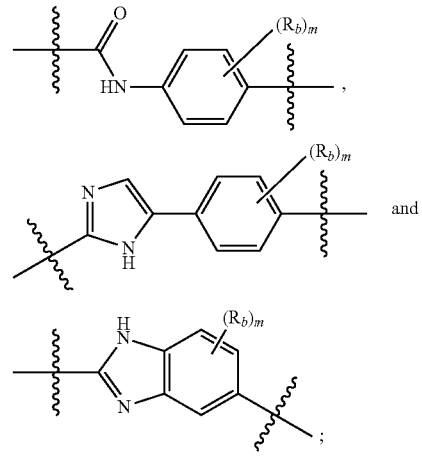

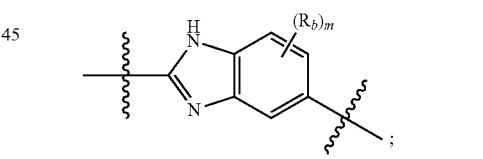

Y is selected from the group consisting of the following groups:

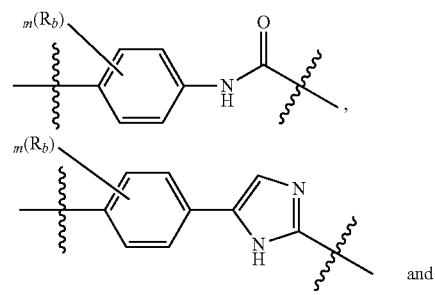

and

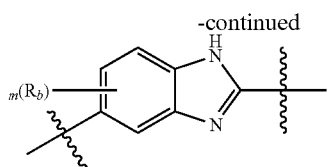

$R_7$ and $R_8$ are each independently selected from the group consisting of —CH(alkyl)(alkoxy), —CH(alkyl)$_2$, —CH(alkoxy)$_2$, —C(alkyl)$_2$(alkoxy), —C(alkyl)(alkoxy)$_2$, —C(alkyl)$_3$ and —C(alkoxy)$_3$;

$R_9$ and $R_{10}$ are each independently selected from the group consisting of hydrogen, halogen, alkyl, alkoxy, and alkoxyalkyl;

each of $R_a$ and $R_b$ is independently selected from the group consisting of hydrogen, halogen, and alkyl;

each m is independently selected from the group consisting of 0, 1, 2, 3, and 4; and n is selected from the group consisting of 0, 1, 2, 3, 4, 5, 6, 7, and 8.

In another aspect, the present application provides a pharmaceutical composition comprising a therapeutically effective amount of the compound of Formula I, a pharmaceutically acceptable salt, a tautomer, a stereoisomer or a deuteride thereof, or a mixture thereof, and one or more pharmaceutically acceptable carriers.

In a further aspect, the present application provides use of the compound of Formula I, a pharmaceutically acceptable salt, a tautomer, a stereoisomer or a deuteride thereof, or a mixture thereof, or the above pharmaceutical composition in the preparation of a medicament for the treatment of hepatitis C virus infection.

In still another aspect, the present application provides a method for treating hepatitis C virus infection, comprising administering to a subject in need of such treatment a therapeutically effective amount of the compound of Formula I, a pharmaceutically acceptable salt, a tautomer, a stereoisomer or a deuteride thereof, or a mixture thereof, or the above pharmaceutical composition.

In yet another aspect, the present application provides the compound of Formula I, a pharmaceutically acceptable salt, a tautomer, a stereoisomer or a deuteride thereof, or a mixture thereof for use in the treatment of hepatitis C virus infection, and the above pharmaceutical composition for use in the treatment of hepatitis C virus infection.

In another aspect, the present application provides use of the compound of Formula I, a pharmaceutically acceptable salt, a tautomer, a stereoisomer or a deuteride thereof, or a mixture thereof, or the above pharmaceutical composition in the treatment of hepatitis C virus infection.

DETAILED DESCRIPTION OF THE INVENTION

In one aspect, the present application provides a compound of Formula I, a pharmaceutically acceptable salt, a tautomer, a stereoisomer or a deuteride thereof, or a mixture thereof:

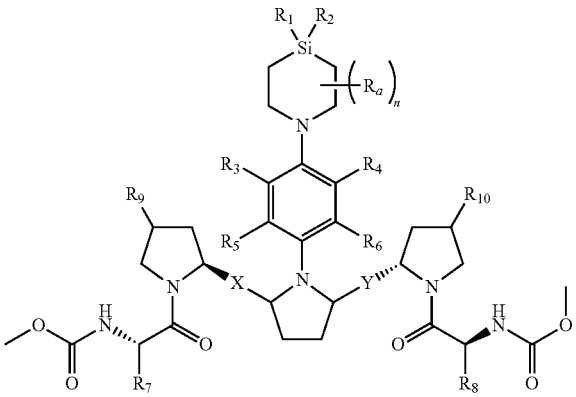

Formula I wherein:

$R_1$ and $R_2$ are each independently selected from the group consisting of hydroxyl, alkyl, alkoxy and aryl, or $R_1$ and $R_2$ are joined to form a silicon-containing saturated aliphatic ring containing 1, 2 or 3 silicon atoms (that is, $R_1$ and $R_2$ together with the silicon atom to which they are attached form a silicon-containing saturated aliphatic ring);

$R_3$, $R_4$, $R_5$ and $R_6$ are each independently selected from the group consisting of hydrogen and halogen;

X is selected from the group consisting of the following groups:

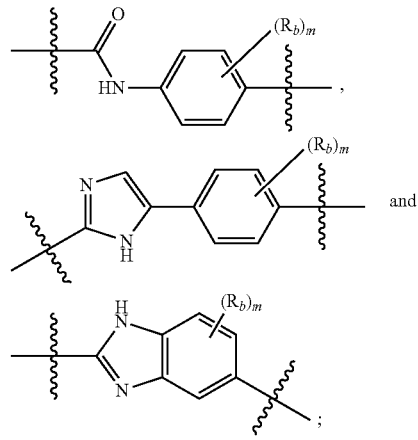

Y is selected from the group consisting of the following groups:

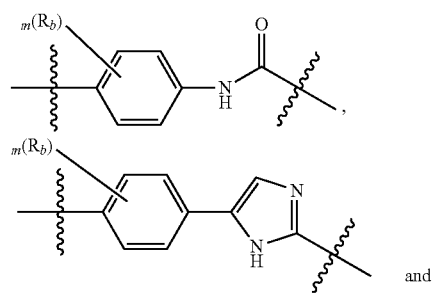

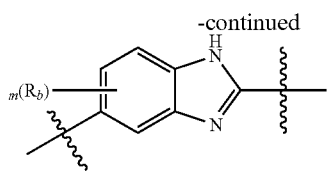

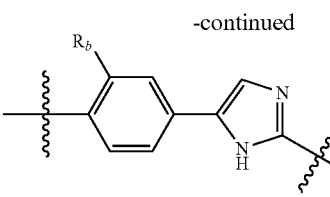

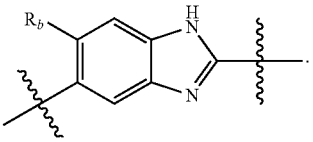

$R_7$ and $R_8$ are each independently selected from the group consisting of —CH(alkyl)(alkoxy), —CH(alkyl)$_2$, —CH(alkoxy)$_2$, —C(alkyl)$_2$(alkoxy), —C(alkyl)(alkoxy)$_2$, —C(alkyl)$_3$ and —C(alkoxy)$_3$;

$R_9$ and $R_{10}$ are each independently selected from the group consisting of hydrogen, halogen, alkyl, alkoxy, and alkoxyalkyl;

each of $R_a$ and $R_b$ is independently selected from the group consisting of halogen and alkyl; or each of $R_a$ and $R_b$ is independently selected from the group consisting of hydrogen, halogen, and alkyl;

each m is independently selected from the group consisting of 0, 1, 2, 3, and 4; and n is selected from the group consisting of 0, 1, 2, 3, 4, 5, 6, 7, and 8.

The relative stereochemistry of the 2- and 5-positions of the pyrrole ring in which N (wherein N is at the 1-position) is attached to the benzene ring may be cis or trans. In some specific embodiments, the configurations of the 2- and 5-positions on the pyrrole ring include (2S, 5S), (2S, 5R), (2R, 5S) and (2R, 5R). The compound of Formula I may be a stereoisomer or may be a mixture of two or more stereoisomers in an arbitrary ratio.

In some embodiments, in the above compound of Formula I, the substitution position of each $R_a$ is optionally at the carbon atom in the ortho or meta position of the silicon atom.

In some embodiments, in the above compound of Formula I, the substitution position of each $R_b$ may be arbitrary; preferably, X is selected from the group consisting of

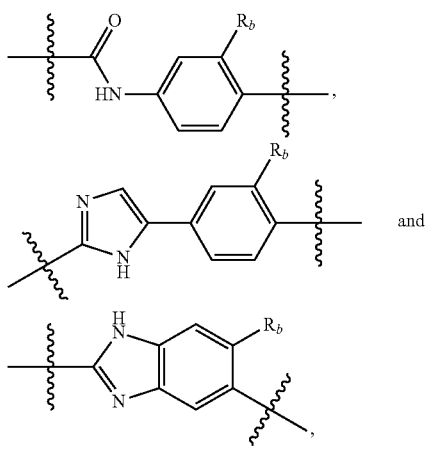

and Y is selected from the group consisting of

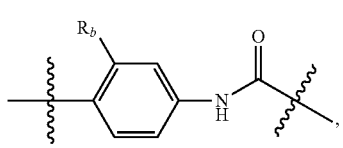

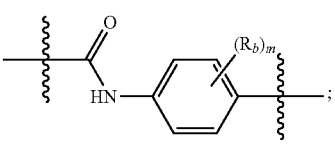

In some embodiments, in the above compound of Formula I, the alkyl involved in the definitions of $R_1$, $R_2$, $R_7$, $R_8$, $R_9$, $R_{10}$, $R_a$ and $R_b$ is $C_{1-6}$ alkyl or $C_{1-4}$ alkyl, the alkoxy involved in the definitions of $R_1$, $R_2$, $R_7$, $R_8$, $R_9$ and $R_{10}$ is $C_{1-6}$ alkoxy or $C_{1-4}$ alkoxy, the alkoxyalkyl involved in the definitions of $R_9$ and $R_{10}$ is $C_{1-6}$ alkoxy$C_{1-6}$ alkyl, $C_{1-6}$ alkoxy$C_{1-4}$ alkyl or $C_{1-4}$ alkoxy$C_{1-2}$ alkyl, the aryl involved in the definitions of $R_1$ and $R_2$ is $C_{6-12}$ aryl; and the silicon-containing saturated aliphatic ring involved in the definitions of $R_1$ and $R_2$ is a 3- to 8-membered or 4- to 6-membered silicon-containing saturated aliphatic ring.

In some embodiments, $R_1$ and $R_2$ are each independently selected from the group consisting of hydroxy, $C_{1-6}$ alkyl, $C_{1-6}$ alkoxy, and $C_{6-12}$ aryl, or $R_1$ and $R_2$ are joined to form a 3- to 8-membered silicon-containing saturated aliphatic ring containing 1, 2 or 3 silicon atoms.

In some embodiments, $R_1$ and $R_2$ are each independently selected from $C_{1-6}$ alkyl, or $R_1$ and $R_2$ are joined to form a 3- to 8-membered silicon-containing saturated aliphatic ring containing 1 silicon atom.

In some embodiments, $R_1$ and $R_2$ are each independently selected from the group consisting of methyl, ethyl, n-propyl, isopropyl, t-butyl, n-butyl, isobutyl and phenyl, or $R_1$ and $R_2$ are joined to form a 3-, 4-, 5-, 6-, 7- or 8-membered silicon-containing saturated aliphatic ring, wherein the silicon-containing saturated aliphatic ring contains 1 silicon atom.

In some embodiments, $R_1$ and $R_2$ are each independently selected from methyl, or $R_1$ and $R_2$ are joined to form a 4-, 5- or 6-membered silicon-containing saturated aliphatic ring, wherein the silicon-containing saturated aliphatic ring contains 1 silicon atom.

In some embodiments, $R_3$, $R_4$, $R_5$ and $R_6$ are each independently selected from the group consisting of hydrogen, fluoro, and chloro.

In some embodiments, $R_3$ and $R_4$ are each independently selected from the group consisting of hydrogen and fluoro, and $R_5$ and $R_6$ are selected from hydrogen. In some embodiments, one of $R_3$ and $R_4$ is fluoro, and the other is hydrogen, and $R_5$ and $R_6$ are selected from hydrogen. Preferably, $R_3$ and $R_4$ are selected from fluoro, and $R_5$ and $R_6$ are selected from hydrogen.

In some embodiments, X is selected from and Y is selected from the group consisting of
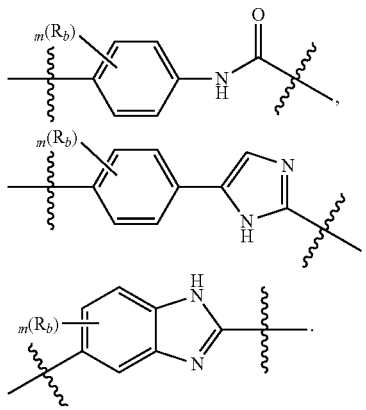
In some embodiments, X is selected from
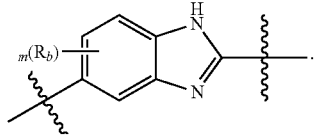
and Y is selected from the group consisting of
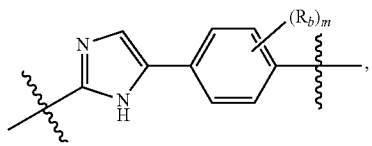
In some embodiments, X is selected from
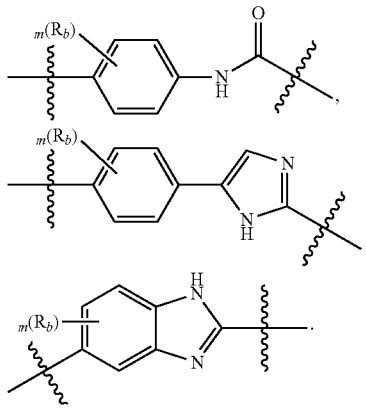
and Y is selected from the group consisting of
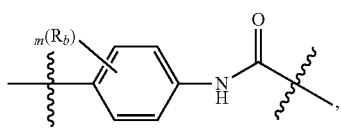
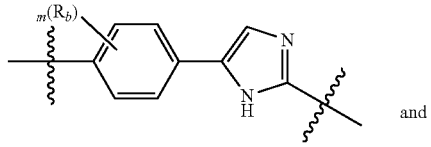
In some embodiments, X is selected from
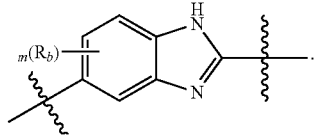
and Y is selected from
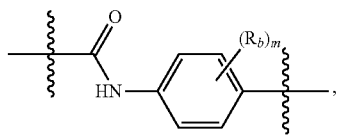
or X is selected from
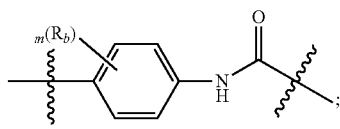
and Y is selected from
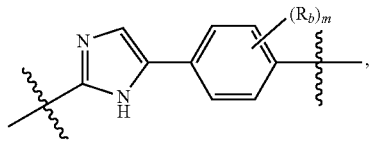
or X is selected from
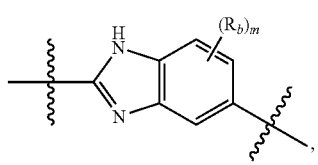

and Y is selected from
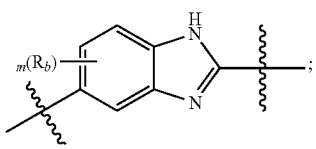
preferably, X is selected from
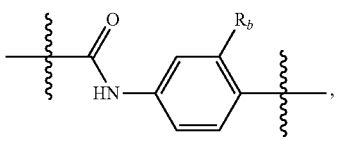
and Y is selected from
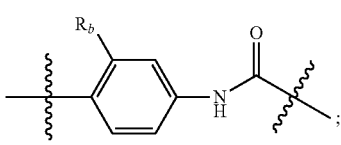
or X is selected from
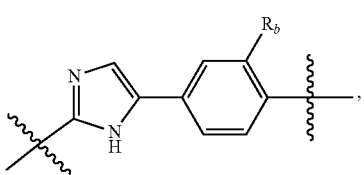
and Y is selected from
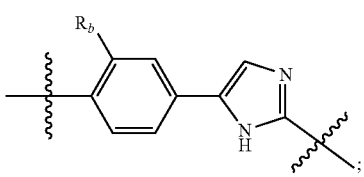
or X is selected from
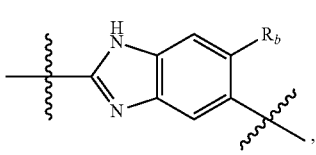
and Y is selected from
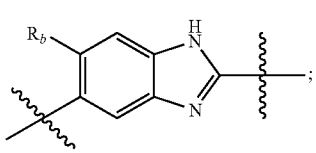
preferably, X is selected from
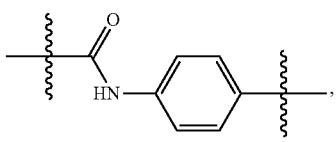
and Y is selected from
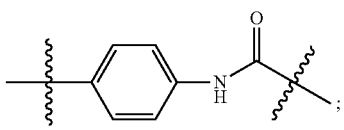 [SMILES: *C(=O)Nc1ccc(*)cc1]
or X is selected from
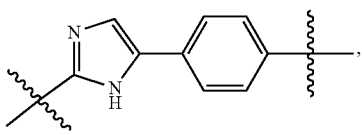 [SMILES: *c1ccc(-c2cnc(*)[nH]2)cc1]
and Y is selected from
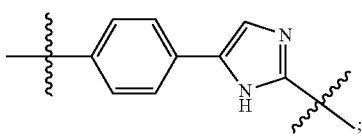 [SMILES: *c1ccc(-c2cnc(*)[nH]2)cc1]
or X is selected from
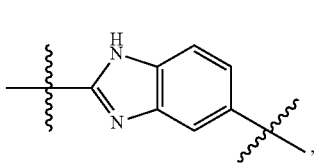
and Y is selected from
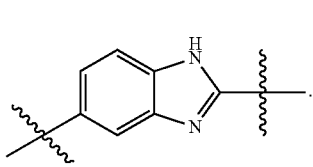 [SMILES: *c1ccc2[nH]c(*)nc2c1]
In some embodiments, X is selected from
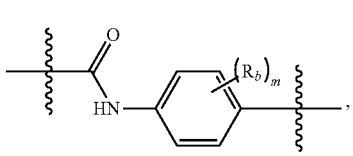

and Y is selected from

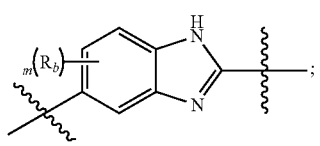

or X is selected from

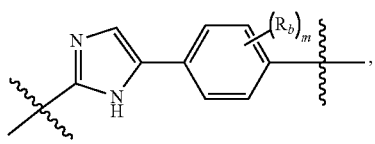

and Y is selected from the group consisting of

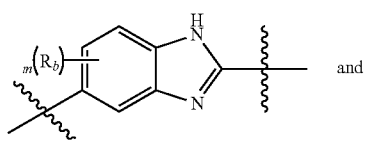 and

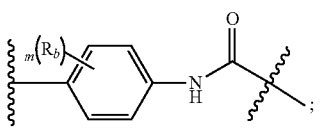

preferably, X is selected from

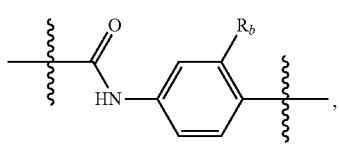

and Y is selected from

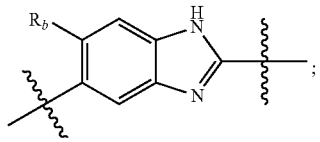

or X is selected from

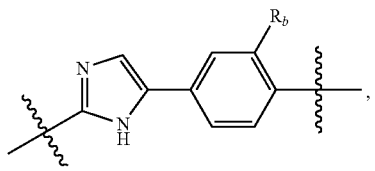

and Y is selected from the group consisting of

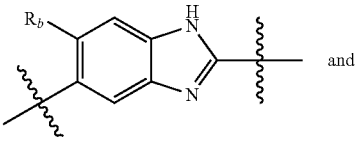 and

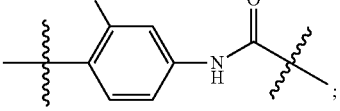

preferably, X is selected from

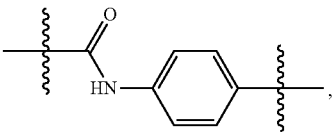

and Y is selected from

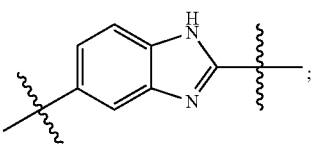 [SMILES: *c1ccc2[nH]c(*)nc2c1]

or X is selected from

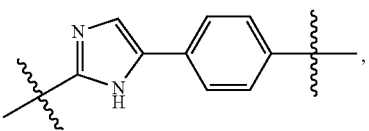

and Y is selected from the group consisting of

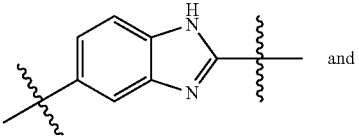 and

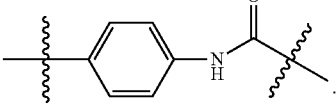

In some embodiments, X is selected from the group consisting of

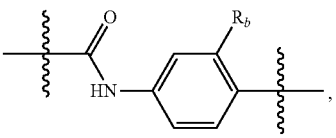

-continued

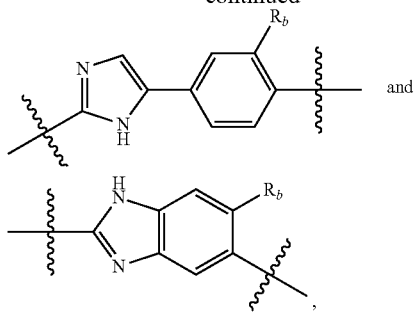

and and Y is selected from the group consisting of

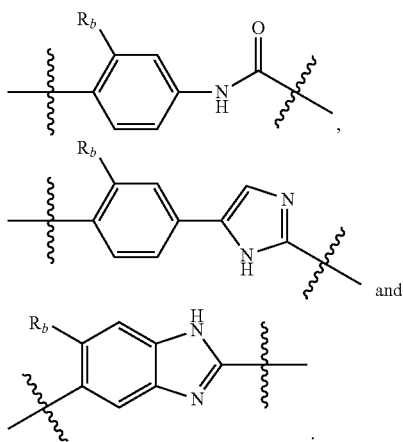

In some embodiments, X is selected from the group consisting of

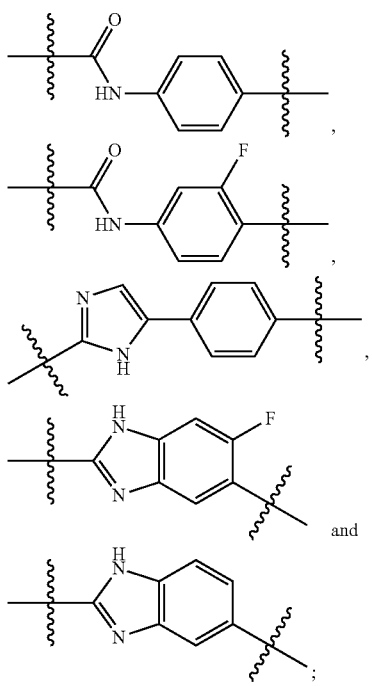

and Y is selected from the group consisting of

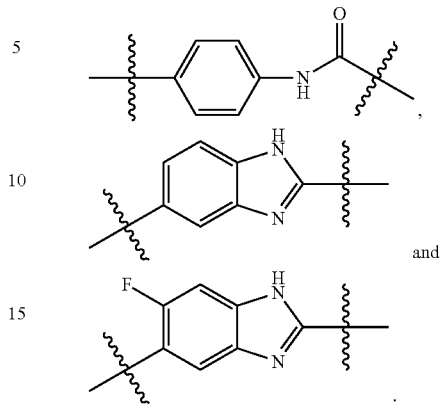

In some embodiments, $R_7$ and $R_8$ are each independently selected from the group consisting of —CH($C_{1-6}$ alkyl)($C_{1-6}$ alkoxy), —CH($C_{1-6}$ alkyl)$_2$, —CH($C_{1-6}$ alkoxy)$_2$, —C($C_{1-6}$ alkyl)$_2$($C_{1-6}$ alkoxy), —C($C_{1-6}$ alkyl) ($C_{1-6}$ alkoxy)$_2$, —C($C_{1-6}$ alkyl)$_3$ and —C($C_{1-6}$ alkoxy)$_3$. In some embodiments, $R_7$ and $R_8$ are the same.

In some embodiments, $R_7$ and $R_8$ are each independently selected from the group consisting of —CH(CH$_3$)(OCH$_3$), —CH(CH$_3$)$_2$, —CH(OCH$_3$)$_2$, —C(CH$_3$)$_2$(OCH$_3$), —C(CH$_3$)(OCH$_3$)$_2$, —C(CH$_3$)$_3$, —C(OCH$_3$)$_3$, —CH(CH$_2$CH$_3$)(OCH$_2$CH$_3$), —CH(CH$_3$)(OCH$_2$CH$_3$), —CH(CH$_2$CH$_3$)(OCH$_3$), —CH(CH$_2$CH$_3$)$_2$, —CH(CH$_3$)(CH$_2$CH$_3$), —CH(OCH$_2$CH$_3$)$_2$, —CH(OCH$_2$CH$_3$)(OCH$_3$), —C(CH$_2$CH$_3$)$_2$(OCH$_2$CH$_3$), —C(CH$_3$)$_2$(OCH$_2$CH$_3$), —C(CH$_2$CH$_3$)$_2$(OCH$_3$), —C(CH$_2$CH$_3$)(OCH$_2$CH$_3$)$_2$, —C(CH$_3$)(OCH$_2$CH$_3$)$_2$, —C(CH$_2$CH$_3$)(OCH$_3$)$_2$, —C(CH$_2$CH$_3$)$_3$, —C(CH$_3$)(CH$_2$CH$_3$)$_2$, —C(CH$_3$)$_2$(CH$_2$CH$_3$) and —C(OCH$_2$CH$_3$)$_3$.

In some embodiments, $R_9$ and $R_{10}$ are each independently selected from the group consisting of hydrogen, halogen, alkyl, and alkoxy. In some embodiments, $R_9$ and $R_{10}$ are each independently selected from the group consisting of hydrogen and alkoxyalkyl.

In some embodiments, $R_9$ and $R_{10}$ are each independently selected from the group consisting of hydrogen, halogen, $C_{1-6}$ alkyl, and $C_{1-6}$ alkoxy. In some embodiments, $R_9$ and $R_{10}$ are each independently selected from the group consisting of hydrogen and $C_{1-6}$ alkoxy$C_{1-6}$ alkyl. In some embodiments, $R_9$ and $R_{10}$ are the same.

In some embodiments, $R_9$ and $R_{10}$ are each independently selected from the group consisting of hydrogen, fluoro, chloro, methyl, ethyl, n-propyl, isopropyl, t-butyl, n-butyl, isobutyl, methoxy, ethoxy, n-propoxy, isopropoxy, tert-butoxy, n-butoxy and isobutoxy. In some embodiments, $R_9$ and $R_{10}$ are each independently selected from the group consisting of hydrogen, methoxymethyl, methoxyethyl, ethoxymethyl, and ethoxyethyl. In some embodiments, $R_9$ and $R_{10}$ are each independently selected from the group consisting of hydrogen and methoxymethyl. In some embodiments, both $R_9$ and $R_{10}$ are hydrogen. In some embodiments, one of $R_9$ and $R_{10}$ is hydrogen and the other is methoxymethyl. In some embodiments, both $R_9$ and $R_{10}$ are methoxymethyl.

In some embodiments, $R_7$ and $R_8$ are each independently selected from the group consisting of —CH(alkyl)(alkoxy), —CH(alkyl)$_2$, and —CH(alkoxy)$_2$. In some embodiments, $R_7$ and $R_8$ are each independently selected from the group consisting of —CH($C_{1-6}$ alkyl)($C_{1-6}$ alkoxy), —CH($C_{1-6}$ alkyl)$_2$, and —CH($C_{1-6}$ alkoxy)$_2$. In some embodiments, both $R_7$ and $R_8$ are —CH(CH$_3$)(OCH$_3$).

In some embodiments, $R_7$ and $R_8$ are each independently selected from the group consisting of —CH(CH$_3$)(OCH$_3$) and —CH(CH$_3$)$_2$; and $R_9$ and $R_{10}$ are each independently selected from the group consisting of hydrogen and methoxymethyl.

In some embodiments, $R_7$ and $R_8$ are each independently selected from the group consisting of —CH(CH$_3$)(OCH$_3$) and —CH(CH$_3$)$_2$; and $R_9$ and $R_{10}$ are selected from hydrogen.

In some embodiments, $R_7$ and $R_8$ are each independently selected from the group consisting of —CH(CH$_3$)(OCH$_3$) and —CH(CH$_3$)$_2$, wherein the chiral carbon atom of —CH(CH$_3$)(OCH$_3$) is in R configuration; and $R_9$ and $R_{10}$ are each independently selected from the group consisting of hydrogen and methoxymethyl.

In some embodiments, $R_7$ and $R_8$ are each independently selected from the group consisting of —CH(CH$_3$)(OCH$_3$) and —CH(CH$_3$)$_2$, wherein the chiral carbon atom of —CH(CH$_3$)(OCH$_3$) is in R configuration; and $R_9$ and $R_{10}$ are selected from hydrogen.

In some embodiments, the chiral carbon atom on the tetrahydropyrrole ring attached to $R_9$ or $R_{10}$ is in S configuration.

In some embodiments, each of $R_a$ and $R_b$ is independently selected from the group consisting of hydrogen, halogen, and $C_{1-6}$ alkyl.

In some embodiments, each of $R_a$ and $R_b$ is independently selected from the group consisting of halogen and $C_{1-6}$ alkyl.

In some embodiments, each of $R_a$ and $R_b$ is independently selected from the group consisting of fluoro, chloro, methyl, ethyl, n-propyl, isopropyl, t-butyl, n-butyl, and isobutyl.

In some embodiments, each of $R_a$ and $R_b$ is independently selected from the group consisting of hydrogen, fluoro, chloro, methyl, ethyl, n-propyl, isopropyl, t-butyl, n-butyl, and isobutyl.

In some embodiments, n is selected from 0, and $R_b$ is selected from fluoro.

In some embodiments, $R_1$ and $R_2$ are methyl, or $R_1$ and $R_2$ are joined to form a 4-, 5- or 6-membered silicon-containing saturated aliphatic ring containing 1 silicon atom; one of $R_3$ and $R_4$ is fluoro, and the other is hydrogen, or both $R_3$ and $R_4$ are fluoro; $R_5$ and $R_6$ are hydrogen; X is

[structures]

Y is

[structures]

both $R_7$ and $R_8$ are —CH(CH$_3$)(OCH$_3$); both $R_9$ and $R_{10}$ are hydrogen or methoxymethyl; and n is 0.

Further, the present application provides a compound of Formula Ia, Formula Ib, Formula Ic or Formula Id, a pharmaceutically acceptable salt, a tautomer, a stereoisomer or a deuteride thereof, or a mixture thereof, Formula Ia Formula Ib

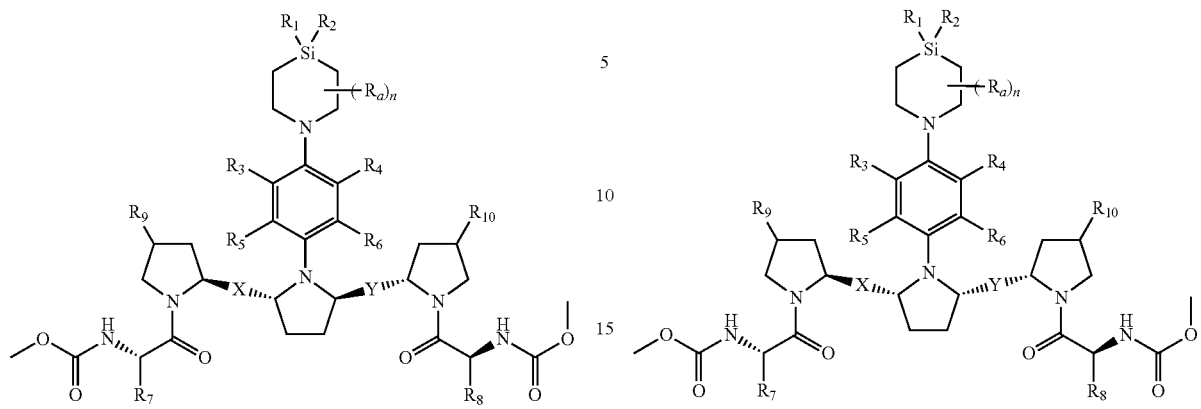

Formula Id

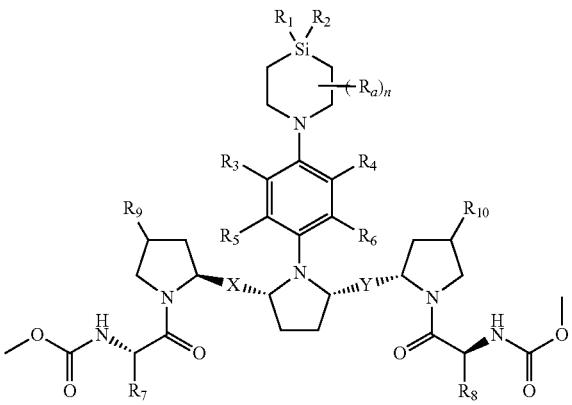

Formula Ic

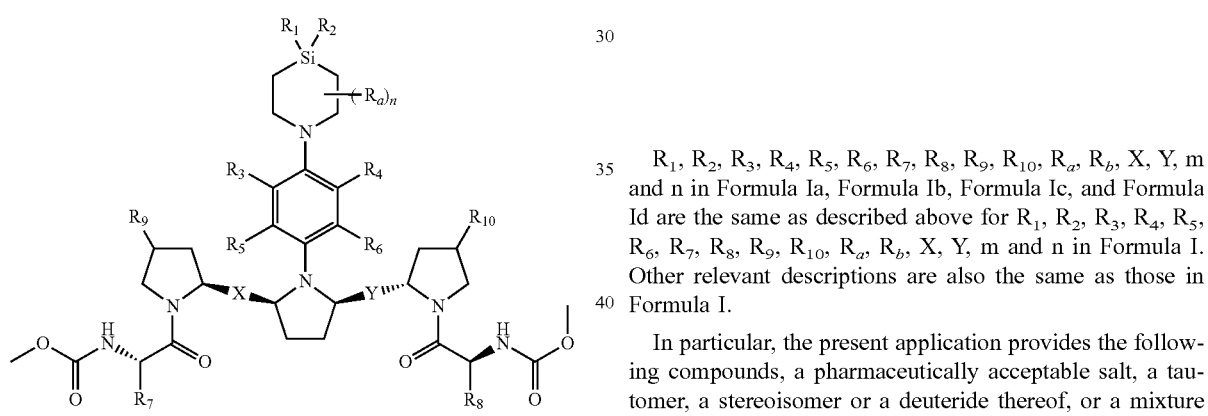

R$_1$, R$_2$, R$_3$, R$_4$, R$_5$, R$_6$, R$_7$, R$_8$, R$_9$, R$_{10}$, R$_a$, R$_b$, X, Y, m and n in Formula Ia, Formula Ib, Formula Ic, and Formula Id are the same as described above for R$_1$, R$_2$, R$_3$, R$_4$, R$_5$, R$_6$, R$_7$, R$_8$, R$_9$, R$_{10}$, R$_a$, R$_b$, X, Y, m and n in Formula I. Other relevant descriptions are also the same as those in Formula I.

In particular, the present application provides the following compounds, a pharmaceutically acceptable salt, a tautomer, a stereoisomer or a deuteride thereof, or a mixture thereof:

1a

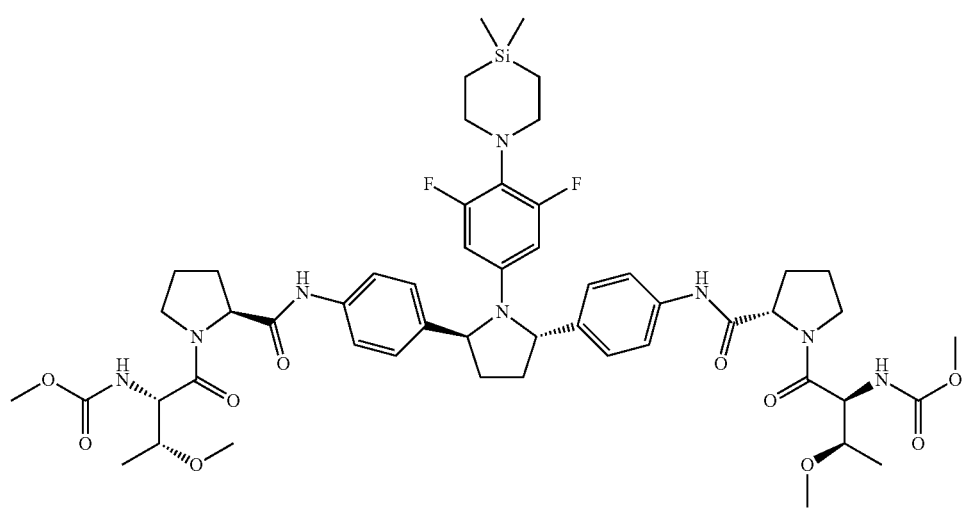

-continued
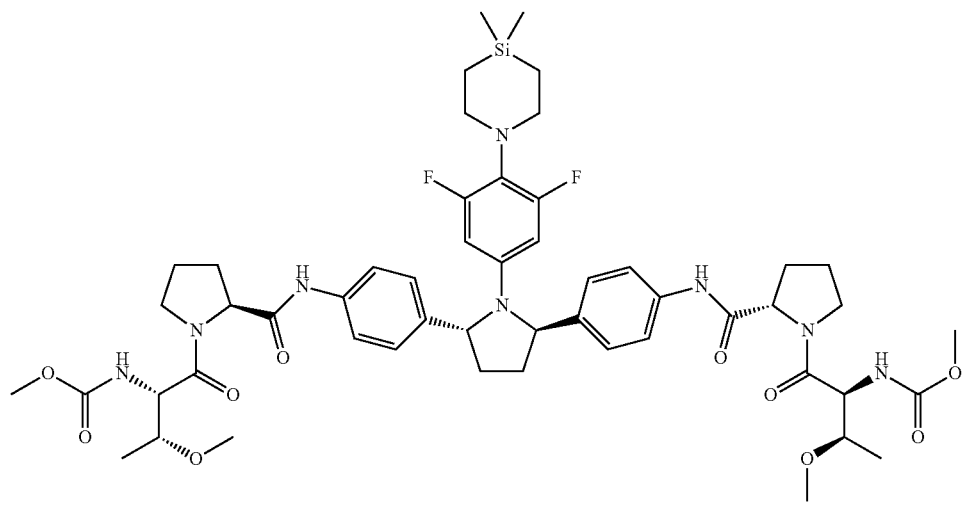
1b
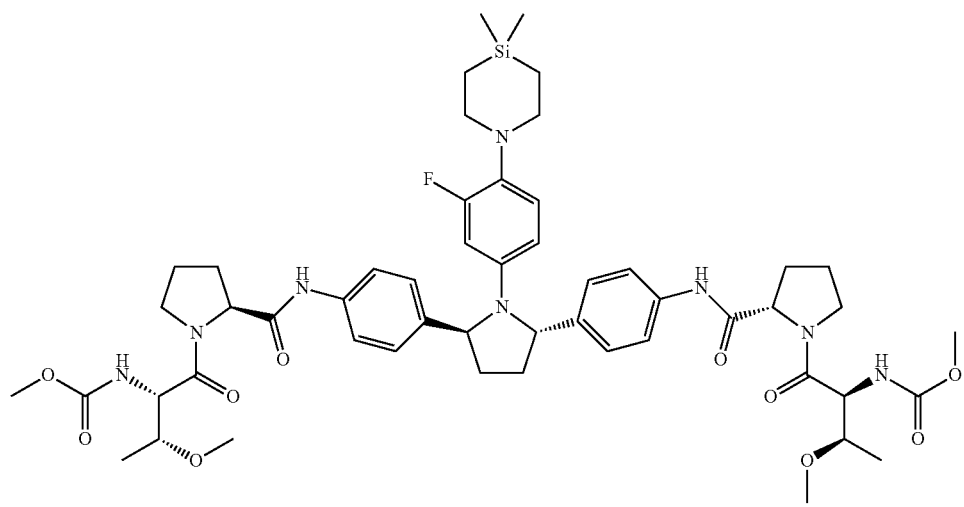
2a
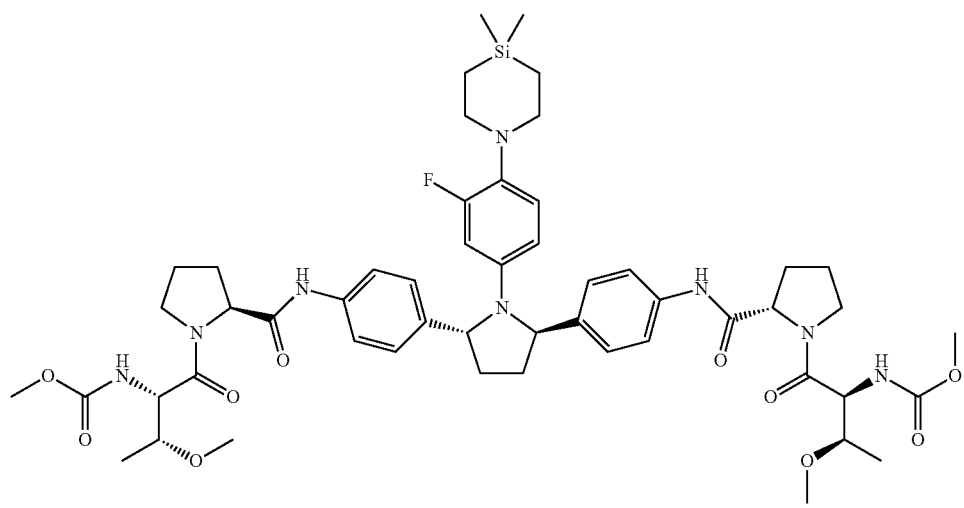
2b

-continued
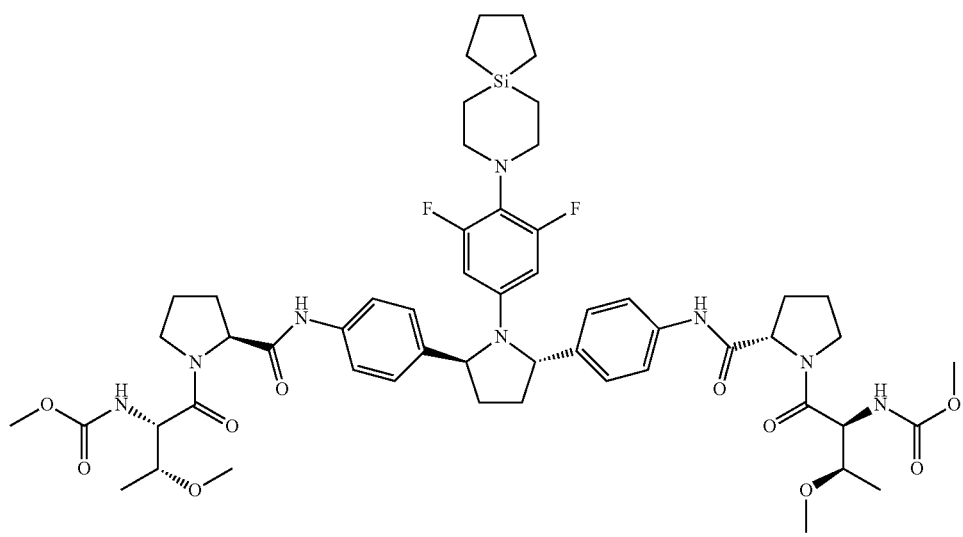
3a
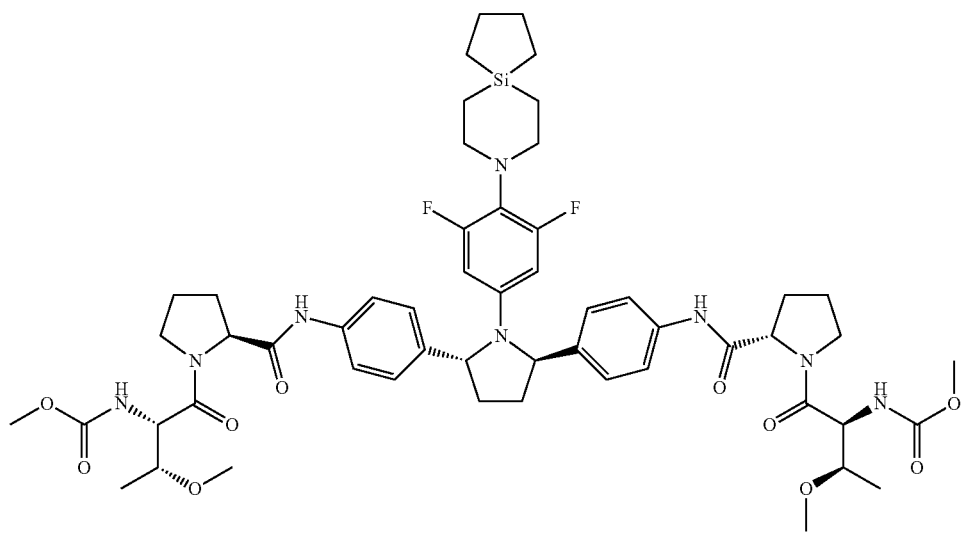
3b
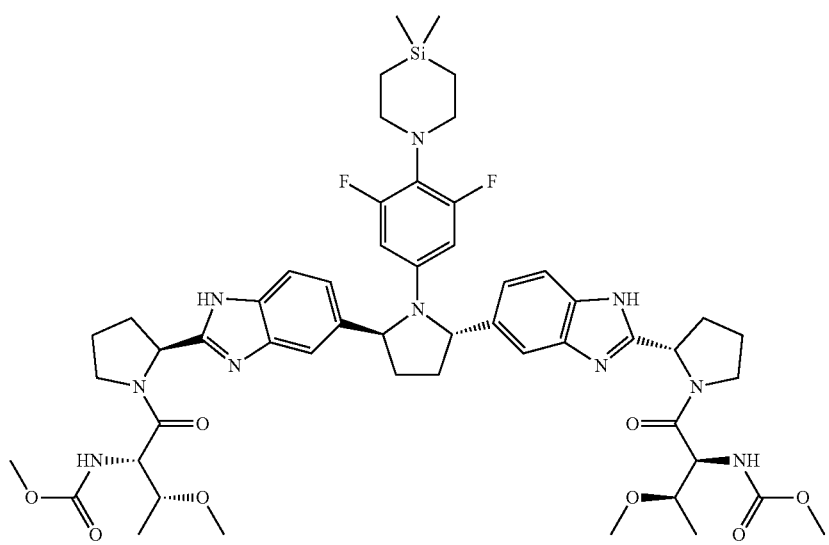
4a

-continued
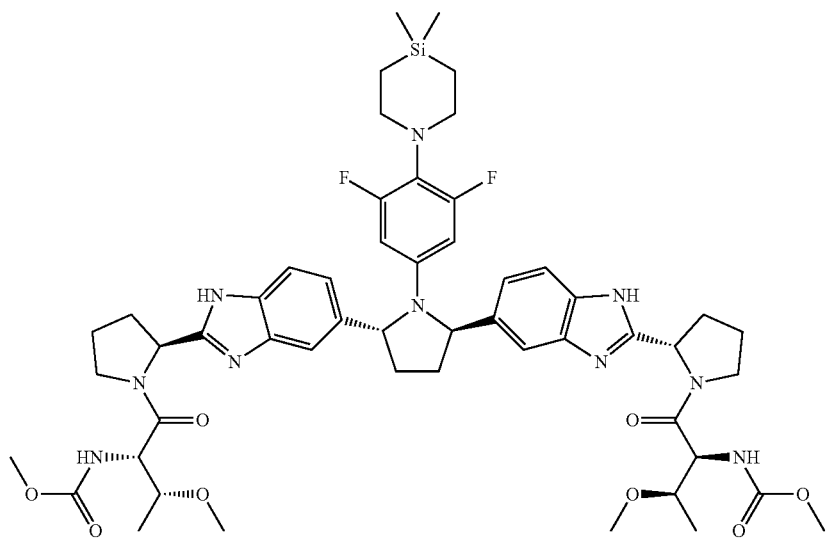
4b
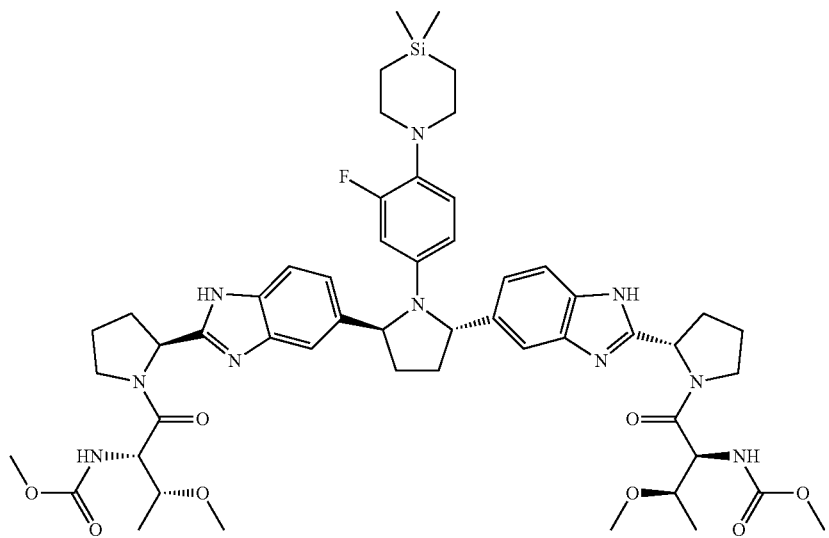
5a
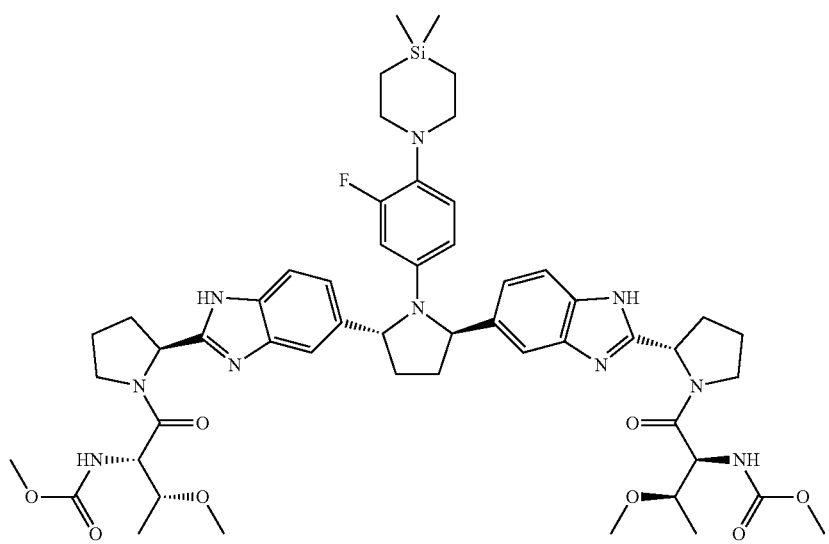
5b

-continued
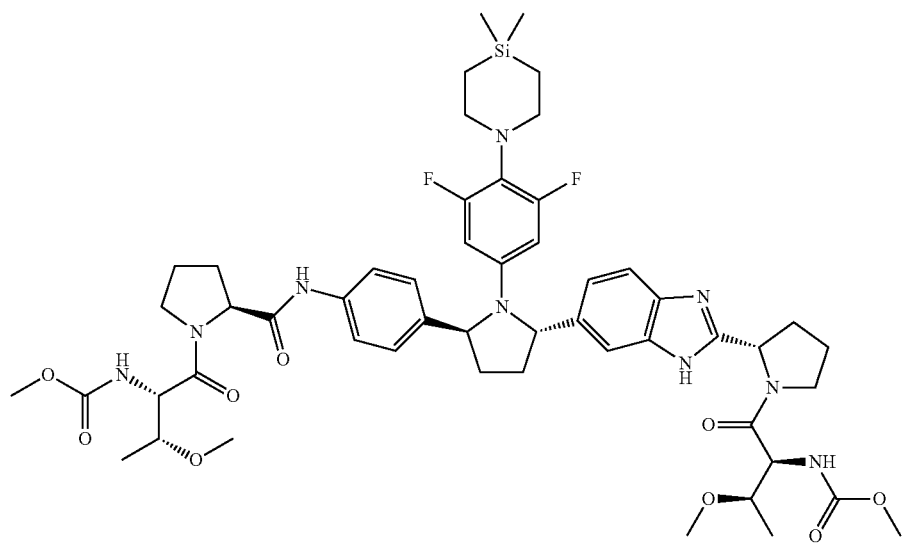
6a
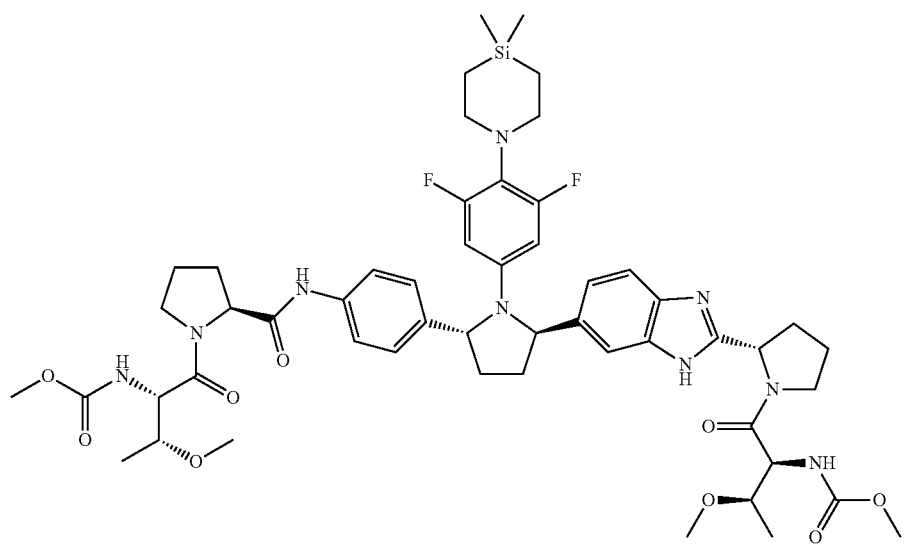
6b
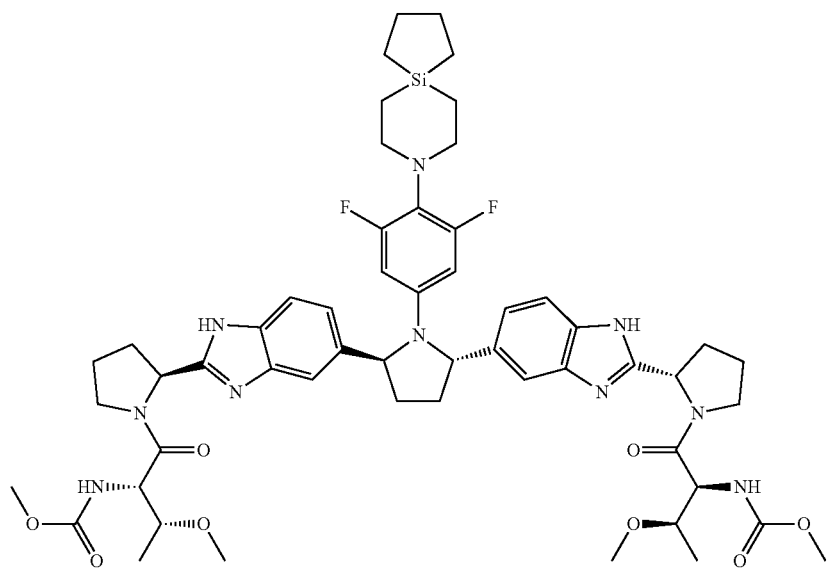
7a

-continued
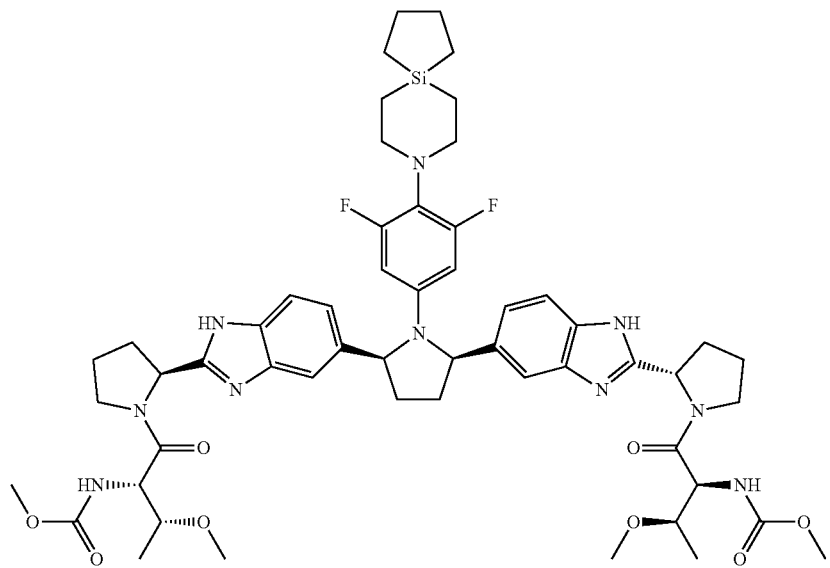
7b
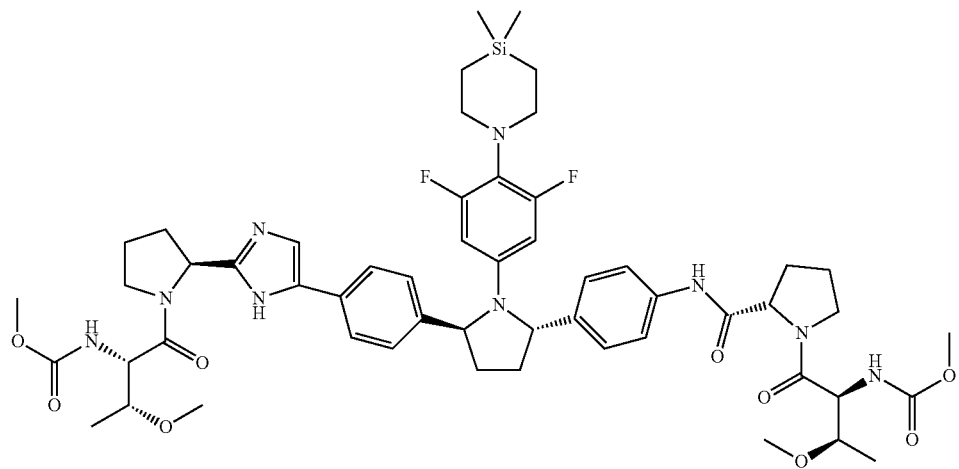
8a
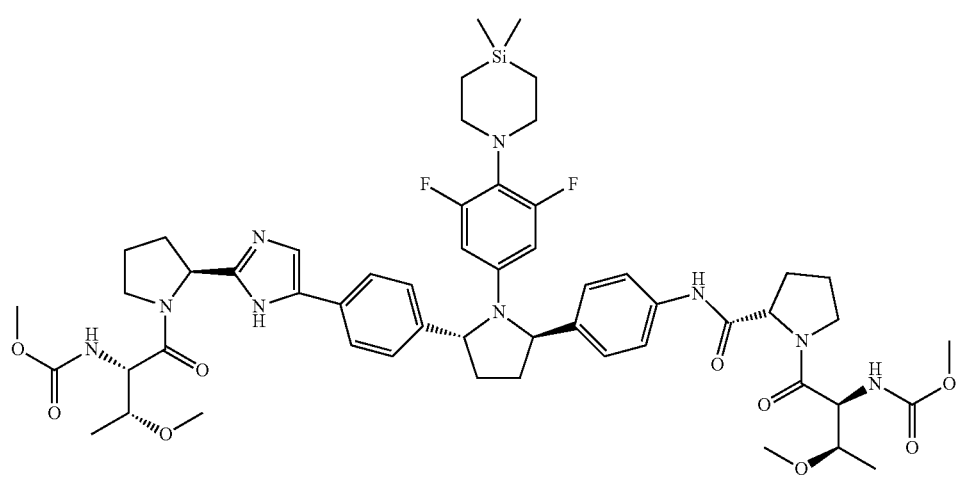
8b

-continued
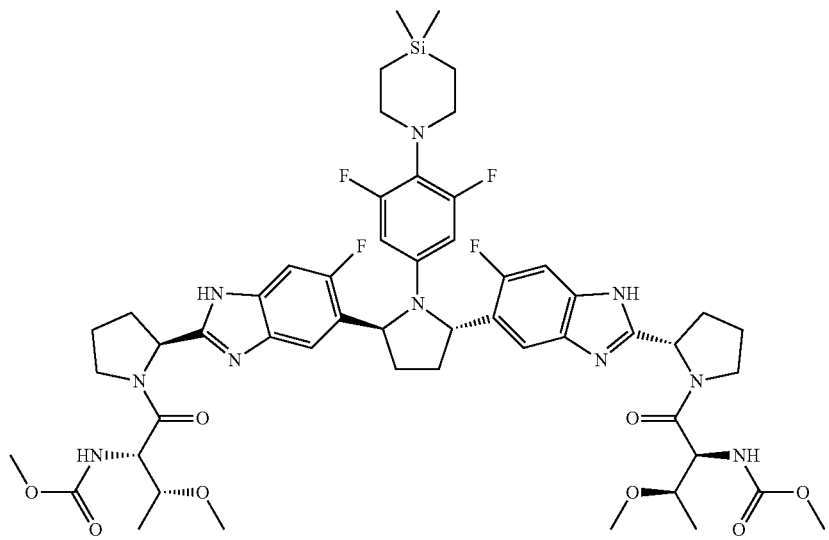
9a
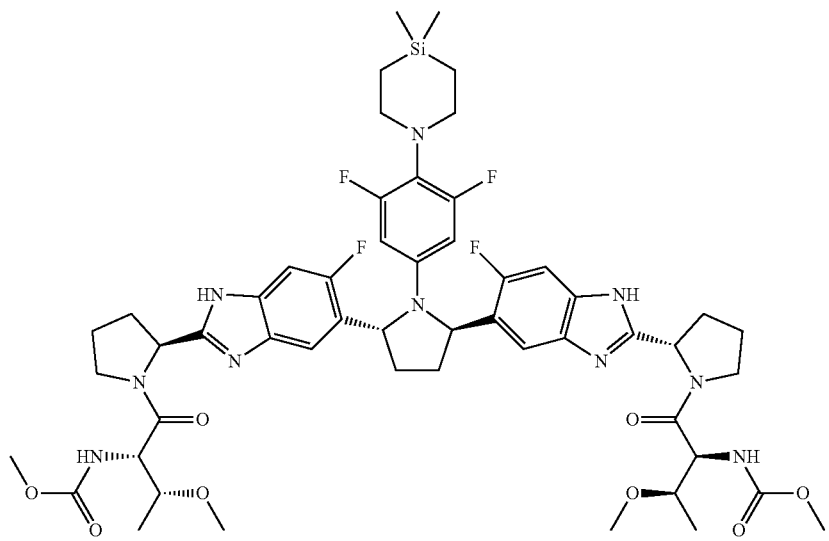
9b
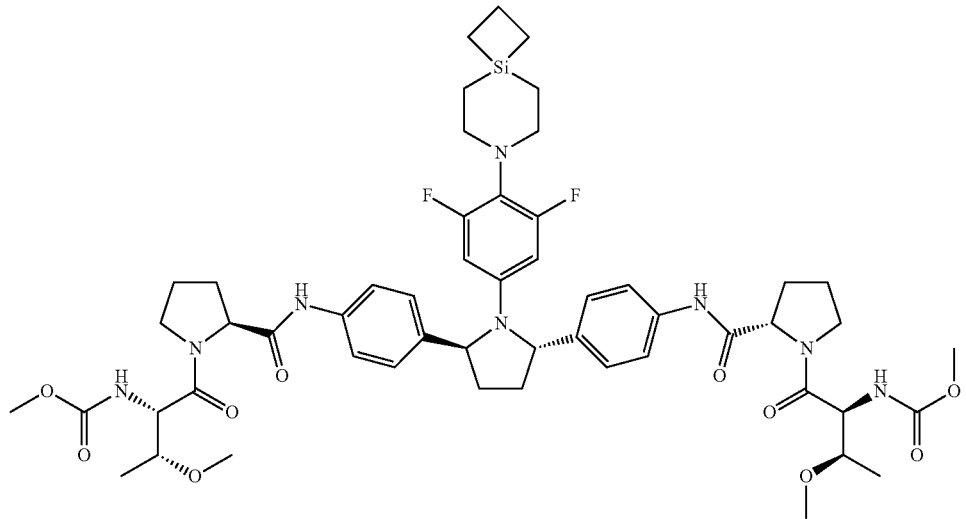
10a

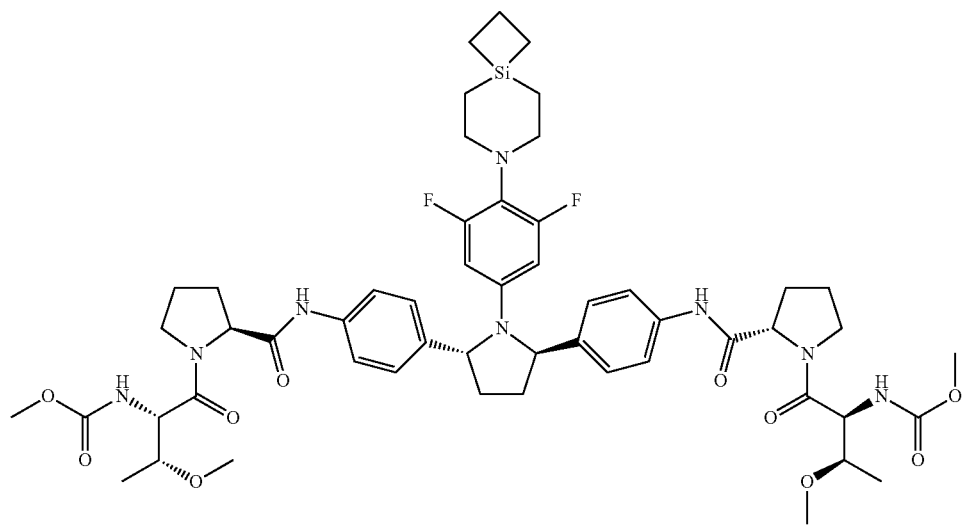
10b
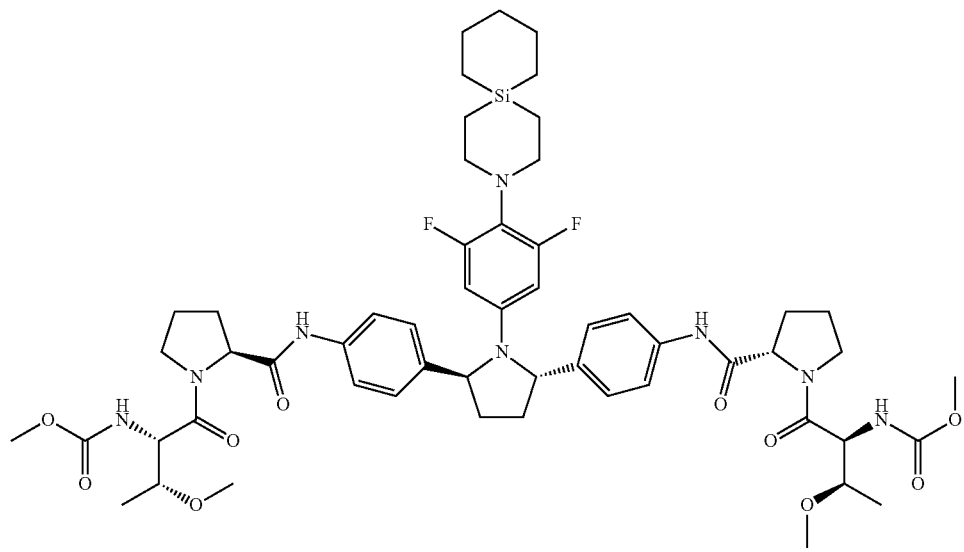
11a
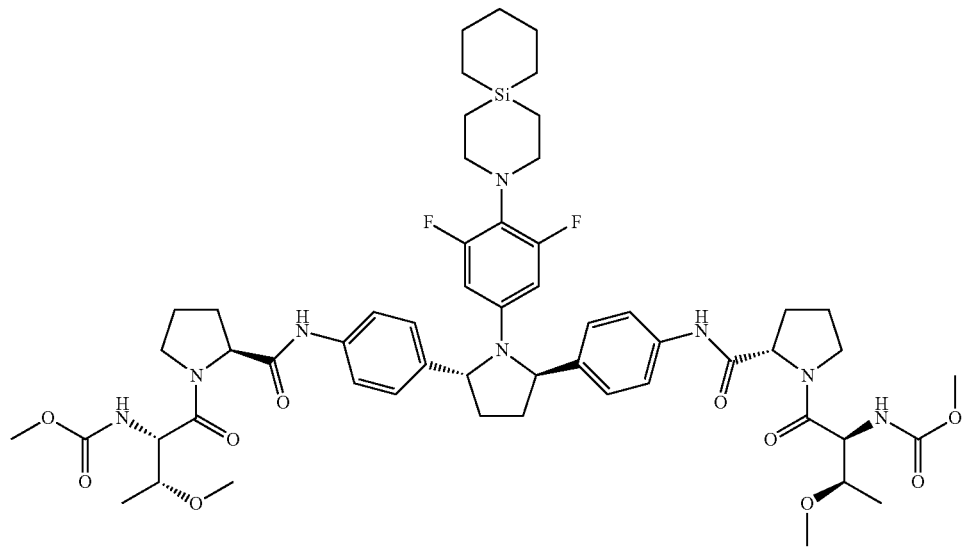
11b

12a
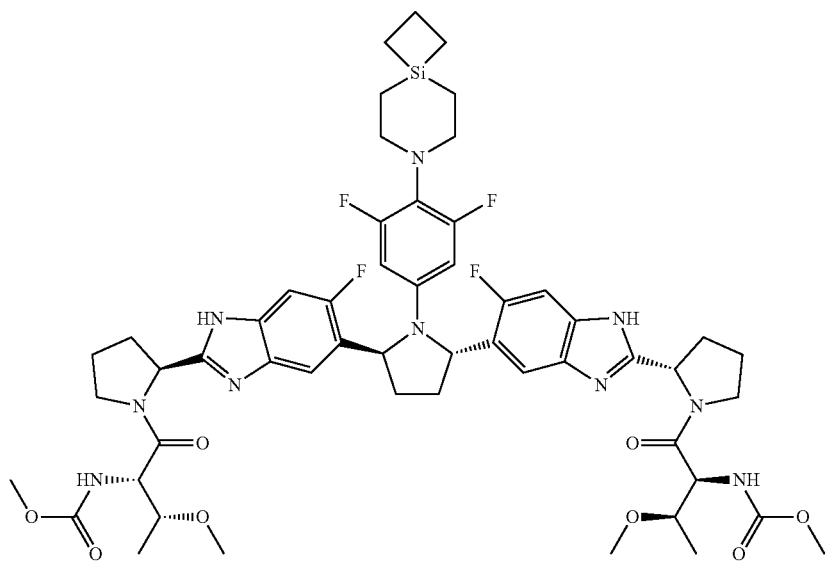
12b
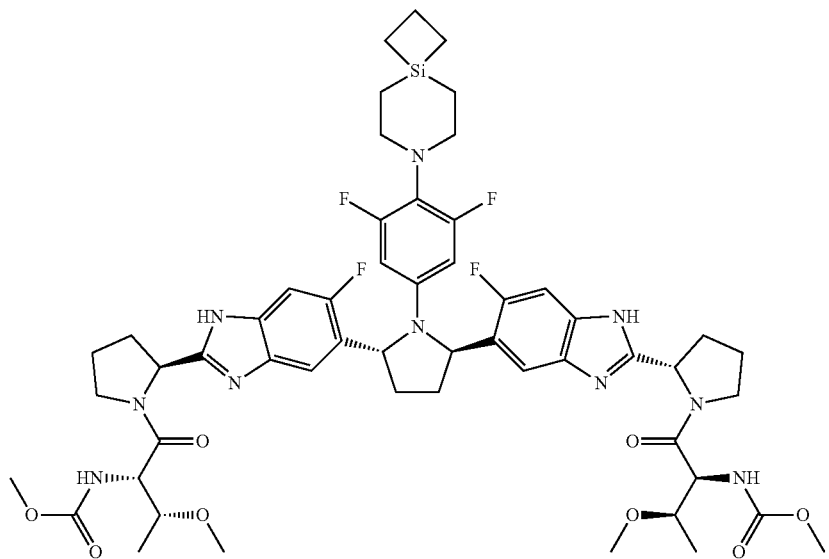
13a
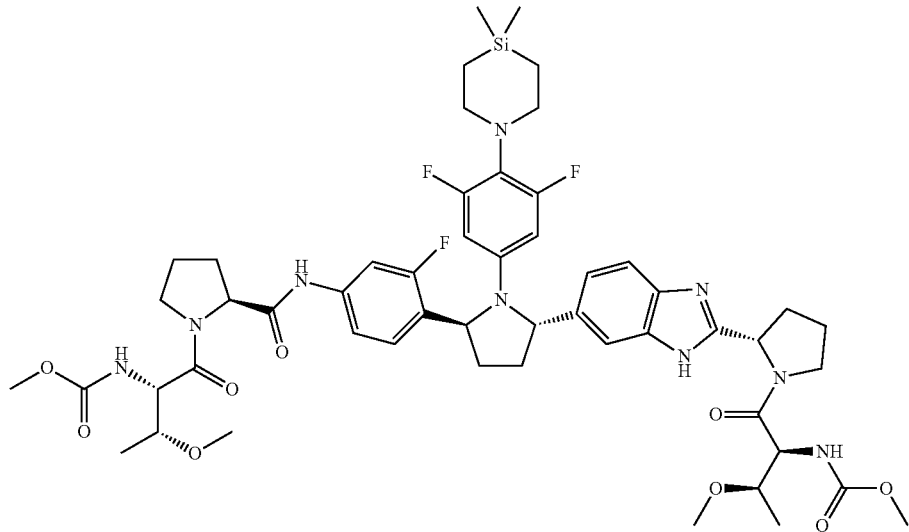

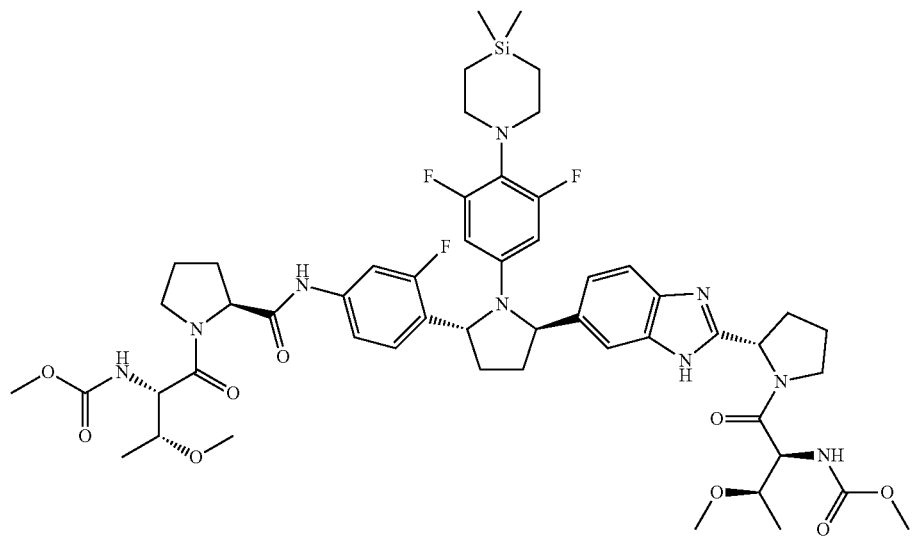
13b
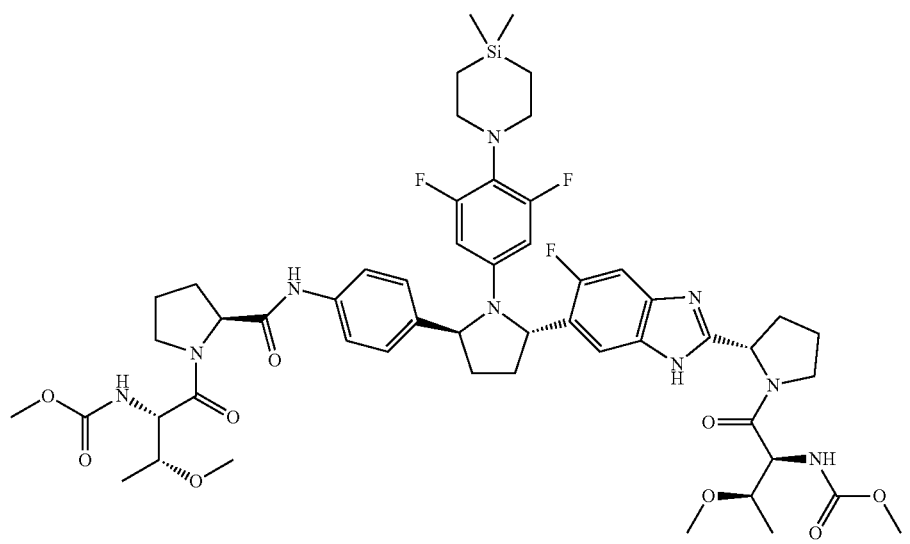
14a
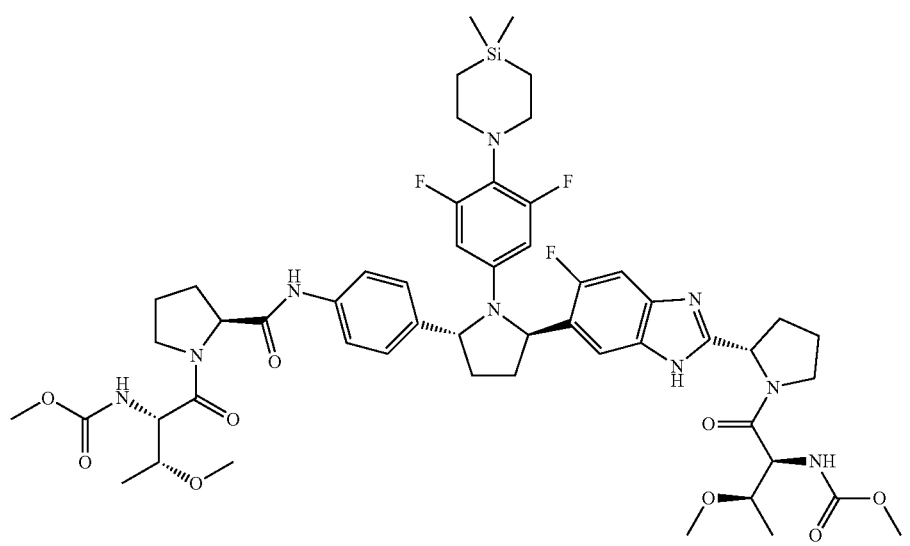
14b

15a
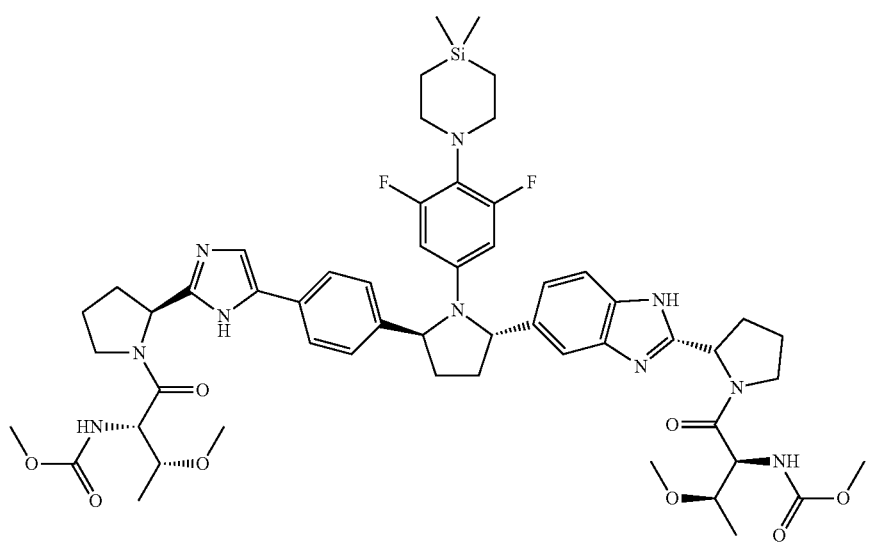
15b
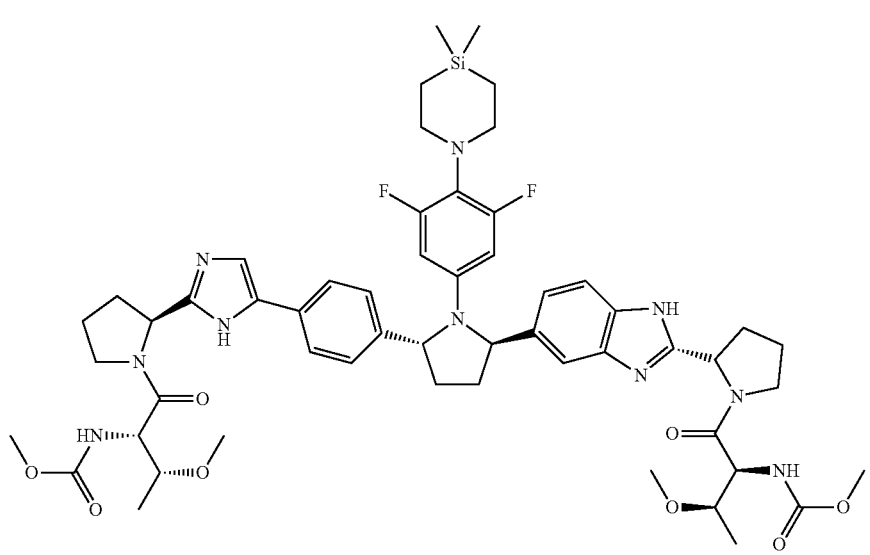
16a
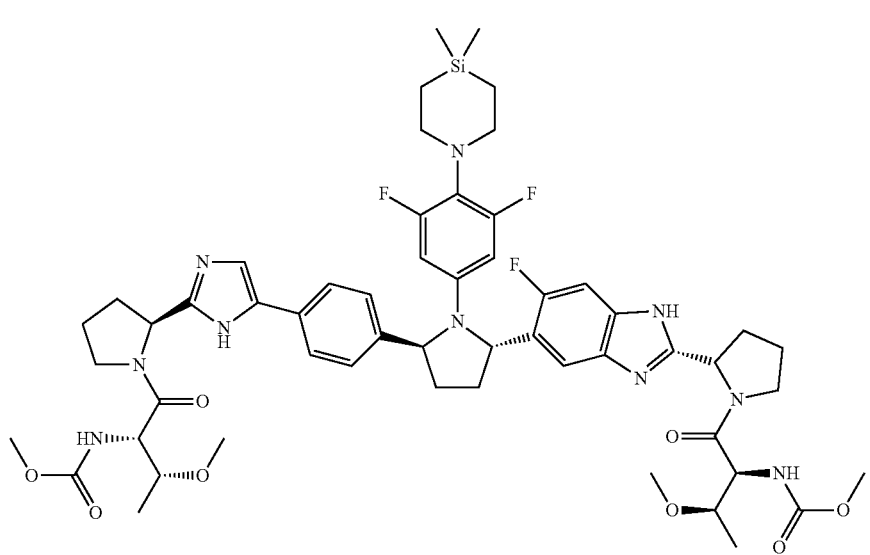

-continued
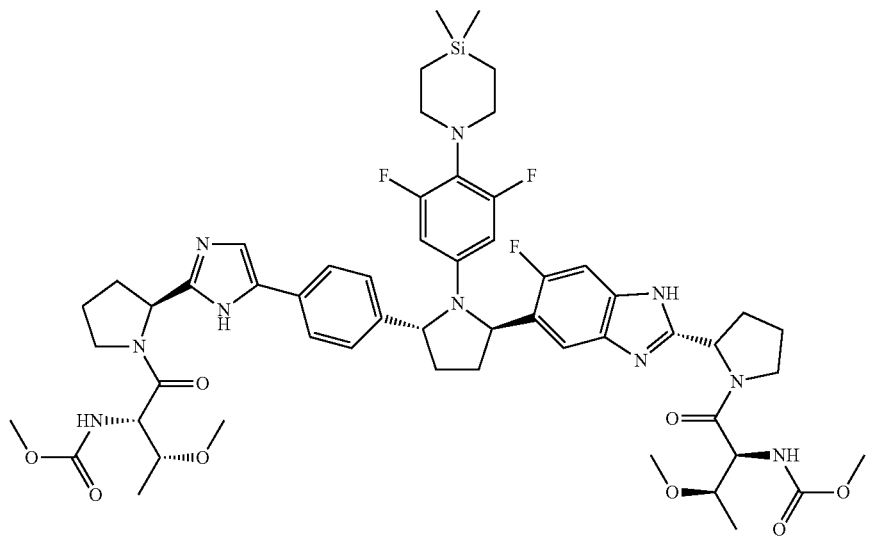
16b
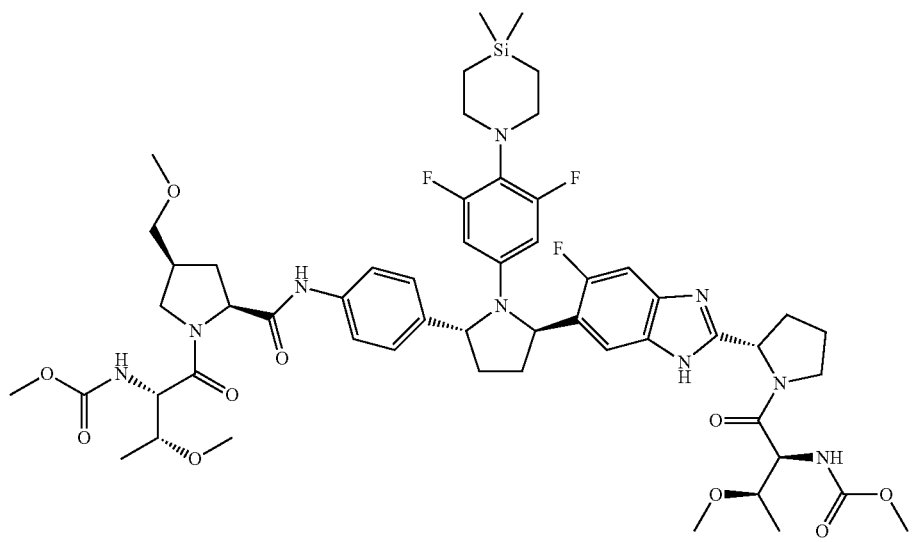
17b
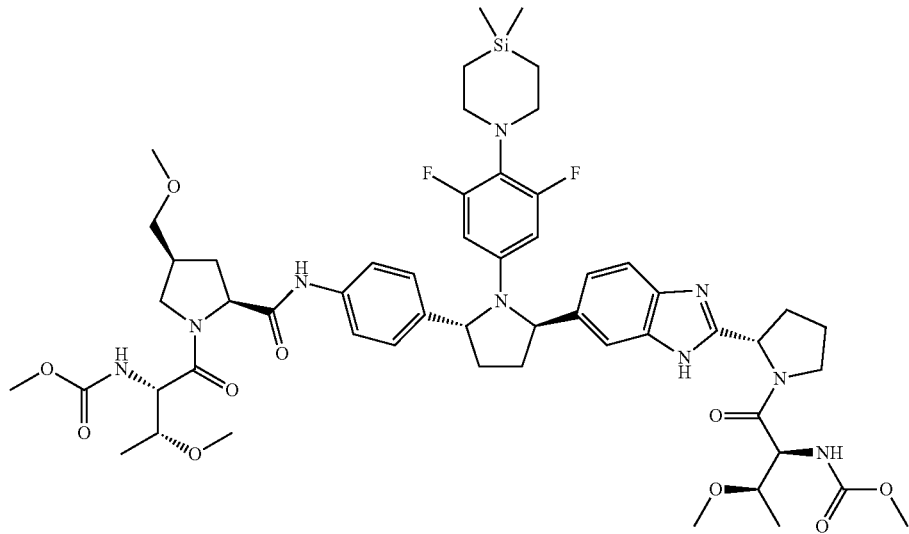
18b

-continued
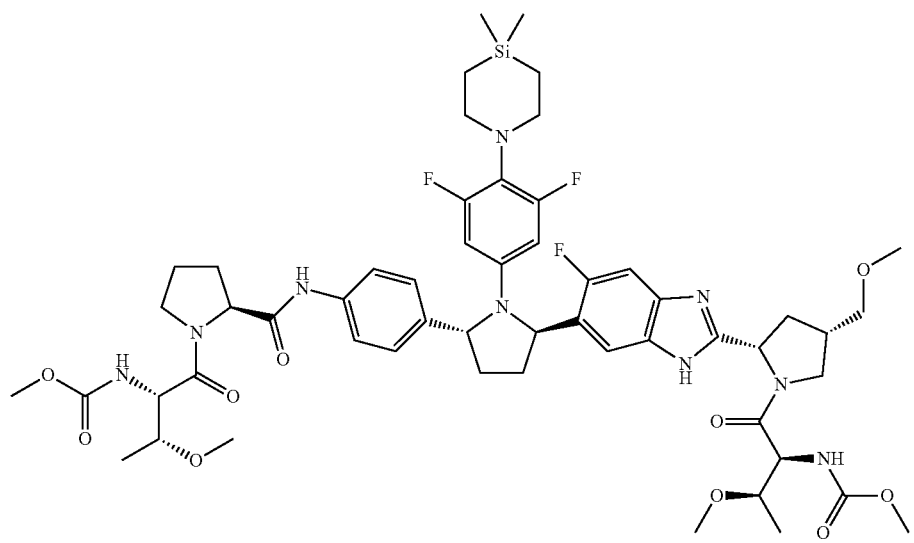
19b
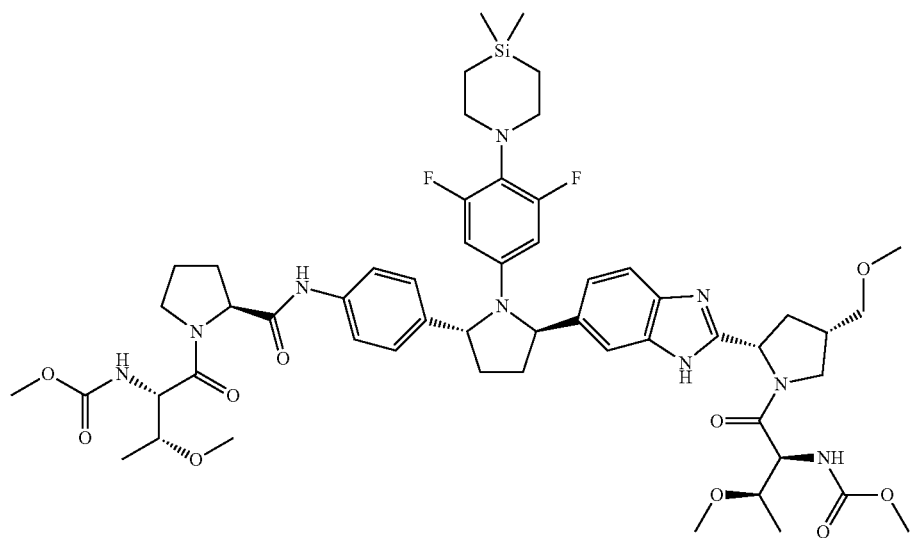
20b
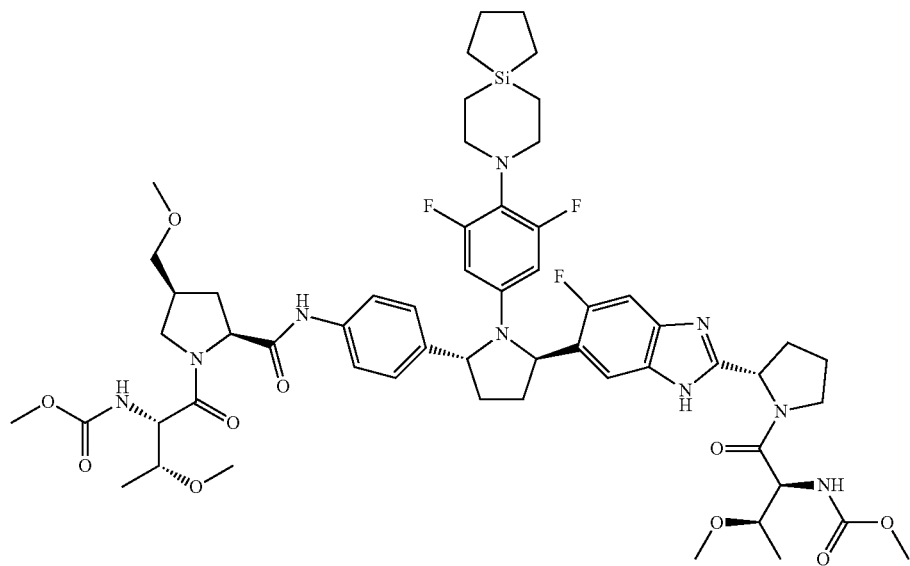
21b

-continued
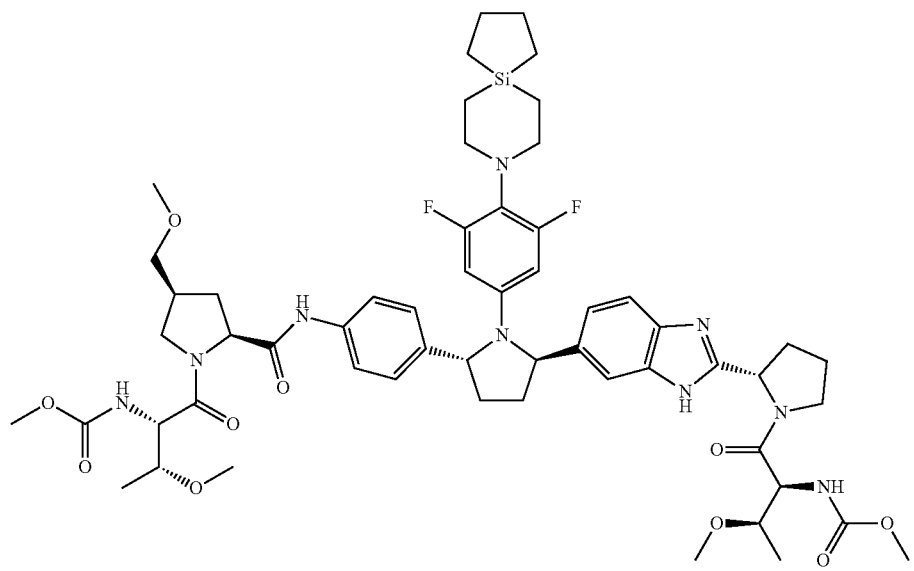
22b
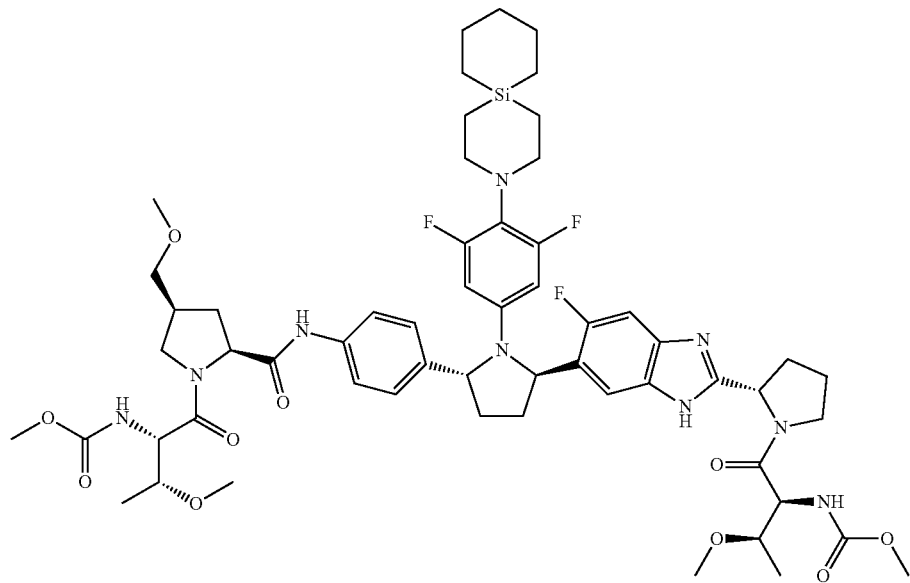
23b

-continued
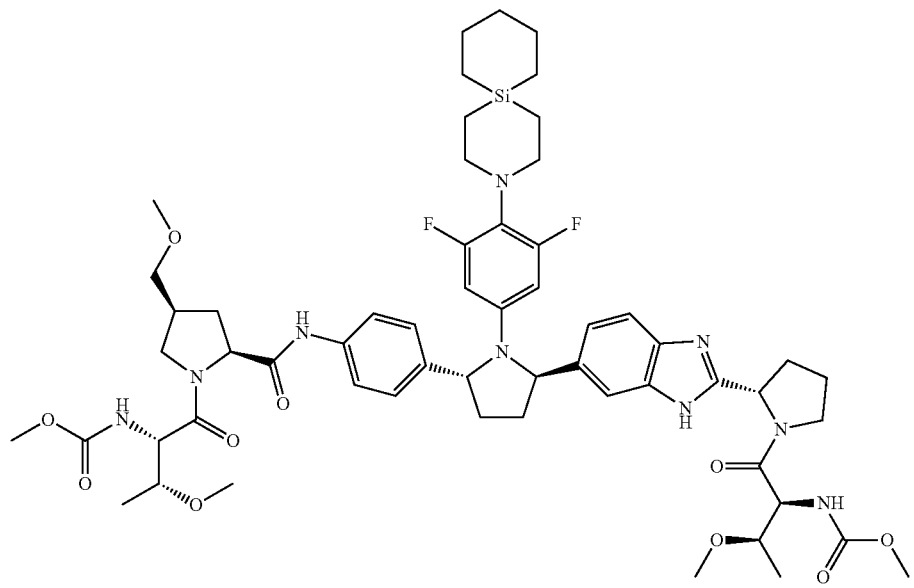
24b
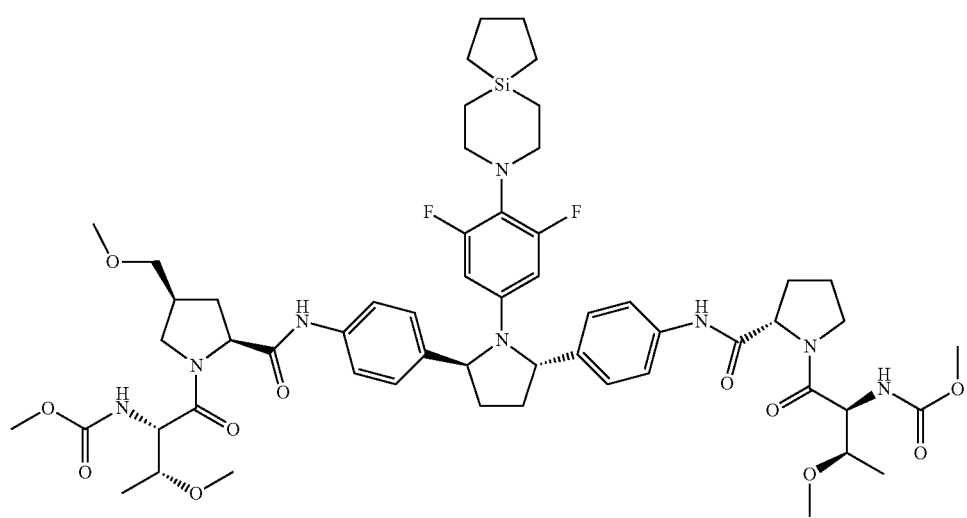
25a
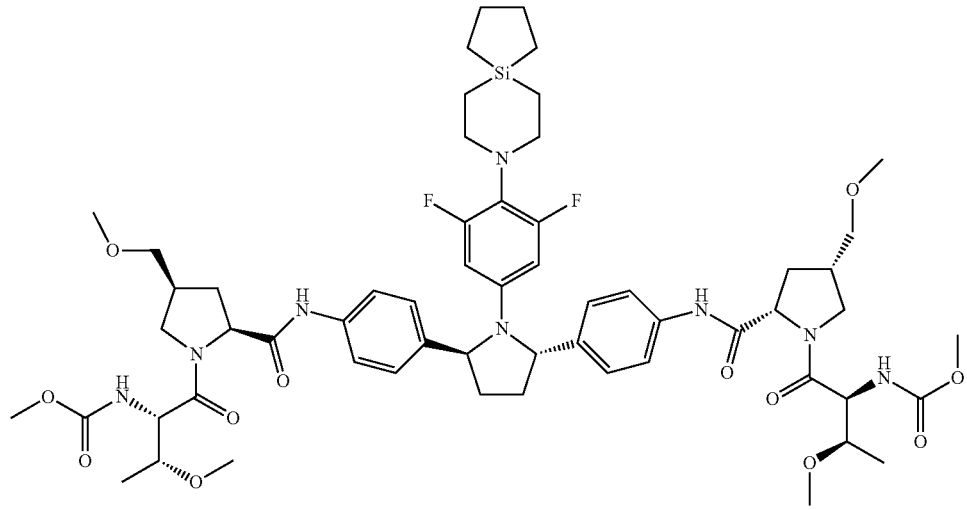
26a

-continued
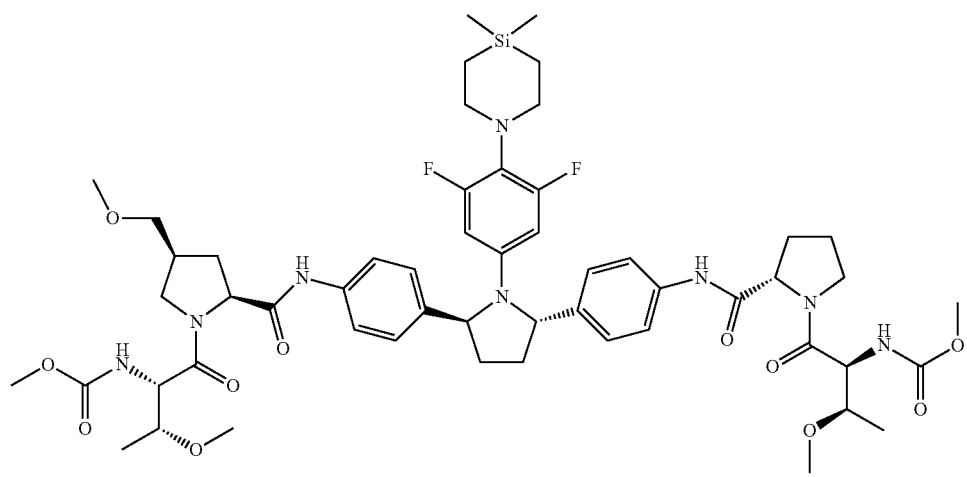
27a
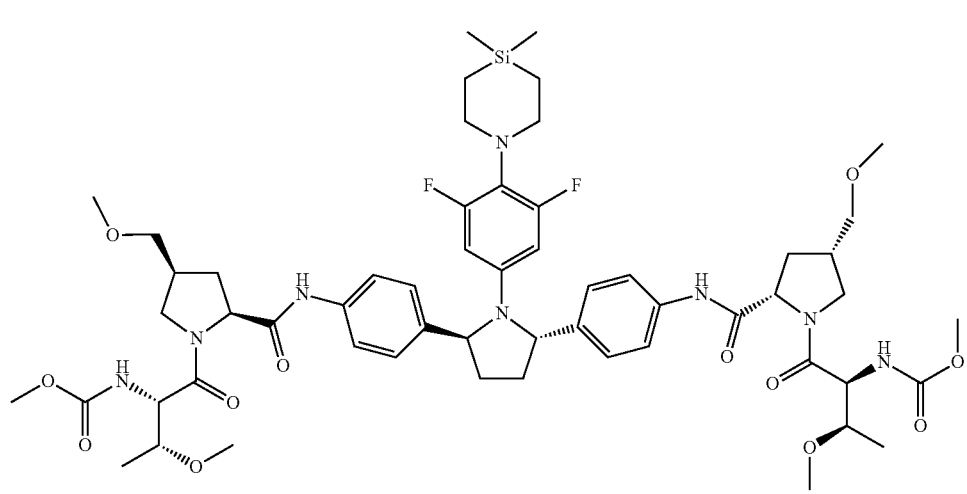
28a
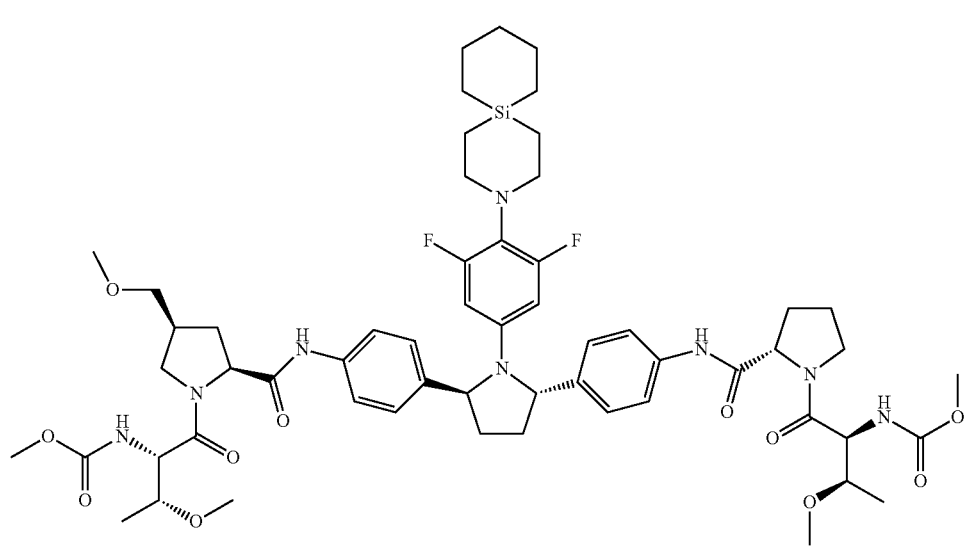
29a

-continued
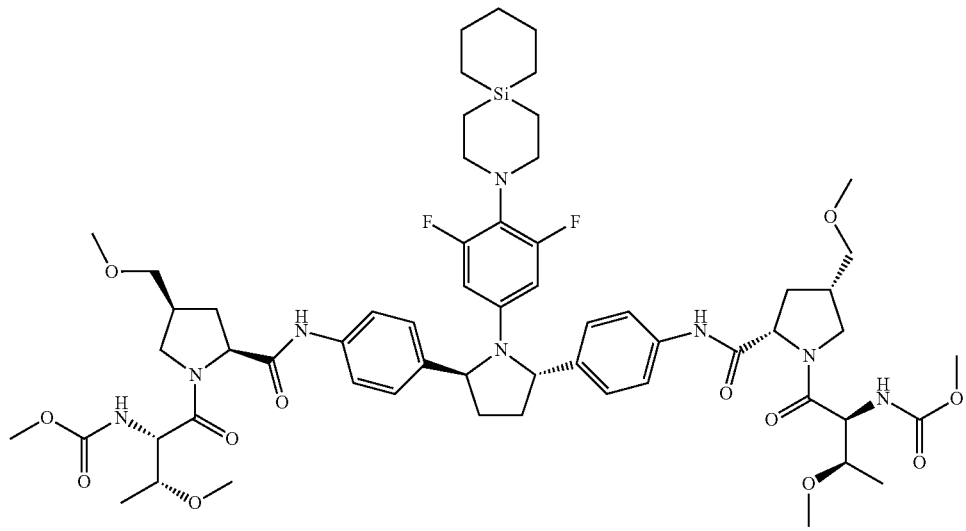
30a
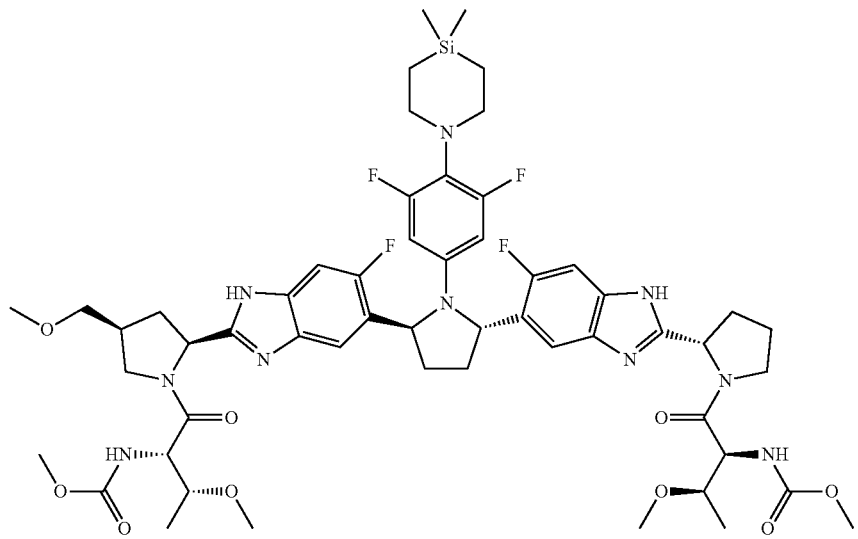
31a
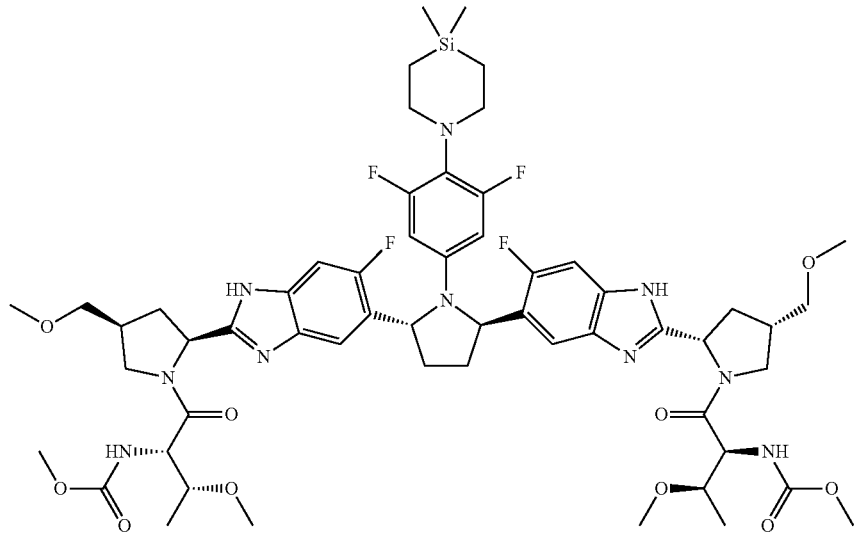
32b

-continued
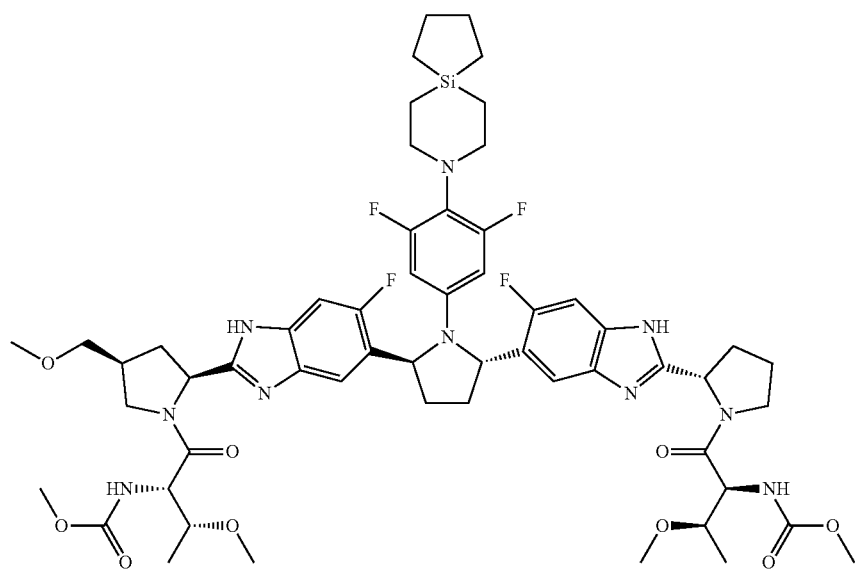
33a
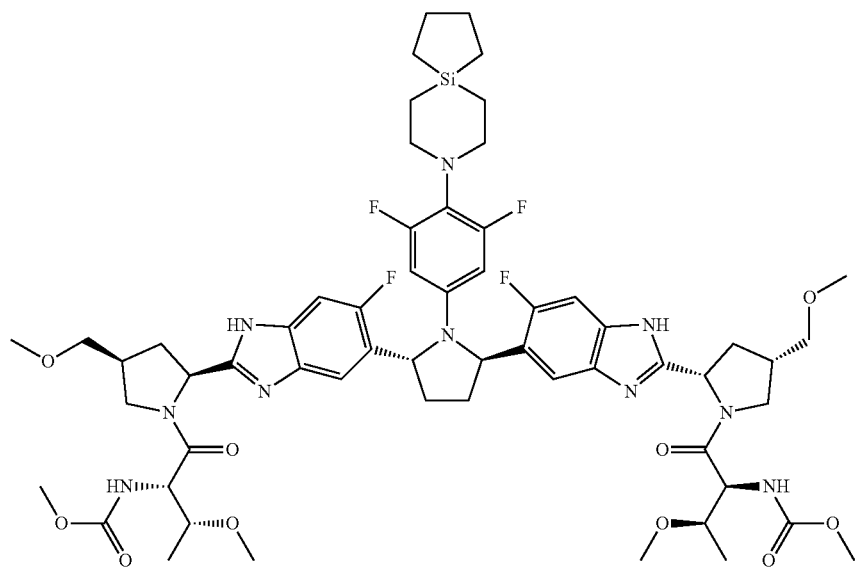
34b

-continued

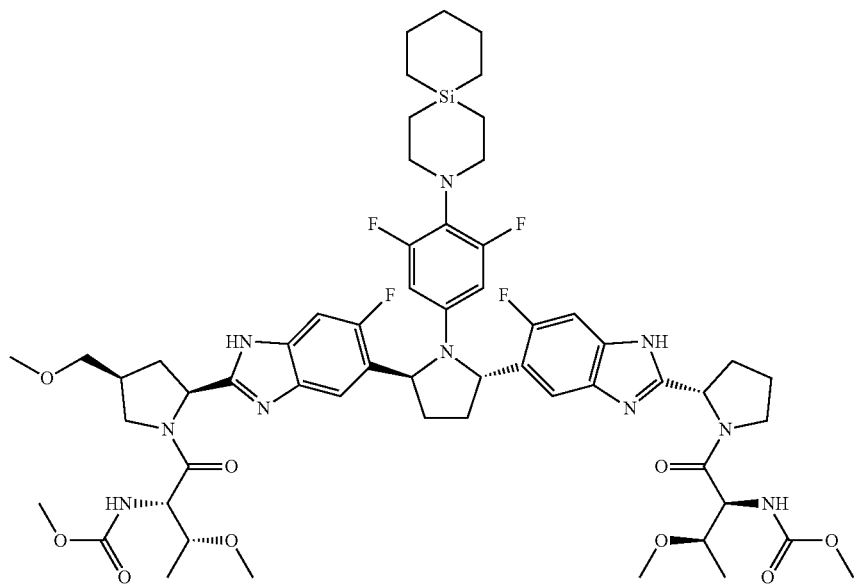

35a

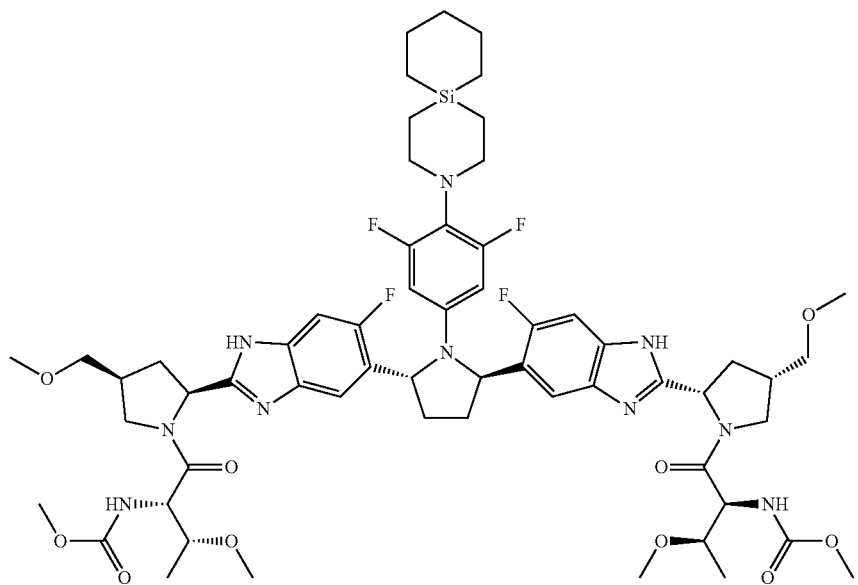

36b

In particular, the present application provides the following compounds, a pharmaceutically acceptable salt, a tautomer, a stereoisomer or a deuteride thereof, or a mixture thereof: Compound 1a, Compound 1b, Compound 2a, Compound 2b, Compound 3a, Compound 4a, Compound 4b, Compound 5a, Compound 5b, Compound 6a, Compound 6b, Compound 7b, Compound 8b, Compound 17b and Compound 18b.

In particular, the present application provides the following compounds, a pharmaceutically acceptable salt, a tautomer, a stereoisomer or a deuteride thereof, or a mixture thereof: Compound 1a, Compound 1b, Compound 2a, Compound 2b, Compound 3a, Compound 4a, Compound 4b, Compound 5a, Compound 5b, Compound 6a, Compound 6b, Compound 7b, Compound 8a, Compound 8b, Compound 9b, Compound 11a, Compound 14b, Compound 15b, Compound 17b and Compound 18b.

In another aspect, the present application provides a pharmaceutical composition comprising a therapeutically effective amount of the compound of Formula I or Formula Ia or Formula Ib or Formula Ic or Formula Id, a pharmaceutically acceptable salt, a tautomer, a stereoisomer or a deuteride thereof, or a mixture thereof, and one or more pharmaceutically acceptable carriers.

The pharmaceutical composition according to the present application may be prepared by combining the compound according to the present application, a pharmaceutically acceptable salt, a tautomer, a stereoisomer or a deuteride thereof, or a mixture thereof with a suitable pharmaceutically acceptable carrier; for example, it may be formulated into solid, semisolid, liquid or gaseous formulations, such as tablets, pills, capsules, powders, granules, ointments, emulsions, suspensions, solutions, suppositories, injections, inhalants, gels, microspheres, aerosols, and the like.

Typical administration routes of the compound according to the present application, a pharmaceutically acceptable salt, a tautomer, a stereoisomer or a deuteride thereof, or a mixture thereof, or the pharmaceutical composition thereof include, but are not limited to, oral, rectal, transmucosal and enteral administration, or topical, transdermal, inhalation, parenteral, sublingual, intravaginal, intranasal, intraocular, intraperitoneal, intramuscular, subcutaneous, and intravenous administration.

The pharmaceutical composition according to the present application may be prepared by using methods well-known in the art, such as a conventional mixing method, dissolution method, granulation method, dragee manufacture method, grinding method, emulsification method, lyophilization method and the like.

For oral administration, the pharmaceutical composition may be formulated by mixing an active compound with a pharmaceutically acceptable carrier well-known in the art. Such carrier enables the compound according to the present application to be formulated into tablets, pills, pastilles, dragees, capsules, liquids, gels, slurries, suspensions, and the like, which are used for oral administration to a patient.

A solid oral composition may be prepared by a conventional mixing, filling or tabletting method, for example, may be obtained by the following method: mixing the active compound with a solid excipient, optionally grinding the resulting mixture, if necessary, adding other appropriate adjuvants, and then processing the mixture into granules to obtain the core of a tablet or dragee. Appropriate adjuvants include, but are not limited to, binders, diluents, disintegrating agents, lubricants, glidants, sweetening agents, flavoring agents, and the like. The core of the dragee may be optionally coated through well-known processes in general pharmaceutical practice, especially by enteric coating.

The pharmaceutical composition may also be suitable for parenteral administration, such as a sterile solution, a suspension, or a lyophilized product in an appropriate unit dosage form. A suitable excipient such as a filler, a buffering agent or a surfactant can be used.

In a further aspect, the compounds of the present application (comprising the compounds having the specific structures) have an inhibitory activity against hepatitis C virus (HCV) NS5A and can be used as an HCV NS5A inhibitor for the treatment of hepatitis C virus infection, and specifically can be used for the treatment of liver diseases such as hepatitis, cirrhosis, and the like caused by hepatitis C virus infection.

In particular, the compounds of the present application (comprising the compounds having the specific structures) have an inhibitory activity against hepatitis C virus (HCV) NS5A, and specifically have an excellent inhibitory activity against various gene subtypes of HCV, and these gene subtypes include 1a, 1b, 2a, 2b, 3a, 3b, 4a, 4b, 5a and 6a; and also include some chimeric types 1b/3a, 1b/4a, 1b/5a, 1b/6a and the like.

In particular, the compounds of the present application (comprising the compounds having the specific structures) have a good affinity for liver tissue and can be targeted to the liver tissue.

In particular, the compounds of the present application (comprising the compounds having the specific structures) also have a certain drug resistance.

The present application provides use of the compound of Formula I or Formula Ia or Formula Ib or Formula Ic or Formula Id, a pharmaceutically acceptable salt, a tautomer, a stereoisomer or a deuteride thereof, or a mixture thereof in the preparation of a medicament for the treatment of hepatitis C virus (HCV) infection.

The present application provides use of the compound of Formula I or Formula Ia or Formula Ib or Formula Ic or Formula Id, a pharmaceutically acceptable salt, a tautomer, a stereoisomer or a deuteride thereof, or a mixture thereof and at least one other active compound in the preparation of a medicament for the treatment of hepatitis C virus (HCV) infection.

The present application provides use of the pharmaceutical composition comprising the compound of Formula I or Formula Ia or Formula Ib or Formula Ic or Formula Id, a pharmaceutically acceptable salt, a tautomer, a stereoisomer or a deuteride thereof, or a mixture thereof in the preparation of a medicament for the treatment of hepatitis C virus (HCV) infection.

The present application provides use of the pharmaceutical composition comprising the compound of Formula I or Formula Ia or Formula Ib or Formula Ic or Formula Id, a pharmaceutically acceptable salt, a tautomer, a stereoisomer or a deuteride thereof, or a mixture thereof and at least one other active compound in the preparation of a medicament for the treatment of hepatitis C virus (HCV) infection.

In some embodiments, the other active compounds include, but are not limited to, other compounds that are resistant to HCV activity. In some embodiments, the other active compounds include, but are not limited to, immunomodulators and other antivirals.

The HCV includes a plurality of genotypes and a plurality of gene subtypes, such as 1a, 1b, 2a, 2b, 3a, 3b, 4a, 4b, 5a, 6a.

The present application provides a method for treating hepatitis C virus infection, comprising administering to a subject in need of such treatment a therapeutically effective amount of the compound of Formula I or Formula Ia or Formula Ib or Formula Ic or Formula Id, a pharmaceutically acceptable salt, a tautomer, a stereoisomer or a deuteride thereof, or a mixture thereof, or the above pharmaceutical composition.

The therapeutically effective amount of the compound of Formula I or Formula Ia or Formula Ib or Formula Ic or Formula Id, a pharmaceutically acceptable salt, a tautomer, a stereoisomer or a deuteride thereof, or a mixture thereof according to the present application is from about 0.0001 to 20 mg/Kg body weight per day, for example, from 0.001 to 10 mg/Kg body weight per day.

The dosing frequency of the compound of Formula I or Formula Ia or Formula Ib or Formula Ic or Formula Id depends on the requirements of an individual patient, for example one or two or more times per day. Administration may be intermittent, for example, during the period of several days, the patient receives the daily dosage of the compound of Formula I or Formula Ia or Formula Ib or Formula Ic or Formula Id, and then during the period of several days or a longer time, the patient does not receive the daily dosage of the compound of Formula I or Formula Ia or Formula Ib or Formula Ic or Formula Id.

The present application provides the compound of Formula I or Formula Ia or Formula Ib or Formula Ic or Formula Id, a pharmaceutically acceptable salt, a tautomer, a stereoisomer or a deuteride thereof, or a mixture thereof for use in the treatment of hepatitis C virus infection, and the above pharmaceutical composition for use in the treatment of hepatitis C virus infection.

The present application provides use of the compound of Formula I or Formula Ia or Formula Ib or Formula Ic or Formula Id, a pharmaceutically acceptable salt, a tautomer, a stereoisomer or a deuteride thereof, or a mixture thereof, or the above pharmaceutical composition in the treatment of hepatitis C virus infection.

Relevant Definitions

Unless stated otherwise, the following terms and phrases used herein have the following meanings. A specific term or phrase shall not be considered unclear or indefinite when it is not specially defined. It should be understood according to its common meaning.

The term "optional" or "optionally" means that the subsequently described event or circumstance may or may not occur, and that the description includes instances where said event or circumstance occurs and instances where said event or circumstance does not occurs.

The expression $C_{m-n}$ used herein means that this moiety has m to n carbon atoms. For example, "$C_{1-6}$ alkyl" means that said alkyl has 1 to 6 carbon atoms.

A numerical range herein refers to each of the integers within this given range. For example, "$C_{1-6}$" means that this group may have 1 carbon atom, 2 carbon atoms, 3 carbon atoms, 4 carbon atoms, 5 carbon atoms or 6 carbon atoms.

When any variable (e.g. R) occurs more than one time in the composition or structure of a compound, its definition in each occurrence is independent. Therefore, for example, if a group is substituted by 2 R, each R has independent options.

When the bond of a substituent is cross-connected to a ring between two atoms, the substituent can be bonded with any atom on the ring. For example, the structural unitError! Objects cannot be created from editing field codes.or Error! Objects cannot be created from editing field codes.means that it may be substituted at any position on cyclohexyl or cyclohexadiene.

The term "halogen" refers to fluoro, chloro, bromo or iodo.

The term "alkyl" refers to a straight or branched saturated aliphatic hydrocarbon group consisting of carbon atoms and hydrogen atoms, such as methyl, ethyl, propyl, butyl, pentyl, hexyl, heptyl, octyl, nonyl, decyl, etc. The specific alkyl includes all isomeric forms thereof. For example, propyl includes —$CH_2CH_2CH_3$ and —$CH(CH_3)_2$. For example, butyl includes —$CH_2CH_2CH_2CH_3$, —$CH(CH_3)(CH_2CH_3)$, —$C(CH_3)_3$ and —$CH_2CH(CH_3)_2$.

The term "$C_{1-6}$ alkyl" refers to an alkyl group having 1 to 6 carbon atoms. The term "$C_{1-4}$ alkyl" refers to an alkyl group having 1 to 4 carbon atoms.

The term "$C_{1-6}$ alkoxy" refers to an —O-alkyl group having 1 to 6 carbon atoms. The term "$C_{1-4}$ alkoxy" refers to an —O-alkyl group having 1 to 4 carbon atoms.

The term "alkoxyalkyl" refers to an alkyl group substituted with at least one alkoxy group (namely, at least one hydrogen atom of the alkyl group is substituted with an alkoxy group), for example, methoxymethyl, ethoxymethyl, methoxyethyl, ethoxyethyl, methoxypropyl, ethoxypropyl and isopropoxymethyl, and for example, 2-methoxy-ethyl, 1-, 2- or 3-methoxypropyl, and 2-ethoxyethyl.

The term "aryl" refers to an all-carbon monocyclic or polycyclic fused aromatic ring group having a conjugated π-electron system, preferably having 6 to 14 carbon atoms, more preferably having 6 to 12 carbon atoms, and most preferably having 6 carbon atoms. For example, a monocyclic aromatic ring group is selected from phenyl; a bicyclic fused aromatic ring group consists of phenyl fused to a 4- to 6-membered aromatic or non-aromatic carbocyclic ring, including naphthyl.

The term "saturated aliphatic ring" refers to a carbocyclic ring that is fully saturated and may exist as a monocyclic ring, bridged ring or spirocyclic ring. Unless otherwise indicated, the carbocyclic ring is typically a 3- to 10-membered ring. Non-limiting examples of the saturated aliphatic ring include, but are not limited to, cyclopropane, cyclobutane, cyclopentane, cyclohexane, cycloheptane, cyclooctane, bicyclo[2.2.1]heptane, bicyclo[2.2.2]octane, adamantane, etc.

The term "silicon-containing saturated aliphatic ring" means that 1, 2 or 3 carbon atoms in the above "saturated aliphatic ring" are replaced by silicon atoms.

The term "membered" refers to the number of ring-forming atoms. For example, "3- to 8-membered" or "4- to 6-membered" means that the number of ring-forming atoms is 3 to 8 or 4 to 6, and the number of ring-forming atoms in a 4-membered saturated aliphatic ring containing 1 silicon atom is four, of which three are carbon atoms and one is a silicon atom.

The term "pharmaceutically acceptable" refers to those compounds, materials, compositions and/or dosage forms that are, within the scope of sound medical judgment, suitable for use in contact with the tissues of human being and animals without excessive toxicity, irritation, allergic response or other problems or complications, commensurate with a reasonable benefit/risk ratio.

The term "pharmaceutically acceptable salt" refers to a salt that retains the biological efficacy of the free acids and free bases of a specific compound, without biological adverse effects. Pharmaceutically acceptable salts may refer to, for example, metal salts, ammonium salts, salts formed with organic bases, salts formed with inorganic acids, salts formed with organic acids, salts formed with basic or acidic amino acids, and the like.

The pharmaceutically acceptable salt of the present application can be synthesized from a parent compound containing an acidic or alkaline group by a conventional chemical method. Generally, such a salt is prepared by a method of allowing these compounds in the form of a free acid or base to react with a stoichiometric amount of an appropriate base or acid in water or an organic solvent or a mixture thereof, in general, preferably non-aqueous media such as ether, ethyl acetate, ethanol, isopropanol, acetonitrile, etc.

The intermediates and compounds according to the present application may also exist in the form of different tautomers, and all such forms are included in the scope of the present application. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Examples of proton tautomers are an imidazole moiety, wherein a proton can migrate between the two nitrogen atoms of the ring. Valence tautomers include interconversions by reorganization of some of the bond-forming electrons. Non-limiting examples of tautomers include, but are not limited to,

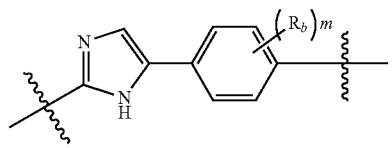

and

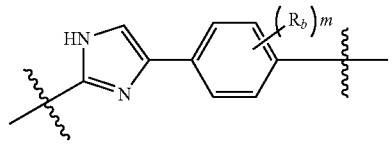

; and

-continued

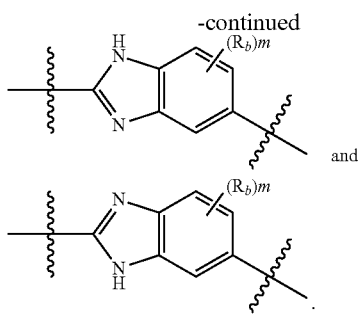

and

The term "stereoisomer" refers to isomers having the same molecular structure of the compounds, but which differ in stereostructure, such as enantiomers and diastereomers.

As for a pharmaceutical or pharmacological active agent, the term "effective amount" or "therapeutically effective amount" refers to the amount of a medicament or agent which is not toxic but sufficient to achieve the desired effect. With respect to the oral formulation in the present application, the "effective amount" for an active substance in the composition refers to the amount required to achieve the desired effect in combination with another active substance in the composition. The effective amount may be determined individually and depends on the age and general condition of the subject as well as the specific active substance. The effective amount in a specific case can be determined by a person skilled in the art through conventional tests.

The compound according to the present application may contain atomic isotope in non-natural ratio at one or more atoms constituting said compound. For example, the compound may be labeled with radioisotope, such as deuterium ($^2$H), tritium ($^3$H), iodine-125($^{125}$I) or C-14($^{14}$C). The changes of all the isotopes of the compound, radioactive or not, is encompassed within the scope of the present application.

Furthermore, the substitution (for example, forming a deuteride) with heavier isotopes (such as deuterium, i.e. $^2$H) may afford certain therapeutic advantages resulting from greater metabolic stability, for example, increased in vivo half-life or reduced dosage requirements, and thus may be preferable in some circumstances, wherein the deuterium substitution may be partial or complete, and partial deuterium substitution means that at least one hydrogen is substituted with at least one deuterium. Furthermore, as for the specific position of the deuteration, the hydrogen atoms in the methoxy of the compound of Formula I or Formula Ia or Formula Ib or Formula Ic or Formula Id may be substituted by one, two or three deuterium atoms; the hydrogen atoms in the phenyl ring may be substituted by one, two, three, four or five deuterium atoms.

Exemplary deuterated compounds are shown below, but are not limited thereto.

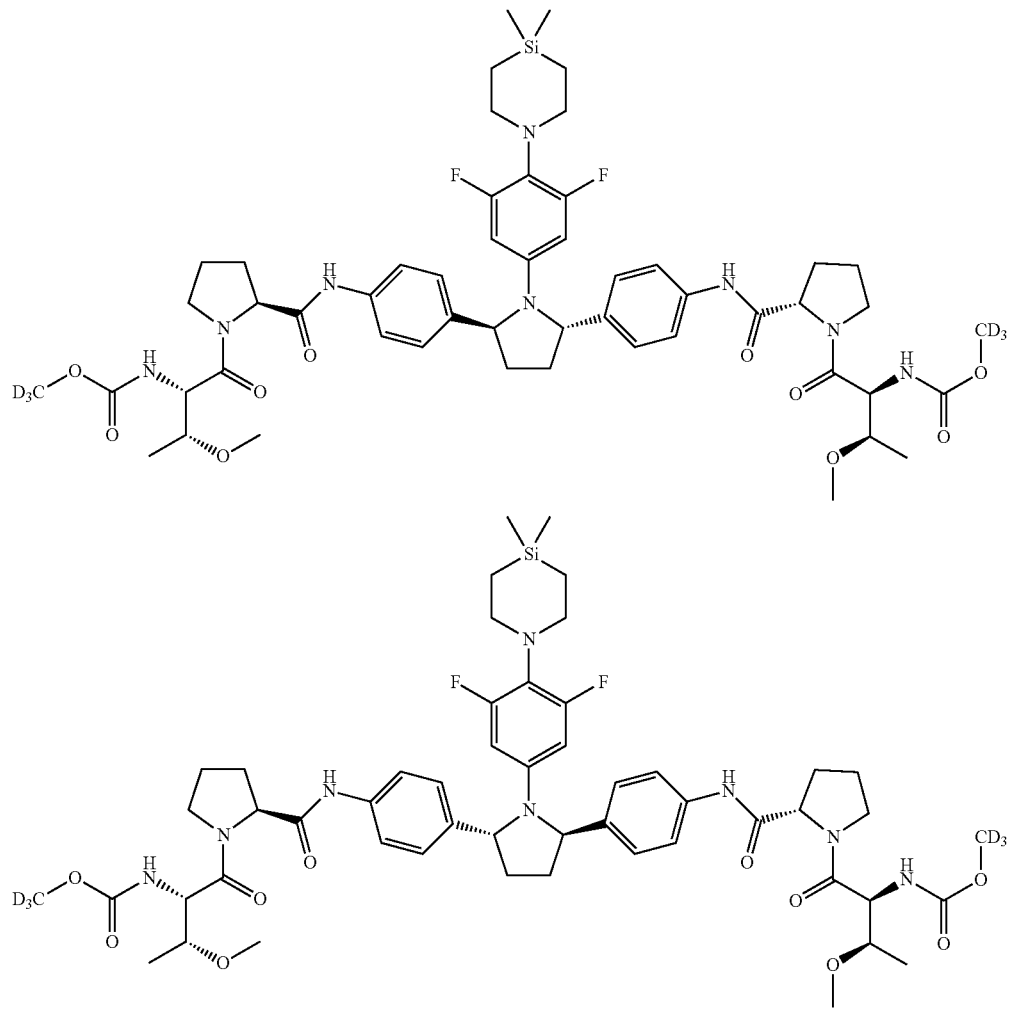

The compounds of the present application may comprise asymmetrically substituted carbon atoms known as chiral centers. These compounds may exist, without limitation, as a single stereoisomer (e.g., a single enantiomer or single diastereomer), a mixture of stereoisomers (e.g. a mixture of enantiomers or diastereomers), or racemic mixtures. Compounds identified in the present application as a single stereoisomer are meant to describe compounds that are present in a form that is substantially free from other stereoisomers. The term "substantially free" means that at least 95%, 96%, 97%, 98% or 99% of the compound in a composition is the described stereoisomer. Where the stereochemistry of a chiral carbon is not specified in the chemical structure of a compound, the chemical structure is intended to encompass either stereoisomer compound of the chiral center. For example, $R_7$ and $R_8$ in the compound of Formula I or Formula Ia or Formula Ib or Formula Ic or Formula Id may contain a chiral carbon atom. Specifically, when $R_7$ and $R_8$ are —CH($C_{1-4}$ alkyl)($C_{1-4}$ alkoxy), $R_7$ and $R_8$ have at least one chiral carbon atom and are —C*H($C_{1-4}$ alkyl)($C_{1-4}$ alkoxy), wherein C* is a chiral carbon atom and may be S configuration or R configuration. More specifically, when $R_7$ and $R_8$ are —CH($CH_3$)($OCH_3$), the specific configurations include:

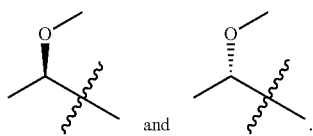

Individual stereoisomers of the compounds of the present application can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographical separation of the diastereomers and regeneration of the individual enantiomers, and enzymatic resolution.

The compounds of the present application can be prepared by a variety of synthetic methods well known to those skilled in the art, including the specific embodiments listed below, the embodiments obtained by combining the specific embodiments listed below with other chemical synthesis methods, and equivalents well known to those skilled in the art. The preferred embodiments include, but are not limited to, the examples of the present application.

The reaction raw materials and reaction reagents of the present application can be commercially available or obtained by preparation.

The chemical reactions of the specific embodiments of the present application are carried out in suitable solvents which are suitable for the chemical changes of the present application and the required reagents and materials thereof. In order to obtain the compounds of the present application, it is sometimes necessary for those skilled in the art to modify or select the synthetic steps or reaction schemes based on the existing embodiments.

The compounds of Formula I of the present application can be prepared by using conventional methods in the art through the following schemes, wherein, $R_1$, $R_2$, $R_3$, $R_4$, $R_5$, $R_6$, $R_7$, $R_8$, $R_9$, $R_{10}$, $R_a$, $R_b$, X, Y, m and n are as defined above.

1. When X is selected from

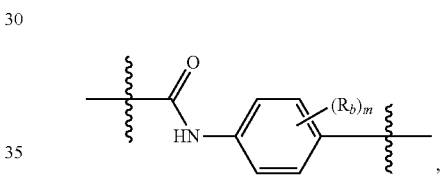

and Y is selected from

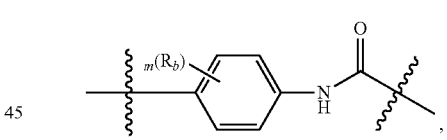

the scheme is as follows:

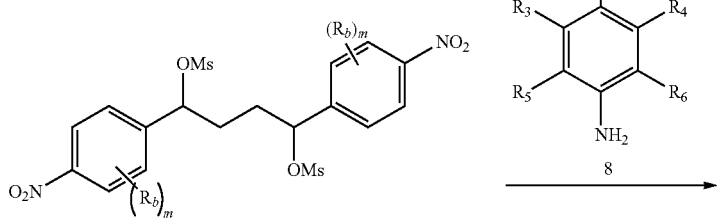

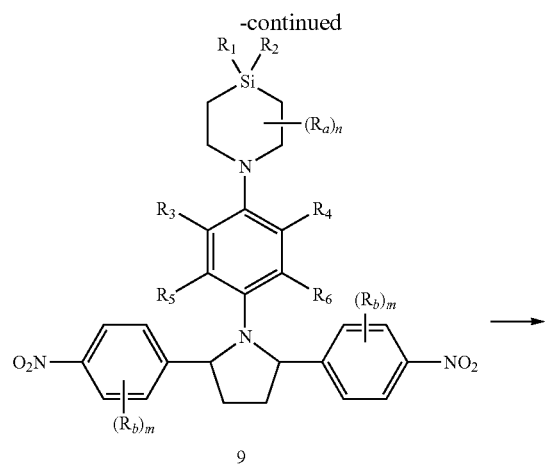
9
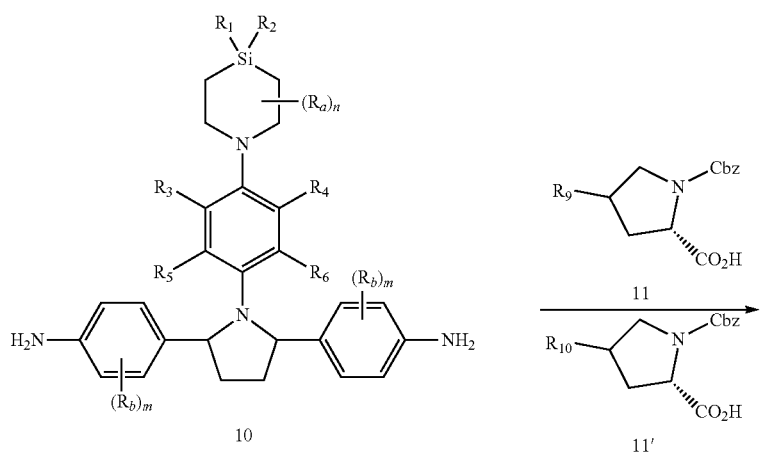
10    11    11'
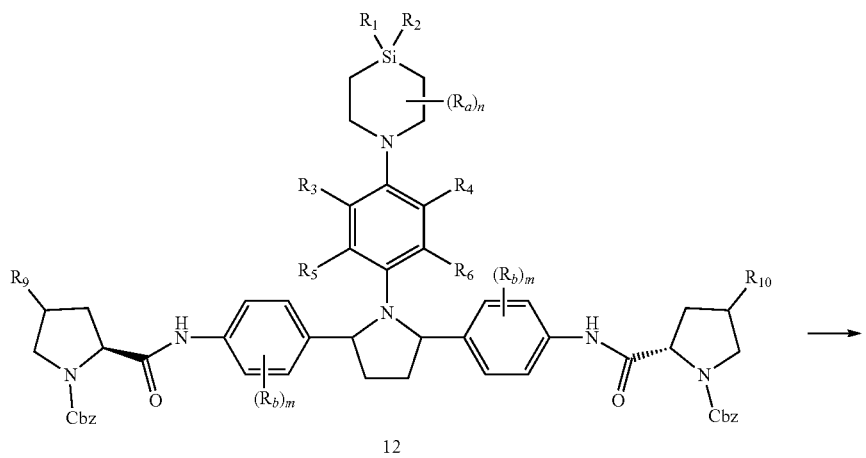
12

-continued

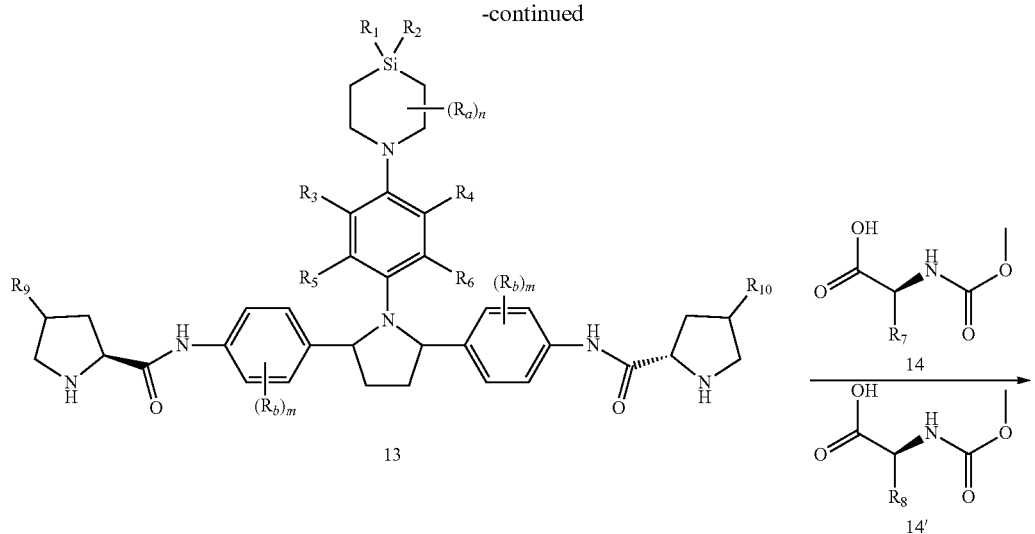

Compound 7 and Compound 8 were cyclized to give Compound 9, the nitro groups of which were further reduced to obtain Compound 10. Compound 10 was subjected to an amidation reaction with Compound 11 and/or Compound 11' to give Compound 12, the amino-protecting group Cbz of which was further removed to obtain Compound 13. Then Compound 13 was further subjected to an amidation reaction with Compound 14 and/or Compound 14' to give the compound of Formula I.

2. When X is selected from
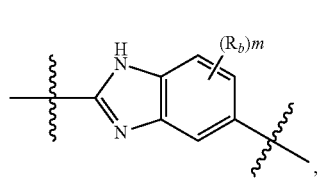
and Y is selected from
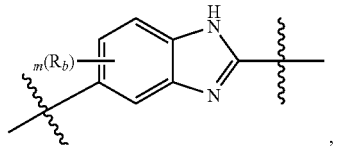
the scheme is as follows:
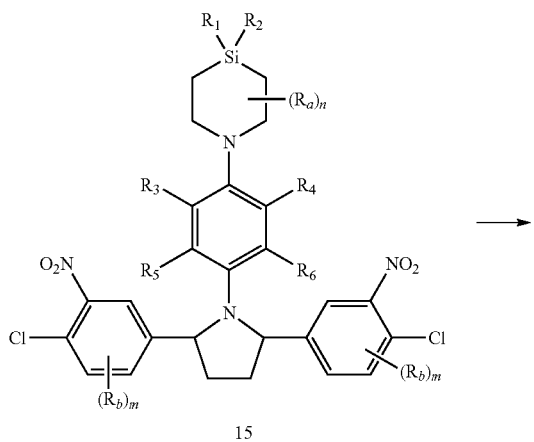
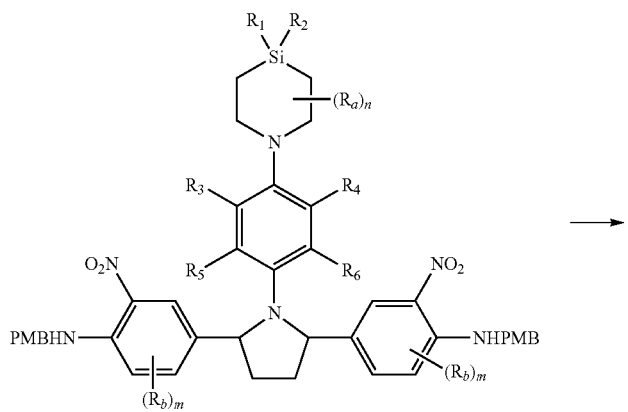
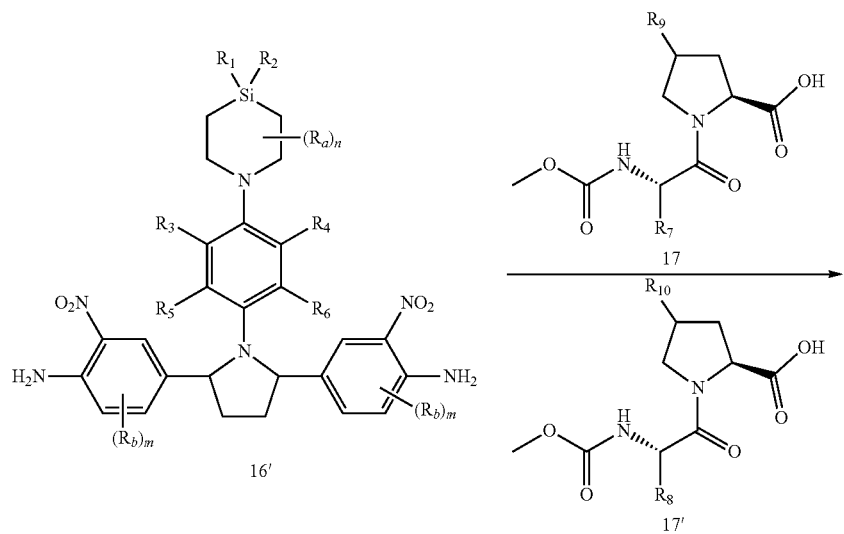

-continued
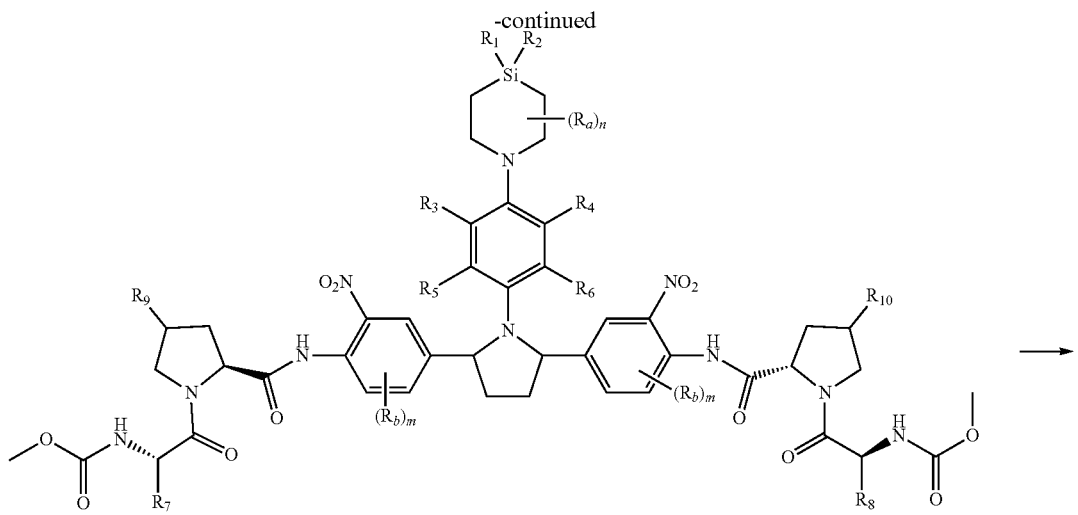
18
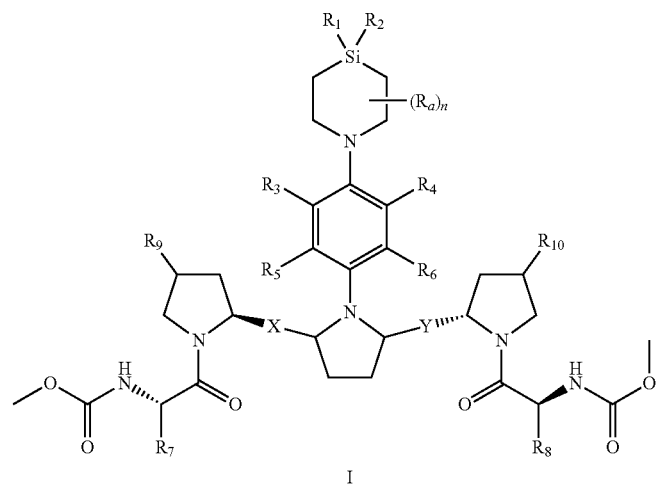
I
Compound 15 was subjected to an amino substitution reaction to obtain Compound 16 which was then hydrolyzed to give Compound 16'. Compound 16' was subjected to an amidation reaction with Compound 17 and/or Compound 17' to give Compound 18, the nitro groups of which were further reduced to amino groups followed by cyclization to give the compound of Formula I.

3. When X is selected from 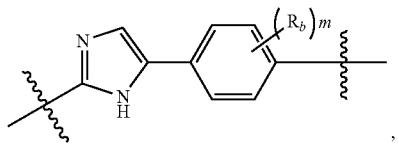 and Y is selected from 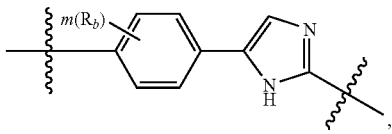,
the scheme is as follows:
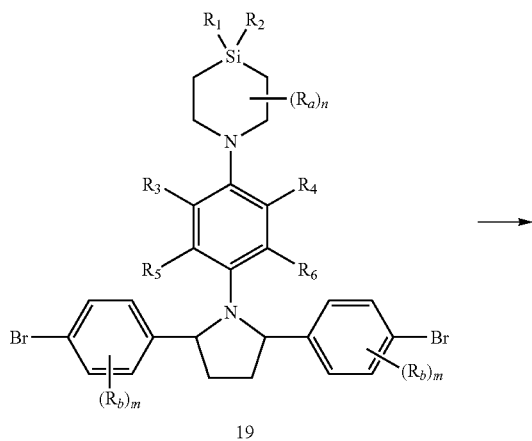
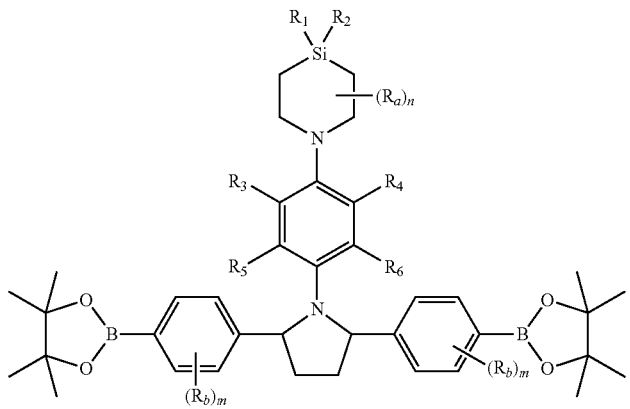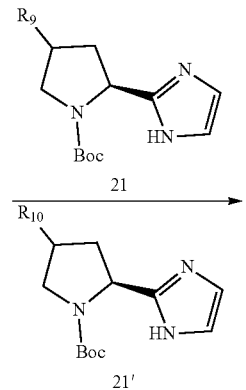
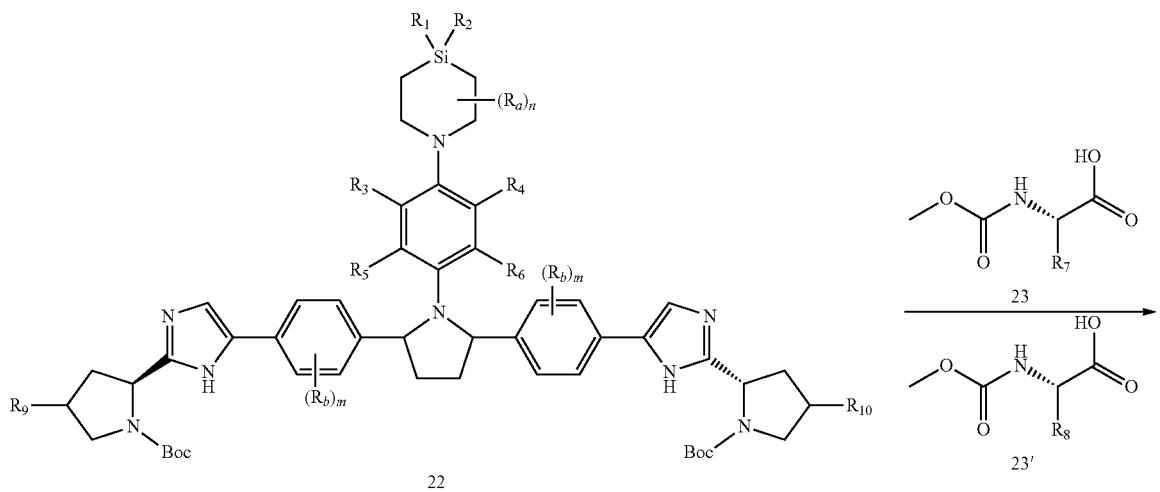

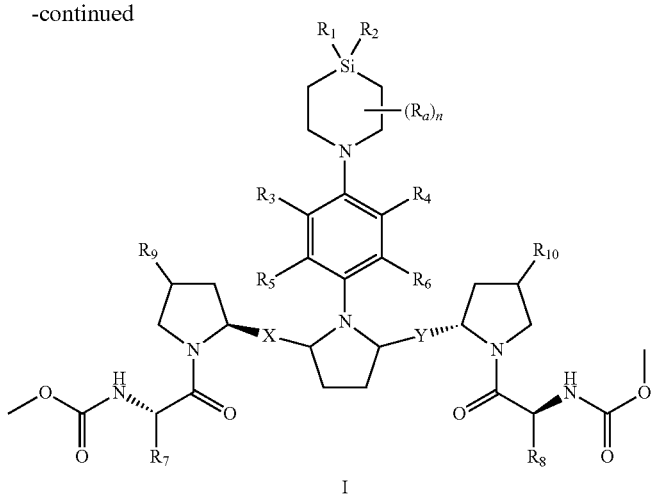

I

Compound 19 was first reacted with bis(pinacolato)diboron to give Compound 20 which was then subjected to a coupling reaction with Compound 21 and/or Compound 21' to give Compound 22. After the removal of the protecting group, Compound 22 was subjected to an amidation reaction with Compound 23 and/or Compound 23' to give the compound of Formula I.

When X and Y are selected from different types of fragments, any one of the structural fragments can be constructed first and then another different structural fragment was constructed in turn with reference to the above methods for constructing the structural fragments

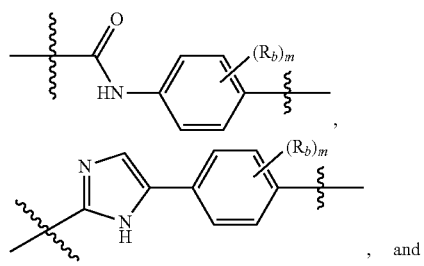

,

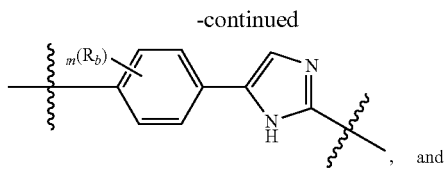

, and

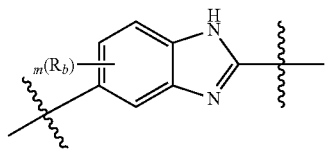

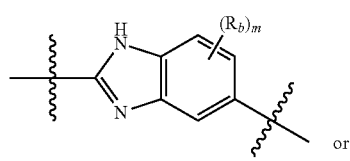

or

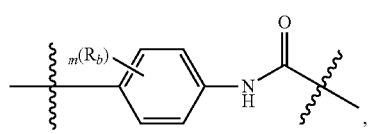

,

Compound 8 can be prepared according to the following process:

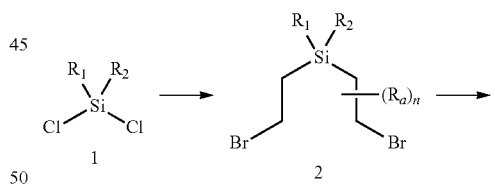

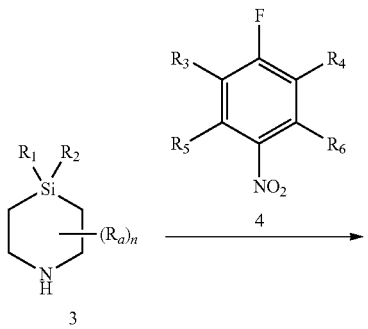

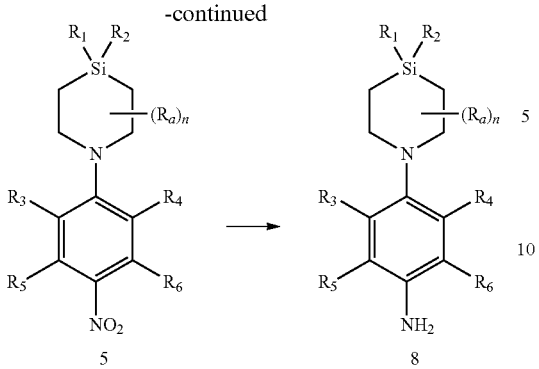

Compound 1 was subjected to a substitution reaction to obtain Compound 2 which was then condensed with benzylamine into a ring in the presence of a base followed by the removal of the benzyl-protecting group to give Compound 3. Then Compound 3 was subjected to N-alkylation reaction with Compound 4 in the presence of a base to give Compound 5, the nitro group of which was further reduced to give Compound 8.

The present application also provides methods for preparing the compounds of Formula Ia, Formula Ib, Formula Ic, and Formula Id.

The compounds of Formula Ia, Formula Ib, Formula Ic and Formula Id in different configurations can be obtained by directly separating the prepared compound of Formula I by chromatographic column chromatography.

The compounds of Formula Ia, Formula Ib, Formula Ic and Formula Id in different configurations can also be obtained by respectively preparing different chiral intermediate fragments such as Compound 10, Compound 15, and Compound 19 in different configurations.

Specific Embodiments

The following specific examples are provided to enable those skilled in the art to more clearly understand and implement the present application. They should not be construed as a limitation to the scope of the present application, but are merely exemplary illustrations and typical representatives of the present application. Those skilled in the art will understand that there are other synthetic routes involved for preparing the compounds of the present application, and ones provided below are non-limiting examples.

Unless indicated otherwise, raw materials used in the present application are commercially available and directly used without further purification.

All operations involving raw materials that are susceptible to oxidation or hydrolysis are carried out under a nitrogen protection atmosphere. Column chromatography was performed using silica gel (200-300 mesh) produced by Qingdao Chemical Co., Ltd. Thin Layer Chromatography was performed using prefabricated plates (silica gel 60 PF254, 0.25 mm) manufactured by E. Merck. Separation of chiral compounds was performed using a column: Waters XBridge C18, Ø4.6×150 mm, 5 micron, and a chiral column: CHIRALPAK IA Ø4.6×250 mm, 5 micron. Nuclear magnetic resonance spectrum (NMR) was performed using Varian VNMRS-400 nuclear magnetic resonance spectrometer; and LC/MS was performed using FINNIGAN Thermo LCQ Advantage MAX, Agilent LC 1200 series (column: Waters Symmetry C18, Ø4.6×50 mm, 5 micron, 35° C.), and ESI (+) ion mode was used.

Unless otherwise indicated, TEA represents triethylamine; DMF represents N,N-dimethylformamide; THF represents tetrahydrofuran; "h" represents hour, for example, "24 h" represents 24 hours; "room temperature" represents 20-25° C.; Boc-represents tert-butoxycarbonyl; PMB-represents p-methoxybenzyl; and Ms-represents methylsulfonyl.

Example 1: 4-(4,4-Dimethyl-1,4-azasilinan-1-yl)-3,5-difluoroaniline

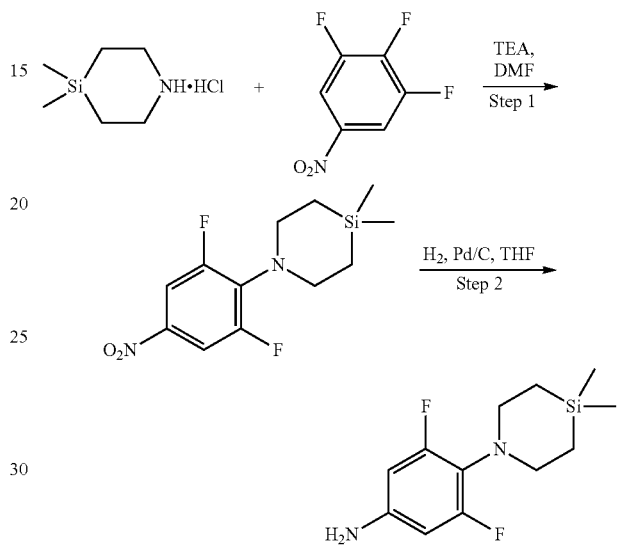

Step 1: 1-(2,6-Difluoro-4-nitrophenyl)-4,4-dimethyl-1,4-azasilinane 4,4-Dimethyl azasilinane hydrochloride (20.6 g, 124.4 mmol) and triethylamine (51.6 g, 3373.0 mmol) were dispersed in N,N-dimethylformamide (200 mL). The resulting mixture was stirred at room temperature for 10 min, and then transferred to an ice water bath and stirred. 3,4,5-Trifluoronitrobenzene (20.0 g, 113.0 mmol) was added dropwise. After the completion of the dropwise addition, the resulting mixture was stirred for 30 min in an ice water bath, and then stirred at room temperature overnight. Then the reaction mixture was poured into 1 L of water, stirred for 10 min, suction-filtered, washed with water (10 mL×3), and dried to give 1-(2,6-difluoro-4-nitrophenyl)-4,4-dimethyl-1,4-azasilinane (31.2 g).

$^1$H NMR (500 MHz, DMSO-d$_6$): δ7.93 (dd, J=10.0 Hz, 1.0 Hz, 2H), 3.49-3.51 (m, 4H), 0.85-0.88 (m, 4H), 0.12 (s, 6H).

Step 2: 4-(4,4-Dimethyl-1,4-azasilinan-1-yl)-3,5-difluoroaniline 1-(2,6-Difluoro-4-nitrophenyl)-4,4-dimethyl-1,4-azasilinane (31.0 g, 108.3 mmol) was dissolved in tetrahydrofuran (200 mL), and then Pd/C (5.0 g, 10%, water content: 56%) was added. The resulting mixture reacted at room temperature overnight under a hydrogen atmosphere. The resulting mixture was suction-filtered, and the filtrate was concentrated. The residue was refined with petroleum ether, suction filtered, and dried to give 4-(4,4-dimethyl-1,4-azasilinan-1-yl)-3,5-difluoroaniline (23.4 g).

$^1$H NMR (500 MHz, DMSO-d$_6$): δ6.10-6.12 (m, 2H), 5.34 (s, 2H), 3.10-3.13 (m, 4H), 0.77-0.79 (m, 4H), 0.08 (s, 6H).

Example 2: 4-(4,4-Dimethyl-1,4-azasilinan-1-yl)-3-fluoroaniline

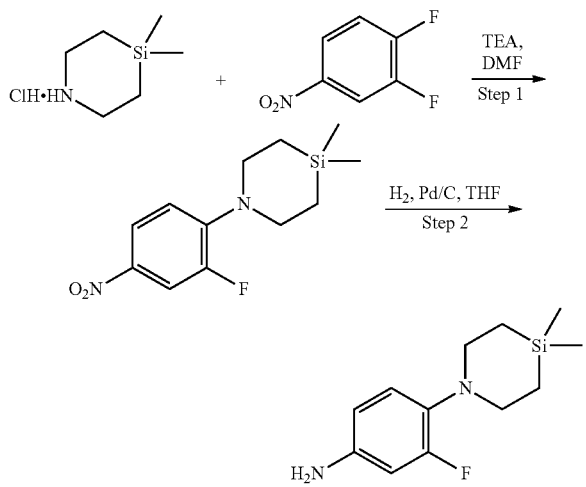

Step 1: 1-(2-Fluoro-4-nitrophenyl)-4,4-dimethyl-1,4-azasilinane 4,4-Dimethyl azasilinane hydrochloride (19.3 g, 105.8 mmol) and triethylamine (48.2 g, 349.1 mmol) were dispersed in N,N-dimethylformamide (200 mL). The resulting mixture was stirred at room temperature for 10 min, and then transferred to an ice water bath and stirred. 3,4-Difluoronitrobenzene (16.8 g, 105.8 mmol) was added dropwise. After the completion of the dropwise addition, the resulting mixture was stirred for 30 min in an ice water bath, and then stirred at room temperature overnight. The reaction mixture was poured into 1 L of water, stirred for 10 min, suction-filtered, and washed with a large amount of water. The resulting solid was collected and dried to give 1-(2-fluoro-4-nitrophenyl)-4,4-dimethyl-1,4-azasilinane (28.1 g).

$^1$H NMR (300 MHz, DMSO-d$_6$): δ7.91-7.95 (m, 2H), 7.10-7.14 (m, 1H), 3.71-3.73 (m, 4H), 0.85-0.88 (m, 4H), 0.11 (s, 6H).

Step 2: 4-(4,4-Dimethyl-1,4-azasilinan-1-yl)-3-fluoroaniline 1-(2-Fluoro-4-nitrophenyl)-4,4-dimethyl-1,4-azasilinane (28.0 g, 104.3 mmol) was dissolved in tetrahydrofuran (200 mL), and then Pd/C (5.0 g, 10%, water content: 56%) was added. The resulting mixture reacted at room temperature overnight under a hydrogen atmosphere. The reation mixture was suction-filtered, and the filtrate was concentrated. The residue was refined with petroleum ether (200 mL), suction-filtered, and dried to give 4-(4,4-dimethyl-1,4-azasilinan-1-yl)-3-fluoroaniline (1.2 g).

$^1$H NMR (500 MHz, DMSO-d$_6$): δ6.75-6.79 (m, 1H), 6.25-6.31 (m, 2H), 4.90 (s, 2H), 3.04-3.06 (m, 4H), 0.79-0.81 (m, 4H), 0.08 (s, 6H).

Example 3: 8-aza-5-silaspiro[4.5]decane Hydrochloride

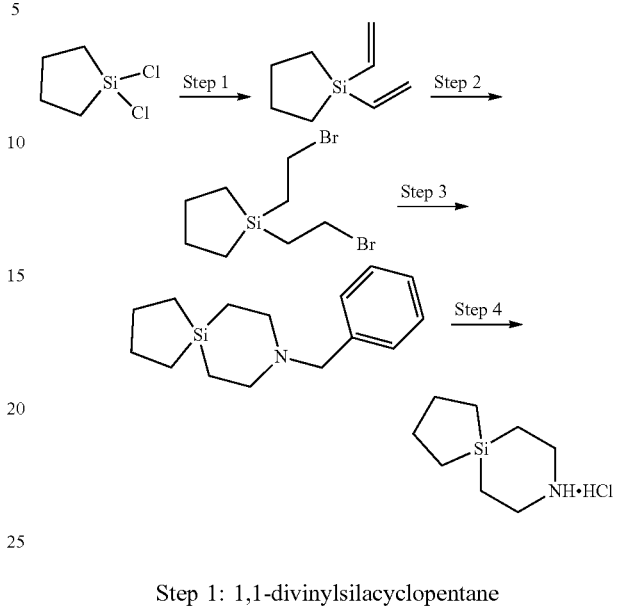

Step 1: 1,1-divinylsilacyclopentane

To a 1 L dried three-necked flask were added 1,1-dichlorosilacyclopentane (purity: 90%, 15.53 g, 90 mmol) and dried tetrahydrofuran (100 mL), and the temperature was cooled to 0° C. under nitrogen gas protection. Then 1 M/L vinylmagnesium bromide (220 mmol, 220 mL) was slowly added dropwise, and the internal temperature of the mixture was controlled to 0° C. to 5° C. during the dropwise addition. After the completion of the dropwise addition, the resulting mixture was naturally warmed to room temperature and stirred for 5 h, and then cooled to 0° C. Water (200 mL) was then slowly poured thereto under stirring. The resulting mixture was layered, and the aqueous layer was extracted with diethyl ether (60 mL×2). The combined organic layer was washed with a saturated saline solution (100 mL), dried over anhydrous sodium sulfate and filtered. Then tetrahydrofuran and diethyl ether were distilled off under atmospheric pressure, and the residue was distilled under reduced pressure to give 1, 1-divinylsilacyclopentane (4.97 g).

$^1$H NMR (500 MHz, CDCl$_3$): δ 6.27-6.20 (m, 2H), 6.07 (d, J=3.5 Hz, 1H), 6.04 (d, J=4.0 Hz, 1H), 5.83 (d, J=3.5 Hz, 1H), 5.79 (d, J=4.0 Hz, 1H), 1.66-1.63 (m, 4H), 0.75-0.73 (m, 4H).

Step 2: Preparation of 1,1-bis(2-bromoethyl)silacyclopentane 1, 1-Divinylsilacyclopentane (19.64 g, 142.4 mmol) was dissolved in 150 mL of n-heptane, and benzoyl peroxide (0.06 g, 0.23 mmol) was then added thereto, and the resulting mixture was stirred at 40° C. for 1 h. Dried hydrogen bromide gas was continuously supplied to the reaction solution until the reaction was completed. Then the reaction solution was cooled to room temperature, and washed with saturated aqueous sodium carbonate solution (100 mL×3). The organic layer was washed with a saturated saline solution (60 mL), dried over anhydrous sodium sulfate and filtered. Then the solvent was distilled off under reduced pressure, and the residue was subjected to silica gel column chromatography (petroleum ether/ethyl acetate=20/1 as mobile phase) to give 1,1-bis(2-bromoethyl)silacyclopentane (21.4 g).

¹H-NMR (DMSO-d₆, 500 MHz): δ 3.69 (t, J=9.0 Hz, 4H), 1.5 (m, 8H), 0.63 (t, J=3.0 Hz, 4H).

Step 3: 8-Benzyl-8-aza-5-silaspiro[4.5]decane

A mixture of 1,1-bis(2-bromoethyl)silacyclopentane (21.4 g, 71.83 mmol), benzylamine (9.24 g, 86.2 mmol), and triethylamine (15.99 g, 158.02 mmol) in chloroform (100 mL) was heated to reflux for 13 h, and then cooled to room temperature. A 5% aqueous NaOH solution (150 mL) was added and stirred for 30 min. The resulting mixture was extracted with dichloromethane (100 mL×3), and the organic phase was washed with a saturated saline solution and dried over anhydrous sodium sulfate. Then the solvents were distilled off under reduced pressure, and the residue was subjected to silica gel column chromatography (petroleum ether/ethyl acetate=15/1 as mobile phase) to give 8-benzyl-8-aza-5-silaspiro[4.5]decane (8.0 g).

¹H-NMR (DMSO-d₆, 500 MHz): δ7.30 (m, 4H), 7.22 (m, 1H), 3.50 (s, 2H), 2.65 (t, J=6 Hz, 4H), 1.53 (m, 4H), 0.78 (t, J=12.5 Hz, 4H), 0.57 (t, J=1.0 Hz, 4H).

MS (ESI) m/z: 246.2[M+H]⁺.

Step 4: 8-Aza-5-silaspiro[4.5]decane Hydrochloride

8-Benzyl-8-aza-5-silaspiro[4.5]decane (8.0 g, 32.63 mmol) was dissolved in 80% anhydrous methanol (100 mL), and then 0.8 g of 10% Pd—C and 36% concentrated hydrochloric acid (9.92 g, 97.9 mmol) were added in sequence, and replacement with hydrogen gas was carried out for three times. The resulting mixture was heated to 50° C. and a hydrogenation reduction reaction was carried out for 15 h. Then the resulting mixture was cooled to room temperature and filtered by using Celite as a filter aid. The solvent was distilled off under reduced pressure to give a white solid, which was then refined with ethyl acetate/dichloromethane (1/1) and suction-filtered to give 8-aza-5-silaspiro[4.5]decane hydrochloride (5.2 g).

¹H-NMR (DMSO-d₆, 500 MHz): δ 3.21 (t, J=6.0 Hz, 4H), 1.56 (m, 4H), 1.06 (t, J=6.5 Hz, 4H), 0.64 (t, J=7.0 Hz, 4H).

MS (ESI) m/z: 156.2[M+H]⁺.

Example 4: 3,5-Difluoro-4-(8-aza-5-silaspiro[4.5]dec-8-yl)aniline

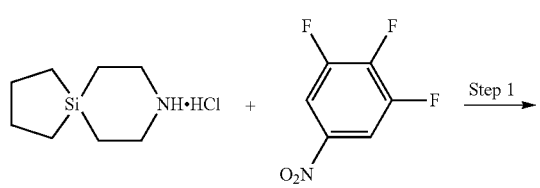

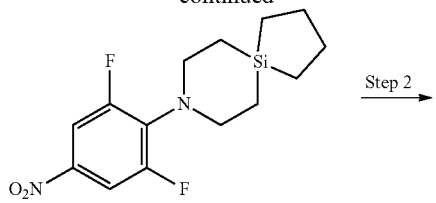

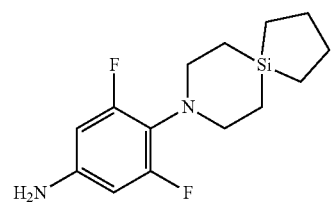

Step 1: 8-(2,6-Difluoro-4-nitrophenyl)-8-aza-5-silaspiro[4.5]decane

8-Aza-5-silaspiro[4.5]decane hydrochloride (5.0 g, 26.1 mmol) and triethylamine (12.0 g, 86.1 mmol) were dispersed in N,N-dimethylformamide (50 mL), stirred at room temperature for 10 min, and then transferred to an ice water bath and stirred. 3,4,5-Trifluoronitrobenzene (5.1 g, 28.7 mmol) was added dropwise. After the completion of the dropwise addition, the resulting mixture was stirred for 30 min in an ice water bath, and then stirred at room temperature overnight. Then the reaction mixture was poured into water (300 mL), stirred for 10 min, suction-filtered, washed with water (10 mL×3), and dried to give 8-(2,6-difluoro-4-nitrophenyl)-8-aza-5-silaspiro[4.5]decane (2.9 g).

¹H NMR (500 MHz, CDCl₃): δ 7.70-7.77 (m, 2H), 3.55 (t, J=6.5 Hz, 4H), 1.60-1.63 (m, 4H), 1.00 (t, J=6.5 Hz, 4H), 0.66 (t, J=7.0 Hz, 4H).

Step 2: 3,5-Difluoro-4-(8-aza-5-silaspiro[4.5]dec-8-yl)aniline 8-(2,6-Difluoro-4-nitrophenyl)-8-aza-5-silaspiro[4.5]decane (2.9 g, 9.3 mmol) was dissolved in tetrahydrofuran (30 mL), and then Pd/C (0.5 g, 10%, water content: 56%) was added. A hydrogenation reduction reaction was carried out at room temperature for 2.5 h. Then the reaction mixture was suction-filtered, and the filtrate was concentrated. The residue was refined with petroleum ether (30 mL), suction-filtered, and dried to give 3,5-difluoro-4-(8-aza-5-silaspiro[4.5]dec-8-yl) aniline (2.45 g).

¹H NMR (500 MHz, CDCl₃): δ6.14-6.18 (m, 2H), 3.63 (s, 2H), 3.27-3.29 (t, J=6.5 Hz, 4H), 1.59-1.62 (m, 4H), 0.96 (t, J=6.0 Hz, 4H), 0.64-0.66 (m, 4H).

MS (ESI) m/z: 283.1 [M+H]⁺.

Example 5: Methyl ((2S,2'S,3R,3'R)-((2S,2'S)-(((((2S,5S)-1-(4-(4,4-dimethyl azasilinan-1-yl)-3,5-difluorophenyl)pyrrolidin-2,5-diyl)bis(4,1-phenylene))bis(azanediyl)) bis(carbonyl))bis(pyrrolidin-2,1-diyl))bis(3-methoxy-1-oxobutan-1,2-diyl)) dicarbamate (1a)
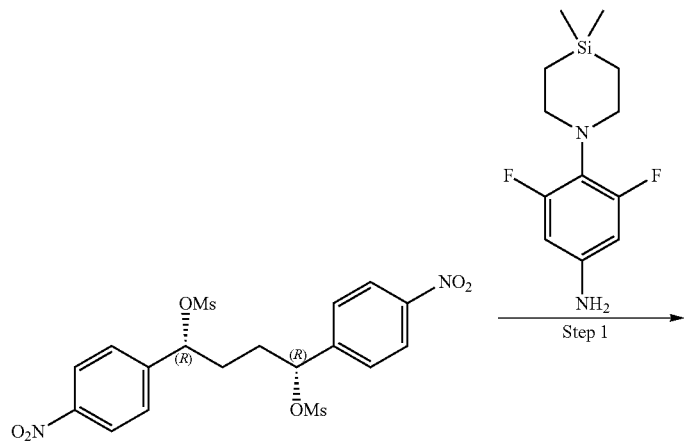
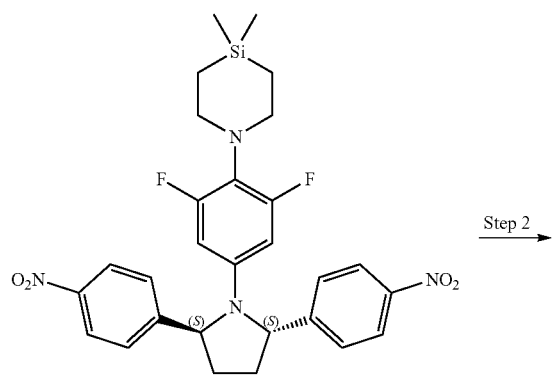
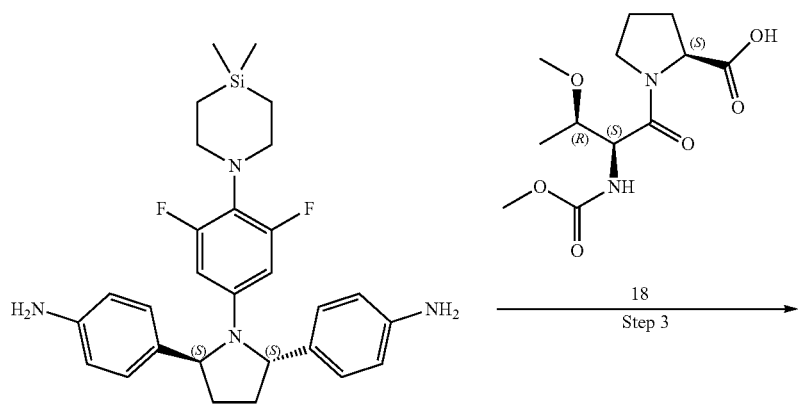

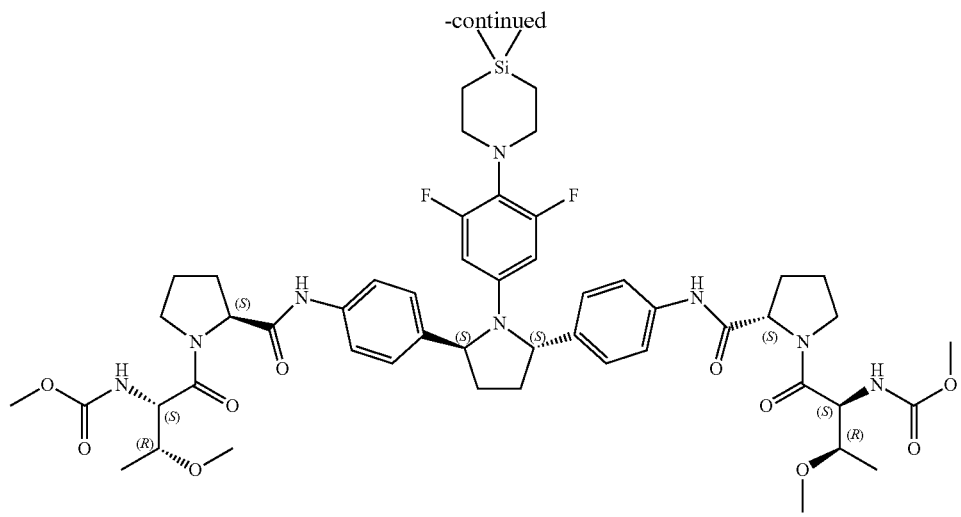

1a

Step 1: 1-(4-((2S, S)-2,5-bis(4-nitrophenyl)pyrrolidin-1-yl)-2,6-difluorophenyl)-4,4-dimethylazasilinane (1R,4R)-1,4-bis(4-nitrophenyl)butane-1,4-diyldimesylate (1.5 g, 3.0 mmol) was added to 10 mL of N,N-dimethylformamide in a 100 mL three-necked flask, and then 4-(4,4-dimethylazasilinan-1-yl)-3,5-difluoroaniline (7.88 g, 30.71 mmol) was added thereto. The resulting mixture was heated to 60° C. under nitrogen gas protection and reacted for 24 h. After the completion of the reaction, the reaction mixture was poured into 200 mL of 2 M hydrochloric acid, and then filtered. The collected solid was redissolved with dichloromethane (50 mL). The resulting mixture was washed with a saturated aqueous sodium chloride solution (30 mL×3), dried over anhydrous sodium sulfate, filtered, concentrated, and then subjected to silica gel column chromatography (petroleum ether:ethyl acetate=10:1 as mobile phase) to give 1-(4-((2S,5S)-2,5-bis(4-nitrophenyl) pyrrolidin-1-yl)-2,6-difluorophenyl)-4,4-dimethylazasilinane (1.2 g).

$^1$H NMR (500 MHz, CDCl$_3$): δ 8.24 (d, J=8.5 Hz, 4H), 7.37 (d, J=8.5 Hz, 4H), 5.78 (d, J=11.5 Hz, 2H), 5.25 (d, J=6.5 Hz, 2H), 3.29 (s, 4H), 2.60 (s, 2H), 2.06 (s, 2H), 0.97 (s, 4H), 0.10 (s, 6H).

MS (ESI) m/z: 553.2[M+H]$^+$.

Step 2: 4,4'-((2S,5S)-1-(4-(4,4-dimethylazasilinan-1-yl)-3,5-difluorophenyl) pyrrolidin-2,5-diyl)diphenylamine 1-(4-((2S,5S)-2,5-bis(4-nitrophenyl)pyrrolidin-1-yl)-2,6-difluorophenyl)-4,4-dimethylazasilinane (2.1 g, 3.8 mmol) was dissolved in 30 mL of tetrahydrofuran in a 100 mL single-necked flask, and then platinum dioxide (0.43 g, 1.9 mmol) was added thereto. Replacement with hydrogen gas was carried out for three times, and then the resulting mixture was subjected to a hydrogenation reaction at atmospheric temperature and pressure for 3 h. Then the resulting mixture was filtered by using Celite as a filter aid, and the residue was purified by silica gel column chromatography (petroleum ether:ethyl acetate=5:1 as an eluent) to give 1.25 g of crude product, which was then refined with petroleum ether (15 mL) to afford 4,4'-((2S,5S)-1-(4-(4,4-dimethylazasilinan-1-yl)-3,5-difluorophenyl)pyrrolidin-2,5-diyl) diphenylamine (0.72 g).

$^1$H NMR (500 MHz, CDCl$_3$): δ6.94 (d, J=8.0 Hz, 4H), 6.65 (d, J=8.5 Hz, 4H), 5.82 (d, J=12.0 Hz, 2H), 4.95 (d, J=5.5 Hz, 2H), 3.17 (s, 4H), 2.49 (s, 2H), 1.73 (d, J=5.5 Hz, 2H), 0.82 (s, 4H), 0.07 (s, 6H).

MS (ESI) m/z:493.1 [M+H]$^+$.

Step 3: Methyl ((2S,2'S,3R,3'R)-((2S,2'S)-(((((2S,5S)-1-(4-(4,4-dimethyl azasilinan-1-yl)-3,5-difluorophenyl)pyrrolidin-2,5-diyl)bis(4,1-phenylene))bis(azanediyl))bis(carbonyl))bis(pyrrolidin-2,1-diyl))bis(3-methoxy-1-oxobutan-1,2-diyl))dicarbamate (1a)

4,4'-((2S,5S)-1-(4-(4,4-dim ethyl azasilinan-1-yl)-3,5-difluorophenyl) pyrrolidin-2,5-diyl)diphenylamine (0.5 g, 1.02 mmol) was dissolved in 10 mL of N,N-dimethylformamide in a 100 mL single-necked flask, and then N-(methoxycarbonyl)-O-methyl-L-threonyl-L-proline (0.9 g, 3.05 mmol), 1-(3-dimethylaminopropyl)-3-ethylcarbodiimide hydrochloride (0.58 g, 3.05 mmol), 1-hydroxybenzotriazole (0.42 g, 3.05 mmol), and N-methylmorpholine (0.62 g, 6.1 mmol) were added in sequence. The resulting mixture was heated to 55° C. and reacted for 12 h. Then the reaction mixture was poured into water and filtered. The filter cake was redissolved with dichloromethane (50 mL). The resulting mixture was washed with a saturated aqueous sodium chloride solution (30 mL), dried over anhydrous sodium sulfate, and then subjected to silica gel column chromatography (petroleum ether:ethyl acetate=1:2 (v/v)) to give Compound 1a (0.6 g).

$^1$H NMR (500 MHz, DMSO-d$_6$): δ 9.95 (s, 2H), 7.52 (d, J=8.5 Hz, 4H), 7.29 (d, J=8.0 Hz, 2H), 7.14 (d, J=8.5 Hz, 4H), 5.81 (d, J=12.5 Hz, 2H), 5.15 (d, J=6.0 Hz, 2H), 4.44 (dd, J=4.5 Hz, 8.0 Hz, 2H), 4.28 (d, J=8.0 Hz, 2H), 3.83 (m, 2H), 3.68 (d, J=7.0 Hz, 2H), 3.54 (s, 6H), 3.49 (t, J=6.5 Hz, 2H), 3.23 (s, 6H), 3.04 (t, J=5.5 Hz, 4H), 2.45 (m, 2H), 2.16 (m, 2H), 2.00 (d, J=6.0 Hz, 2H), 1.90 (m, 4H), 1.62 (d, J=5.5 Hz, 2H), 1.15 (d, J=6.0 Hz, 6H), 0.71 (t, J=6.0 Hz, 4H), 0.04 (s, 6H).

MS (ESI) m/z: 1055.3 [M+Na]$^+$.

Example 6: Methyl ((2S,2'S,3R,3'R)-((2S,2'S)-(((((2R,5R)-1-(4-(4,4-dimethylazasilinan-1-yl)-3,5-difluorophenyl)pyrrolidin-2,5-diyl)bis(4,1-phenylene))bis(azanediyl))bis(carbonyl))bis(pyrrolidin-2,1-diyl))bis (3-methoxy-1-oxobutan-1,2-diyl)) dicarbamate (1b)
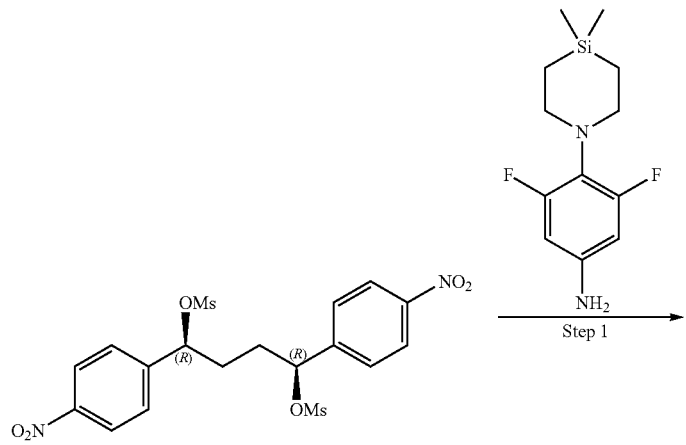
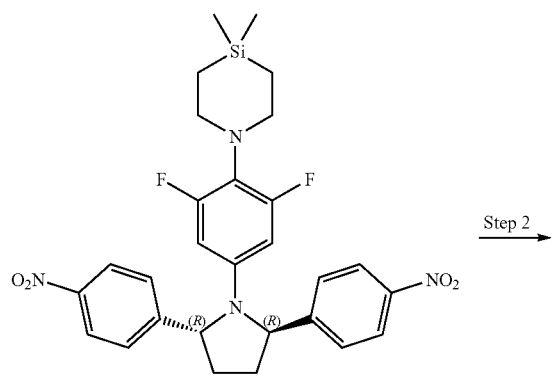
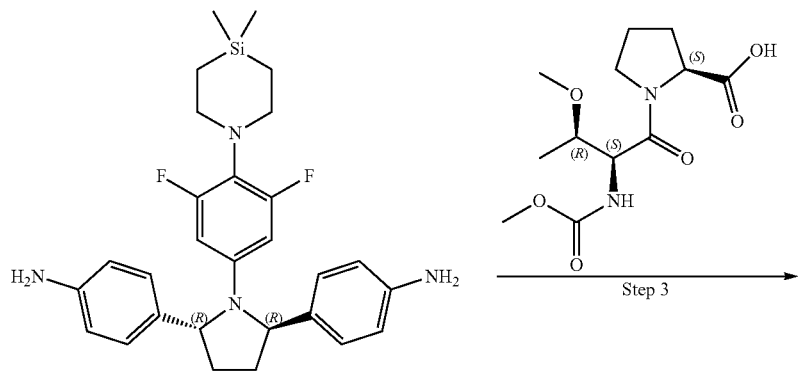

-continued

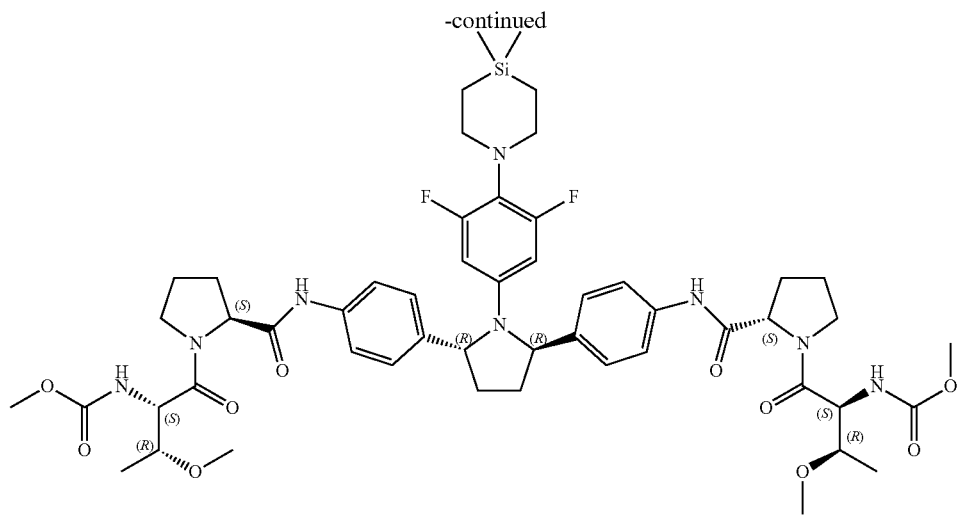

1b

Compound 1b (320 mg) was obtained with reference to the synthetic steps 1, 2, and 3 of Compound 1a in Example 5.

$^1$H NMR (500 MHz, CDCl$_3$): δ 8.92 (s, 2H), 7.45 (d, J=8.5 Hz, 4H), 7.06 (d, J=8.5 Hz, 4H), 5.76 (d, J=12 Hz, 2H), 5.70 (d, J=8 Hz, 2H), 5.01-4.99 (m, 2H), 4.83-4.82 (m, 2H), 4.70-4.68 (m, 2H), 3.80-3.79 (m, 2H), 3.78-3.77 (m, 4H), 3.69 (s, 6H), 3.38 (s, 6H), 3.33-3.20 (m, 3H), 2.48-2.44 (m, 4H), 2.06-2.01 (m, 7H), 1.74-1.73 (m, 4H), 1.23-1.22 (m, 6H), 0.08 (s, 6H).

MS (ESI) m/z: 1055.5 [M+Na]$^+$.

Example 7: Methyl ((2S, 2'S, 3R, 3'R)-((2S, 2'S)-(((((2S, 5S)-1-(4-(4,4-dimethylazasilinan-1-yl)-3-fluorophenyl) pyrrolidin-2,5-diyl)bis(4,1-phenylene)) bis(azanediyl))bis(carbonyl))bis(pyrrolidin-2,1-diyl))bis(3-methoxy-1-oxobutan-1,2-diyl)) dicarbamate (2a)

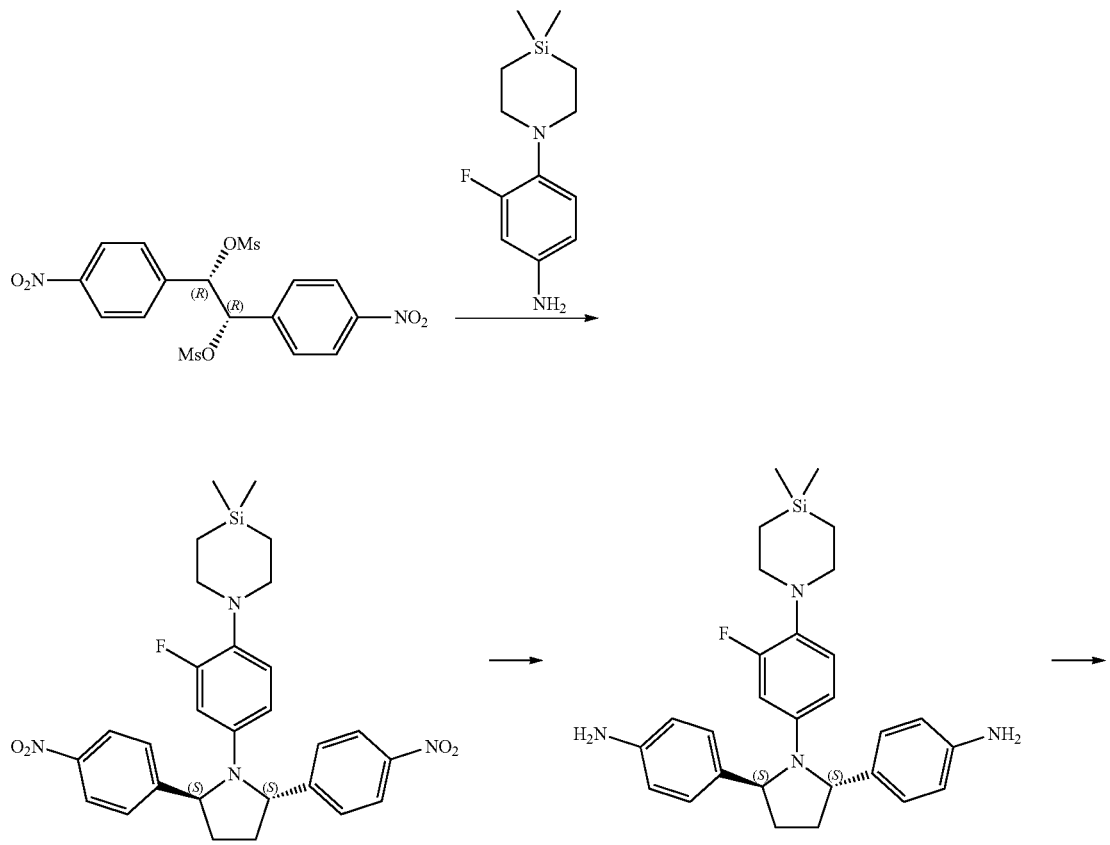

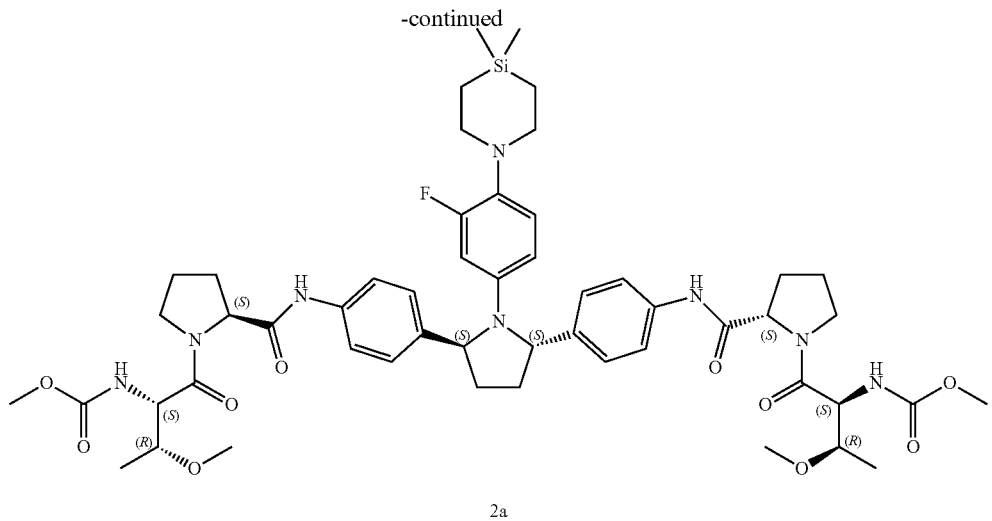

2a

Step 1: 1-(4-((2S, 5S)-2,5-bis(4-nitrophenyl)pyrrolidin-1-yl)-2-fluorophenyl)-4,4-dimethylazasilinane (1R,4R)-1,4-bis(4-nitrophenyl)butan-1,4-diyldimesylate (1.5 g, 3.1 mmol), N,N-dimethylformamide (15 mL) and 4-(4,4-dimethylazasilinan-1-yl)-3-fluoroaniline (7.32 g, 31 mmol) were added respectively to a 100 mL three-necked flask. The resulting mixture was heated to 60° C. in an oil bath under nitrogen gas protection and reacted for 24 h. Then the reaction mixture was poured into 2 M hydrochloric acid (100 mL), and a solid was precipitated. The solid was collected by filtration, and then redissolved with dichloromethane (50 mL). The resulting mixture was washed with a saturated aqueous sodium chloride solution (30 mL), dried over anhydrous sodium sulfate, filtered, concentrated, and then purified by silica gel column chromatography (petroleum ether:ethyl acetate=10:1 as an eluent) to give 1-(4-((2S, 5S)-2,5-bis(4-nitrophenyl) pyrrolidin-1-yl)-2-fluorophenyl)-4,4-dimethylazasilinane (1.2 g).

$^1$H-NMR (500 MHz, CDCl$_3$): δ 8.24 (s, 4H), 7.36 (d, J=8.0 Hz, 4H), 6.71 (s, 1H), 6.00 (m, 2H), 5.29 (s, 2H), 3.11 (s, 2H), 2.63 (s, 2H), 1.96 (s, 2H), 1.58 (m, 2H), 0.85 (m, 4H), 0.07 (s, 6H).

MS (ESI) m/z: 535.1[M+H]$^+$.

Step 2: 4,4'-((2S,5S)-1-(4-(4,4-dimethylazasilinan-1-yl)-3-fluorophenyl) pyrrolidin-2,5-diyl)diphenylamine 1-(4-((2S,5S)-2,5-bis(4-nitrophenyl)pyrrolidin-1-yl)-2-fluorophenyl)-4,4-dimethylazasilinane (1.67 g, 3.13 mmol) was dissolved in 20 mL of tetrahydrofuran in a 100 mL single-necked flask, and then platinum dioxide (0.7 g, 3.13 mmol) was added thereto. The resulting mixture was subjected to a hydrogenation reaction at atmospheric temperature and pressure for 3 h. Then the resulting mixture was filtered by using Celite as a filter aid. The solvent was distilled off under reduced pressure, and the residue was purified by silica gel column chromatography (petroleum ether: ethyl acetate=5:1 as an eluent) to give 4,4'-((2S,5S)-1-(4-(4,4-dimethylazasilinan-1-yl)-3-fluorophenyl)pyrrolidin-2,5-diyl)diphenylamine (1.2 g).

$^1$H NMR (500 MHz, CDCl$_3$): δ 6.95 (d, J=8.0 Hz, 4H), 6.64 (d, J=8.5 Hz, 4H), 6.06 (m, 3H), 4.98 (d, J=7.0 Hz, 2H), 3.12 (s, 2H), 2.50 (s, 2H), 1.75 (d, J=5.0 Hz, 2H), 1.26 (m, 2H), 0.88 (m, 4H), 0.12 (s, 6H).

MS (ESI) m/z: 475.1 [M+H]$^+$.

Step 3: Methyl ((2S, 2'S, 3R, 3'R)-((2S, 2'S)-(((((2S, 5S)-1-(4-(4,4-dimethylazasilinan-1-yl)-3-fluorophenyl)pyrrolidin-2,5-diyl)bis(4,1-phenylene))bis (azanediyl))bis(carbonyl))bis(pyrrolidin-2,1-diyl))bis(3-methoxy-1-oxobutan-1,2-diyl)) dicarbamate (2a)

4,4'-((2S,5S)-1-(4-(4,4-dimethylazasilinan-1-yl)-3-fluorophenyl)pyrrolidin-2,5-diyl)diphenylamine (0.53 g, 1.12 mmol) was dissolved in 10 mL of N,N-dimethylformamide in a 100 mL single-necked flask, and then N-(methoxycarbonyl)-O-methyl-L-threonyl-L-proline (0.97 g, 3.35 mmol), 1-(3-dimethylaminopropyl)-3-ethylcarbodiimide hydrochloride (0.64 g, 3.35 mmol), 1-hydroxybenzotriazole (0.45 g, 3.35 mmol) and N-methylmorpholine (0.68 g, 6.71 mmol) were added in sequence. The resulting mixture was heated to 55° C. and reacted for 12 h. Then the reaction mixture was poured into water and filtered. The filter cake was redissolved with dichloromethane. The organic phase was washed with a saturated aqueous sodium chloride solution, dried and then purified by column chromatography (petroleum ether:ethyl acetate=1:2 (v/v) as mobile phase) to give Compound 2a (0.5 g).

$^1$H NMR (500 MHz, CDCl$_3$): δ9.93 (s, 2H), 7.50 (d, J=8.5 Hz, 4H), 7.29 (d, J=8.0 Hz, 2H), 7.13 (d, J=8.5 Hz, 4H), 6.71 (m, 1H), 5.96 (m, 2H), 5.13 (d, J=6.0 Hz, 4H), 4.44 (m, 2H), 4.28 (m, 2H), 3.82 (m, 2H), 3.65 (m, 2H), 3.54 (s, 6H), 3.48 (m, 2H), 3.26 (s, 6H), 2.98 (m, 4H), 2.45 (m, 2H), 2.16 (m, 2H), 2.09 (m, 2H), 1.89 (m, 4H), 1.62 (d, J=5.5 Hz, 2H), 1.14 (d, J=6.0 Hz, 6H), 0.73 (t, J=5.5 Hz, 2H), 0.04 (s, 6H).

MS (ESI) m/z: 1015.5[M+H]$^+$.

Example 8: Methyl ((2S, 2'S, 3R, 3'R)-((2S, 2'S)-(((((2R, 5R)-1-(4-(4,4-dimethylazasilinan-1-yl)-3-fluorophenyl)pyrrolidin-2,5-diyl)bis(4,1-phenylene))bis(azanediyl))bis(carbonyl))bis(pyrrolidin-2,1-diyl))bis(3-methoxy-1-oxobutan-1,2-diyl))dicarbamate (2b)
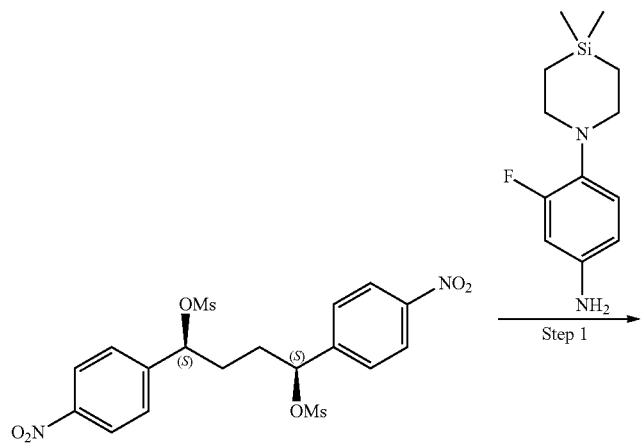
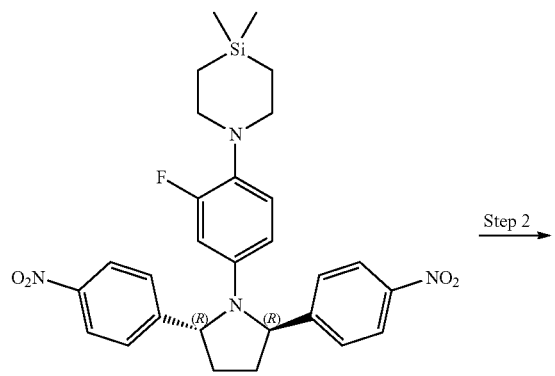
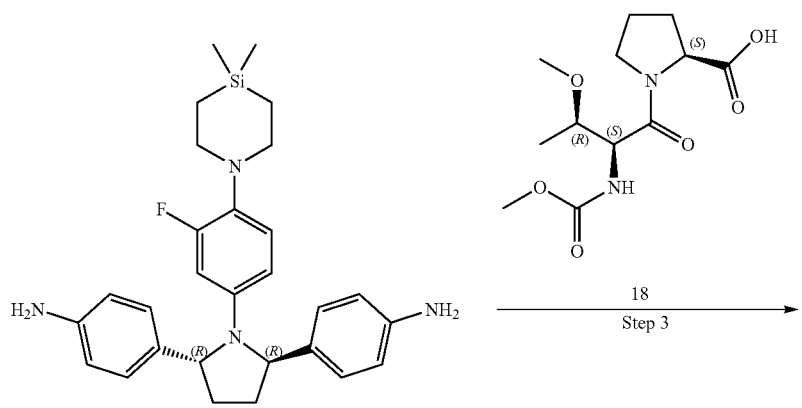

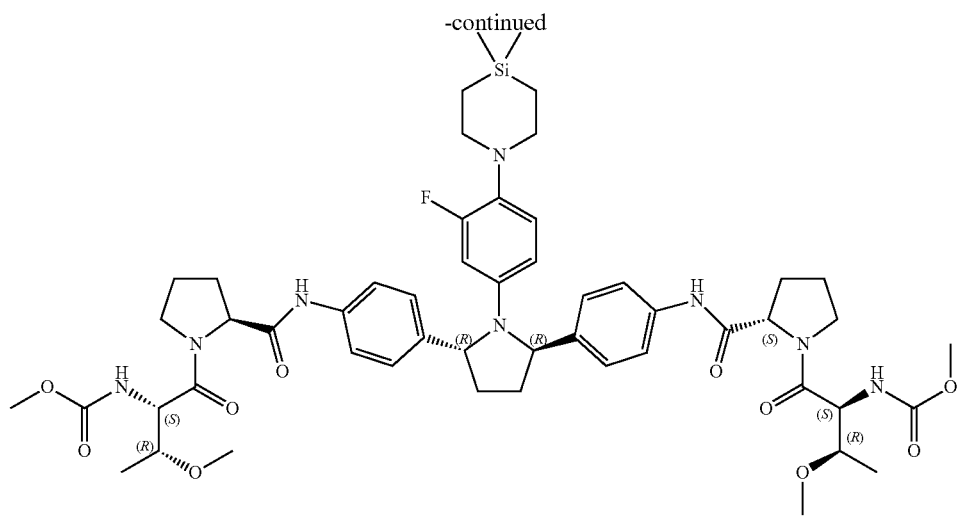

2b

Compound 2b (0.55 g) was obtained with reference to the synthetic steps 1, 2, and 3 of Compound 2a in Example 7.

$^1$HNMR (500 MHz, DMSO-$d_6$): δ 9.94 (s, 2H), 7.51 (d, J=8.5 Hz, 4H), 7.29 (d, J=7.5 Hz, 2H), 7.13 (d, J=8.5 Hz, 4H), 6.70 (m, 1H), 5.96 (m, 2H), 5.13 (d, J=6.0 Hz, 2H), 4.44 (dd, J=5.0 Hz, 8.0 Hz, 2H), 4.28 (t, J=7.5 Hz, 2H), 0.3.69 (m, 2H), 3.54 (m, 2H), 3.49 (s, 6H), 3.47 (d, J=6.5 Hz, 2H), 3.25 (s, 6H), 2.98 (m, 4H), 2.44 (m, 2H), 2.15 (m, 2H), 2.00 (d, J=6.0 Hz, 2H), 1.89 (m, 4H), 1.62 (d, J=5.5 Hz, 2H), 1.13 (d, J=6.5 Hz, 6H), 0.73 (t, J=6.0 Hz, 4H), 0.04 (s, 6H). MS (ESI) m/z: 1037.50[M+Na]$^+$.

Example 9: Methyl ((2S,2'S,3R,3'R)-((2S,2'S)-(((((2S,5S)-1-(3,5-difluoro-4-(8-aza-5-silaspiro[4.5]dec-8-yl)phenyl)pyrrolidin-2,5-diyl)bis(4,1-phenylene))bis (azanediyl))bis(carbonyl))bis(pyrrolidin-2,1-diyl)(3-methoxy-1-oxobutan-1,2-diyl)) dicarbamate (3a)

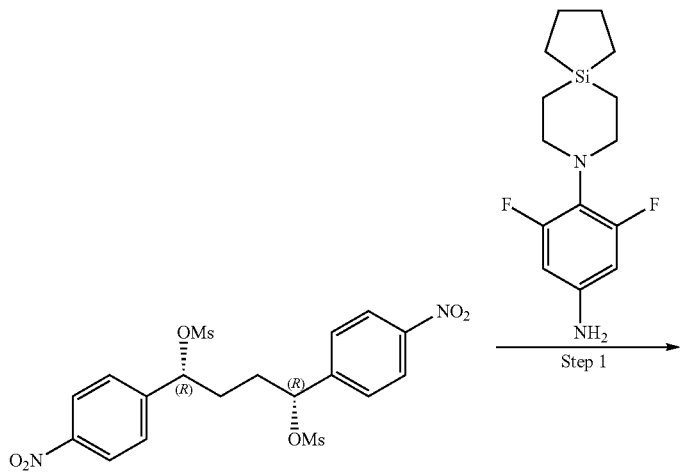

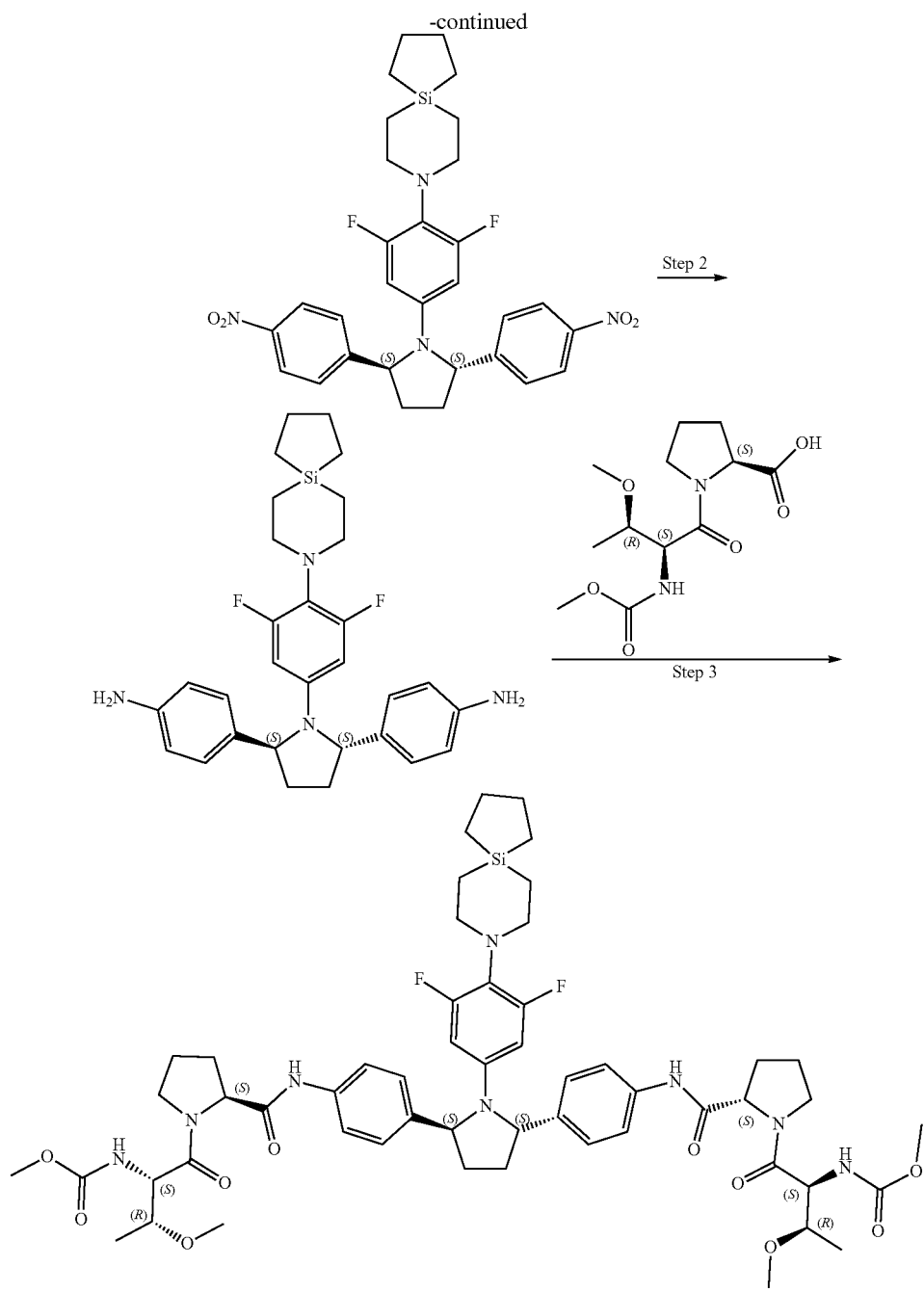

3a

Step 1: 8-(4-((2S, 5S)-2,5-bis(4-nitrophenyl)pyrrolidin-1-yl)-2,6-difluorophenyl)-8-aza-5-silaspiro[4.5]decane In a 100 mL single-necked flask, (1R, 4R)-1,4-bis(4-nitrophenyl)butan-1,4-diyldimesylate (0.39 g, 0.79 mmol) and 3, 5-difluoro-4-(8-aza-5-silaspiro[4.5]dec-8-yl)aniline (0.45 g, 1.59 mmol) were dissolved in acetonitrile (4 mL) at room temperature, and then to the mixture was added N,N-diisopropylethylamine (0.51 g, 3.95 mmol), and the resulting mixture was heated to 75° C. and stirred overnight. The reaction mixture was cooled to room temperature, and then poured into 6N aqueous hydrochloric acid solution (50 mL). The resulting mixture was extracted with ethyl acetate (20 mL×2). The organic phase was washed with water (100 mL) and a saturated saline solution (100 mL), respectively, dried over anhydrous sodium sulfate, filtered and concentrated. The resulting crude product was subjected to silica gel column chromatography (petroleum ether:ethyl acetate=10:1) to separate the isomers to give 8-(4-((2S, 5S)-2,5-bis(4-nitrophenyl)pyrrolidin-1-yl)-2,6-difluorophenyl)-8-aza-5-silaspiro[4.5]decane (0.25 g).

$^1$H NMR (500 MHz, DMSO-d$_6$): δ 8.22 (d, J=8.5 Hz, 4H), 7.52 (d, J=8 Hz, 4H), 5.88 (d, J=11.5 Hz, 2H), 5.50-5.49 (m,

2H), 3.07-3.04 (m, 4H), 1.75-1.74 (m, 2H), 1.52-1.49 (m, 4H), 1.25-1.23 (m, 2H), 0.81-0.78 (m, 4H), 0.55-0.52 (m, 4H).

MS(ESI) m/z 579.5 [M+H]$^+$.

Step 2: 4,4'-((2S,5S)-1-(3,5-difluoro-4-(8-aza-5-silaspiro[4.5]dec-8-yl)phenyl) pyrrolidin-2,5-diyl) diphenylamine 8-(4-((2S,5S)-2,5-bis(4-nitrophenyl)pyrrolidin-1-yl)-2,6-difluorophenyl)-8-aza-5-silaspiro[4.5]decane (0.25 g, 0.43 mmol) was dissolved in tetrahydrofuran (4 mL) in a 100 mL single-necked flask. Then, to this solution was added platinum dioxide (0.1 g, 0.43 mmol), and replacement with hydrogen gas was carried out for three times. The resulting mixture reacted overnight at room temperature under a hydrogen atmosphere. The reaction mixture was filtered through Celite, and the filtrate was concentrated to give 4,4'-((2S,5S)-1-(3,5-difluoro-4-(8-aza-5-silaspiro[4.5]dec-8-yl) phenyl)pyrrolidin-2,5-diyl)diphenylamine (0.19 g).

MS(ESI) m/z: 519.5 [M+H]$^+$.

Step 3: Methyl ((2S,2'S,3R,3'R)-((2S,2'S)-(((((2S,5S)-1-(3,5-difluoro-4-(8-aza-5-silaspiro [4.5]dec-8-yl)phenyl)pyrrolidin-2,5-diyl)bis(4,1-phenylene))bis(azanediyl)) bis(carbonyl))bis(pyrrolidin-2,1-diyl)(3-methoxy-1-oxobutan-1,2-diyl))dicarbamate (3a)

In a 100 mL single-necked flask, 4,4'-((2S,5S)-1-(3,5-difluoro-4-(8-aza-5-silaspiro[4.5]dec-8-yl)phenyl)pyrrolidin-2,5-diyl)diphenylamine (0.14 g, 0.27 mmol) and N-(methoxycarbonyl)-O-methyl-L-threonyl-L-proline (0.23 g, 0.81 mmol) were dissolved in N,N-dimethylformamide (5 mL) at room temperature, and then 1-ethyl-(3-dimethylaminopropyl)carbonyldiimide hydrochloride (0.16 g, 0.81 mmol), 1-hydroxybenzotriazole (0.11 g, 0.81 mmol) and N-methylmorpholine (0.14 g, 1.35 mmol) were added in sequence. The resulting mixture was heated to 60° C. and reacted for 1 hour. After the completion of the reaction, the reaction mixture was poured into water (50 mL) and then extracted with ethyl acetate (100 mL). The organic phase was washed with water (100 mL) and a saturated saline solution (100 mL), respectively, dried over anhydrous sodium sulfate, filtered, concentrated and purified to give Compound 3a (0.14 g).

$^1$H NMR (500 MHz, DMSO-d$_6$): δ 9.95 (s, 2H), 7.52 (d, J=10 Hz, 4H), 7.31 (d, J=10 Hz, 2H), 7.14 (d, J=5 Hz, 4H), 5.80 (d, J=10 Hz, 2H), 5.15 (s, 2H), 4.45-4.42 (m, 2H), 4.29-4.26 (m, 2H), 3.85-3.81 (m, 2H), 3.69-3.65 (m, 2H), 3.53 (s, 6H), 3.49-3.45 (m, 2H), 3.25 (s, 6H), 3.08-3.05 (m, 4H), 2.44 (s, 2H), 2.17-2.12 (m, 2H), 2.01-1.96 (m, 2H), 1.91-1.84 (m, 4H), 1.62-1.61 (m, 2H), 1.51-1.50 (m, 4H), 1.15-1.13 (m, 6H), 0.81-0.79 (m, 4H), 0.56-0.53 (m, 4H).

MS(ESI) m/z 1081.3 [M+Na]$^+$.

Example 10: Methyl (2S, 2'S, 3R, 3'R)-((2S,2'S)-(((2S,5S)-1-(4-(4,4-dimethyl-1,4-diazocan-1-yl)-3,5-difluorophenyl)pyrrolidin-2,5-diyl)bis(1H-benzo[d]imidazol-5,2-diyl))bis(pyrrolidin-2,1-diyl))bis(3-methoxy-1-oxobutan-1,2-diyl))dicarbamate (4a)

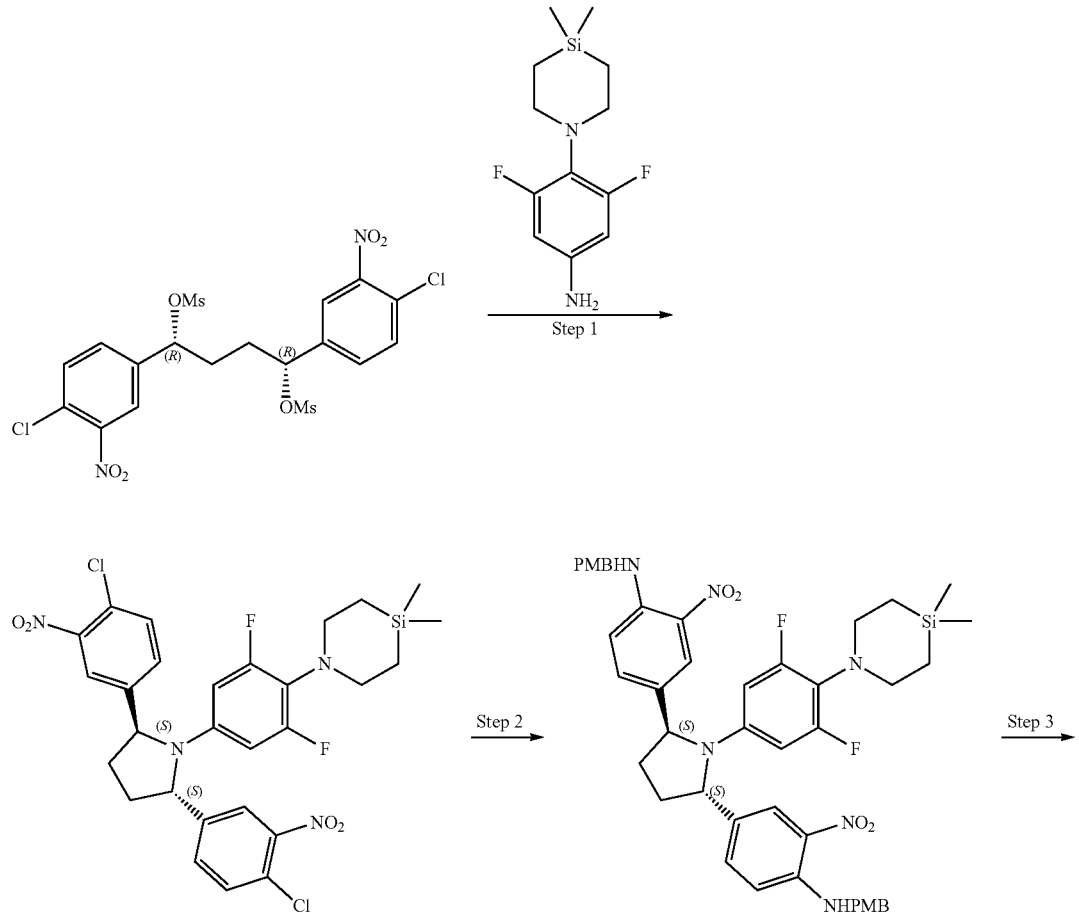

-continued
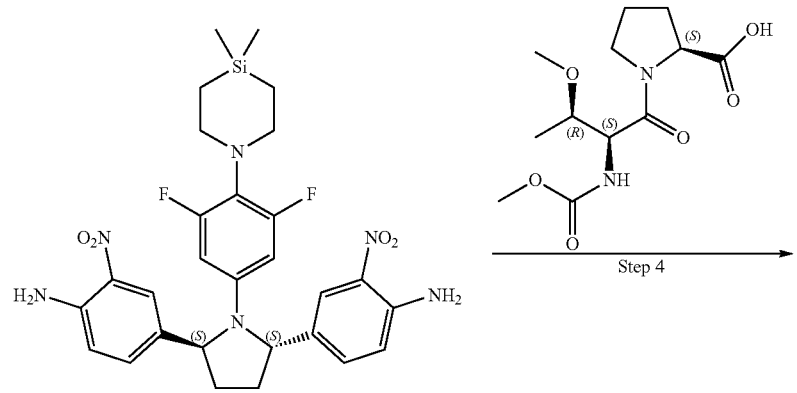
Step 4
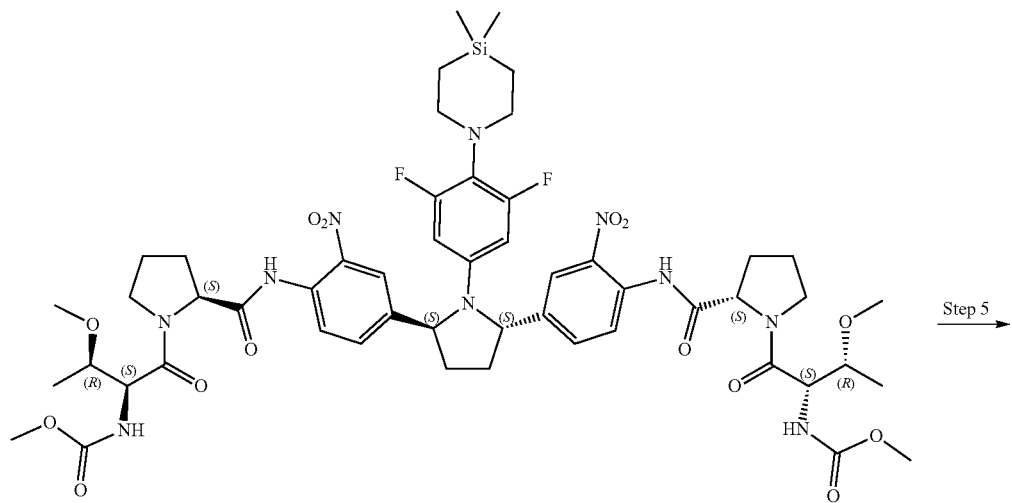
Step 5
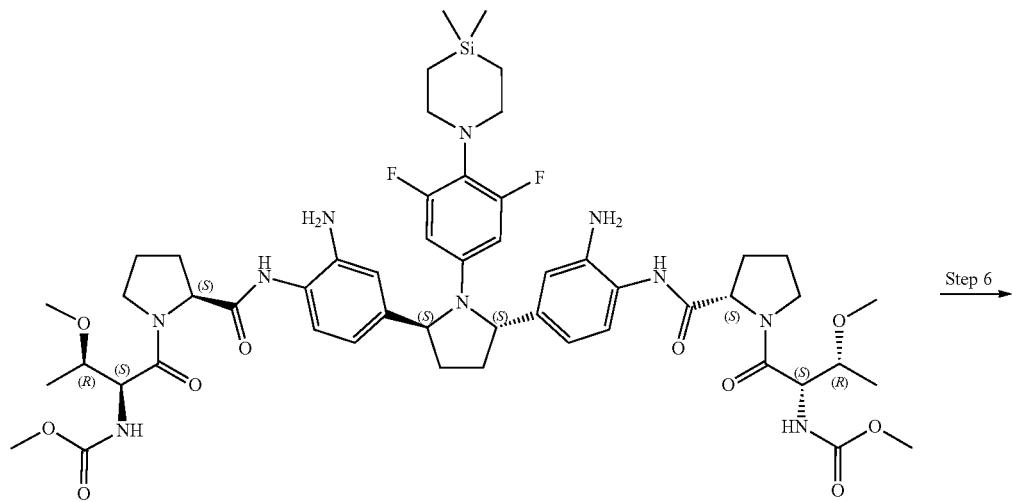
Step 6

-continued

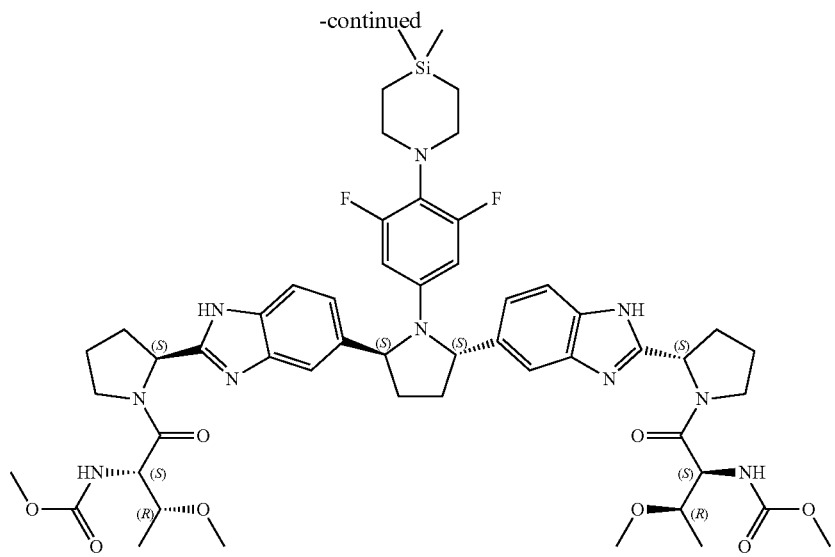

4a

Step 1: 1-(4-((2S,5S)-2,5-bis(4-chloro-3-nitrophenyl)pyrrolidin-1-yl)-2,6-difluorophenyl)-4,4-dimethyl-1,4-azasilinane In a 100 mL single-necked flask, (1R,4R)-1,4-bis(4-chloro-3-nitrophenyl)butan-1,4-diyldimesylate (2.5 g, 4.49 mmol) and 4-(4,4-dimethyl-1,4-azasilinan-1-yl)-3,5-difluoroaniline (9.2 g, 35.88 mmol) were dissolved in N,N-dimethylformamide (30 mL) at room temperature, and then the resulting mixture was heated to 60° C. overnight. The reaction mixture was cooled to room temperature, poured into 1N hydrochloric acid (50 mL), and then extracted with ethyl acetate (20 mL×2). The combined organic phase was dried, filtered and concentrated to give a crude product, which was purified by silica gel column chromatography (petroleum ether:ethyl acetate=10:1) to give 1-(4-((2S,5S)-2,5-bis(4-chloro-3-nitrophenyl)pyrrolidin-1-yl)-2,6-difluorophenyl)-4,4-dimethyl-1,4-azasilinane (2.5 g).
$^1$H NMR (500 MHz, CDCl$_3$): δ=7.70 (d, J=1 Hz, 2H), 7.52 (d, J=8.5 Hz, 2H), 7.34-7.28 (m, 2H), 6.02-5.99 (m, 1H), 5.98-5.93 (m, 1H), 5.22 (d, J=6.5 Hz, 2H), 3.14-3.13 (m, 4H), 2.60-2.50 (m, 2H), 1.90-1.892 (m, 2H), 0.86-0.85 (m, 4H), 0.08 (s, 6H).
MS (ESI) m/z 621.1 [M+H]$^+$.

Step 2: 5,5'-((2S,5S)-1-(4-(4,4-dimethyl-1,4-azasilinan-1-yl)-3,5-difluorophenyl) pyrrolidin-2,5-diyl)bis(N-(4-methoxybenzyl)-2-nitroaniline)

In a 100 mL single-necked flask, 4-methoxybenzylamine (3.53 g, 25.74 mmol) was added to 1-(4-((2S,5S)-2,5-bis(4-chloro-3-nitrophenyl)pyrrolidin-1-yl)-2,6-difluorophenyl)-4,4-dimethyl-1,4-azasilinane (2.0 g, 3.22 mmol). The resulting mixture was heated to 145° C. in an oil bath and reacted for 1 h. The reaction mixture was cooled to room temperature, diluted with ethyl acetate (100 mL), and then washed successively with 2N hydrochloric acid (50 mL×2) and a saturated saline solution (20 mL). The organic phase was dried, filtered and concentrated to give a crude product, which was purified by silica gel column chromatography (petroleum ether:ethyl acetate=10:1) to give 5,5'-((2S,5S)-1-(4-(4,4-dimethyl-1,4-azasilinan-1-yl)-3,5-difluorophenyl)pyrrolidin-2,5-diyl)bis(N-(4-methoxybenzyl)-2-nitroaniline) (2.1 g). MS (ESI) m/z 845.3 [M+Na]$^+$.

Step 3: 5,5'-((2S,5S)-1-(4-(4,4-dimethyl-1,4-azasilinan-1-yl)-3,5-difluorophenyl)pyrrolidine-2,5-diyl)bis(2-nitroaniline)

In a 100 mL single-necked flask, 5,5'-((2S,5S)-1-(4-(4,4-dimethyl-1,4-azasilinan-1-yl)-3,5-difluorophenyl)pyrrolidin-2,5-diyl)bis(N-(4-methoxybenzyl)-2-nitroaniline) (2.1 g, 2.55 mmol) was dissolved in trifluoroacetic acid (20 mL), and stirred at room temperature for 1 h. The reaction mixture was concentrated to remove the solvent, and the residue was diluted with ethyl acetate (20 mL), and then washed successively with a saturated sodium bicarbonate solution (20 mL) and a saturated saline solution (10 mL). The organic phase was dried, filtered and concentrated to give a crude product, which was purified by silica gel column chromatography (petroleum ether:ethyl acetate=3:1) to give 5,5'-((2S,5S)-1-(4-(4,4-dimethyl-1,4-azasilinan-1-yl)-3,5-difluorophenyl)pyrrolidin-2,5-diyl)bis(2-nitroaniline) (1.5 g).
MS (ESI) m/z 583.1 [M+H]$^+$.

Step 4: Methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-nitro-4,1-phenylene) bis(azanediyl))bis(carbonyl))bis(pyrrolidin-2,1-diyl))bis(3-methoxy-1-oxobutan-1,2-diyl)) dicarbamate In a 100 mL single-necked flask, 5,5'-((2S,5S)-1-(4-(4,4-dimethyl-1,4-azasilinan-1-yl)-3,5-difluorophenyl)pyrrolidin-2,5-diyl)bis(2-nitroaniline) (1.4 g, 2.4 mmol) and N-(methoxycarbonyl)-O-methyl-L-threonyl-L-proline (2.08 g, 7.2 mmol) were dissolved in pyridine (15 mL), and then phosphorus oxychloride (1.11 g, 7.2 mmol) was added dropwise under an ice bath and continuously reacted for 15 min. Then the reaction mixture was diluted with ethyl acetate (30 mL), and then washed successively with 1N hydrochloric acid (20 mL×2), a saturated sodium bicarbonate solution (20 mL) and a saturated saline solution (20 mL).

The organic phase was dried, filtered and concentrated to give a crude product, which was purified by silica gel column chromatography (petroleum ether:ethyl acetate=2:3) to give methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-nitro-4,1-phenylene)bis(azanediyl))bis (carbonyl))bis(pyrrolidin-2,1-diyl))bis(3-methoxy-1-oxobutan-1,2-diyl)) dicarbamate (1.6 g).

MS (ESI) m/z 1145.5 [M+Na]+.

Step 5: Methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-amino-4,1-phenylene) bis(azanediyl))bis(carbonyl))bis (pyrrolidin-2,1-diyl))bis(3-methoxy-1-oxobutan-1,2-diyl))dicarbamate In a 100 mL single-necked flask, methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-nitro-4,1-phenyl ene)bis(azanediyl))bis(carbonyl))bis(pyrrolidin-2,1-diyl))bis(3-methoxy-1-oxobutan-1,2-diyl))dicarbamate (1.6 g, 1.42 mmol) was dissolved in tetrahydrofuran (20 mL). Then platinum dioxide (200 mg, 0.88 mmol) was added thereto and reacted at room temperature for 1 h under hydrogen condition. The reaction mixture was filtered through Celite, and the filtrate was concentrated to give methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-amino-4,1-phenylene)bis(azanediyl))bis(carbonyl))bis(pyrrolidin-2,1-diyl))bis(3-methoxy-1-oxobutan-1,2-diyl))dicarbamate (1.2 g).

MS (ESI) m/z 1085.4 [M+Na]+.

Step 6: Methyl (2S, 2'S, 3R, 3'R)-((2S,2'S)-(((2S,5S)-1-(4-(4,4-dimethyl-1,4-azasilinan-1-yl)-3,5-difluorophenyl)pyrrolidin-2,5-diyl)bis(1H-benzo[d]imidazol-5,2-diyl))bis(pyrrolidin-2,1-diyl))bis(3-methoxy-1-oxobutan-1,2-diyl))dicarbamate (4a)

Acetic acid (10 mL) was added to methyl ((2S,2'S,3R,3'R)-((2S,2'S)-(((((2S,5S)-1-(4-(4,4-dimethyl-1,4-azasilinan-1-yl)-3,5-difluorophenyl)pyrrolidin-2,5-diyl)bis(2-amino-4,1-phenylene)bis(azanediyl))bis(carbonyl))bis(pyrrolidin-2,1-diyl))bis(3-methoxy-1-oxobutan-1,2-diyl)) dicarbamate (1.2 g, 1.13 mmol) in a 100 mL single-necked flask. The resulting mixture was heated to 70° C. in an oil bath, and reacted for 2 h. Then the reaction mixture was concentrated to remove the solvent. The residue was diluted with ethyl acetate (30 mL), and then washed successively with a saturated sodium bicarbonate solution (30 mL) and a saturated saline solution (20 mL). The organic phase was dried, filtered and concentrated to give a crude product, which was purified by silica gel column chromatography (dichloromethane:methanol=20:1) and prep-HPLC to give Compound 4a (88 mg).

$^1$H NMR (500 MHz, CDCl$_3$): δ=10.39 (s, 1H), 10.26 (s, 1H), 7.73-7.71 (m, 1H), 7.53-7.50 (m, 1H), 7.33-7.30 (m, 1H), 7.15-7.15 (m, 3H), 5.80-5.75 (m, 2H), 5.72-5.68 (m, 2H), 5.55-5.51 (m, 2H), 5.22-5.17 (m, 2H), 4.64 (s, 1H), 4.57 (s, 1H), 3.80-3.78 (m, 3H), 3.77-3.74 (m, 8H), 3.73-3.72 (m, 1H), 3.31-3.09 (m, 3H), 3.10-3.07 (m, 4H), 2.98-2.90 (m, 4H), 2.62-2.57 (m, 2H), 2.30-2.27 (m, 4H), 2.20-2.10 (m, 2H), 1.75-1.72 (m, 2H), 1.29-1.27 (m, 2H), 1.18-1.14 (m, 5H), 0.77-0.74 (m, 4H), 0.04 (s, 6H).

MS (ESI) m/z 1049.4 [M+Na]+.

Example 11: Methyl (2S, 2'S, 3R, 3'R)-((2S,2'S)-(((2R,5R)-1-(4-(4,4-dimethylazasilinan-1-yl)-3,5-difluorophenyl)pyrrolidin-2,5-diyl)bis(1H-benzo[d]imidazol-5,2-diyl))bis(pyrrolidin-2,1-diyl))bis(3-methoxy-1-oxobutan-1,2-diyl))dicarbamate (4b)

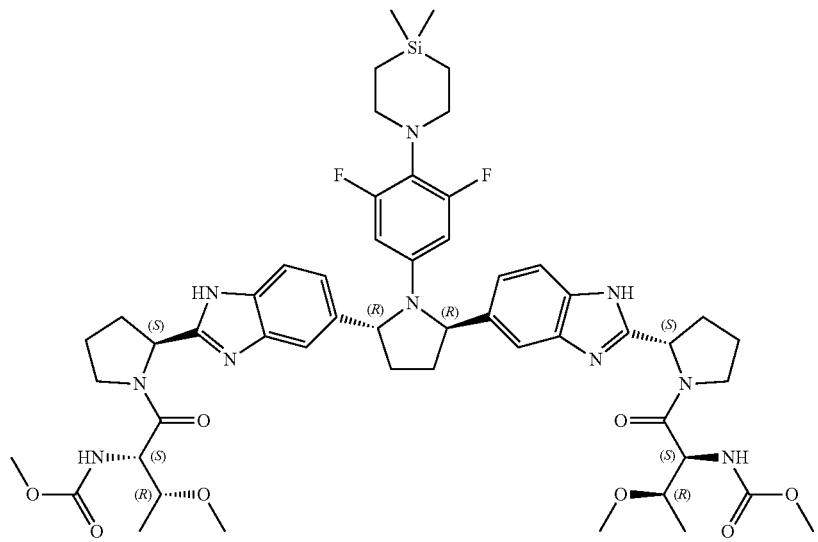

4b

Methyl (2S, 2'S, 3R, 3'R)-((2S,2'S)-(((2R,5R)-1-(4-(4,4-dimethylazasilinan-1-yl)-3,5-difluorophenyl)pyrrolidin-2,5-diyl)bis(1H-benzo[d]imidazol-5,2-diyl))bis (pyrrolidin-2,1-diyl))bis(3-methoxy-1-oxobutan-1,2-diyl))dicarbamate (4b) (0.7 g) was obtained by synthesis with reference to the synthesis method of Compound 4a in Example 10.

$^1$H NMR (500 MHz, DMSO-d$_6$): δ 12.08 (s, 1H), 12.00 (s, 1H), 7.49 (d, J=8.5 Hz, 1H), 7.41 (d, J=8.0 Hz, 2H), 7.19 (s, 1H), 7.08 (m, 4H), 5.87 (t, J=6.0 Hz, 2H), 5.35 (d, J=7.5

Hz, 2H), 5.16 (t, J=3.5 Hz, 2H), 4.29 (d, J=4.5 Hz, 2H), 3.85 (d, J=6.0 Hz, 4H), 3.55 (s, 6H), 3.48 (d, J=5.5 Hz, 2H), 3.18 (m, 6H), 3.00 (m, 4H), 2.54 (m, 2H), 2.20 (s, 4H), 2.02 (m, 4H), 1.69 (s, 2H), 1.04 (m, 6H), 0.69 (s, 4H), 0.02 (s, 6H).
MS (ESI) m/z: 1027.4[M+H]⁺.
Example 12: Methyl (2S, 2'S, 3R, 3'R)-((2S,2'S)-(((2S,5S)-1-(4-(4,4-dimethyl-1,4-azasilinan-1-yl)-3-fluorophenyl)pyrrolidin-2,5-diyl)bis(1H-benzo[d]imidazol-5,2-diyl))bis(pyrrolidin-2,1-diyl))bis(3-methoxy-1-oxobutan-1,2-diyl))dicarbamate (5a)
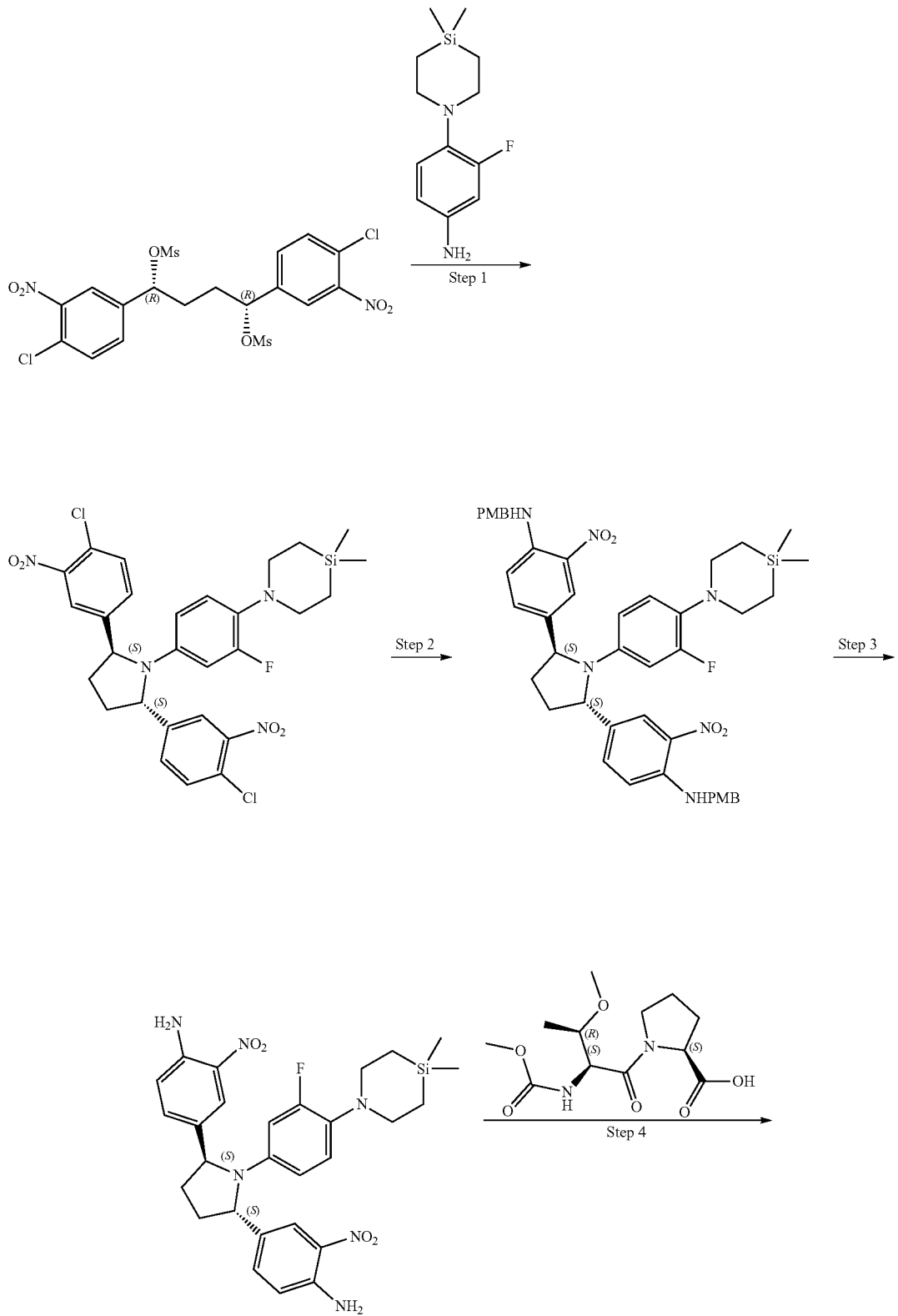

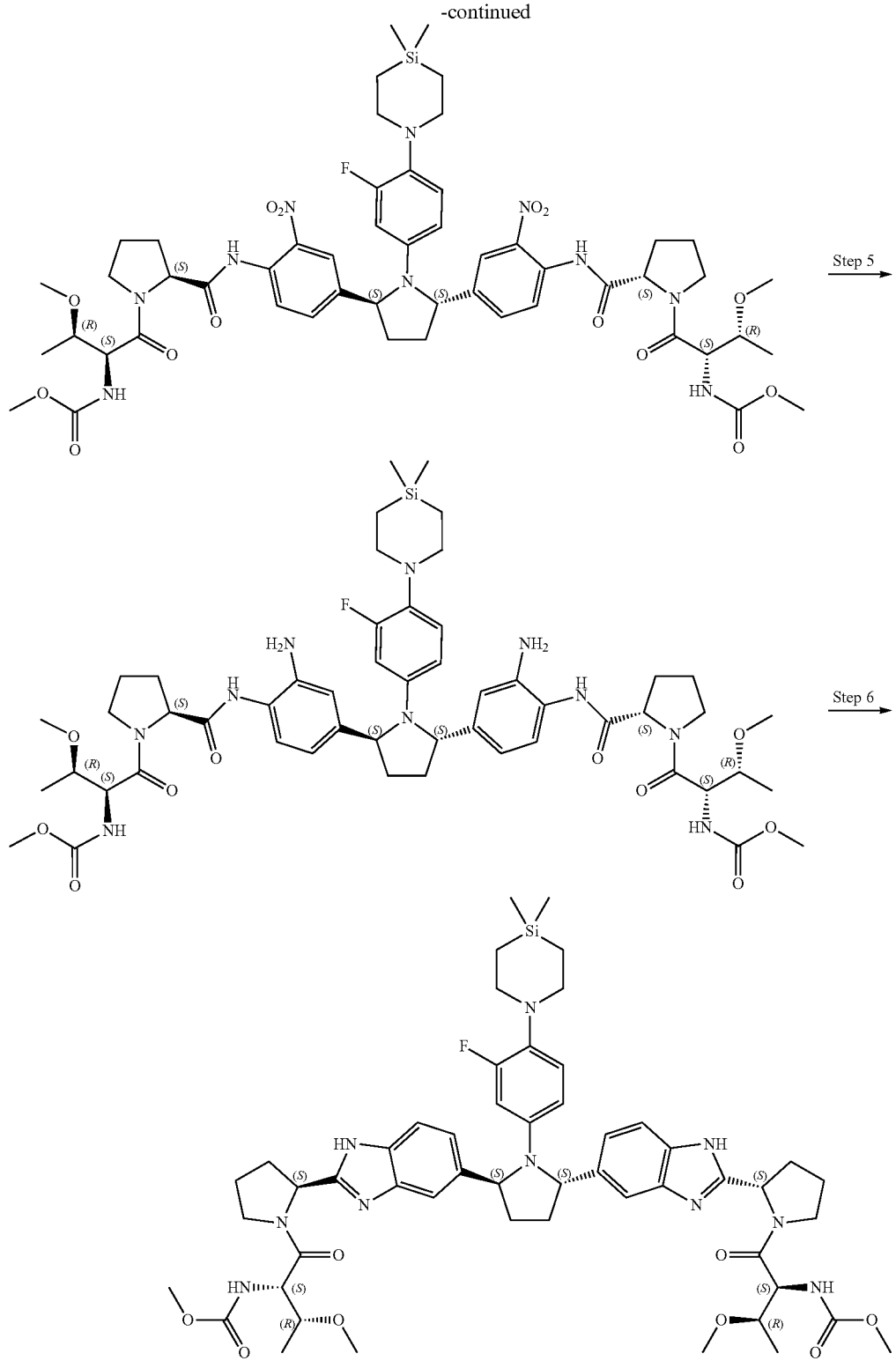
5a
Methyl (2S, 2'S, 3R, 3'R)-((2S,2'S)-(((2S,5S)-1-(4-(4,4-dimethyl-1,4-azasilinan-1-yl)-3-fluorophenyl)pyrrolidin-2,5-diyl)bis(1H-benzo[d]imidazol-5,2-diyl)) bis(pyrrolidin-2,1-diyl))bis(3-methoxy-1-oxobutan-1,2-diyl))dicarbamate 5a (44 mg) was obtained by synthesis with reference to the synthesis method of Compound 4a in Example 10.
$^1$H-NMR (500 MHz, CDCl$_3$): δ=10.40 (s, 1H), 10.26 (s, 1H), 7.72-7.04 (m, 1H), 7.56-7.55 (m, 1H), 7.31-7.30 (m, 1H), 7.17-7.08 (m, 3H), 6.59 (s, 1H), 6.08-5.95 (m, 2H), 5.76-5.68 (m, 2H), 5.57-5.50 (m, 2H), 5.28-5.21 (m, 2H), 4.64-4.61 (s, 1H), 4.60-4.57 (s, 1H), 3.82-3.80 (m, 4H), 3.79-3.67 (m, 9H), 3.63-3.57 (m, 1H), 3.33-3.26 (m, 3H), 3.08-2.95 (m, 9H), 2.67-2.54 (m, 2H), 2.30-2.22 (m, 4H), 2.18-2.13 (m, 2H), 1.85-1.80 (m, 3H), 1.20-1.03 (m. 3H), 0.81-0.79 (m, 4H), 0.04 (s, 6H).

MS (ESI) m/z 1031.3 [M+Na]+.

Example 13: Methyl (2S, 2'S, 3R, 3'R)-((2S,2'S)-(((2R,5R)-1-(4-(4,4-dimethylazasilinan-1-yl)-3-fluorophenyl)pyrrolidin-2,5-diyl)bis(1H-benzo[d]imidazol-5,2-diyl))bis(pyrrolidin-2,1-diyl))bis(3-methoxy-1-oxobutan-1,2-diyl))dicarbamate (5b)

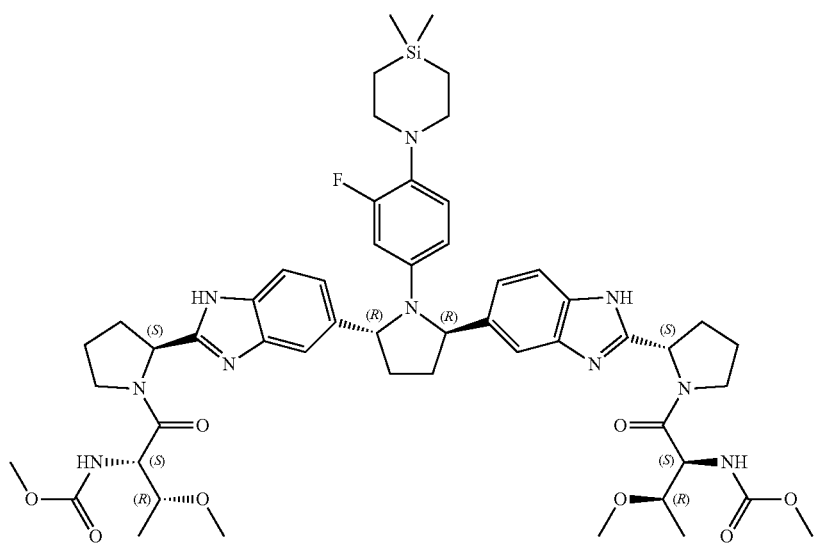

5b

Methyl (2S, 2'S, 3R, 3'R)-((2S,2'S)-(((2R,5R)-1-(4-(4,4-dimethylazasilinan-1-yl)-3-fluorophenyl)pyrrolidin-2,5-diyl)bis(1H-benzo[d]imidazol-5,2-diyl))bis (pyrrolidin-2,1-diyl))bis(3-methoxy-1-oxobutan-1,2-diyl))dicarbamate (5b) (0.4 g) was obtained by synthesis with reference to the synthesis method of Compound 4a in Example 10.

1H NMR (DMSO-d6, 500 MHz): δ 12.04 (s, 1H), 11.98 (s, 1H), 7.47 (d, J=8.0 Hz, 2H), 7.39 (d, J=8.5 Hz, 2H), 7.07 (m, 4H), 6.65 (m, 1H), 6.02 (d, J=7.0 Hz, 2H), 5.32 (d, J=5.0 Hz, 2H), 5.15 (d, J=7.0 Hz, 2H), 4.29 (s, 2H), 3.85 (s, 4H), 3.55 (s, 6H), 3.48 (m, 2H), 3.27 (s, 6H), 2.94 (m, 4H), 2.54 (m, 2H), 2.21 (d, J=5.5 Hz, 4H), 2.01 (m, 4H), 1.70 (s, 2H), 1.05 (t, J=6.0 Hz, 6H), 0.71 (t, J=3.0 Hz, 4H), 0.02 (s, 6H).

MS (ESI) m/z: 1009.5[M+H]+.

Example 14: Methyl ((2S,3R)-1-((S)-2-(6-((2S,5S)-1-(4-(4,4-dimethylazasilinan-1-yl)-3,5-difluorophenyl)-5-(4-((S)-1-(N-(methoxycarbonyl)-O-methyl-L-threonyl)pyrrolidin-2-formylamino)phenyl) pyrrolidin-2-yl)-1H-benzo[d]imidazol-2-yl) pyrrolidin-1-yl)-3-methoxy-1-oxobutan-2-yl) carbamate (6a)

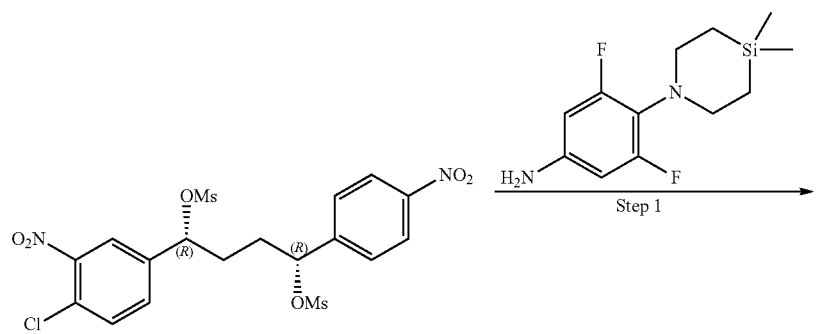

-continued
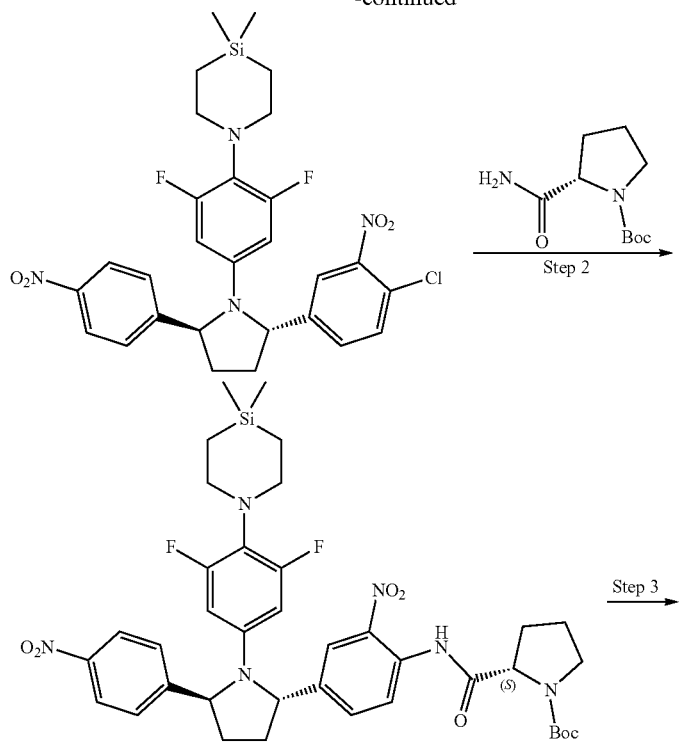
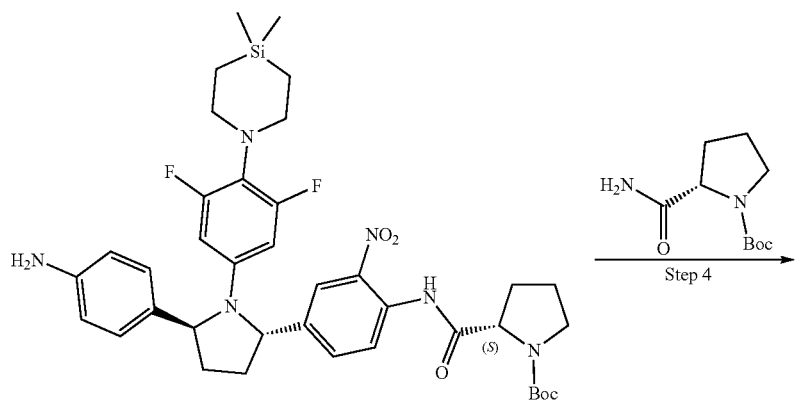
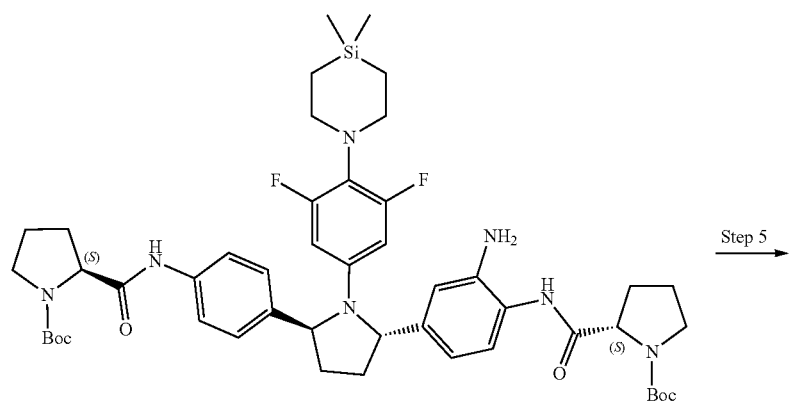

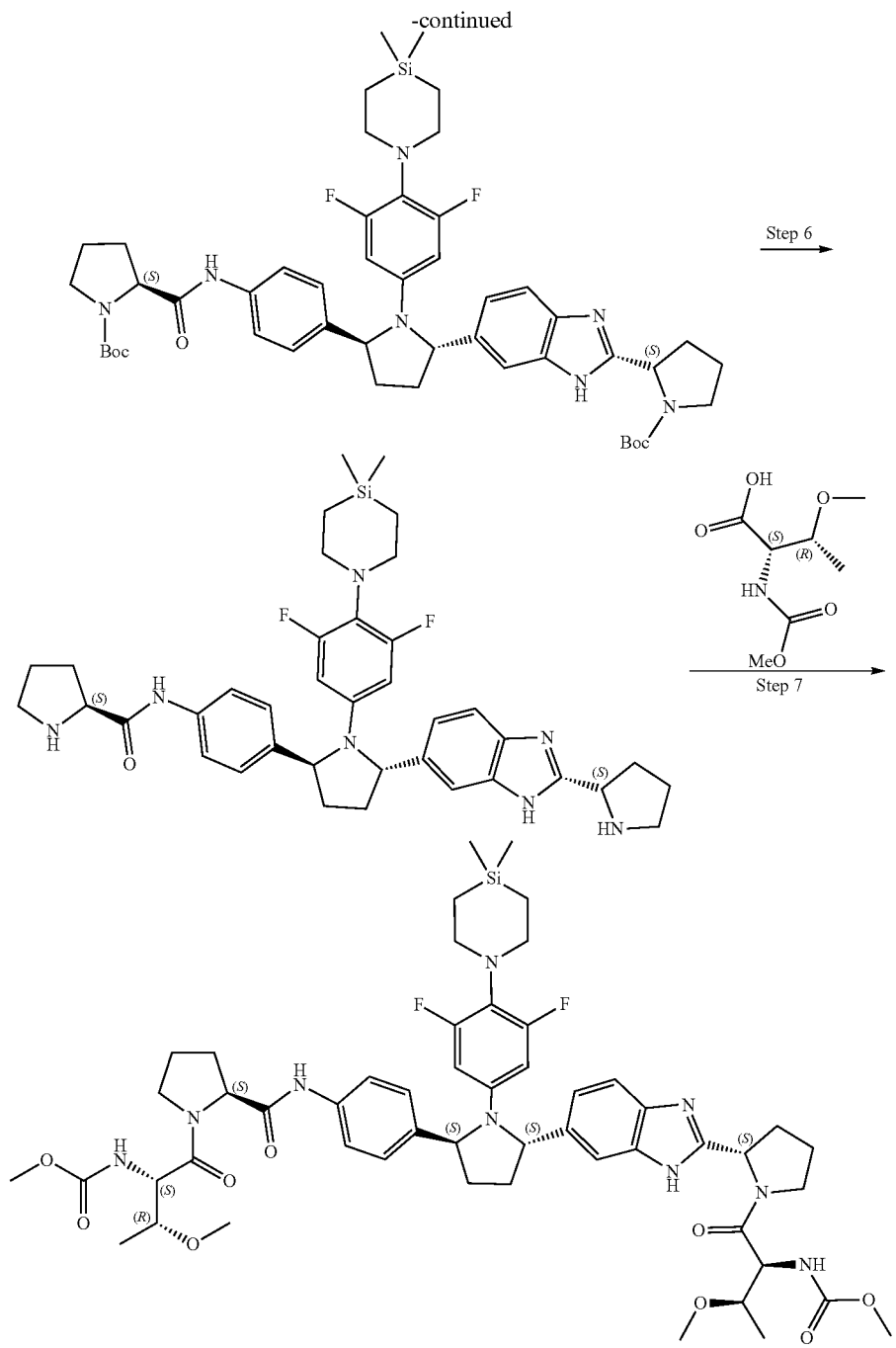

6a

Step 1: 1-(4-((2S,5S)-2-(4-chloro-3-nitrophenyl)-5-(4-nitrophenyl)pyrrolidin-1-yl)-2,6-difluorophenyl)-4,4-dimethyl-1,4-azasilinane A mixture of (1R,4R)-1-(4-chloro-3-nitrophenyl)-4-(4-nitrophenyl)butane-1,4-diyldimesylate (2.00 g, 4.5 mmol), 4-(4,4-dimethyl-1,4-azasilinan-1-yl)-3,5-difluoroaniline (9.20 g, 36.0 mmol), and N,N-diisopropylethylamine (5.85 g, 45.0 mmol) in N,N-dimethylformamide (45 mL) was heated to 60° C. and reacted in an oil bath under stirring overnight. After the completion of the reaction, the reaction mixture was poured into 2M/hydrochloric acid (200 mL), stirred for 10 min, and then extracted with ethyl acetate (60 mL×2). The organic phase was washed with 2M hydrochloric acid (60 mL) and a saturated saline solution (60 mL), respectively, dried over anhydrous sodium sulfate, and concentrated. The residue was subjected to silica gel column chromatography (mobile phase: petroleum ether: ethyl acetate=15:1) to give 1-(4-((2S,5S)-2-(4-chloro-3-nitrophenyl)-5-(4-nitrophenyl)pyrrolidin-1-yl)-2,6-difluorophenyl)-4,4-dimethyl-1,4-azasilinane (1.31 g).

$^1$H NMR (500 MHz, DMSO-d$_6$): δ 8.21 (d, J=8.5 Hz, 2H), 7.96 (d, J=2.0 Hz, 1H), 7.75 (d, J=8.5 Hz, 1H), 7.48-7.55 (m,

3H), 5.92 (d, J=12.0 Hz, 2H), 5.43-5.50 (m, 2H), 3.04 (t, J=6.0 Hz, 4H), 1.94-2.03 (m, 2H), 1.72-1.79 (m, 2H), 0.72 (t, J=6.0 Hz, 4H), 0.03 (s, 6H).

MS (ESI) m/z: 587.1.

Step 2: Tert-butyl (S)-2-((4-((2S,5S)-1-(4-(4,4-dimethylazasilinan-1-yl)-3,5-difluorophenyl)-5-(4-nitrophenyl)pyrrolidin-2-yl)-2-nitrophenyl)carbamoyl) pyrrolidine-1-carboxylate 1-(4-((2S, 5S)-2-(4-chloro-3-nitrophenyl)-5-(4-nitrophenyl)pyrrolidin-1-yl)-2,6-difluorophenyl)-4,4-dimethyl-1,4-azasilinane (1.47 g, 2.49 mmol), tert-butyl (S)-2-carbamoylpyrrolidine-1-carboxylate (0.81 g, 3.75 mmol), cesium carbonate (1.23 g, 3.75 mmol), tris(dibenzylideneacetone) dipalladium (0.12 g, 0.12 mmol), and 4,5-bis(diphenylphosphino)-9,9-dimethylxanthene (0.42 g, 0.75 mmol) were dispersed in 1,4-dioxane (40 mL), and the resulting mixture was reacted at 100° C. for 4 h in an oil bath under $N_2$ atmosphere with stirring. Then the reaction mixture was cooled to room temperature, and suction-filtered. The filtrate was poured into 200 mL of water, and then extracted with ethyl acetate (60 mL×2), washed with water (60 mL×3), dried and concentrated. The residue was purified by silica gel column chromatography (mobile phase: petroleum ether: ethyl acetate=10:1) to give tert-butyl (S)-2-((4-((2S,5 S)-1-(4-(4,4-dimethylazasilinan-1-yl)-3,5-difluorophenyl)-5-(4-nitro phenyl)pyrrolidin-2-yl)-2-nitrophenyl)carbamoyl) pyrrolidine-1-carboxylate (1.1 g).

$^1$H NMR (500 MHz, DMSO-$d_6$): δ 10.52 (s, 1H), 8.21-8.28 (m, 2H), 7.85-7.86 (m, 1H), 7.49-7.66 (d, J=8.5 Hz, 1H), 7.50-7.58 (m, 3H), 5.91 (d, J=12.5 Hz, 2H), 5.45 (dd, J=8.0 Hz, J=34.5 Hz, 2H),4.30 (s, 1H), 3.34-3.43 (m, 2H), 3.02-3.10 (m, 4H), 2.42-2.45 (m, 1H), 2.13-2.28 (m, 1H), 1.72-1.97 (m, 6H), 1.3 (s, 9H), 0.69-0.72 (m, 4H), 0.03 (s, 6H).

MS (ESI) m/z: 765.3.

Step 3: Tert-butyl (S)-2-((2-amino-4-((2S,5S)-5-(4-aminophenyl)-1-(4-(4,4-dimethylazasilinan-1-yl)-3,5-difluorophenyl)pyrrolidin-2-yl)phenyl)carbamoyl) pyrrolidine-1-carboxylate Tert-butyl (S)-2-((4-((2S,5S)-1-(4-(4,4-dimethylazasilinan-1-yl)-3,5-difluorophenyl)-5-(4-nitrophenyl)pyrrolidin-2-yl)-2-nitrophenyl)carbamoyl)pyrrolidine-1-carboxylate (1.00 g, 1.30 mmol) was dissolved in tetrahydrofuran (15 mL). Then platinum oxide (0.1 g) was added thereto and reacted at room temperature for 6 h under a hydrogen atmosphere with stirring. Then the reaction mixture was suction-filtered, and the filtrate was concentrated. The residue was refined with methyl tert-butyl ether (15 mL) to give tert-butyl (S)-2-((2-amino-4-((2S,5S)-5-(4-aminophenyl)-1-(4-(4,4-dimethylazasilinan-1-yl)-3,5-difluorophenyl)pyrrolidin-2-yl)phenyl)carbamoyl)pyrrolidine-1-carboxylate (0.58 g, 63%).

$^1$H NMR (500 MHz, DMSO-$d_6$) δ 9.24 (s, 1H), 7.06 (d, J=9.0 Hz, 1H), 6.84-6.85 (m, 2H), 6.50-6.58 (m, 3H), 6.43 (d, J=7.5 Hz, 1H), 5.81 (d, J=12.5 Hz, 2H), 4.95 (s, 4H), 4.79-4.93 (m, 2H), 4.24 (s, 1H), 3.34-3.43 (m, 2H), 3.03-3.08 (m, 4H), 2.35-2.41 (m, 2H), 2.13-2.22 (m, 1H), 1.89-1.91 (m, 2H), 1.76-1.79 (m, 1H), 1.57-1.61 (m, 2H), 1.32-1.41 (m, 9H), 0.71-0.73 (m, 4H), 0.04 (s, 6H).

MS (ESI) m/z: 705.3.

Step 4: Tert-butyl (S)-2-((2-amino-4-((2S,5S)-5-(4-((S)-1-(tert-butoxycarbonyl) pyrrolidin-2-formylamino)phenyl)1-(4-(4,4-dimethylazasilinan-1-yl)-3, 5-difluorophenyl) pyrrolidin-2-yl)phenyl)carbamoyl) pyrrolidine-1-carboxylate Tert-butyl (S)-2-((2-amino-4-((2S,5S)-5-(4-aminophenyl)-1-(4-(4,4-dimethylazasilinan-1-yl)-3,5-difluorophenyl) pyrrolidin-2-yl)phenyl)carbamoyl)pyrrolidine-1-carboxylate (0.40 g, 0.57 mmol), L-Boc-proline (0.13 g, 0.60 mmol), 2-(7-oxobenzotriazole)-N,N,N',N'-tetramethyluronium hexafluorophosphate (0.33 g, 0.86 mmol), and N,N-diisopropylethylamine (0.20 mL, 1.14 mmol) were dissolved in N,N-dimethylformamide (10 mL), and the resulting mixture reacted at room temperature under stirring for 2 h. The reaction mixture was poured into water (50 mL), stirred for 10 min, and suction-filtered. The filter cake was washed with water (5 mL×3), and the solid was collected and dried to give tert-butyl (S)-2-((2-amino-4-((2S,5 S)-5-(4-((S)-1-(tert-butoxycarbonyl)pyrrolidin-2-formylamino)phenyl) 1-(4-(4, 4-dimethylazasilinan-1-yl)-3,5-difluorophenyl)pyrrolidin-2-yl)phenyl)carbamoyl) pyrrolidine-1-carboxylate (0.46 g).

$^1$H NMR (500 MHz, DMSO-$d_6$): δ 9.92 (s, 1H), 9.15-9.23 (m, 1H), 7.53 (d, J=8.0 Hz, 1H), 7.14-7.15 (m, 2H), 7.07 (d, J=8.0 Hz, 1H), 6.57-6.61 (m, 2H), 5.81 (d, J=12.5 Hz, 2H), 5.06 (dd, J=7.5 Hz, J=34.0 Hz, 2H), 4.380-4.93 (m, 2H), 4.19-4.25 (m, 2H), 3.33-3.41 (m, 4H), 3.03-3.05 (m, 4H), 2.43-2.47 (m, 2H), 2.19-2.20 (m, 2H), 1.80-1.89 (m, 6H), 1.64-1.67 (m, 2H), 1.36-1.41 (m, 18H), 0.70-0.72 (m, 4H), 0.03 (s, 6H).

MS (ESI) m/z: 902.6.

Step 5: Tert-butyl (S)-2-((4-((2S,5S)-5-(2-((S)-1-(tert-butoxycarbonyl)pyrrolidin-2-yl)-1H-benzo[d] imidazol-6-yl)-1-(4-(4,4-dimethylazasilinan-1-yl)-3, 5-difluorophenyl) pyrrolidin-2-yl)phenyl)carbamoyl) pyrrolidine-1-carboxylate Tert-butyl (S)-2-((4-((2S,5S)-5-(2-((S)-1-(tert-butoxycarbonyl)pyrrolidin-2-yl)-1H-benzo[d]imidazol-6-yl)-1-(4-(4, 4-dimethylazasilinan-1-yl)-3,5-difluorophenyl) pyrrolidin-2-yl)phenyl)carbamoyl)pyrrolidine-1-carboxylate (0.45 g, 0.50 mmol), and acetic acid (2.7 mL) were dissolved in toluene (9 mL), and the resulting mixture reacted at 55° C. in an oil bath with stirring for 5 h. Then the pH of the reaction mixture was adjusted to be alkaline with a saturated aqueous solution of sodium carbonate. The resulting mixture was extracted with ethyl acetate (30 mL×2), dried over anhydrous sodium sulfate, filtered, and then concentrated. The residue was purified by silica gel column chromatography (mobile phase: petroleum ether:ethyl acetate=10:1) to give tert-butyl (S)-2-((4-((2S,5S)-5-(2-((S)-1-(tert-butoxycarbonyl) pyrrolidin-2-yl)-1H-benzo[d]imidazol-6-yl)-1-(4-(4,4-dimethylazasilinan-1-yl)-3,5-difluorophenyl)pyrrolidin-2-yl)phenyl)carbamoyl)pyrrolidine-1-carboxylate (0.21 g).

$^1$H NMR (500 MHz, DMSO-$d_6$): δ 9.95 (s, 1H), 7.55 (d, J=8.0 Hz, 2H), 7.46 (d, J=7.5 Hz, 1H), 7.17-7.25 (m, 3H), 7.06 (d, J=8.5 Hz, 1H), 5.82-5.86 (m, 2H), 5.25 (dd, J=5.5 Hz, J=48.5 Hz, 2H), 4.85-4.95 (m, 1H), 4.41-4.42 (m, 2H), 3.39-.356 (m, 4H), 3.02-3.04 (m, 4H), 2.15-2.20 (m, 2H), 1.80-1.99 (m, 8H), 1.68-1.70 (m, 2H), 1.29-1.40 (m, 18H), 0.68-0.71 (m, 4H), 0.02 (s, 6H).

MS (ESI) m/z: 884.4.

Step 6: (S)—N-(4-((2S,5S)-1-(4-(4,4-dimethylazasilinan-1-yl)-3,5-difluorophenyl)-5-(2-((S)-pyrrolidin-2-yl)-1H-benzo[d]imidazol-6-yl)pyrrolidin-2-yl)phenyl) pyrrolidine-2-carboxamide Tert-butyl (S)-2-((4-((2S,5S)-5-(2-((S)-1-(tert-butoxycarbonyl)pyrrolidin-2-yl)-1H-benzo[d]imidazol-6-yl)-1-(4-(4,4-dimethylazasilinan-1-yl)-3,5-difluorophenyl) pyrrolidin-2-yl)phenyl)carbamoyl)pyrrolidine-1-carboxylate (0.17 g, 0.23 mmol) was dissolved in tetrahydrofuran (8 mL) and concentrated hydrochloric acid (2 mL, 24 mL), and the resulting mixture reacted at room temperature for 1 h. Then the reaction mixture was concentrated, and the residue was diluted with water (10 mL) and washed with ethyl acetate. The pH of the aqueous phase was adjusted to be alkaline with a saturated aqueous solution of sodium carbonate, and then extracted with a mixture of dichloromethane and methanol in 10:1. The organic phase was washed with water, dried and concentrated to give (S)—N-(4-((2S,5S)-1-(4-(4,4-dimethylazasilinan-1-yl)-3,5-difluorophenyl)-5-(2-((S)-pyrrolidin-2-yl)-1H-benzo[d]imidazol-6-yl)pyrrolidin-2-yl)phenyl)pyrrolidine-2-carboxamide (0.15 g).

$^1$H NMR (500 MHz, DMSO-$d_6$): δ 9.92 (s, 1H), 7.61 (d, J=8.5 Hz, 2H), 7.46 (d, J=7.5 Hz, 1H), 7.16-7.23 (m, 3H), 7.03 (d, J=8.5 Hz, 1H), 5.85 (d, J=12.5 Hz, 2H), 5.29 (dd, J=5.5, 45.0 Hz, 2H), 4.31-4.32 (m, 1H), 3.66-3.69 (m, 2H), 3.02 (t, J=6.0 Hz, 4H), 2.87-2.94 (m, 4H), 1.95-2.01 (m, 4H), 1.73-1.78 (m, 3H), 1.63-1.67 (m, 4H), 1.23-1.25 (m, 3H), 0.68 (t, J=6.0 Hz, 4H), 0.02 (s, 6H).

MS (ESI) m/z: 684.2.

Step 7: Methyl ((2S,3R)-1-((S)-2-(6-((2S,5S)-1-(4-(4,4-dimethylazasilinan-1-yl)-3,5-difluorophenyl)-5-(4-((S)-1-(N-(methoxycarbonyl)-O-methyl-L-threonyl) pyrrolidin-2-formylamino)phenyl)pyrrolidin-2-yl)-1H-benzo[d]imidazol-2-yl)pyrrolidin-1-yl)-3-methoxy-1-oxobutan-2-yl)carbamate (6a)

(S)—N-(4-((2S,5S)-1-(4-(4,4-dimethylazasilinan-1-yl)-3,5-difluorophenyl)-5-(2-((S)-pyrrolidin-2-yl)-1H-benzo[d]imidazol-6-yl)pyrrolidin-2-yl)phenyl) pyrrolidine-2-carboxamide (0.14 g, 0.21 mmol), (2S,3R)-3-methoxy-2-((methoxycarbonyl)amino)butyric acid (0.09 g, 0.47 mmol), 2-(7-oxobenzotriazole)-N,N,N',N'-tetramethyluronium hexafluophosphate (0.16 g, 0.41 mmol), N,N-diisopropylethylamine (0.21 g, 1.64 mmol), and N,N-dimethylformamide (5 mL) reacted at room temperature for 3 h. After the completion of the reaction, the reaction mixture was poured into water (30 mL), stirred for 10 min, suction-filtered, and washed with water (10 mL×3). The collected crude product was then purified to give methyl ((2S,3R)-1-((S)-2-(6-((2S,5S)-1-(4-(4,4-dimethylazasilinan-1-yl)-3,5-difluorophenyl)-5-(4-((S)-1-(N-(methoxycarbonyl)-O-methyl-L-threonyl) pyrrolidin-2-formylamino)phenyl)pyrrolidin-2-yl)-1H-benzo[d]imidazol-2-yl)pyrrolidin-1-yl)-3-methoxy-1-oxobutan-2-yl)carbamate (6a) (0.065 g).

$^1$H NMR (500 MHz, DMSO-$d_6$): δ 11.97-12.29 (m, 1H), 9.95-10.00 (m, 1H), 7.53 (d, J=8.0 Hz, 2H), 7.43 (dd, J=8.5 Hz, J=34.5 Hz, 1H), 7.30 (d, J=8.0 Hz, 1H), 7.16-7.27 (m, 4H), 7.04 (dd, J=8.0 Hz, J=25.5 Hz, 1H), 5.84 (dd, J=3.5 Hz, J=12.5 Hz, 2H), 5.14-5.34 (m, 3H), 4.43-4.46 (m, 1H), 4.27-4.30 (m, 2H), 3.83-3.84 (m, 2H), 3.66-3.68 (m, 1H), 3.47-3.55 (m, 7H), 3.16-3.28 (m, 6H), 3.02 (t, J=6.0 Hz, 4H), 2.49-2.51 (m, 1H), 2.14-2.24 (m, 3H), 1.97-2.07 (m, 4H), 1.85-1.93 (m, 2H), 1.63-1.70 (m, 2H), 1.23-1.25 (m, 2H), 1.06-1.15 (m, 6H), 0.70 (t, J=5.0 Hz, 4H), 0.03 (s, 6H).

MS (ESI) m/z: 1030.4.

Example 15: Methyl ((2S,3R)-1-((S)-2-(6-((2R,5R)-1-(4-(4,4-dimethylazasilinan-1-yl)-5-(4-((S)-1-(N-(methoxycarbonyl)-O-methyl-L-threonyl) pyrrolidin-2-formylamino)phenyl)pyrrolidin-2-yl)-benzo[d]imidazol-2-yl)pyrrolidin-1-yl)-3-methoxy-1-oxobutan-2-yl)carbamate (6b)

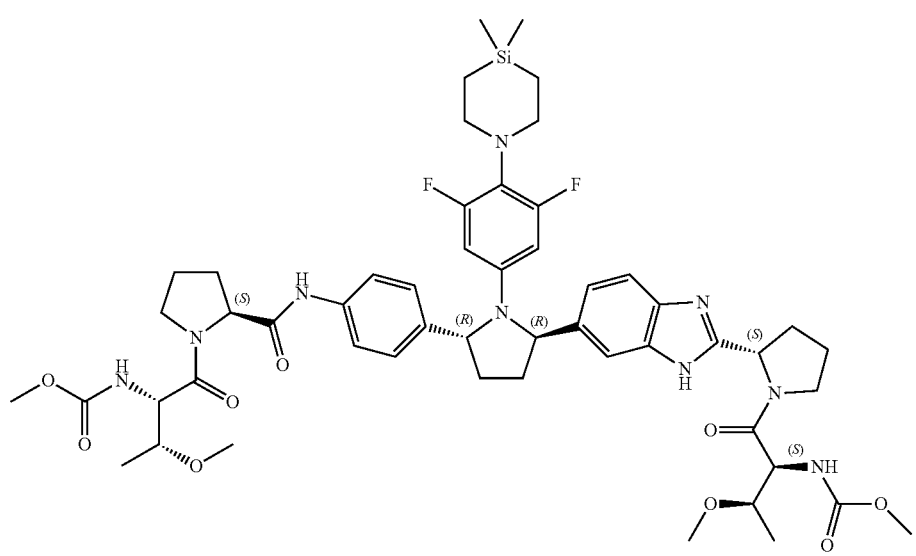

6b

Compound 6b (0.06 g) was obtained by synthesis with reference to the preparation method of Compound 6a.

¹H NMR (500 MHz, DMSO-d₆): δ 11.98-12.28 (m, 1H), 9.96-10.00 (m, 1H), 7.53 (d, J=8.5 Hz, 1H), 7.44 (dd, J=8.0 Hz, J=39.0 Hz, 1H), 7.29 (d, J=4.0 Hz, 1H), 7.12-7.24 (m, 4H), 7.05 (m, 1H), 5.84 (dd, J=6.0 Hz, J=12.0 Hz, 2H), 5.12-5.34 (m, 3H), 4.43-4.46 (m, 1H), 4.26-4.34 (m, 2H), 3.83-3.84 (m, 2H), 3.66-3.68 (m, 1H), 3.46-3.54 (m, 7H), 3.10-3.25 (m, 6H), 3.02 (t, J=6.0 Hz, 4H), 2.47-2.49 (m, 1H), 2.15-2.20 (m, 3H), 1.87-1.92 (m, 6H), 1.62-1.69 (m, 2H), 1.23-1.25 (m, 2H), 0.99-1.14 (m, 6H), 0.69 (t, J=6.0 Hz, 4H), 0.02 (s, 6H).

MS(ESI): m/z 1030.4.

Example 16: Methyl ((2S,2'S,3R,3'R)-((2S,2'S)-(((2R,5R)-1-(3,5-difluoro-4-(8-aza-5-silaspiro[4.5]dec-8-yl)phenyl)pyrrolidin-2,5-diyl)bis(1H-benzo[d]imidazol-5,2-diyl))bis(pyrrolidin-2,1-diyl)bis-1-oxobutan-1,2-diyl))dicarbamate (7b)

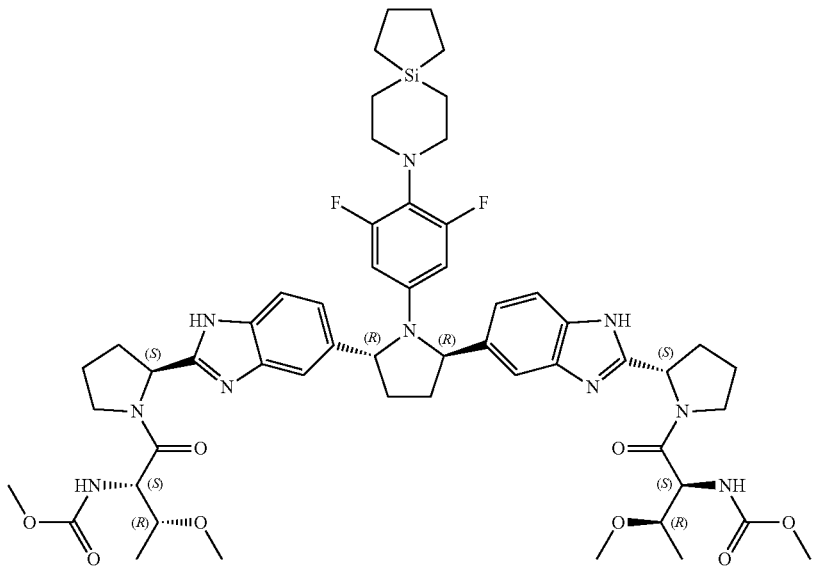

Methyl ((2S,2'S,3R,3'R)-((2S,2'S)-(((2R,5R)-1-(3,5-difluoro-4-(8-aza-5-silaspiro[4.5]dec-8-yl)phenyl)pyrrolidin-2,5-diyl)bis(1H-benzo[d]imidazol-5,2-diyl))bis (pyrrolidin-2,1-diyl)bis-1-oxobutan-1,2-diyl))dicarbamate (7b) was prepared with reference to the preparation method of Compound 4a in Example 10.

Example 17: Methyl ((2S,3R)-1-((S)-2-((4-((2R,5R)-1-(4-(4,4-dimethylazasilinan-1-yl)-3,5-difluorophenyl-5-(4-(2-((S)-1-(N-methoxycarbonyl)-O-methyl-L-threonyl) pyrrolidin-2-yl)-1H-imidazol-5-yl)phenyl)pyrrolidin-2-yl)phenyl)carbamoyl) pyrrolidin-1-yl)-3-methoxy-1-oxobutan-2-yl) carbamate (8b)
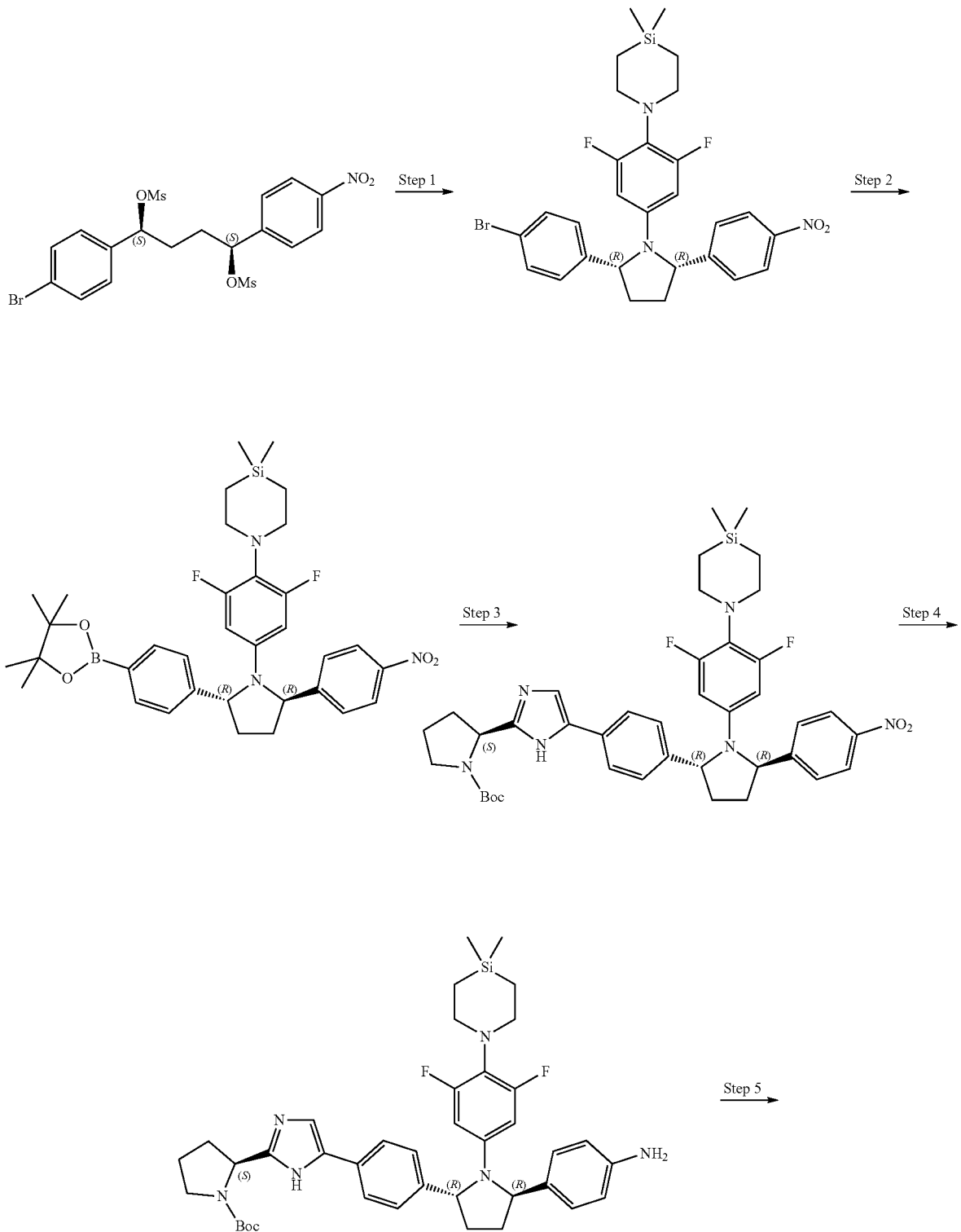

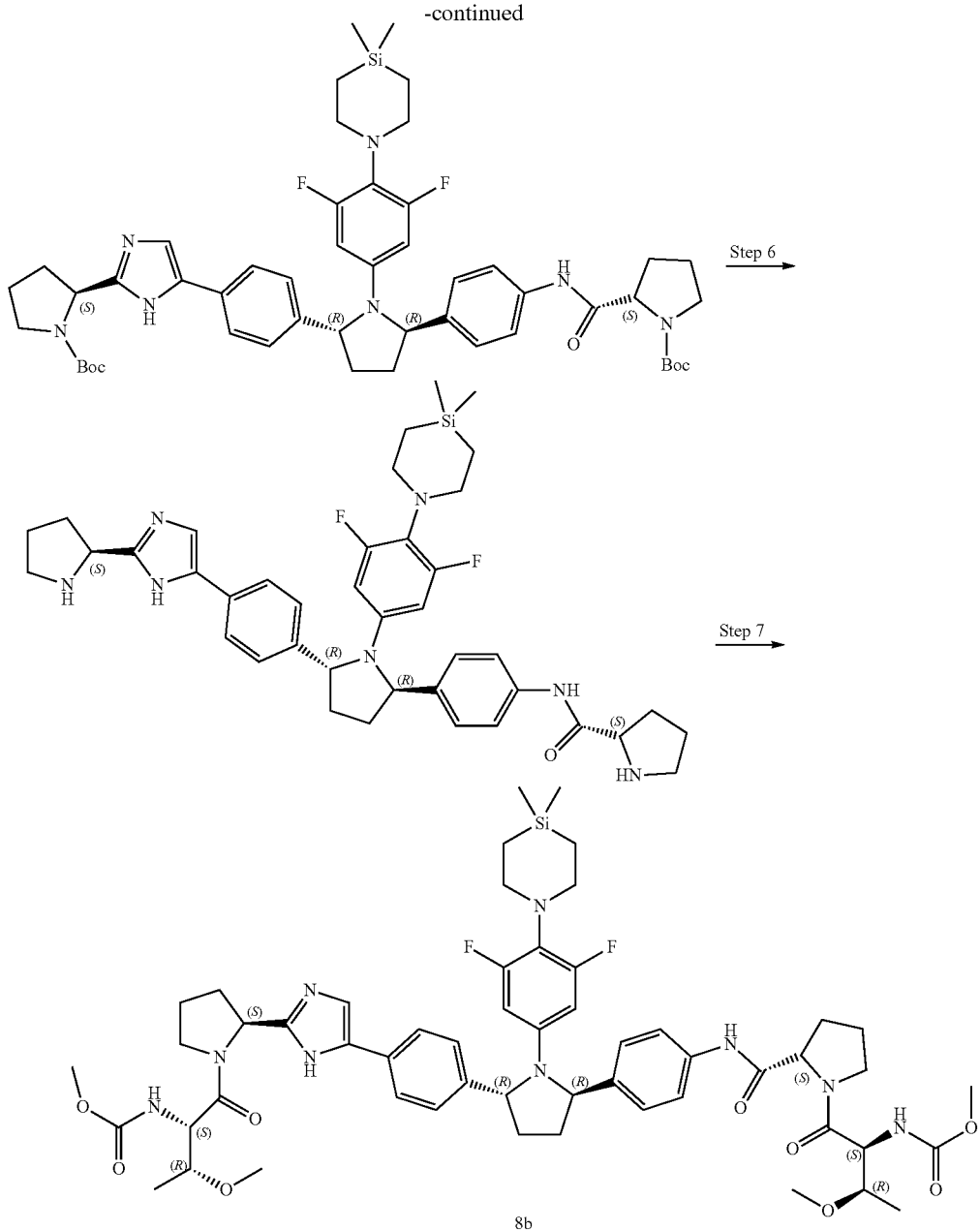

Step 1: 1-(4-((2R,5R)-2-(4-bromophenyl)-5-(4-nitrophenyl)pyrrolidin-1-yl)-2,6-difluorophenyl)-4,4-dimethylazasilinane In a 250 mL single-necked flask, a mixture of (1S,4S)-1-(4-bromophenyl)-4-(4-nitrophenyl)butan-1,4-diyldimesylate (12 g, 23.03 mmol), 4-(4,4-dimethyl-1,4-azasilinan-1-yl)-3,5-difluoroaniline (47.2 g, 184.2 mmol) and N,N-diisopropylethylamine (23.8 g, 184.2 mmol) in N,N-dimethylformamide (100 mL) was heated to 60° C. and stirred for 5 hours. After the completion of the reaction, the reaction mixture was poured into a 2N diluted hydrochloric acid solution (300 mL) and then extracted with ethyl acetate (300 mL). The organic phase was washed with a 6N diluted hydrochloric acid solution (100 mL), water (100 mL) and a saturated saline solution (100 mL), respectively, and then dried over anhydrous sodium sulfate, filtered and concentrated. The resulting crude product was purified by silica gel column chromatography (petroleum ether:ethyl acetate=25:1) to give 1-(4-((2R, 5R)-2-(4-bromophenyl)-5-(4-nitrophenyl)pyrrolidin-1-yl)-2,6-difluorophenyl)-4,4-Dimethylazasilinane (4.7 g).

MS(ESI)m/z: 586.0.

Step 2: 1-(2,6-Difluoro-4-((2R, 5R)-2-(4-nitrophenyl)-5-(4-(4,4,5,5-tetramethyl-1,3,2-dioxaborolan-2-yl)pyridin-2-yl)phenyl)pyrrolidin-1-yl)phenyl)-4,4-dimethylazasilinane 1-(4-((2R,5R)-2-(4-bromophenyl)-5-(4-nitrophenyl)pyrrolidin-1-yl)-2,6-difluoro phenyl)-4,4-dimethylazasilinane (3 g, 5.13 mmol), bis(pinacolato)diboron (1.56 g, 6.16 mmol), potassium acetate (1.51 g, 15.39 mmol) and [1-1'-(diphenylphosphino) ferrocene]palladium dichloride (0.19 g, 0.26 mmol) were added in sequence to a reaction flask, and then N,N-dimethylformamide (75 mL) was added thereto under nitrogen gas protection. The mixture was heated to 100° C. and stirred for 9 h. After the completion of the reaction, the reaction mixture was poured into ice water (200 mL) and then extracted with ethyl acetate (300 mL). The organic phase was washed with water (100 mL) and a saturated saline solution (100 mL), respectively, and then dried over anhydrous sodium sulfate, filtered and concentrated. The resulting crude product was purified by silica gel column chromatography (petroleum ether:ethyl acetate=12:1) to give 1-(2,6-difluoro-4-((2R, 5R)-2-(4-nitrophenyl)-5-(4-(4,4,5,5-tetramethyl-1,3,2-dioxaborolan-2-yl)pyridin-2-yl)phenyl)pyrrolidin-1-yl)phenyl)-4,4-dimethylazasilinane (1.54 g).

MS (ESI): m/z 634.2.

Step 3: Tert-butyl (S)-2-(5-(4-((2R,5R)-1-(4-(4,4-dimethyl-1,4-azasilinan-1-yl)-3,5-difluorophenyl))-5-(4-nitrophenyl)pyrrolidin-2-yl)phenyl)-1H-imidazol-2-yl) pyrrolidine-1-carboxylate 1-(2,6-Difluoro-4-((2R,5R)-2-(4-nitrophenyl)-5-(4-(4,4,5,5-tetramethyl-1,3,2-dioxaborolan-2-yl)pyri din-2-yl)phenyl)pyrrolidin-1-yl)phenyl)-4,4-dimethylazasilinane (1.3 g, 2.05 mmol), tert-butyl (S)-2-(5-bromo-1H-imidazol-2-yl) pyrrolidine-1-carboxylate (0.71 g, 2.26 mmol), potassium carbonate (0.85 g, 6.15 mmol) and tetrakis(triphenylphosphine)palladium (0.12 g, 0.103 mmol) were added in sequence into a reaction flask, and then dioxane (65 mL) and water (13 mL) were added to the flask under nitrogen gas protection. The mixture was heated to 90° C. and stirred for 4 h. After the completion of the reaction, the reaction mixture was poured into water (100 mL) and then extracted with ethyl acetate (200 mL). The organic phase was washed with water (100 mL) and a saturated saline solution (100 mL), respectively, and then dried over anhydrous sodium sulfate, filtered and concentrated. The resulting crude product was purified by silica gel column chromatography (petroleum ether:ethyl acetate=2:1) to give tert-butyl (S)-2-(5-(4-((2R,5R)-1-(4-(4,4-dimethyl-1,4-azasilinan-1-yl)-3,5-difluorophenyl))-5-(4-nitrophenyl)pyrrolidin-2-yl) phenyl)-1H-imidazol-2-yl)pyrrolidine-1-carboxylate (0.8 g).

MS (ESI): m/z 743.2.

Step 4: Tert-butyl (S)-2-(5-(4-((2R,5R)-5-(4-aminophenyl)-1-(4-(4,4-dimethyl-1,4-azasilinan-1-yl)pyridin-2-yl)-3,5-difluorophenyl)pyrrolidin-2-yl)phenyl)-1H-imidazol-2-yl)pyrrolidine-1-carboxylate Tert-butyl (S)-2-(5-(4-((2R,5R)-1-(4-(4,4-dimethyl-1,4-azasilinan-1-yl)-3,5-difluorophenyl))-5-(4-nitrophenyl)pyrrolidin-2-yl)phenyl)-1H-imidazol-2-yl) pyrrolidine-1-carboxylate (0.8 g, 1.08 mmol), tetrahydrofuran (20 mL) and platinum dioxide (0.08 g) were added in sequence to a reaction flask. The resulting mixture was subjected to a hydrogenation reduction reaction at room temperature and atmospheric pressure with stirring for 2 h. After the completion of the reaction, the reaction mixture was filtered by using Celite, and the filtrate was concentrated. The resulting crude product was purified by silica gel column chromatography (petroleum ether: ethyl acetate=2:1) to give tert-butyl (S)-2-(5-(4-((2R,5R)-5-(4-aminophenyl)-1-(4-(4,4-dimethyl-1,4-azasilinan-1-yl)pyridin-2-yl)-3,5-difluorophenyl) pyrrolidin-2-yl) phenyl)-1H-imidazol-2-yl)pyrrolidine-1-carboxylate (0.46 g).

$^1$H NMR (500M, DMSO-d$_6$): δ 11.78 (s, 1H), 7.65 (d, J=5 Hz, 2H), 7.37 (s, 1H), 7.15 (d, J=5 Hz, 2H), 6.86 (d, J=10 Hz, 2H), 6.52 (d, J=10 Hz, 2H), 5.82 (d, J=10 Hz, 2H), 5.12 (d, J=5 Hz, 1H), 5.02 (d, J=10 Hz, 1H), 4.94 (brs, 2H), 4.83-4.76 (m, 1H), 3.52-3.50 (m, 1H), 3.37-3.34 (m, 1H), 3.03 (t, J=5 Hz, 4H), 2.47-2.39 (m, 2H), 2.21-2.14 (m, 1H), 2.03-1.96 (m, 2H), 1.86-1.83 (m, 1H), 1.66-1.58 (m, 2H), 1.39 (s, 3H), 1.23 (s, 1H), 1.16 (s, 5H), 0.72-0.69 (m, 4H), 0.02 (s, 6H);

MS(ESI) m/z: 713.3.

Step 5: Tert-butyl (S)-2-((4-((2R,5R)-5-(4-(2-((S)-1-(tert-butoxycarbonyl)pyrrolidin-2-yl)-5-yl)phenyl)-1-(4-(4,4-dimethyl-1,4-azasilinan-1-yl)-3,5-difluorophenyl)pyrrolidin-2-yl)phenyl)carbamoyl)-1-carboxylate Tert-butyl (S)-2-(5-(4-((2R,5R)-5-(4-aminophenyl)-1-(4-(4,4-dimethyl-1,4-azasilinan-1-yl)pyridin-2-yl)-3,5-difluorophenyl)pyrrolidin-2-yl)phenyl)-1H-imidazol-2-yl) pyrrolidine-1-carboxylate (0.36 g, 0.51 mmol), (tert-butoxycarbonyl)-L-proline (0.13 g, 0.61 mmol), 2-(7-oxobenzotriazole)-N,N,N',N'-tetramethyluronium hexafluorophosphate (0.29 g, 0.765 mmol), N,N-diisopropylethylamine (0.13 g, 1.02 mmol) and N,N-dimethyl formamide (20 mL) were added in sequence to a reaction flask, and the resulting mixture was stirred at room temperature for 3 hours. After the completion of the reaction, the reaction mixture was poured into water (100 mL) and then extracted with ethyl acetate (200 mL). The organic phase was washed with water (100 mL) and a saturated saline solution (100 mL), respectively, and then dried over anhydrous sodium sulfate, filtered and concentrated. The resulting crude product was purified by silica gel column chromatography (petroleum ether:ethyl acetate=2:1) to give tert-butyl (S)-2-((4-((2R,5R)-5-(4-(2-((S)-1-(tert-butoxycarbonyl)pyrrolidin-2-yl)-5-yl)phenyl)-1-(4-(4,4-dimethyl-1,4-azasilinan-1-yl)-3,5-difluorophenyl)pyrrolidin-2-yl)phenyl)carbamoyl)-1-carboxylate (0.27 g).

$^1$H NMR (500M, DMSO-d$_6$): δ11.85 (s, 1H), 9.94 (d, J=5 Hz, 1H), 7.66 (d, J=10 Hz, 2H), 7.55 (d, J=5 Hz, 2H), 7.37 (s, 1H), 7.17 (d, J=5 Hz, 4H), 5.83 (d, J=15 Hz, 2H), 5.18 (s, 2H), 4.84-4.76 (m, 1H), 4.26-4.18 (m, 1H), 3.53 (s, 1H), 3.42-3.41 (m, 1H), 3.38-3.34 (m, 2H), 3.03 (t, J=5 Hz, 4H), 2.47-2.43 (m, 2H), 2.21-2.16 (m, 2H), 2.03-2.01 (m, 2H), 1.88-1.76 (m, 4H), 1.68-1.64 (m, 2H), 1.39 (s, 6H), 1.28 (s, 6H), 1.23 (s, 1H), 1.16 (s, 5H), 0.70 (t, J=5 Hz, 4H), 0.02 (s, 6H);

LC-MS(ESI): m/z 732.7.

Step 6: (S)—N-(4-((2R,5R)-1-(4-(4,4-dimethyl-1,4-azasilinan-1-yl)-3,5-difluorophenyl)-5-(2-((S)-pyrrolidin-2-yl)-1H-imidazol-5-yl)phenyl)pyrrolidin-2-yl) phenyl)pyrrolidine-2-formamide (S)-2-((4-((2R,5R)-5-(4-(2-((S)-1-(tert-butoxycarbonyl) pyrrolidin-2-yl)-5-yl)phenyl)-1-(4-(4,4-dimethyl-1,4-azasilinan-1-yl)-3,5-difluorophenyl)pyrrolidin-2-yl)phenyl) carbamoyl)-carboxylic acid (0.2 g, 0.22 mmol) was dissolved in tetrahydrofuran (5 mL), and then concentrated hydrochloric acid (2.5 mL) was added dropwise thereto. After the completion of the dropwise addition, the resulting mixture was stirred at room temperature for 2 hours. After the completion of the reaction, the solvent was distilled off under reduced pressure, and the pH of the resulting concentrated solution was adjusted to be alkaline with a saturated sodium carbonate solution. The resulting mixture was then extracted with a dichloromethane/methanol solution (200 mL, dichloromethane:methanol=10:1) and the organic phase was dried over anhydrous sodium sulfate, filtered and concentrated to give the title compound (0.15 g).

MS(ESI)m/z 710.3.

Step 7: Methyl ((2S,3R)-1-((S)-2-((4-((2R,5R)-1-(4-(4,4-dimethyl-1,4-azasilinan-1-yl)-3,5-difluorophenyl-5-(4-(2-((S)-1-(N-methoxycarbonyl)-O-methyl-L-threonyl)pyrrolidin-2-yl)-1H-imidazol-5-yl)phenyl)pyrrolidin-2-yl)phenyl)carbamoyl)pyrrolidin-1-yl)-3-methoxy-1-oxobutan-2-yl)carbamate (8b)

(S)—N-(4-((2R,5R)-1-(4-(4,4-dimethyl-1,4-azasilinan-1-yl)-3,5-difluorophenyl)-5-(2-((S)-pyrrolidin-2-yl)-1H-imidazol-5-yl)phenyl)pyrrolidin-2-yl)phenyl)pyrrolidine-2-formamide (0.13 g, 0.183 mmol), N-(methoxycarbonyl)-O-methyl-L-threonine (0.081 g, 0.421 mmol), 2-(7-oxobenzotriazole)-N,N,N',N'-tetramethyluronium hexafluorophosphate (0.16 g, 0.421 mmol), N,N-diisopropylethylamine (0.189 g, 1.464 mmol) and N,N-dimethylformamide (6 mL) were added in sequence to a reaction flask, and the mixture was stirred at room temperature for 3 hours. After the completion of the reaction, the reaction mixture was poured into water (150 mL) and then extracted with ethyl acetate (200 mL). The organic phase was washed with water (100 mL) and a saturated saline solution (100 mL), respectively, and then dried over anhydrous sodium sulfate, filtered and concentrated. The resulting crude product was purified by preparative liquid chromatography to give the title compound (0.06 g).

$^1$H NMR (500M, DMSO-$d_6$): δ 11.69 (s, 1H), 9.97 (s, 1H), 7.65 (d, J=5 Hz, 2H), 7.53 (d, J=10 Hz, 2H), 7.40 (s, 1H), 7.32 (d, J=5 Hz, 1H), 7.25-7.21 (m, 1H), 7.15-7.14 (m, 4H), 5.82 (d, J=10 Hz, 2H), 5.17 (s, 2H), 5.06 (s, 1H), 4.44 (s, 1H), 4.29-4.26 (m, 2H), 3.84-3.80 (m, 2H), 3.70-3.65 (m, 1H), 3.57 (s, 1H), 3.54 (s, 5H), 3.49-3.40 (m, 3H), 3.27 (s, 1H), 3.24 (s, 3H), 3.17 (s, 2H), 3.04-3.01 (m, 4H), 2.46 (s, 2H), 2.18-2.13 (m, 3H), 2.01-1.95 (m, 3H), 1.91-1.86 (m, 2H), 1.66-1.63 (m, 2H), 1.19-1.13 (m, 3H), 1.09-1.05 (m, 3H), 0.71-0.69 (m, 4H), 0.02 (s, 6H);

LC-MS(ESI)m/z 1056.4 [M+H]$^+$

Example 18: Methyl ((2S,3R)-1-((2S,4S)-2-((4-((2R,5R)-1-(4-(4,4-dimethyl-1,4-azasilinan-1-yl)-3,5-difluorophenyl)-5-(6-fluoro-2-((S)-1-(N-(methoxycarbonyl)-O-methyl-L-threonyl)pyrrolidin-2-yl)-1H-benzo[d]imidazol-5-yl)pyrrolidin-2-yl)phenyl)formamido)-4-(methoxymethyl)pyrrolidin-1-yl)-3-methoxy-1-oxobutan-2-yl) carbamate (17b)

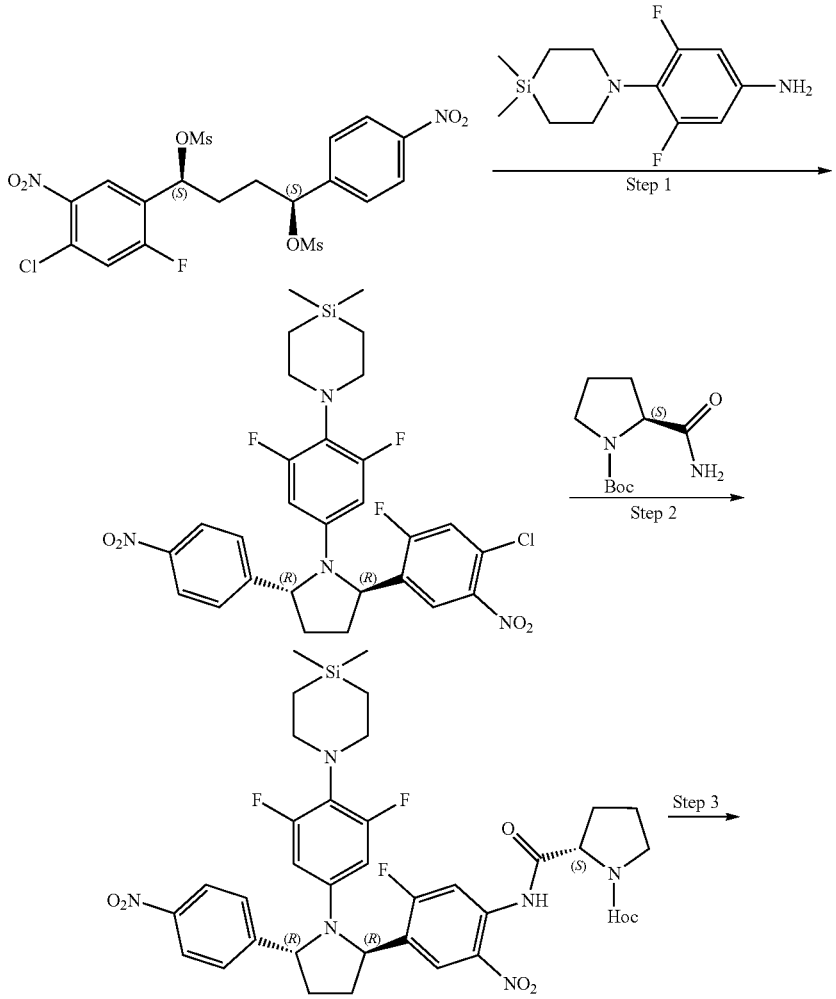

-continued
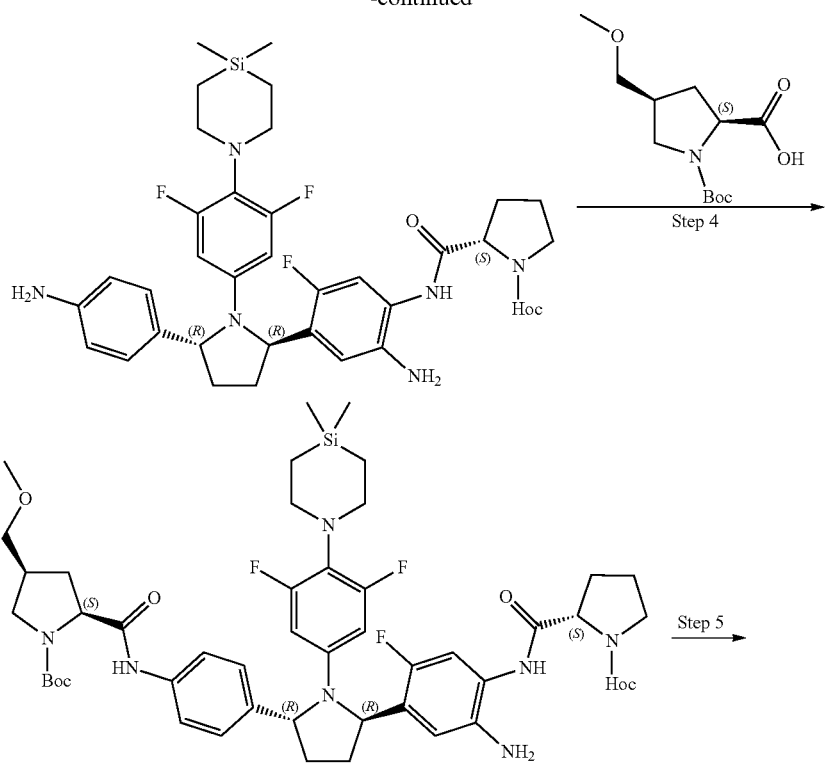
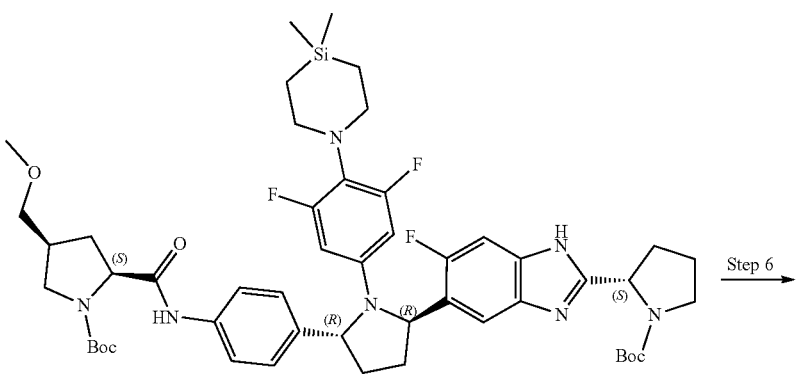
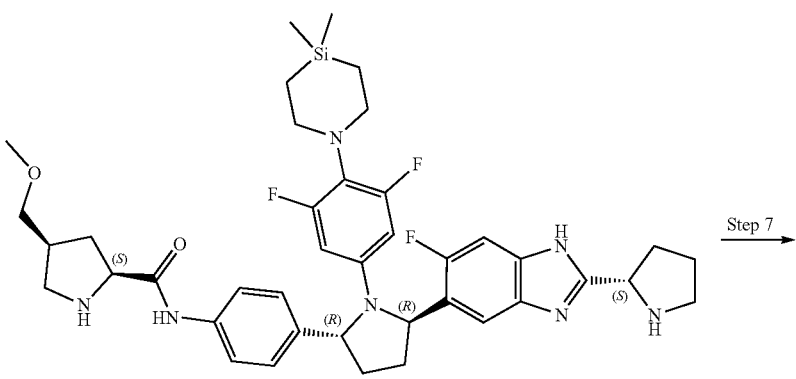

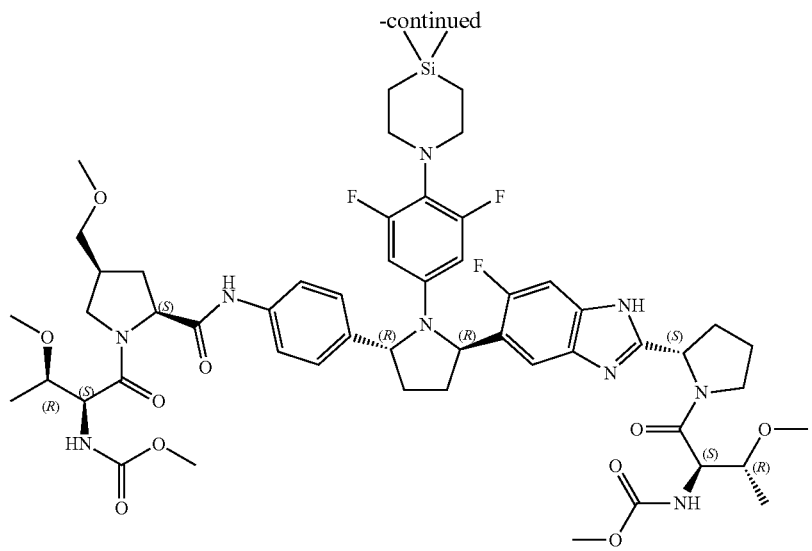

Step 1: 1-(4-((2R,5R)-2-(4-chloro-2-fluoro-5-nitrophenyl)-5-(4-nitrophenyl) pyrrolidin-1-yl)-2,6-difluorophenyl)-4,4-dimethyl-1,4-azasilinane (1S,4S)-1-(4-chloro-2-fluoro-5-nitrophenyl)-4-(4-nitrophenyl)butan-1,4-diyldimesylate (15 g, 27.7 mmol), 4-(4,4-dimethyl-1,4-azasilinan-1-yl)-3,5-difluoroaniline (14.3 g, 55.46 mmol), acetonitrile (60 mL) and N,N-diisopropylethylamine (18 g, 138.5 mmol) were added to a single-necked flask, and the resulting mixture was heated to 75° C. and reacted overnight. After the completion of the reaction, the reaction mixture was cooled to room temperature, and then poured into a 6N aqueous hydrochloric acid solution (200 mL) and extracted with ethyl acetate (200 mL×2). The organic phase was washed with water (200 mL) and a saturated saline solution (200 mL), respectively, and then dried over anhydrous sodium sulfate, filtered and concentrated. The resulting crude product was separated by silica gel column chromatography (petroleum ether:ethyl acetate=10:1) to give the title compound (1.5 g).

LC-MS(ESI)m/z 605.8 [M+H]$^+$.

Step 2: Tert-butyl (S)-2-((4-((2R, 5R)-1-(4-(4,4-dimethyl-1,4-azasilinan-1-yl)-3,5-difluorophenyl)-5-(4-nitrophenyl)pyrrolidin-2-yl)-5-fluoro-2-nitrophenyl)carbamoyl) pyrrolidine-1-formate 1-(4-((2R,5R)-2-(4-chloro-2-fluoro-5-nitrophenyl)-5-(4-nitrophenyl)pyrrolidin-1-yl)-2,6-difluorophenyl)-4,4-dimethyl-1,4-azasilinane (1 g, 1.66 mmol), tert-butyl (S)-2-carbamoylpyrrolidine-1-carboxylate (0.53 g, 2.48 mmol), tris(dibenzylideneacetone)dipalladium (0.23 g, 0.248 mmol), 4,5-bis(diphenylphosphino)-9,9-dimethylxanthene (0.287 g, 0.496 mmol), cesium carbonate (0.81 g, 2.48 mmol) and dioxane (12.5 ml) were added to a single-necked flask, and the resulting mixture reacted at 100° C. under nitrogen gas protection for 12 hours. The resulting mixture was filtered through Celite, and concentrated. The resulting crude product was purified by silica gel column chromatography (petroleum ether:ethyl acetate=5:1) to give the title compound (0.54 g).

LC-MS(ESI)m/z 783.8 [M+H]$^+$.

Step 3: Tert-butyl (S)-2-((2-amino-4-((2R,5R)-5-(4-aminophenyl)-1-(4-(4,4-dimethyl-1,4-azasilinan-1-yl)-3,5-difluorophenyl)pyrrolidin-2-yl)-5-fluorophenyl) carbamoyl)pyrrolidine-1-formate Tert-butyl (S)-2-((4-((2R,5R)-1-(4-(4,4-dimethyl-1,4-azasilinan-1-yl)-3,5-difluorophenyl)-5-(4-nitrophenyl)pyrrolidin-2-yl)-5-fluoro-2-nitrophenyl)carbamoyl)pyrrolidine-1-formate (0.54 g, 0.69 mmol), tetrahydrofuran (10 mL) and platinum dioxide (0.054 g) were added to a single-necked flask, and the resulting mixture reacted at room temperature overnight under a hydrogen atmosphere. The resulting mixture was filtered through Celite, and concentrated to give the title compound (0.5 g).

LC-MS(ESI)m/z 723.5 [M+H]$^+$

Step 4: Tert-butyl (2S,4S)-2-((4-((2R,5R)-5-(5-amino-4-((S)-1-(tert-butoxycarbonyl) pyrrolidine-2-formamido)-2-(4-(4,4-dimethyl-1,4-azasilinan-1-yl)-3,5-difluorophenyl) pyrrolidin-2-yl)phenyl) carbamoyl)-4-(methoxymethyl)pyrrolidine-1-formate Tert-butyl (S)-2-((2-amino-4-((2R,5R)-5-(4-aminophenyl)-1-(4-(4,4-dimethyl-1,4-azasilinan-1-yl)-3,5-difluorophenyl)pyrrolidin-2-yl)-5-fluorophenyl)carbamoyl)pyrrolidine-1-formate (0.22 g, 0.297 mmol), (2S,4S)-1-(tert-butoxycarbonyl)-4-(methoxymethyl) pyrrolidine-2-carboxylic acid (0.085 g, 0.327 mmol), 2-(7-oxobenzotriazole)-N,N,N',N'-tetramethyluronium hexafluorophosphate (0.17 g, 0.446 mmol), N,N-diisopropylethylamine (0.077 g, 0.594 mmol) and N,N-dimethylformamide (6 mL) were added to a single-necked flask, and the resulting mixture reacted at room temperature for 1 hour. Then the reaction mixture was poured into water (150 mL) and filtered to give the title compound (0.32 g).

LC-MS(ESI)m/z 986.8[M+Na]$^+$.

Step 5: Tert-butyl (2S,4S)-2-((4-((2R,5R)-5-(2-((S)-1-(tert-butoxycarbonyl) pyrrolidin-2-yl)-6-fluorobenzo[d]imidazol-5-yl)-1-(4-(4,4-dimethyl-1,4-azasilinan-1-yl)-3,5-difluorophenyl)pyrrolidin-2-yl) phenyl)carbamoyl)-4-(methoxymethyl)pyrrolidine-1-formate Tert-butyl (2S,4S)-2-((4-((2R,5R)-5-(5-amino-4-((S)-1-(tert-butoxycarbonyl) pyrrolidin-2-formamido)-2-(4-(4,4-dimethyl-1,4-azasilinan-1-yl)-3,5-difluorophenyl) pyrrolidin-2-yl)phenyl)carbamoyl)-4-(methoxymethyl) pyrrolidine-1-formate (0.31 g, 0.203 mmol) and acetic acid (2 ml), were added to a single-necked flask, and the resulting mixture was heated to 72° C. and reacted for 30 minutes. Then the pH of the reaction mixture was adjusted to be alkaline with a saturated sodium bicarbonate solution, and then extracted with ethyl acetate. The organic phase was washed with water and a saturated saline solution, respectively, and then dried over anhydrous sodium sulfate, filtered and concentrated to give the title compound (0.26 g).
LC-MS(ESI)m/z 946.9 [M+H]$^+$.

Step 6: (2S,4S)—N-(4-((2R,5R)-1-(4-(4,4-dimethyl-1,4-azasilinan-1-yl)-3,5-difluorophenyl)-5-(6-fluoro-2-((S)-pyrrolidin-2-yl)-1H-benzo[d]imidazol-5-yl) pyrrolidin-2-yl)phenyl)-4-(methoxymethyl) pyrrolidine-2-formamide Tert-butyl (2S,4S)-2-((4-((2R,5R)-5-(2-((S)-1-(tert-butoxycarbonyl) pyrrolidin-2-yl)-6-fluoro-benzo[d]imidazol-5-yl)-1-(4-(4,4-dimethyl-1,4-azasilinan-1-yl)-3,5-difluorophenyl)pyrrolidin-2-yl)phenyl)carbamoyl)-4-(methoxymethyl)pyrrolidine-1-formate (0.25 g, 0.26 mmol), concentrated hydrochloric acid (3 mL) and tetrahydrofuran (3 mL) were added to a single-necked flask, and the resulting mixture was stirred at room temperature for 1 hour. Then the pH of the reaction mixture was adjusted to be alkaline with a saturated sodium carbonate solution, extracted with a mixed solution of dichloromethane and methanol (dichloromethane:methanol=10:1), dried over anhydrous sodium sulfate, filtered and then concentrated to give the title compound (0.18 g).
LC-MS(ESI)m/z 746.6 [M+H]$^+$.

Step 7: (2S,4S)—N-(4-((2R,5R)-1-(4-(4,4-dimethyl-1,4-azasilinan-1-yl)-3,5-difluorophenyl)-5-(6-fluoro-2-((S)-pyrrolidin-2-yl)-1H-benzo[d]imidazol-5-yl)pyrrolidin-2-yl) phenyl)-4-(methoxymethyl)pyrrolidine-2-formamide (0.18 g, 0.24 mmol), N-(methoxycarbonyl)-O-methyl-L-threonine (0.11 g, 0.55 mmol), 2-(7-oxobenzotriazole)-N,N,N',N'-tetramethyluronium hexafluorophosphate (0.18 g, 0.48 mmol), N,N-diisopropylethylamine (0.25 g, 1.92 mmol) and N,N-dimethylformamide (6 ml) were added to a single-necked flask, and the resulting mixture was stirred at room temperature for 1 hour. Then the reaction mixture was poured into water (150 mL) and then extracted with ethyl acetate (200 mL). The organic phase was washed with water (100 mL) and a saturated saline solution (100 mL), respectively, and then dried over anhydrous sodium sulfate, filtered and concentrated. The resulting crude product was purified by preparative liquid chromatography to give the title compound (0.083 g).

$^1$H NMR (500M, DMSO-d$_6$) δ 12.23 (brs, 1H), 9.98 (s, 1H), 7.54-7.53 (m, 2H), 7.37-7.29 (m, 2H), 7.20-7.18 (m, 2H), 7.12 (s, 1H), 6.99 (s, 1H), 5.83-5.81 (m, 2H), 5.47-5.45 (m, 1H), 5.22 (s, 1H), 5.11 (s, 1H), 4.42-4.38 (m, 1H), 4.26-4.24 (m, 2H), 4.10-4.08 (m, 1H), 3.81 (s, 2H), 3.54 (s, 6H), 3.45-3.39 (m, 6H), 3.26-3.24 (m, 6H), 3.08-3.03 (m, 6H), 2.44-2.37 (m, 1H), 2.30 (s, 1H), 2.19 (s, 2H), 2.02-1.97 (m, 2H), 1.74 (s, 1H), 1.66-1.59 (m, 2H), 1.25-1.23 (m, 2H), 1.13 (s, 3H), 0.96 (s, 3H), 0.70 (s, 4H), 0.02 (s, 6H).
LC-MS (ESI) m/z 1092.9 [M+H]$^+$.

Example 19: Methyl ((2S,3R)-1-((2S,4S)-2-((4-((2R,5R)-1-(4-(4,4-dimethyl-1,4-azasilinan-1-yl)-3,5-difluorophenyl)-5-(2-((S)-1-(N-(methoxycarbonyl)-O-methyl-L-threonyl)pyrrolidin-2-yl)-1H-benzo[d]imidazol-5-yl)pyrrolidin-2-yl)phenyl) formamido)-4-(methoxymethyl)pyrrolidin-1-yl)-3-methoxy-1-oxobutan-2-yl)carbamate (18b)

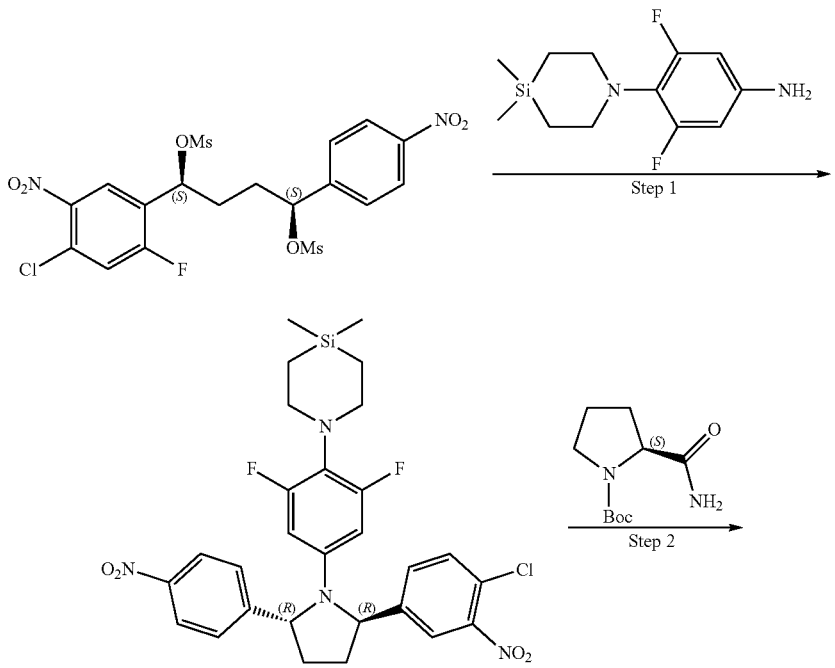

-continued
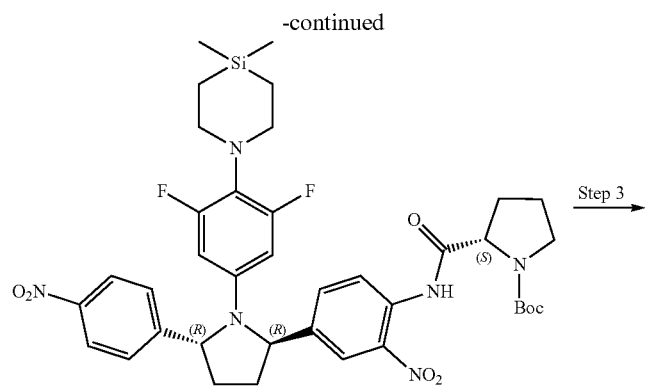
Step 3
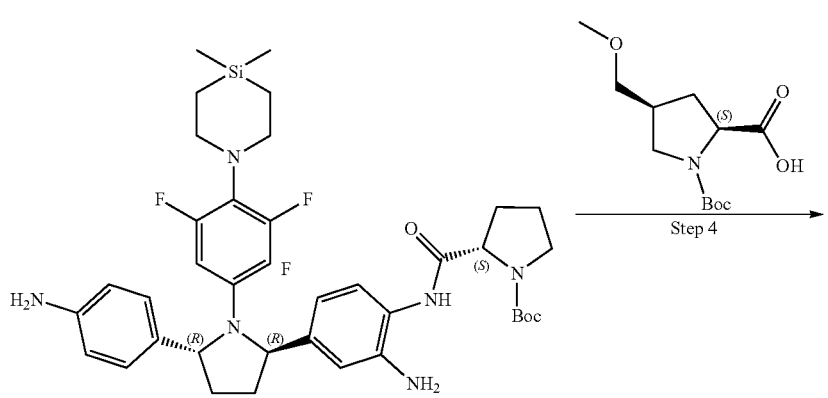
Step 4
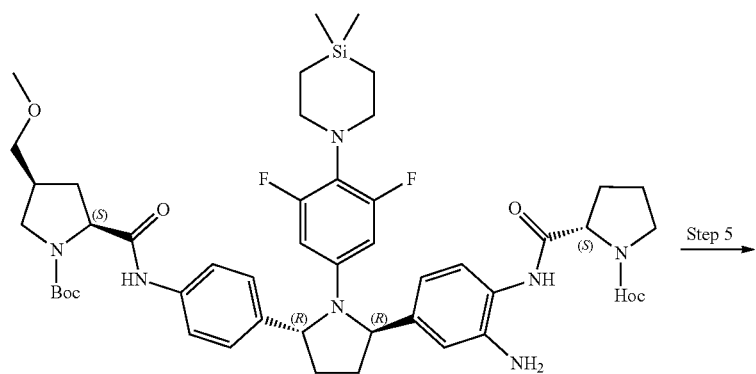
Step 5

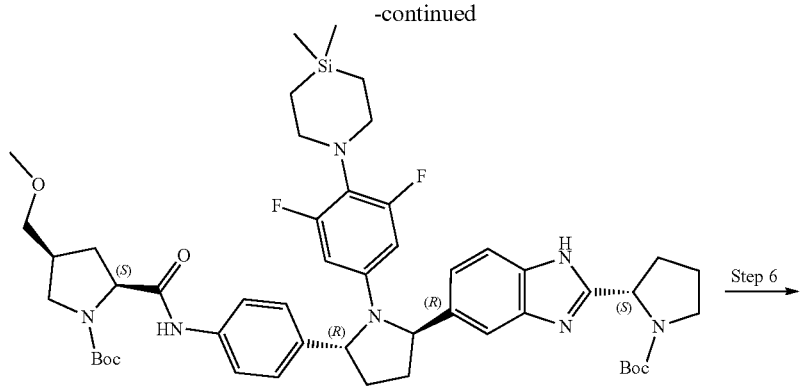

Step 6

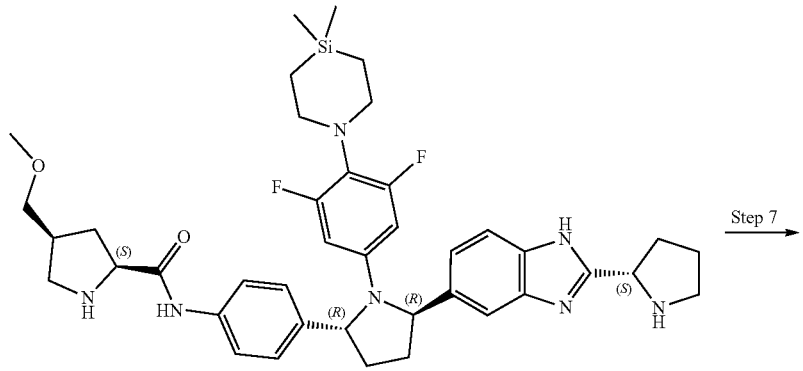

Step 7

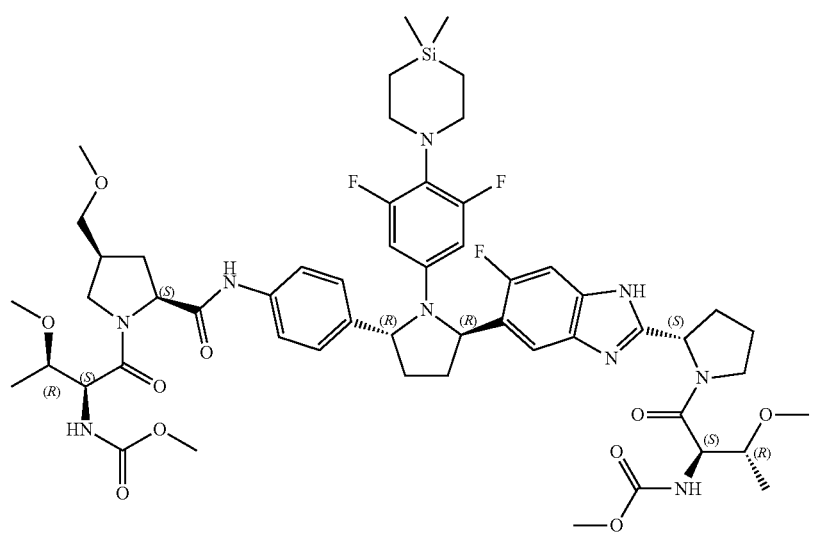

Steps 1-6: (2S, 4S)—N-(4-((2R,5R)-1-(4-(4,4-dimethyl-1,4-azasilinan-1-yl)-3,5-difluorophenyl)-5-(2-((S)-pyrrolidin-2-yl)-1H-benzo[d]imidazol-5-yl)pyrrolidin-2-yl) phenyl)4-(methoxymethyl)pyrrolidine-2-formamide The title compound was obtained with reference to Steps 1-6 in Example 18, except that the starting material (1S, 4S)-1-(4-chloro-2-fluoro-5-nitrophenyl)-4-(4-nitrophenyl)butan-1,4-diyldimesylate was replaced with (1S,4S)-1-(4-chloro-3-nitrophenyl)-4-(4-nitrophenyl)butan-1,4-diyldimesylate.

Step 7: (2S,4S)—N-(4-((2R,5R)-1-(4-(4,4-dimethyl-1,4-azasilinan-1-yl)-3,5-difluorophenyl)-5-(2-((S)-pyrrolidin-2-yl)-1H-benzo[d]imidazol-5-yl)pyrrolidin-2-yl) phenyl)-4-(methoxymethyl)pyrrolidine-2-formamide (0.30 g, 0.41 mmol), N-(methoxycarbonyl)-O-methyl-L-threonine (0.18 g, 0.95 mmol), 2-(7-oxobenzotriazole)-N,N,N',N'-tetramethyluronium hexafluorophosphate (0.31 g, 0.82 mmol), N,N-diisopropylethylamine (0.56 mL, 3.28 mmol), N,N-dimethylformamide (5 mL) were added to a reaction flask, and the mixture reacted at room temperature under stirring for 45 minutes. After the completion of the reaction, the reaction mixture was poured into water (50 mL), stirred for 5 minutes, and then extracted with ethyl acetate (30 mL). The organic phase was washed with water, dried and concentrated. The residue was purified to give Compound 18b (0.26 g).

$^1$H NMR (500 MHz, CDCl$_3$) δ=10.33-10.41 (brs, 1H), 8.81 (s, 1H), 7.44-7.46 (m, 3H), 7.28-7.32 (m, 1H), 7.05-7.10 (m, 3H), 5.70-5.78 (m, 4H), 5.46-5.50 (m, 1H), 5.14-5.17 (m, 1H), 5.03-5.04 (m, 1H), 4.78-4.81 (m, 1H), 4.70-4.72 (m, 1H), 4.61-4.63 (m, 1H), 4.02-4.06 (m, 1H), 3.76-3.77 (m, 3H), 3.70-3.71 (m, 6H), 3.42-3.51 (m, 2H), 3.6 (s, 6H), 3.26-3.27 (m, 3H), 3.12 (t, J=6.0 Hz, 4H), 2.48-2.61 (m, 3H), 2.09-2.37 (m, 5H), 1.71-1.79 (m, 5H), 1.15-1.23 (m, 6H), 0.76-0.79 (m, 4H), 0.05 (s, 6H).

LC-MS(ESI)m/z 1074.8[M+H]$^+$.

Assay Example 1: Determination of the Activity of the Specific Compounds Against Hepatitis C Virus GT1b/3a and GT1b/6a NS5A Chimeric Replicons and GT1b and GT1a Wild-Type Replicons 1. Experimental Materials Cells: Huh 7 cell line and HCV GT1b/3a and GT1b/6a NS5A chimeric replicons and GT1b and GT1a wild-type replicon RNA.

Compounds: 10 mM stock solutions were formulated by using 100% DMSO and stored in a nitrogen cabinet temporarily.

The main reagents are shown in Table 1:

TABLE 1

| Reagent List | |
| --- | --- |
| Reagent Name | Supplier |
| DMEM cell culture | Invitrogen |
| Fetal bovine serum (FBS) | Corning |
| Glutamine (L-Glu) | Invitrogen |
| Penicillin-streptomycin | Hyclone |
| Non-essential amino acid (NEAA) | Invitrogen |
| Dimethyl sulfoxide (DMSO) | Sigma |
| CellTiter-Fluor assay reagent | Promega |
| Britelite plus assay reagent | Perkin Elmer |

2. Assay Method

Treatment of Compound: According to the assay final concentrations of the compounds in Table 2, DMSO stock solutions of the compounds were diluted and then added to a 96-well assay plate. The final concentration of DMSO was 0.5%. The assay final concentrations of the compounds are shown in Table 2.

TABLE 2

| Replicon | Assay final concentration (nM) | | | | | | | | |
| --- | --- | --- | --- | --- | --- | --- | --- | --- | --- |
| GT1a | 0.1 | 0.025 | 0.0063 | 0.0016 | 0.00039 | 0.00010 | 0.000024 | 0.0000061 | 0.0000015 |
| GT1b | 0.1 | 0.025 | 0.0063 | 0.0016 | 0.00039 | 0.00010 | 0.000024 | 0.0000061 | 0.0000015 |
| GT1b/3a | 1 | 0.25 | 0.063 | 0.016 | 0.0039 | 0.00098 | 0.00024 | 0.000061 | 0.000015 |
| GT1b/6a | 100 | 25 | 6.25 | 1.563 | 0.391 | 0.098 | 0.024 | 0.0061 | 0.0015 |

The preparation of cells: After replicon plasmid DNA was linearized with a corresponding restriction enzyme, the DNA was transcribed into RNA by using T7RNA polymerase. Replicon RNA prepared by transcription in vitro was transfected into Huh-7 cells by electroporation. Transfected cells were seeded at a density of 10,000 cells per well into the 96-well assay plate containing the diluted compounds, and then the plate was placed in a 37° C. incubator with 5% CO$_2$ and cultured for 3 days.

Cell viability assay: A cell growth fluorescent titration detection reagent CellTiter-Fluor was added to the 96-well plate of the GT1b wild-type replicon. After the cells were cultured for 1 hour in a 37° C. incubator with 5% CO$_2$, the fluorescence signal value (RFU) was detected by Envision, and the original data (RFU) was used for the calculation of the cytotoxicity of the compounds.

Drug activity assay: Luminescence signal value (RLU) was detected with Envision within 15 minutes using the luciferase assay reagent Britelite plus, and the original data (RLU) was used for the calculation of the activity of the compounds.

Data Processing:

The cytotoxicity of the compounds was calculated by using the equation below:

Cell Viability %=(CPD−HPE)/(ZPE−HPE)×100%*

The activity of the compounds was calculated by using the equation below:

Inhibition %=(ZPE−CPD)/(ZPE−HPE)×100%*

* CPO: signal value of compound well;

HPE (Hundred percent effect): signal value of 100% effective action control well (only DMEM culture solution in the well);

ZPE (zero percent effect): signal value of noneffective action control well (the compound was replaced with 0.5% DMSO).

The cell viability percentages (Viability %) and the inhibition percentages (Inhibition %) were imported into GraphPad Prism software, respectively, and curves were fitted by using nonlinear regression method to obtain the corresponding curves of the compounds, and the cytotoxicity ($CC_{50}$) thereof and inhibitory activity ($EC_{50}$) values against the HCV replicon thereof.

3. The assay results are shown in Table 3.

TABLE 3

Activity $EC_{50}$ values and cytotoxicity $CC_{50}$ values of the compounds against HCV GT1b/3a and GT1b/6a NS5A chimeric replicons and GT1b and GT1a wild-type replicons

| Compounds | $CC_{50}$ value (nM) GT1 b wild-type replicon | $EC_{50}$ value (nM) | | | |
|---|---|---|---|---|---|
| | | GT1 b wild-type replicon | GT1a wild-type replicon | GT1b/3a NS5A chimeric replicon | GT1b/6a NS5A chimeric replicon |
| 1a | >0.1 | 0.00091 | 0.0077 | 0.003 | 0.017 |
| 2a | >0.1 | 0.0029 | 0.012 | 0.006 | 0.242 |
| 2b | >0.1 | 0.016 | 0.065 | 0.014 | 0.454 |
| 5b | >0.1 | 0.017 | 0.013 | 0.0063 | 0.016 |
| 4b | >0.1 | 0.0059 | 0.0041 | 0.0015 | 0.0050 |
| 6a | >0.1 | 0.0057 | 0.014 | 0.0052 | 0.230 |
| 1b | >0.1 | 0.0017 | 0.012 | 0.0048 | 0.114 |
| 6b | >0.1 | 0.0067 | 0.0062 | 0.0024 | 0.0054 |
| 5a | >0.1 | 0.019 | 0.017 | 0.013 | 0.174 |
| 4a | >0.1 | 0.011 | 0.0054 | 0.0039 | 0.026 |

Assay Example 2: Determination of the Activity of the Specific Compounds Against Hepatitis C Virus GT1a and GT1b Wild-Type Replicons and GT1b/3a, GT1b/4a, GT1b/5a and GT1b/6a NS5A Chimeric Replicons 1. Experimental Materials Cells: Huh-7 cells are liver cancer cell strains (from AppTec, USA), HCV GT1a and GT1b wild type (wt) replicons, GT1b/3a, GT1b/4a, GT1b/5a and GT1b/6a NS5A chimeric replicons.

Compounds: 10 mM stock solutions were formulated by using 100% DMSO and stored in a refrigerator at −40° C.

The main reagents are shown in Table 4:

TABLE 4

| Main Reagents | |
|---|---|
| Reagent Name | Supplier |
| DMEM culture | Invitrogen |
| Fetal bovine serum (FBS) | Corning |
| Penicillin-streptomycin | Hyclone |
| Non-essential amino acid (NEAA) | Invitrogen |
| Glutamine (L-Glu) | Invitrogen |
| Dimethyl sulfoxide (DMSO) | Sigma |
| CellTiter-Fluor assay reagent | Promega |
| Britelite plus assay reagent | Perkin Elmer |
| Renilla Luciferase assay reagent | Promega |
| alamarBlue assay reagent | Invitrogen |

2. Assay Method-Transient Transfection

Treatment of Compound: According to the assay final concentrations of the compounds in Table 5, DMSO stock solutions of the compounds were diluted and then added to a 96-well assay plate. The final concentration of DMSO was 0.5%. The assay final concentrations of the compounds are shown in Table 5.

TABLE 5

| Replicon | Compound | Assay Final Concentration (pM) | | | | | | | |
|---|---|---|---|---|---|---|---|---|---|
| GT1a-wt | 8b | 200 | 66.67 | 22.22 | 7.407 | 2.469 | 0.823 | 0.274 | 0.091 | 0.030 |
| | 8a | 200 | 66.67 | 22.22 | 7.407 | 2.469 | 0.823 | 0.274 | 0.091 | 0.030 |
| | 3a | 200 | 66.67 | 22.22 | 7.407 | 2.469 | 0.823 | 0.274 | 0.091 | 0.030 |
| | 7b | 200 | 66.67 | 22.22 | 7.407 | 2.469 | 0.823 | 0.274 | 0.091 | 0.030 |
| | 15b | 200 | 66.67 | 22.22 | 7.407 | 2.469 | 0.823 | 0.274 | 0.091 | 0.030 |
| | 11a | 200 | 66.67 | 22.22 | 7.407 | 2.469 | 0.823 | 0.274 | 0.091 | 0.030 |
| GT1b-wt | 8b | 200 | 66.67 | 22.22 | 7.407 | 2.469 | 0.823 | 0.274 | 0.091 | 0.030 |
| | 8a | 200 | 66.67 | 22.22 | 7.407 | 2.469 | 0.823 | 0.274 | 0.091 | 0.030 |
| | 3a | 200 | 66.67 | 22.22 | 7.407 | 2.469 | 0.823 | 0.274 | 0.091 | 0.030 |
| | 7b | 200 | 66.67 | 22.22 | 7.407 | 2.469 | 0.823 | 0.274 | 0.091 | 0.030 |
| | 15b | 200 | 66.67 | 22.22 | 7.407 | 2.469 | 0.823 | 0.274 | 0.091 | 0.030 |
| | 11a | 200 | 66.67 | 22.22 | 7.407 | 2.469 | 0.823 | 0.274 | 0.091 | 0.030 |
| GT1b/3a-NS5A-wt | 8b | 2000 | 666.67 | 222.22 | 74.074 | 24.691 | 8.230 | 2.743 | 0.914 | 0.305 |
| | 8a | 2000 | 666.67 | 222.22 | 74.074 | 24.691 | 8.230 | 2.743 | 0.914 | 0.305 |
| | 3a | 200 | 66.67 | 22.22 | 7.407 | 2.469 | 0.823 | 0.274 | 0.091 | 0.030 |
| | 7b | 200 | 66.67 | 22.22 | 7.407 | 2.469 | 0.823 | 0.274 | 0.091 | 0.030 |
| | 15b | 200 | 66.67 | 22.22 | 7.407 | 2.469 | 0.823 | 0.274 | 0.091 | 0.030 |
| | 11a | 200 | 66.67 | 22.22 | 7.407 | 2.469 | 0.823 | 0.274 | 0.091 | 0.030 |
| GT1b/6a-NS5A-wt | 8b | 200 | 66.67 | 22.22 | 7.407 | 2.469 | 0.823 | 0.274 | 0.091 | 0.030 |
| | 8a | 200 | 66.67 | 22.22 | 7.407 | 2.469 | 0.823 | 0.274 | 0.091 | 0.030 |
| | 3a | 2000 | 666.67 | 222.22 | 74.074 | 24.691 | 8.230 | 2.743 | 0.914 | 0.305 |
| | 7b | 200 | 66.67 | 22.22 | 7.407 | 2.469 | 0.823 | 0.274 | 0.091 | 0.030 |
| | 15b | 200 | 66.67 | 22.22 | 7.407 | 2.469 | 0.823 | 0.274 | 0.091 | 0.030 |
| | 11a | 200 | 66.67 | 22.22 | 7.407 | 2.469 | 0.823 | 0.274 | 0.091 | 0.030 |
| GT1a-wt | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |
| GT1b-wt | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |

TABLE 5-continued

| Replicon | Compound | Assay Final Concentration (pM) | | | | | | | | |
|---|---|---|---|---|---|---|---|---|---|---|
| GT1b/3a-NS5A-wt | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |
| GT1b/4a-NS5A-wt | 6b | 200 | 66.67 | 22.22 | 7.407 | 2.469 | 0.823 | 0.274 | 0.091 | 0.030 |
| | 1a | 200 | 66.67 | 22.22 | 7.407 | 2.469 | 0.823 | 0.274 | 0.091 | 0.030 |
| | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |
| GT1b/5a-NS5A-wt | 6b | 200 | 66.67 | 22.22 | 7.407 | 2.469 | 0.823 | 0.274 | 0.091 | 0.030 |
| | 1a | 200 | 66.67 | 22.22 | 7.407 | 2.469 | 0.823 | 0.274 | 0.091 | 0.030 |
| | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |
| GT1b/6a-NS5A-wt | 18b | 200 | 66.67 | 22.22 | 7.407 | 2.469 | 0.823 | 0.274 | 0.091 | 0.030 |
| | 9b | 200 | 66.67 | 22.22 | 7.407 | 2.469 | 0.823 | 0.274 | 0.091 | 0.030 |
| | 14b | 200 | 66.67 | 22.22 | 7.407 | 2.469 | 0.823 | 0.274 | 0.091 | 0.030 |
| | 17b | 200 | 66.67 | 22.22 | 7.407 | 2.469 | 0.823 | 0.274 | 0.091 | 0.030 |

The preparation of cells: After replicon plasmid DNA was linearized with a corresponding restriction enzyme, the DNA was transcribed into RNA by using T7 RNA polymerase. Replicon RNA prepared by transcription in vitro was transfected into Huh-7 cells by electroporation. Transfected cells were seeded at a density of 10,000 cells per well into the 96-well assay plate containing the diluted compounds, and then placed in a 37° C. incubator with 5% $CO_2$ and cultured for 3 days.

Cell viability assay: A cell growth fluorescent titration detection reagent CellTiter-Fluor was added to the 96-well plate of the GT1b wild-type replicon. After the cells were cultured for 1 hour in a 37° C. incubator with 5% $CO_2$, the fluorescence signal value (RFU) was detected by Envision, and the original data (RFU) was used for the calculation of the cytotoxicity of the compounds.

Drug activity assay: Luminescence signal value (RLU) was detected with Envision within 15 minutes using the luciferase assay reagent Britelite plus, and the original data (RLU) was used for the calculation of the activity of the compounds.

Data Processing:

The cytotoxicity of the compounds was calculated by using the equation below:

Cell Viability %=(CPD−HPE)/(ZPE−HPE)×100%*

The activity of the compounds was calculated by using the equation below:

Inhibition %=(ZPE−CPD)/(ZPE−HPE)×100%*

* CPO: signal value of compound well;

HPE (Hundred percent effect): signal average value of 100% effective action control well (only DMEM culture solution in the well);

ZPE (zero percent effect): signal value of noneffective action control well (the compound was replaced with 0.5% DMSO).

The cell viability percentages (Viability %) and the inhibition percentages (Inhibition %) were imported into GraphPad Prism software, respectively, and curves were fitted by using nonlinear regression method to obtain the corresponding curves of the compounds, and the cytotoxicity ($CC_{50}$) thereof and the inhibitory activity ($EC_{50}$) values against the HCV replicon thereof.

Assay Example 3: Determination of the Activity of the Specific Compounds Against Infective Hepatitis C Virus HCVcc (GT2a, JFH-1)

1. Experimental Materials

Cells: Huh7.5.1 cells and hepatitis C virus HCVcc (GT2a, JFH-1) infection system.

Compounds: 10 mM stock solutions were formulated by using 100% DMSO and stored in a nitrogen cabinet temporarily.

The main reagents are shown in above Table 4.

2. Assay Method

Treatment of Compound: According to the assay final concentrations of the compounds in Table 6, DMSO stock solutions of the compounds were diluted and then added to a 96-well assay plate. The final concentration of DMSO was 0.5%. The assay final concentrations of the compounds are shown in Table 6.

TABLE 6

Assay final concentrations of the compounds

| Replicon | Compound | Assay final concentration (pM) | | | | | | | |
|---|---|---|---|---|---|---|---|---|---|
| HCVcc (GT2a, JFH-1) | 6b | 100.0 | 33.33 | 11.11 | 3.704 | 1.235 | 0.412 | 0.137 | 0.046 |
| | 1a | 100.0 | 33.33 | 11.11 | 3.704 | 1.235 | 0.412 | 0.137 | 0.046 |
| | 18b | 100.0 | 33.33 | 11.11 | 3.704 | 1.235 | 0.412 | 0.137 | 0.046 |
| | 9b | 100.0 | 33.33 | 11.11 | 3.704 | 1.235 | 0.412 | 0.137 | 0.046 |
| | 14b | 100.0 | 33.33 | 11.11 | 3.704 | 1.235 | 0.412 | 0.137 | 0.046 |
| | 17b | 100.0 | 33.33 | 11.11 | 3.704 | 1.235 | 0.412 | 0.137 | 0.046 |

Viral infection: Huh7.5.1 cells were seeded in a 96-well cell culture plate, and the cells were cultured overnight at 37° C. in an incubator with 5% $CO_2$ for later use. The compound and the HCVcc virus solution (MOI=0.1) were simultaneously added to the cells, and the virus infection was cultured for 3 days. Parallel cytotoxicity assay was identical to the method for the inhibition of the virus but without viral infection.

Drug activity assay: The activity of hRLuc was detected by the addition of *Renilla* luciferase assay reagent. The original data (RLU) was used for the calculation of the activity of the compounds.

Cell viability assay: Cell viability was detected by the addition of alamarBlue assay reagent. The original data (RFU) was used for the calculation of the cytotoxicity of the compounds.

Data Processing:

The cytotoxicity of the compounds was calculated by using the equation below:

Cell Viability %=CPD/CC×100%*

The activity of the compounds was calculated by using the equation below:

Inhibition %=(CPD−VC)/(CC−VC)×100%*

* CPD: signal value of compound well.

VC: Virus Control. The average signal of the DMSO control wells containing cells and viruses.

CC: Cell Control. Cell control wells containing cells only and no viruses.

The cell viability percentages (Cell Viability %) and the compound activity percentages (Inhibition %) were imported into GraphPad Prism software, respectively, and curves were fitted by using nonlinear regression method to obtain the corresponding curves of the compounds, and the cytotoxicity ($CC_{50}$) thereof and inhibitory activity ($EC_{50}$) values against the HCV replicon thereof.

3. The assay results of Assay Examples 2 and 3 are shown in Table 7.

Assay Example 4: Evaluation of the Distribution of the Specific Compounds in Rat Liver Tissue Eighteen male rats were randomly divided into two groups of 9 rats each, fasted (free access to water) overnight, and then intragastrically administered with 10 mg/kg of Compound 1a and Compound 6b, respectively. The subject animals were sacrificed by bloodletting at 0.5 h, 3 h and 8 h after administration. About 1 mL of blood was taken, and anticoagulated with EDTA-K2. The blood samples were immediately placed in ice, and then transferred within 30 min to centrifuge and separate plasma at 4° C. and 4,000 rpm for 10 min. Meanwhile, the whole liver was taken out at the various time points, rinsed with ice-cold physiological saline, blotted dry, weighed, and prepared into a homogenate with physiological saline (W/V=1:5). All plasma and liver homogenates were collected and then immediately stored at −20° C. for testing.

The rats can be fed at 4 h after administration.

After being completely melted, all the samples were vortexed to mix evenly. 50 μL of the samples were pipetted into a 1.5 mL centrifuge tube respectively and then 300 μL of IS-D (20 ng/ml diazepam acetonitrile) solution was added to each sample (200 μL of acetonitrile was added to the blank sample). The samples were vortexed for 10 min and then centrifuged at 12,000 rpm and 4° C. for 10 min. After 80 μL of pure water was added to a 96-well plate, 80 μL of the supernatants were pipetted respectively from the centrifuge tubes to the 96-well plate, vortexed for 3 min, and then kept at 4° C. until LC-MS/MS injection analysis. The drug concentrations in plasma and liver are shown in Table 8.

TABLE 7

| Compound | $EC_{50}$ Value (pM) | | | | | | | | $CC_{50}$ Value (pM) | |
| --- | --- | --- | --- | --- | --- | --- | --- | --- | --- | --- |
| | GT1a-wt | GT2a HCVcc | GT1b/3a-NS5A-wt | GT1b/4a-NS5A-wt | GT1b/5a-NS5A-wt | GT1b/6a-NS5A-wt | GT1b-wt | GT1b-wt | HCVcc | |
| 8b | 0.434 | ND | 67.94 | ND | ND | 6.734 | 1.593 | >200 | ND | |
| 8a | 0.913 | ND | 79.73 | ND | ND | 9.048 | 2.079 | >200 | ND | |
| 3a | 0.543 | ND | 6.348 | ND | ND | 4.5 | 1.332 | >200 | ND | |
| 7b | 1.438 | ND | 10.31 | ND | ND | 0.280 | 3.304 | >200 | ND | |
| 15b | 0.757 | ND | 7.284 | ND | ND | 0.488 | 2.954 | >200 | ND | |
| 11a | 0.824 | ND | 8.796 | ND | ND | 1.688 | 1.345 | >200 | ND | |
| 6b | ND | 1.369 | ND | 0.985 | 4.324 | ND | ND | ND | >100 | |
| 1a | ND | 0.381 | ND | 0.331 | 1.62 | ND | ND | ND | >100 | |
| 18b | 0.893 | 1.148 | 7.137 | 0.999 | 4.495 | 1.752 | 2.591 | >200 | >100 | |
| 9b | 1.014 | 0.912 | 3.799 | 2.488 | 6.085 | 1.129 | 5.284 | >200 | >100 | |
| 14b | 1.067 | 0.998 | 6.111 | 1.594 | 5.365 | 1.117 | 2.916 | >200 | >100 | |
| 17b | 0.965 | 2.68 | 5.705 | 1.661 | 4.663 | 1.095 | 3.058 | >200 | >100 | |

ND: not detected

TABLE 8

The concentration data of the compounds in rat plasma and liver

| Time (h) | Compound 1a | | | Compound 6b | | |
|---|---|---|---|---|---|---|
| | Plasma | Liver | Ratio (L/P) | Plasma | Liver | Ratio (L/P) |
| 0.5 | 54.7 ± 7.82 | 384 ± 121 | 7.01 | 19.8 ± 8.31 | 212 ± 57.2 | 10.7 |
| 3 | 70.1 ± 20.6 | 1711 ± 485 | 24.4 | 34.8 ± 14.7 | 495 ± 171 | 14.2 |
| 8 | 59 ± 33.7 | 1087 ± 822 | 18.4 | 5.82 ± 0.99 | 77.5 ± 20.6 | 13.3 |

Assay Example 5: Evaluation of the Distribution of the Specific Compounds in Mouse Liver Tissue Eighteen male mice were randomly divided into two groups, fasted (free access to water) overnight, and then intragastrically administered with 10 mg/kg of Compound 1a and Compound 6b, respectively. The subject animals were sacrificed by bloodletting at 0.5 h, 3 h and 8 h after administration. About 1 mL of blood was taken, and anti-coagulated with EDTA-K2. The blood samples were immediately placed in ice, and then transferred within 30 min to centrifuge and separate plasma at 4° C. and 4,000 rpm for 10 min. Meanwhile, the whole liver was taken out at the various time points, rinsed with ice-cold physiological saline, blotted dry, weighed, and prepared into a homogenate with physiological saline (W/V=1:5). All plasma and liver homogenates were collected and then immediately stored at −20° C. for testing.

The mice can be fed at 4 h after administration.

After being completely melted, all the samples were vortexed to mix evenly. 50 μL of the samples were pipetted into a 1.5 mL centrifuge tube respectively and then 200 μL of IS-D (20 ng/ml diazepam acetonitrile) solution was added to each sample (200 μL of acetonitrile was added to the blank sample). The samples were vortexed for 10 min and then centrifuged at 12,000 rpm and 4° C. for 10 min. After 80 μL of pure water was added to a 96-well plate, 80 μL of the supernatants were pipetted respectively from the centrifuge tubes to the 96-well plate, vortexed for 3 min, and then kept at 4° C. until LC-MS/MS injection analysis. The drug concentrations in plasma and liver are shown in Table 9.

Assay Example 6: Evaluation of the Drug Resistance of the Specific Compounds—Determination of the In Vitro Activity of the Specific Compounds Against HCV GT1a Wild-Type Replicon and GT1a-NS5A-Y93H and GT1a-NS5A-L31V Mutant Replicons 1. Experimental Materials Cells: Huh-7 cells are liver cancer cell strains (from AppTec, USA), HCVGT1a wild-type replicon and GT1a-NS5A-Y93H and GT1a-NS5A-L31V mutant replicons Compounds: 10 mM stock solutions were formulated by using 100% DMSO and stored in a nitrogen cabinet.

The main reagents are shown in Table 10.

TABLE 10

| Main Reagents | |
|---|---|
| Reagent Name | Supplier |
| DMEM culture | Invitrogen |
| Fetal bovine serum (FBS) | Corning |
| Penicillin-streptomycin | Hyclone |
| Non-essential amino acid (NEAA) | Invitrogen |
| Glutamine (L-Glu) | Invitrogen |
| Dimethyl sulfoxide (DMSO) | Sigma |
| Bright-Glo assay reagent | Promega |

2. Assay Method-Transient Transfection

Treatment of Compound: According to the assay final concentrations of the compounds in Table 11, DMSO stock solutions of the compounds were diluted and then added to a 96-well assay plate. The final concentration of DMSO was 0.5%. The assay final concentrations of the compounds are shown in Table 11.

TABLE 9

The concentration data of the compounds in mouse plasma and liver

| Time (h) | Compound 1a | | | Compound 6b | | |
|---|---|---|---|---|---|---|
| | Plasma | Liver | Ratio (L/P) | Plasma | Liver | Ratio (L/P) |
| 0.5 | 139 ± 16.9 | 337 ± 33.1 | 2.43 | 226 ± 66 | 401 ± 116 | 1.78 |
| 3 | 384 ± 81 | 2644 ± 147.3 | 6.89 | 464 ± 363.3 | 960 ± 530 | 2.07 |
| 8 | 59 ± 7.8 | 334 ± 73.9 | 5.67 | 10 ± 5.8 | 18 ± 1 | 1.76 |

TABLE 11

Assay final concentrations of the compounds

| Replicon | Assay final concentration (nM) | | | | | | | | |
|---|---|---|---|---|---|---|---|---|---|
| GT1a-wt | 0.100 | 0.033 | 0.011 | 0.0037 | 0.0012 | 0.00041 | 0.00014 | 0.000046 | 0.000015 |
| GT1a-NS5A-L31V | 0.300 | 0.100 | 0.033 | 0.011 | 0.0037 | 0.0012 | 0.00041 | 0.00014 | 0.000046 |
| GT1a-NS5A-Y93H | 1.000 | 0.333 | 0.111 | 0.037 | 0.012 | 0.0041 | 0.0014 | 0.00046 | 0.00015 |

The preparation of cells: After replicon plasmid DNA was linearized with a corresponding restriction enzyme, the DNA was transcribed into RNA by using T7 RNA polymerase. Replicon RNA prepared by transcription in vitro was transfected into Huh-7 cells by electroporation. Transfected cells were seeded at a density of 10,000 cells per well into the 96-well assay plate containing the diluted compounds, and then placed in a 37° C. incubator with 5% $CO_2$ and cultured for 3 days.

Compound activity assay: Luminescence signal value (RLU) was detected with Envision within 5 minutes by using the luciferase assay reagent Britelite plus, and the original data (RLU) was used for the calculation of the activity of the compounds.

Data Processing:

The activity of the compounds was calculated by using the equation below:

Inhibition %=(CPD-ZPE)/(HPE-ZPE)×100%*

* CPD: signal value of compound well;

HPE (Hundred percent effect): signal average value of 100% effective action control well (only DMEM culture solution in the well);

ZPE (zero percent effect): signal average value of noneffective action control well (the compound was replaced with 0.5% DMSO).

The compound activity percentages (Inhibition %) were imported into GraphPad Prism software, and curves were fitted by using nonlinear regression method to obtain the corresponding curves of the compounds and the inhibitory activity ($EC_{50}$) values against the HCV replicon thereof.

3. The Assay Results are Shown in Table 12.

TABLE 12

| | GT1a-wt | GT1a-NS5A-L31V | | GT1a-NS5A-Y93H | |
|---|---|---|---|---|---|
| Compound | $EC_{50}$ value(nM) | $EC_{50}$ value (nM) | Fold change | $EC_{50}$ value (nM) | Fold change |
| 6b | 0.0022 | 0.022 | 10.0 | NT | NT |
| 1a | 0.00066 | 0.027 | 40.9 | NT | NT |
| 9b | 0.002 | 0.0017 | 0.9 | 0.04 | 20.0 |
| 14b | 0.0029 | 0.032 | 11.0 | NT | NT |
| 7b | 0.0018 | 0.0061 | 3.4 | 0.903 | 502 |

ND: not detected.

What is claimed is:

1. A compound of Formula I, a pharmaceutically acceptable salt, a tautomer, a stereoisomer or a deuteride thereof, or a mixture thereof:

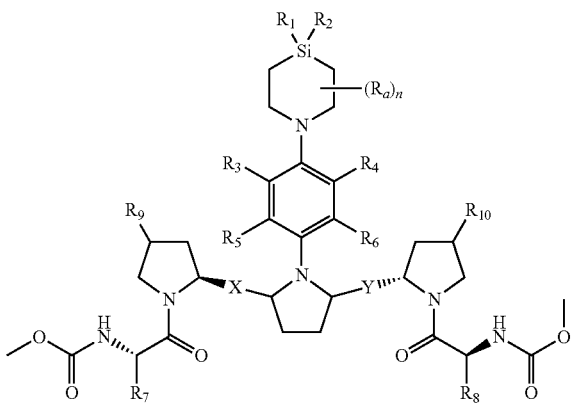

Formula I wherein:

$R_1$ and $R_2$ are each independently selected from the group consisting of hydroxyl, alkyl, alkoxy and aryl, or $R_1$ and $R_2$ are joined to form a silicon-containing saturated aliphatic ring containing 1, 2 or 3 silicon atoms;

$R_3$, $R_4$, $R_5$ and $R_6$ are each independently selected from the group consisting of hydrogen and halogen;

X is selected from the group consisting of the following groups:

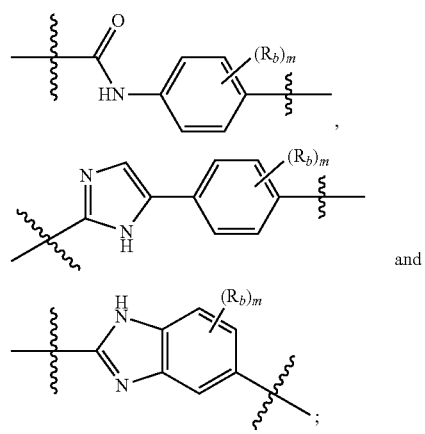

and

Y is selected from the group consisting of the following groups:

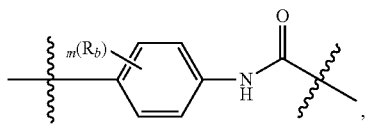

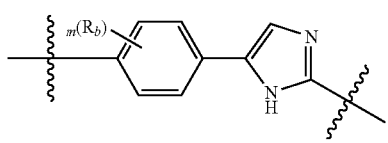 and

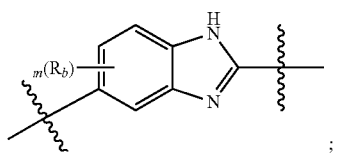 ;

R₇ and R₈ are each independently selected from the group consisting of —CH(alkyl)(alkoxy), —CH(alkyl)₂, —CH(alkoxy)₂, —C(alkyl)₂(alkoxy), —C(alkyl)(alkoxy)₂, —C(alkyl)₃ and —C(alkoxy)₃;

R₉ and R₁₀ are each independently selected from the group consisting of hydrogen, halogen, alkyl, alkoxy, and alkoxyalkyl;

each of Rₐ and R_b is independently selected from the group consisting of hydrogen, halogen, and alkyl;

each m is independently selected from the group consisting of 0, 1, 2, 3, and 4; and n is selected from the group consisting of 0, 1, 2, 3, 4, 5, 6, 7, and 8.

2. The compound according to claim 1, which is a compound of Formula Ia, a compound of Formula Ib, a compound of Formula Ic or a compound of Formula Id:

Formula Ia

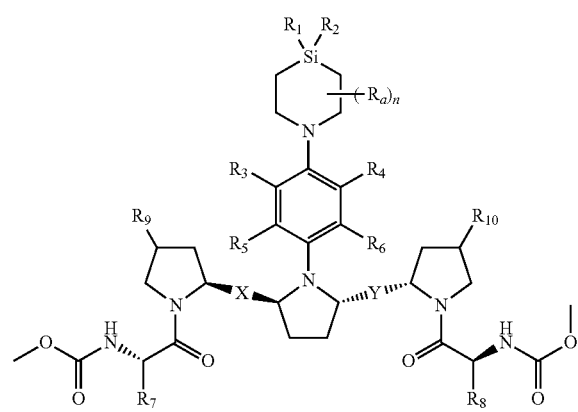

Formula Ib

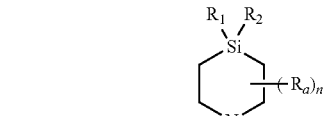

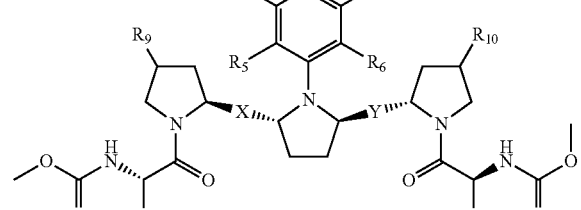

Formula Ic

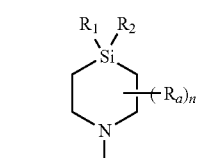

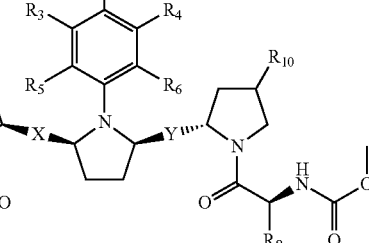

Formula Id

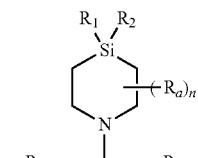

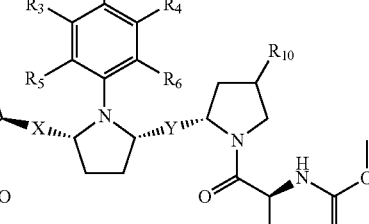

wherein, R₁, R₂, R₃, R₄, R₅, R₆, R₇, R₈, R₉, R₁₀, Rₐ, R_b, X, Y, m and n are as defined in claim 1.

3. The compound according to claim 1, wherein R₁ and R₂ are each independently selected from C₁₋₆ alkyl, or R₁ and R₂ are joined to form a 3- to 8-membered silicon-containing saturated aliphatic ring containing 1 silicon atom.

4. The compound according to claim 1, wherein R₁ and R₂ are each independently selected from the group consisting of methyl, ethyl, n-propyl, isopropyl, t-butyl, n-butyl, isobutyl and phenyl, or R₁ and R₂ are joined to form a 3-, 4-, 5- or 6-membered silicon-containing saturated aliphatic ring, wherein the silicon-containing saturated aliphatic ring contains one silicon atom.

5. The compound according to claim 1, wherein $R_3$, $R_4$, $R_5$ and $R_6$ are each independently selected from the group consisting of hydrogen, fluoro, and chloro.

6. The compound according to claim 1, X is selected from

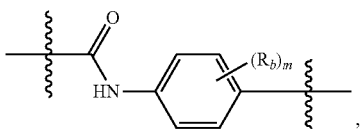
, and Y is selected from

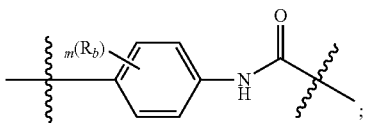
;

or X is selected from

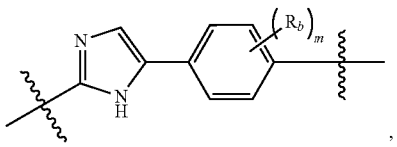
, and Y is selected from

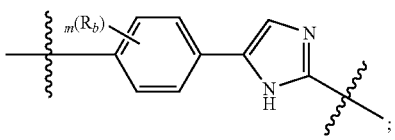
;

or X is selected from

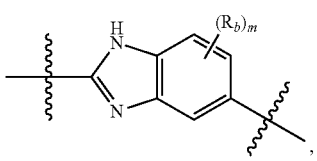
, and Y is selected from

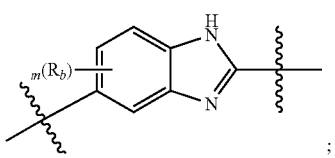
;

or X is selected from

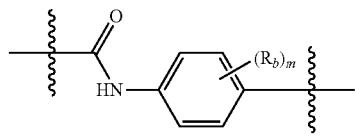
, and Y is selected from

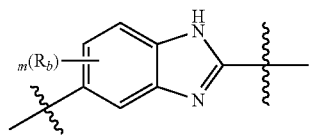
;

or X is selected from

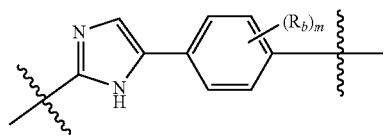
, and Y is selected from the group consisting of

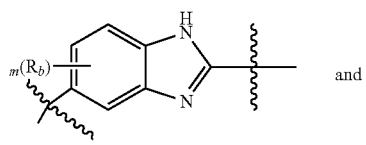 and

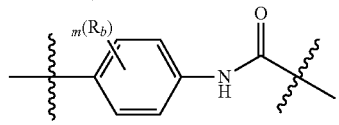
.

7. The compound according to claim 1, wherein X is selected from the group consisting of

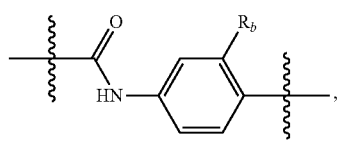
,

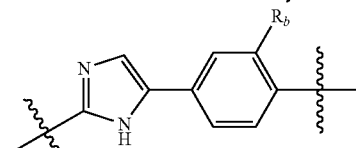 and

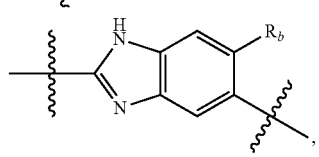
, and Y is selected from the group consisting of

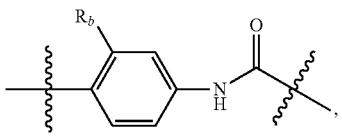

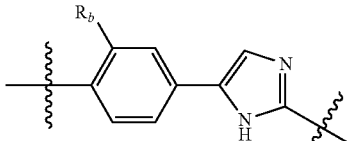
and

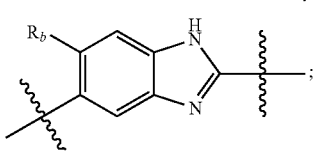
;

or, X is selected from the group consisting of

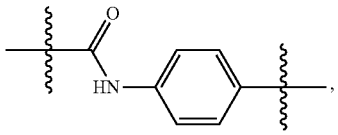 [SMILES: *C(=O)Nc1ccc(*)cc1]

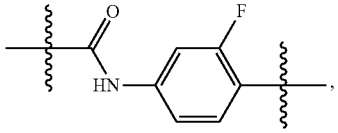

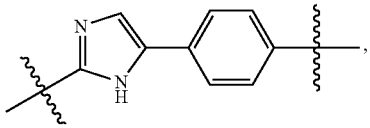

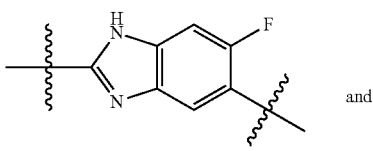
and

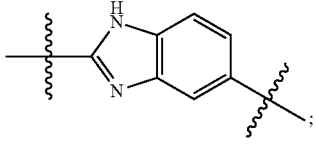
;

and Y is selected from the group consisting of

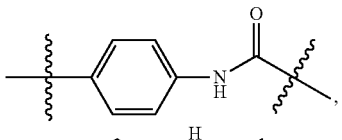

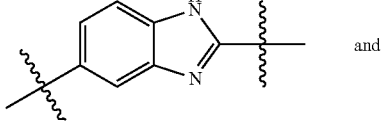
and

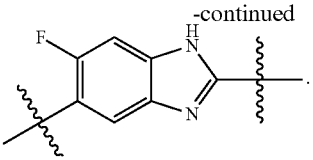
.

8. The compound according to claim 1, wherein $R_7$ and $R_8$ are each independently selected from the group consisting of —CH(CH$_3$)(OCH$_3$), —CH(CH$_3$)$_2$, —CH(OCH$_3$)$_2$, —C(CH$_3$)$_2$(OCH$_3$), —C(CH$_3$)(OCH$_3$)$_2$, —C(CH$_3$)$_3$, —C(OCH$_3$)$_3$, —CH(CH$_2$CH$_3$)(OCH$_2$CH$_3$), —CH(CH$_3$)(OCH$_2$CH$_3$), —CH(CH$_2$CH$_3$)(OCH$_3$), —CH(CH$_2$CH$_3$)$_2$, —CH(CH$_3$)(CH$_2$CH$_3$), —CH(OCH$_2$CH$_3$)$_2$, —CH(OCH$_2$CH$_3$)(OCH$_3$), —C(CH$_2$CH$_3$)$_2$(OCH$_2$CH$_3$), —C(CH$_3$)$_2$(OCH$_2$CH$_3$), —C(CH$_2$CH$_3$)$_2$(OCH$_3$), —C(CH$_2$CH$_3$)(OCH$_2$CH$_3$)$_2$, —C(CH$_3$)(OCH$_2$CH$_3$)$_2$, —C(CH$_2$CH$_3$)(OCH$_3$)$_2$, —C(CH$_2$CH$_3$)$_3$, —C(CH$_3$)(CH$_2$CH$_3$)$_2$, —C(CH$_3$)$_2$(CH$_2$CH$_3$) and —C(OCH$_2$CH$_3$)$_3$.

9. The compound according to claim 1, wherein $R_9$ and $R_{10}$ are each independently selected from the group consisting of hydrogen, fluoro, chloro, methyl, ethyl, n-propyl, isopropyl, t-butyl, n-butyl, isobutyl, methoxy, ethoxy, n-propoxy, isopropoxy, tert-butoxy, n-butoxy, isobutoxy, methoxymethyl, methoxyethyl, ethoxymethyl, and ethoxyethyl.

10. The compound according to claim 1, wherein $R_7$ and $R_8$ are each independently selected from the group consisting of —CH(CH$_3$)(OCH$_3$) and —CH(CH$_3$)$_2$; and $R_9$ and $R_{10}$ are each independently selected from the group consisting of hydrogen and methoxymethyl.

11. The compound according to claim 1, wherein $R_a$ and $R_b$ are each independently selected from the group consisting of hydrogen, fluoro, chloro, methyl, ethyl, n-propyl, isopropyl, t-butyl, n-butyl, and isobutyl.

12. The compound according to claim 1, wherein $R_1$ and $R_2$ are methyl, or $R_1$ and $R_2$ are joined to form a 4-, 5- or 6-membered silicon-containing saturated aliphatic ring containing 1 silicon atom; one of $R_3$ and $R_4$ is fluoro, and the other is hydrogen, or both $R_3$ and $R_4$ are fluoro; $R_5$ and $R_6$ are hydrogen; X is

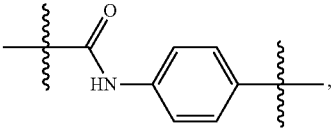

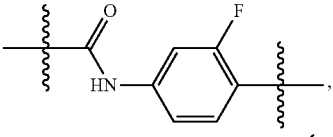

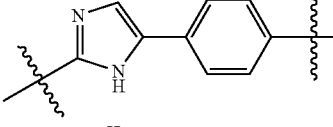

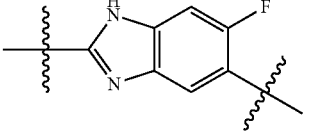
or

157
-continued
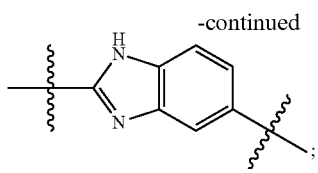
Y is
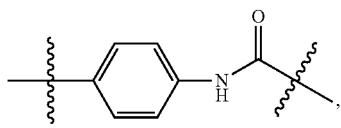
158
-continued
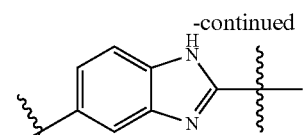 or
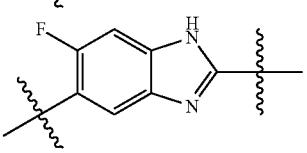
both $R_7$ and $R_8$ are -CH(CH3)(OCH$_3$);
both $R_9$ and $R_{10}$ are hydrogen or methoxymethyl; and n is 0.
13. The compound according to claim 1, which is selected from the following compounds:
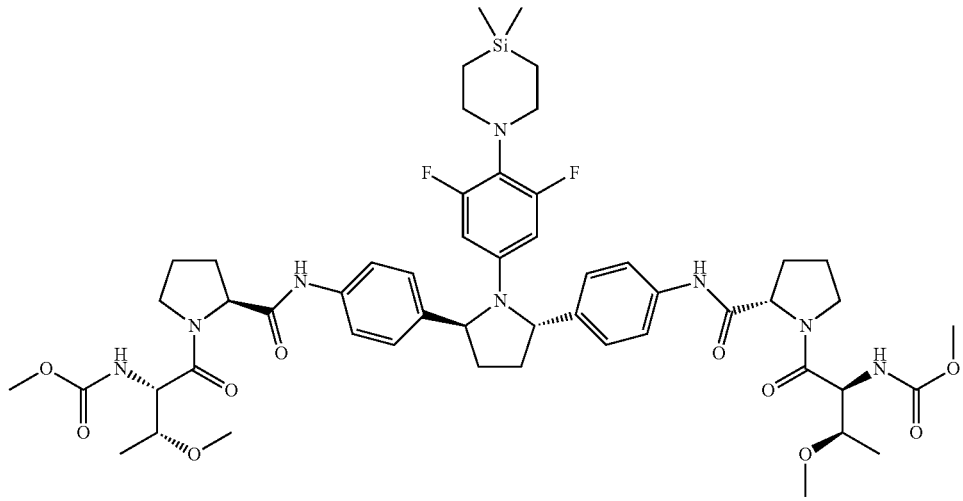
1a
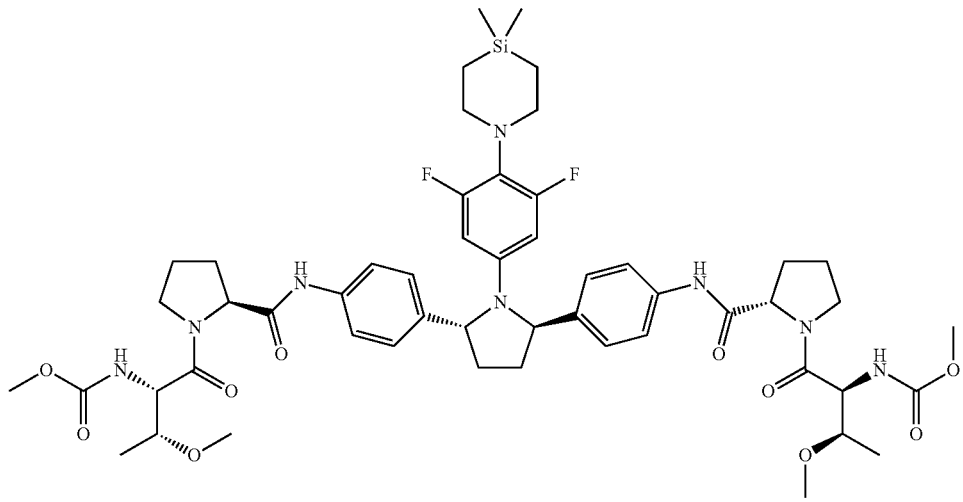
1b -continued
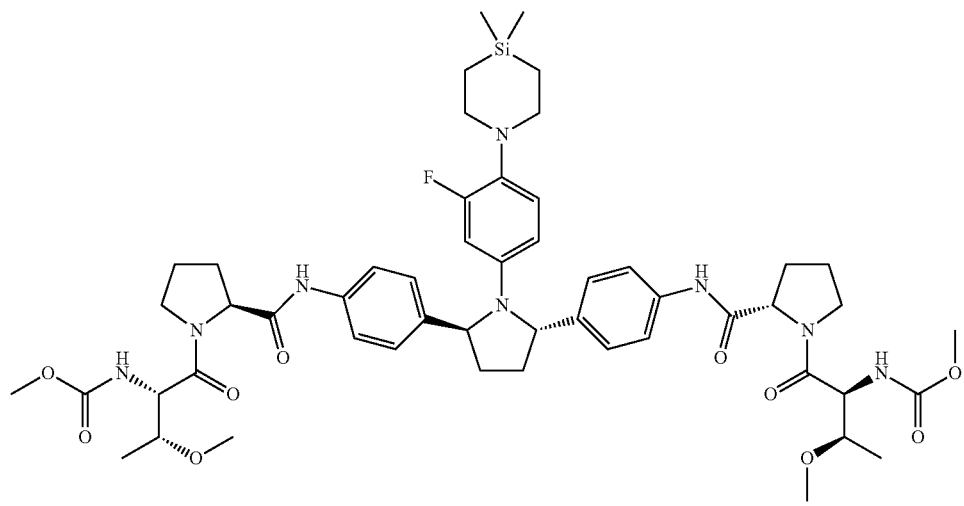
2a
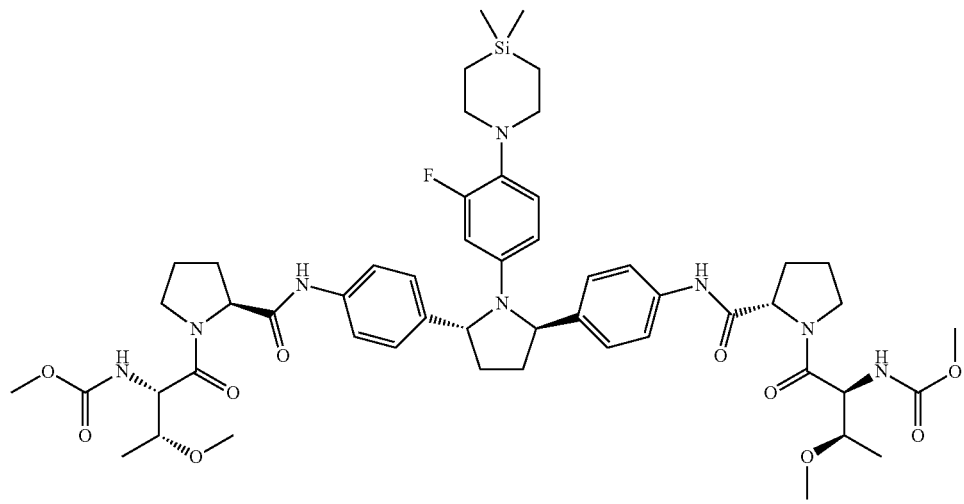
2b
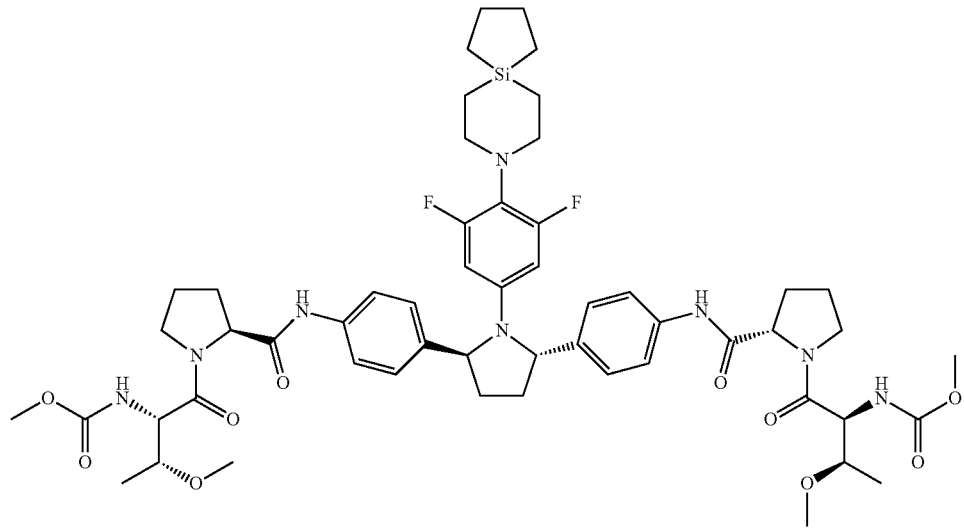
3a -continued
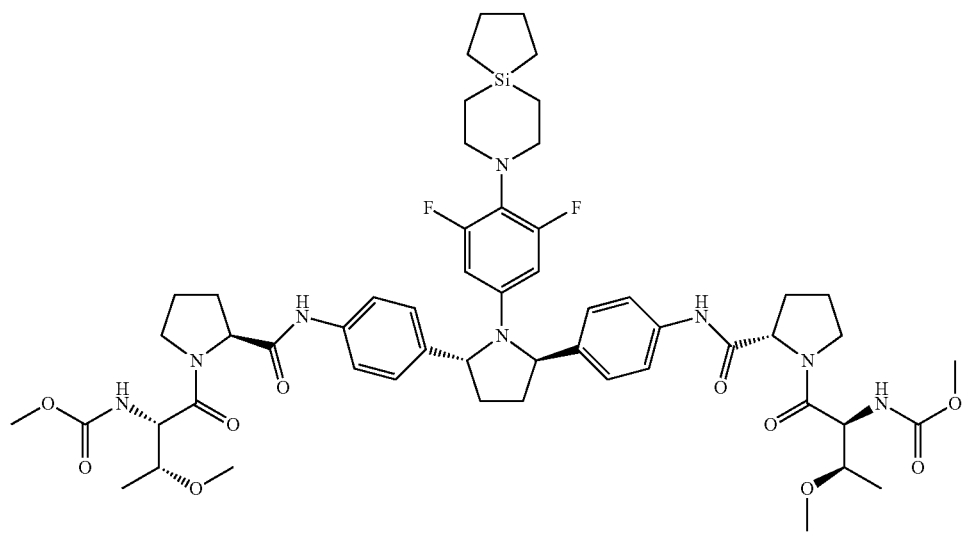
3b
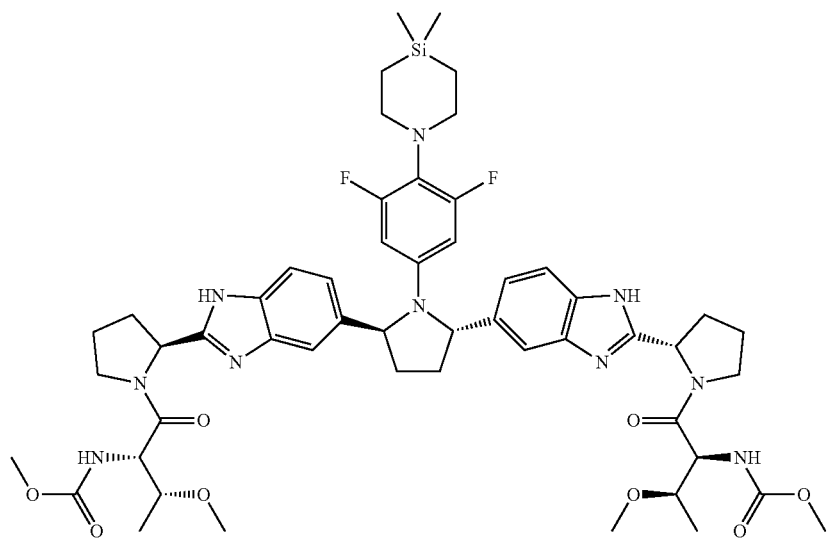
4a
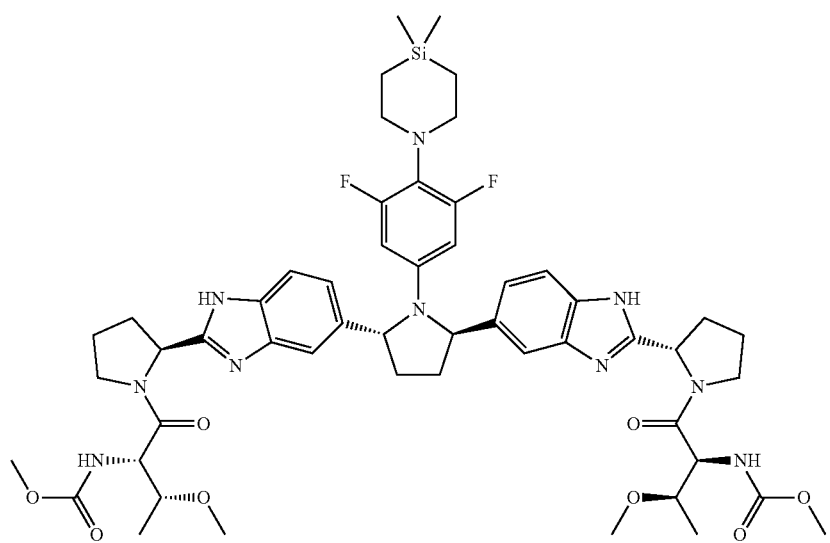
4b -continued
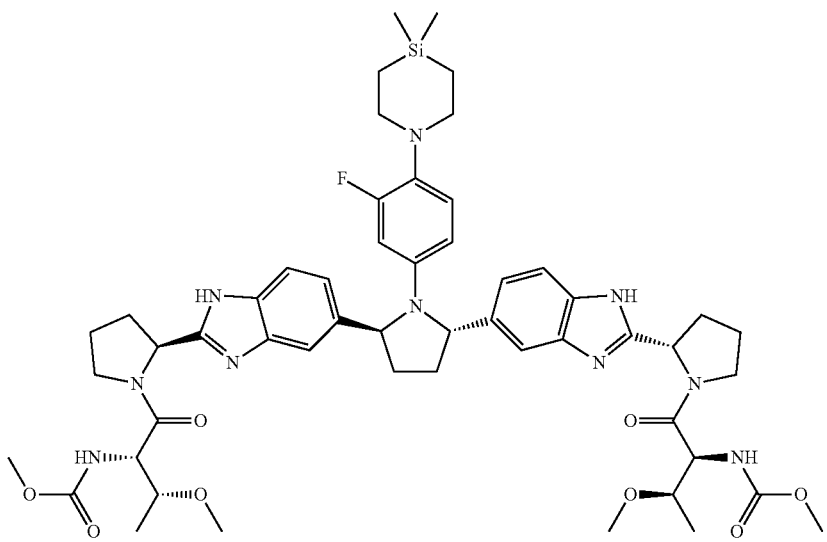
5a
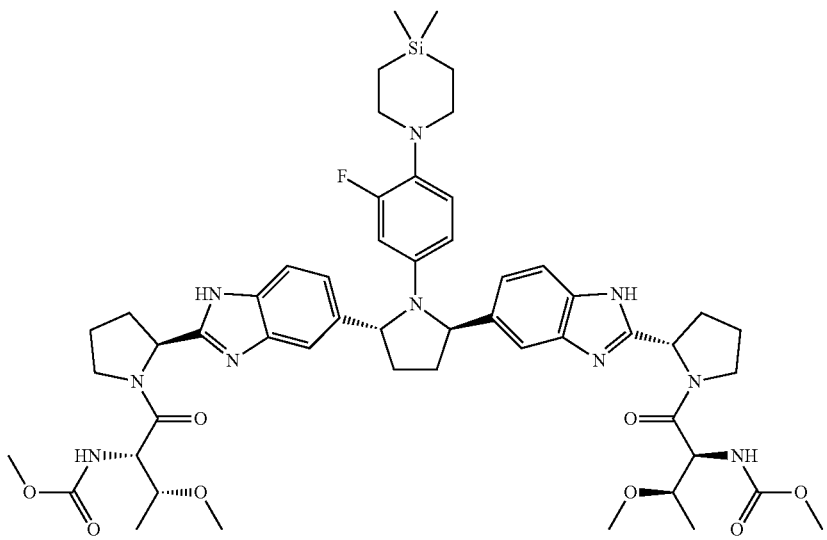
5b
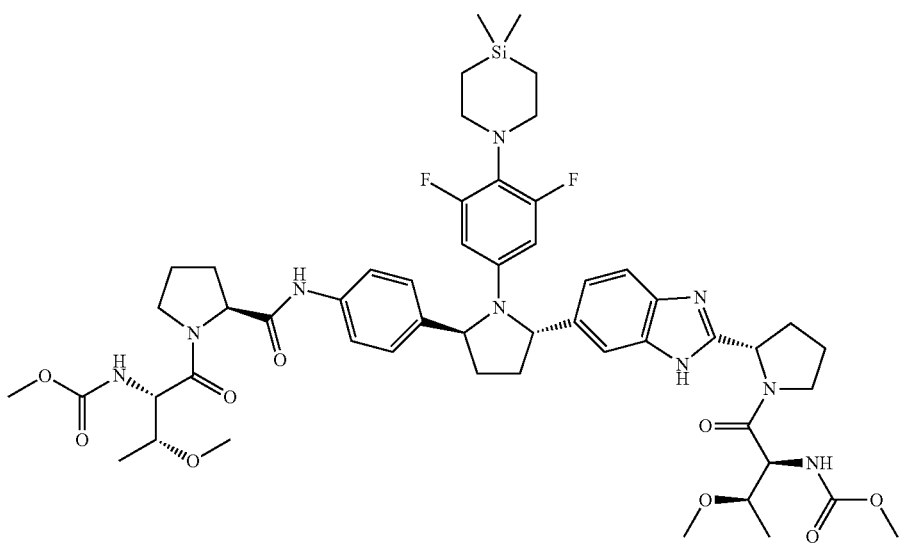
6a -continued
6b
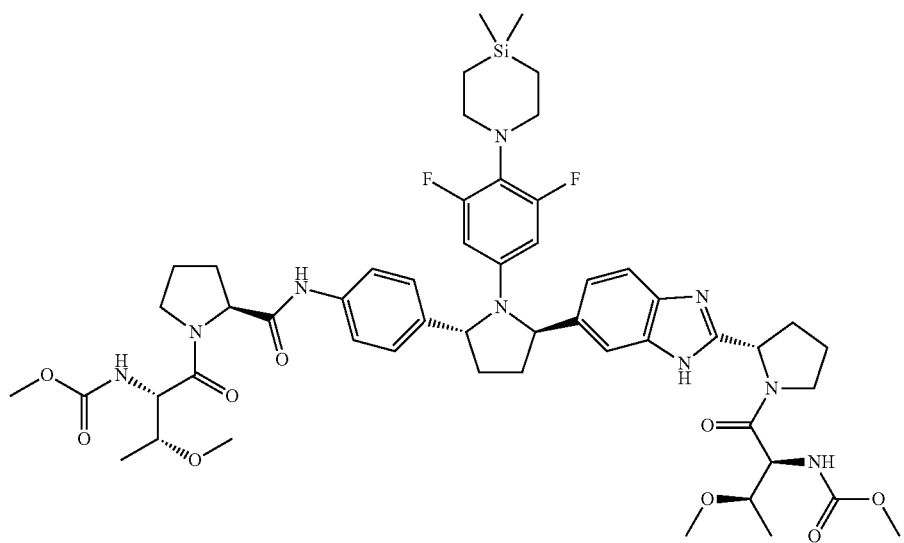
7a
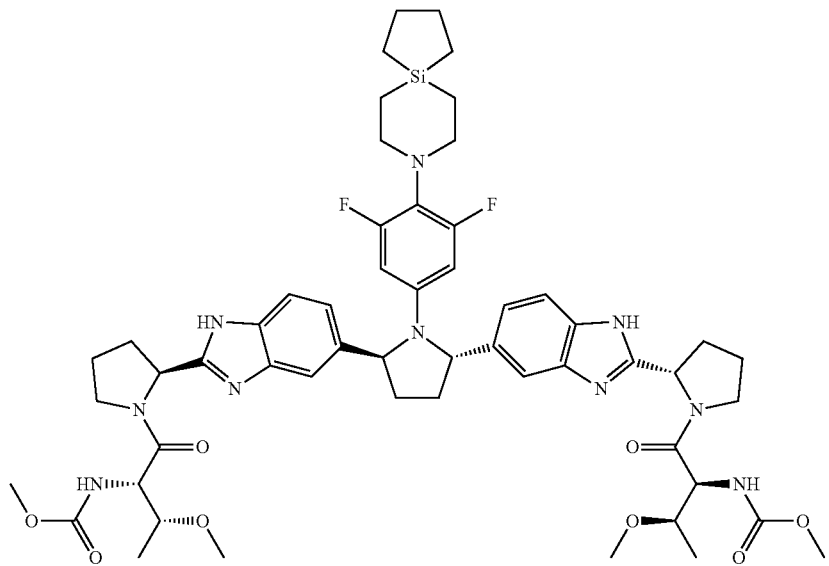
7b
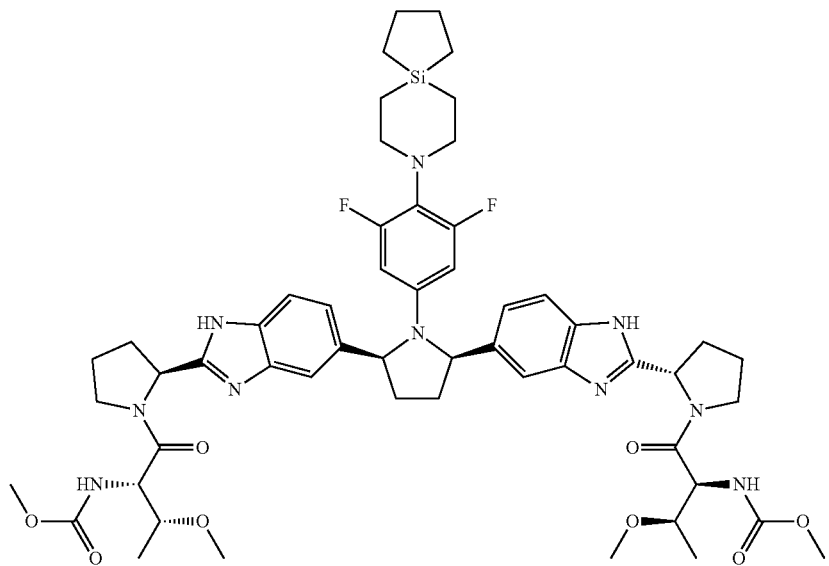

-continued
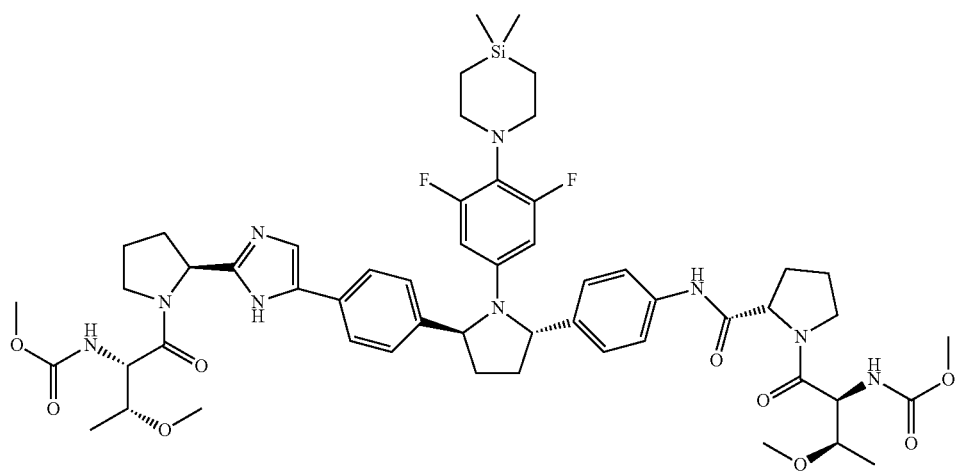
8a
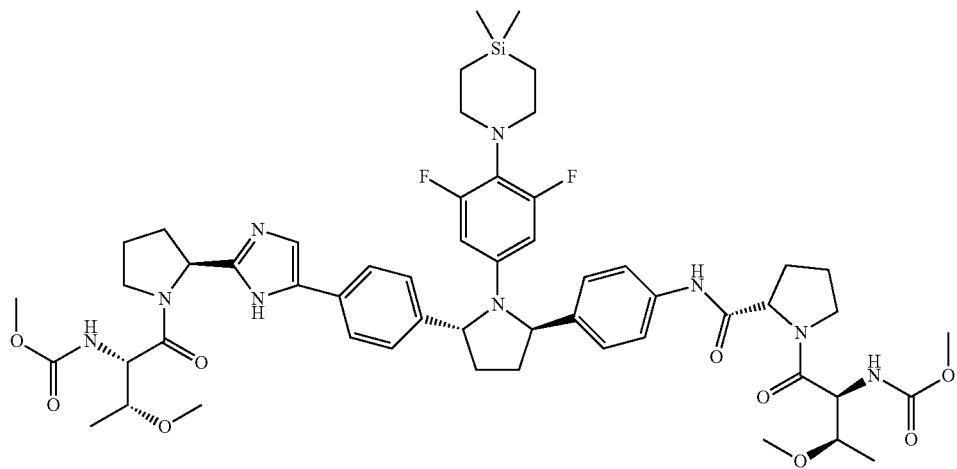
8b
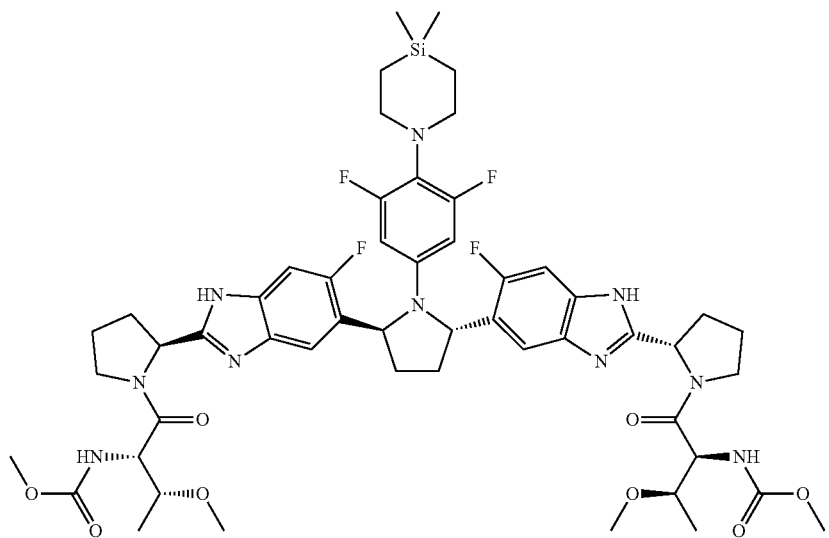
9a

-continued
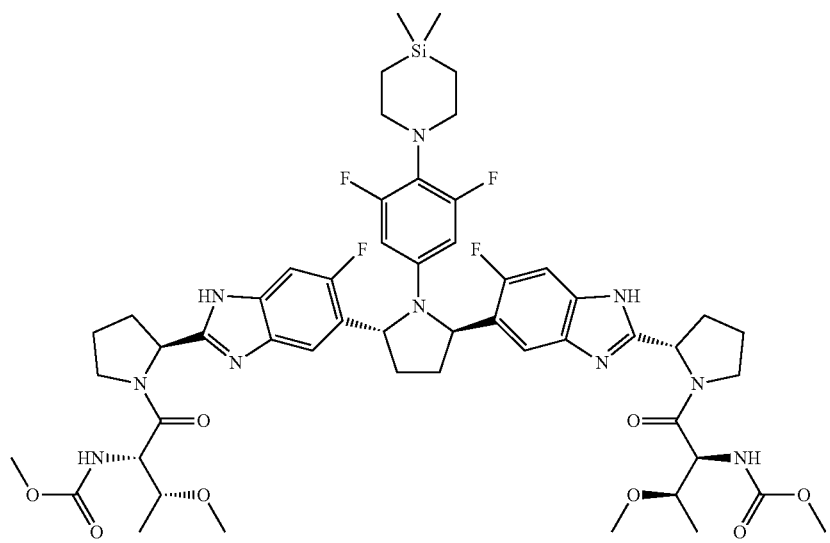
9b
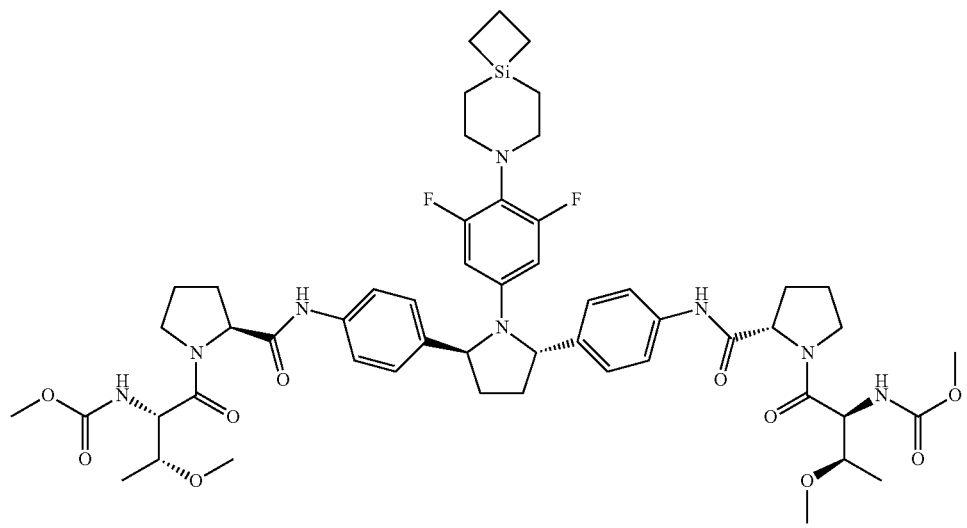
10a
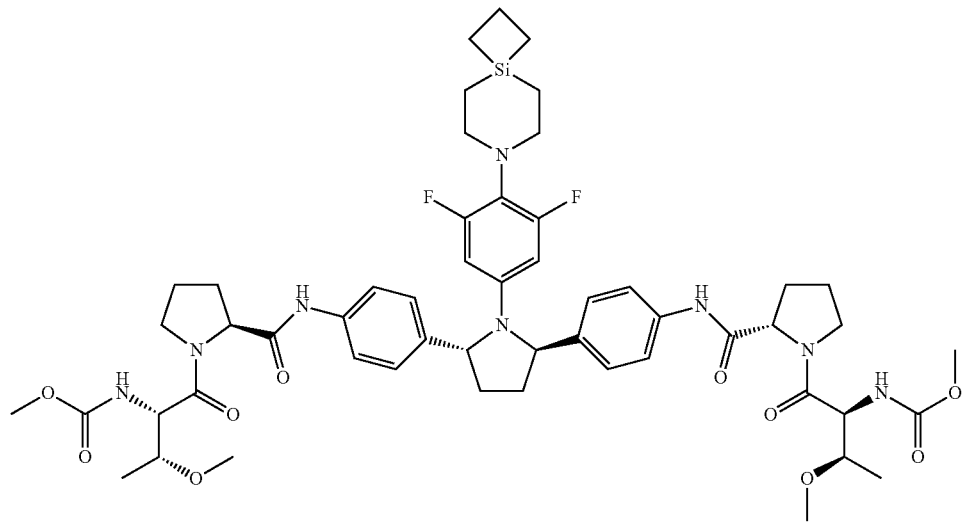
10b

-continued
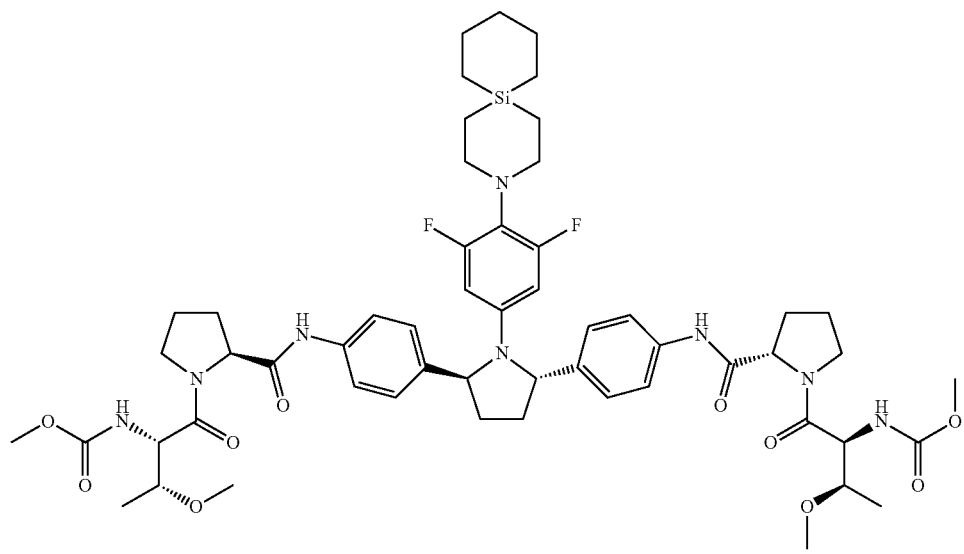
11a
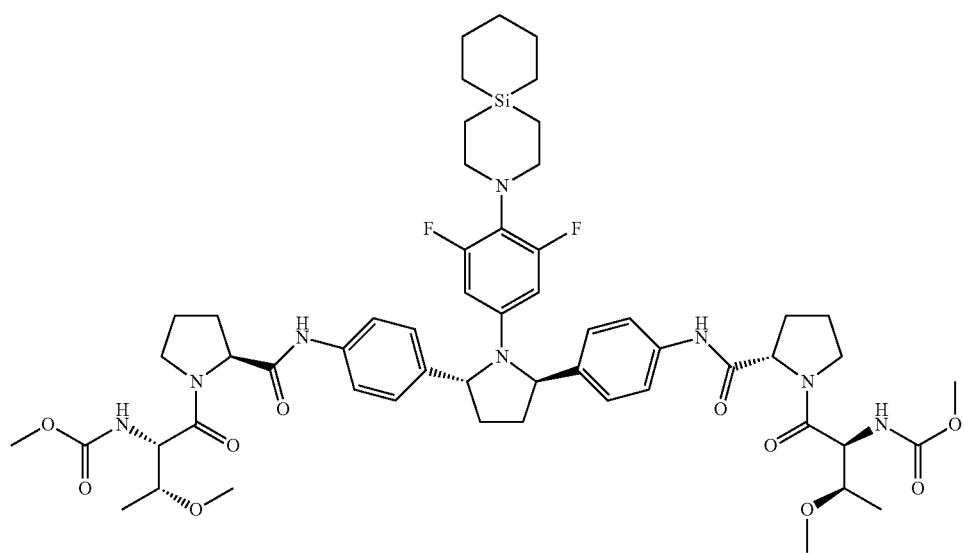
11b
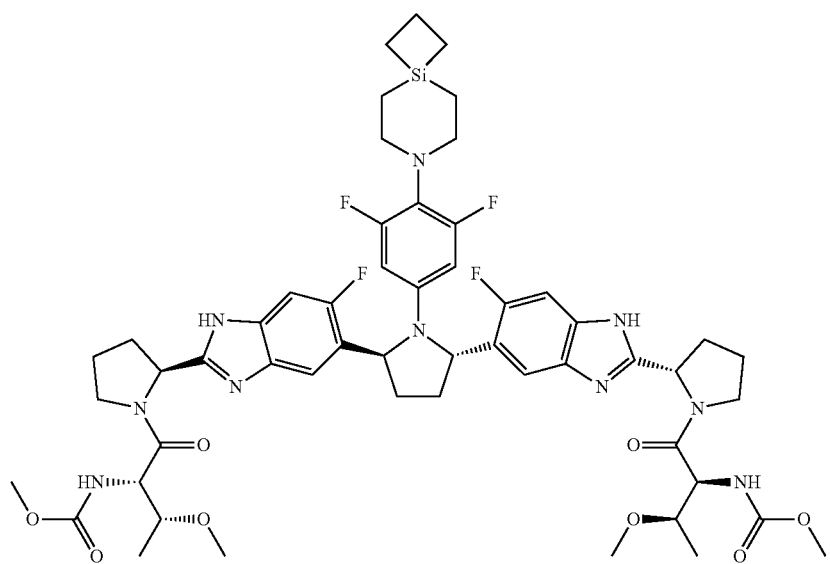
12a

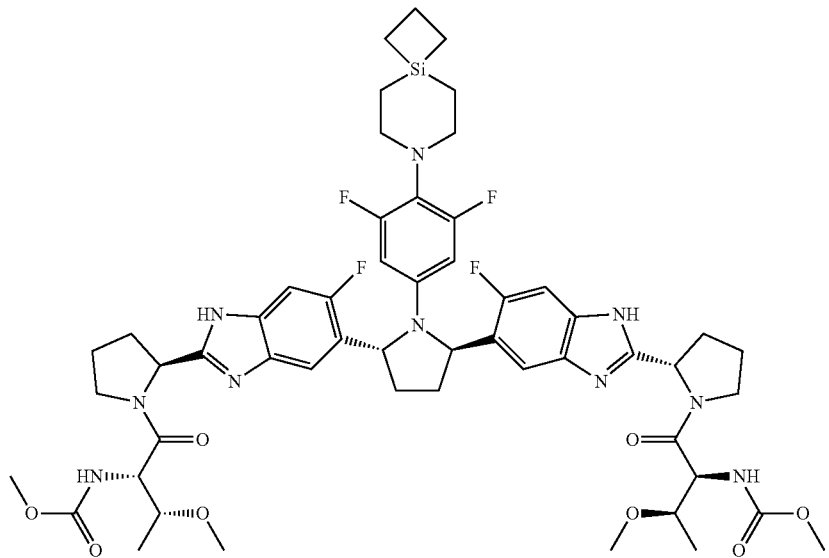
12b
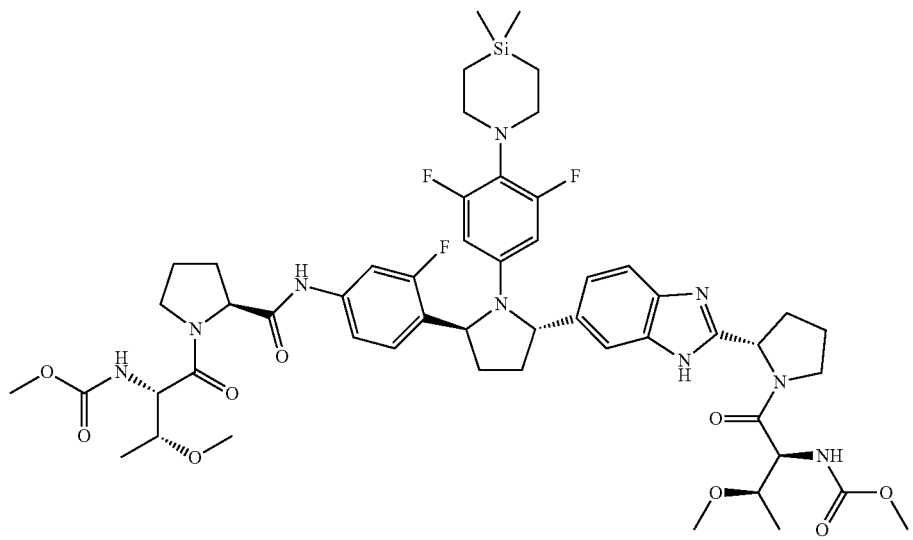
13a
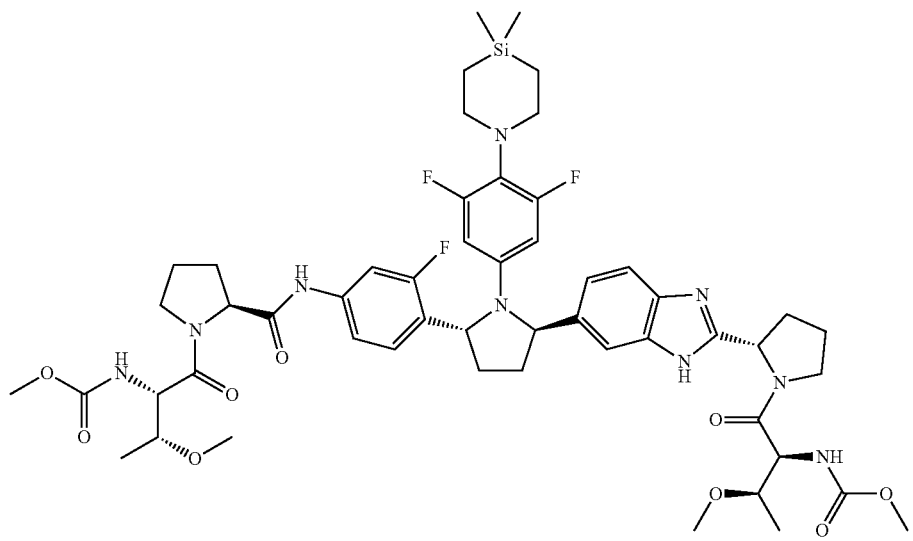
13b

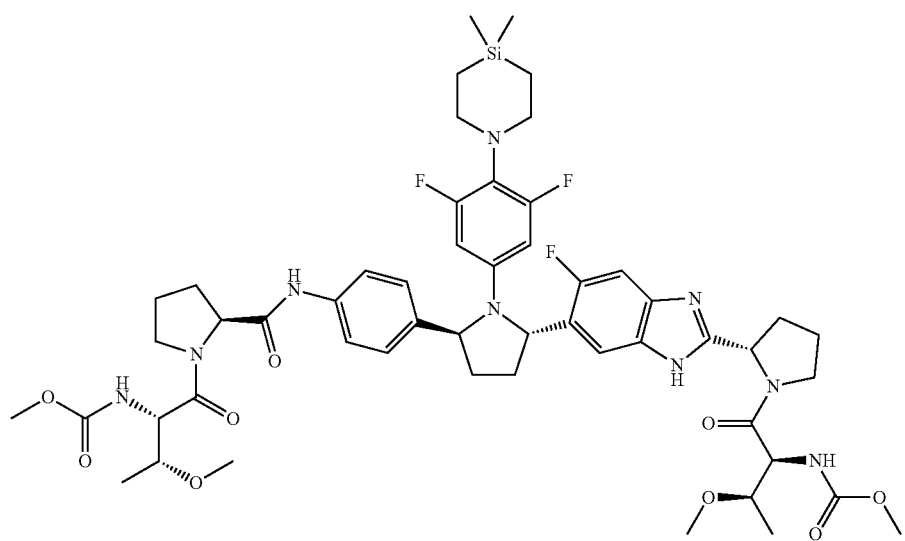
14a
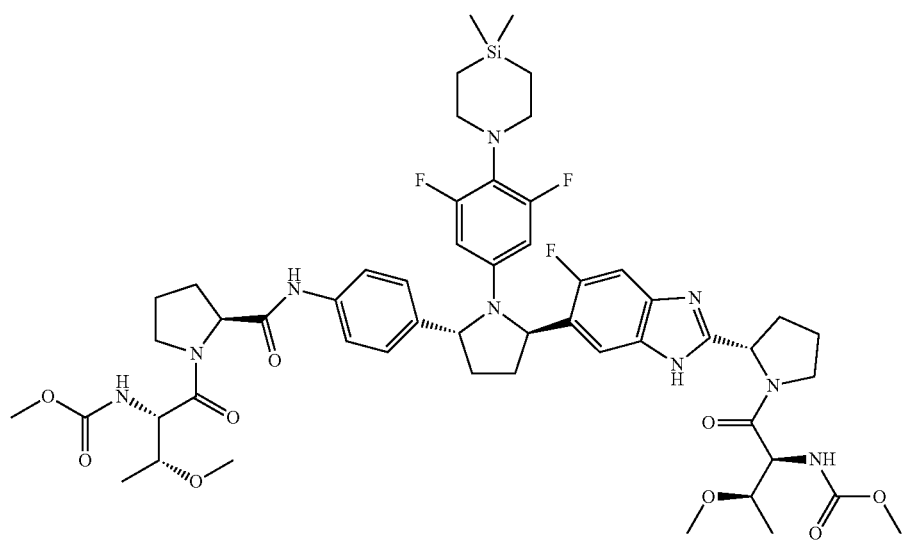
14b
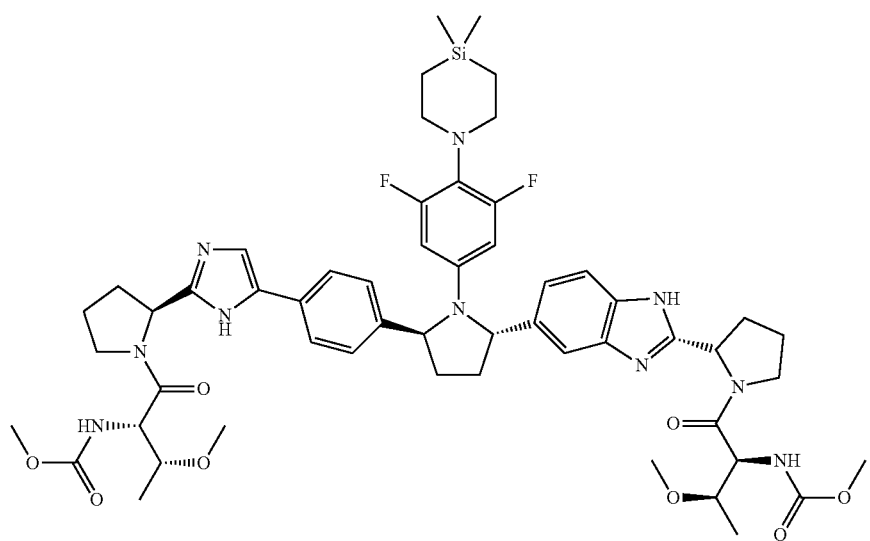
15a

15b
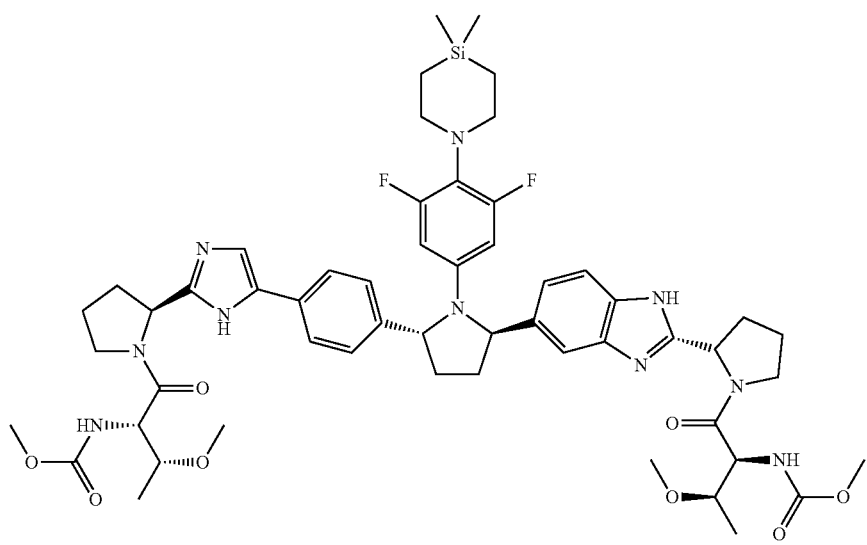
16a
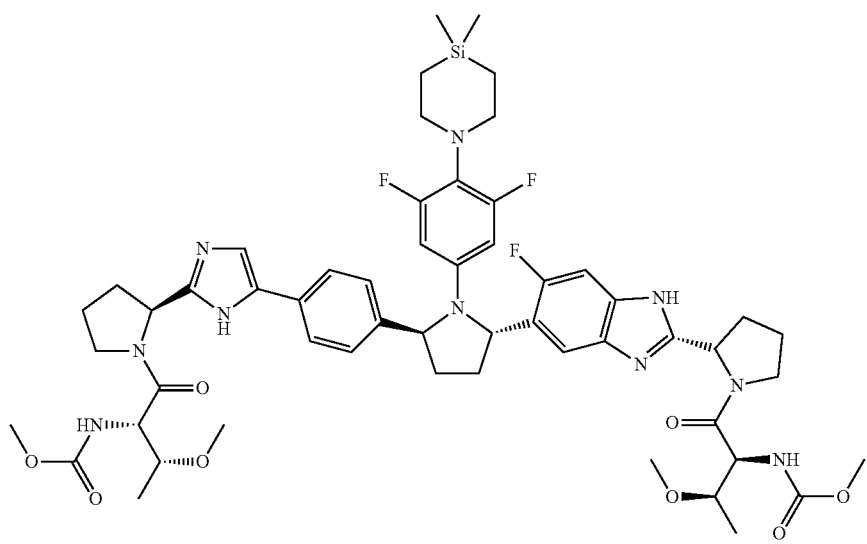
16b
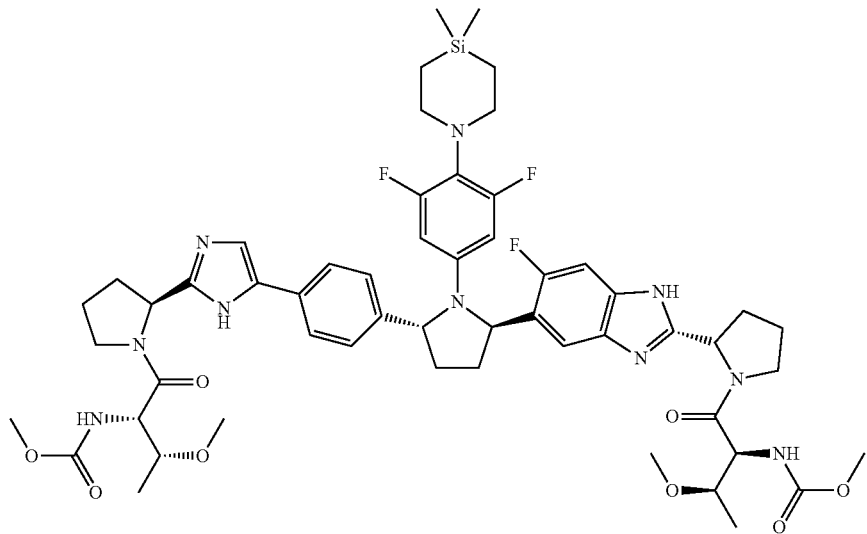

-continued
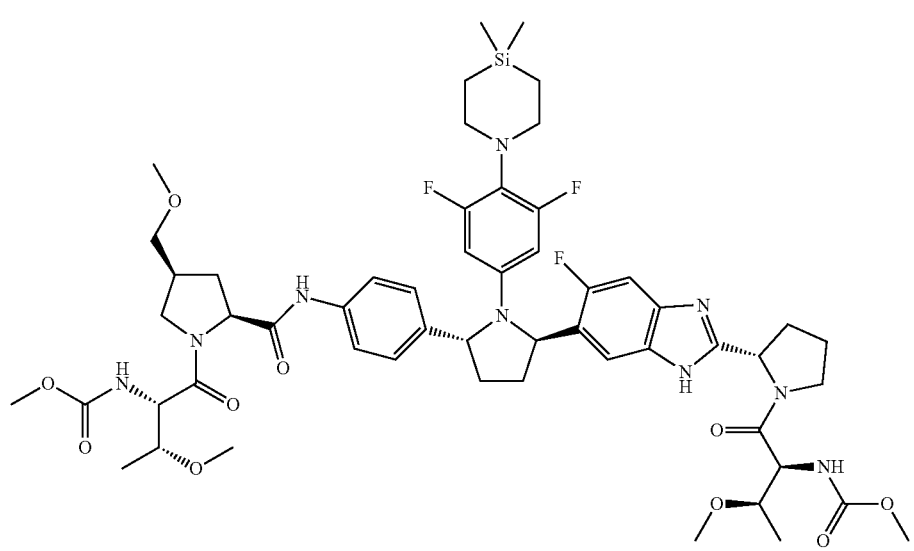
17b
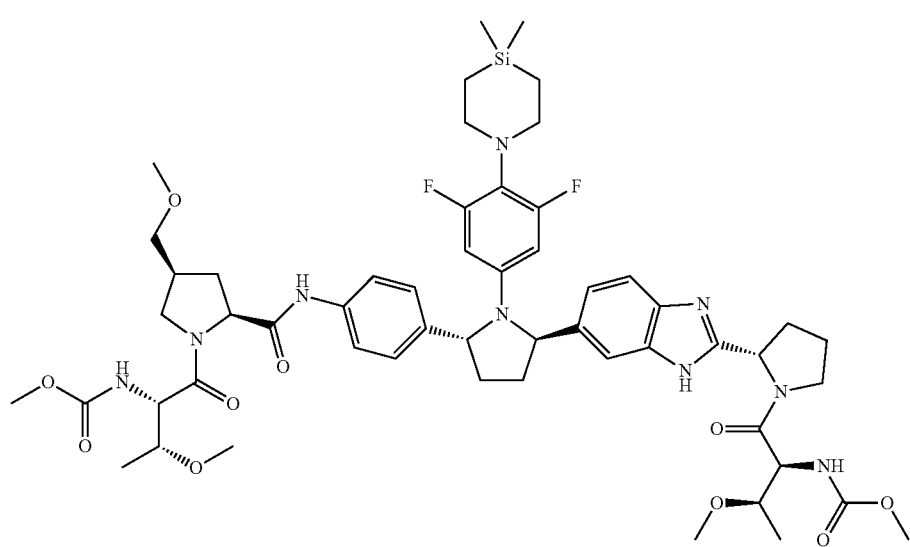
18b
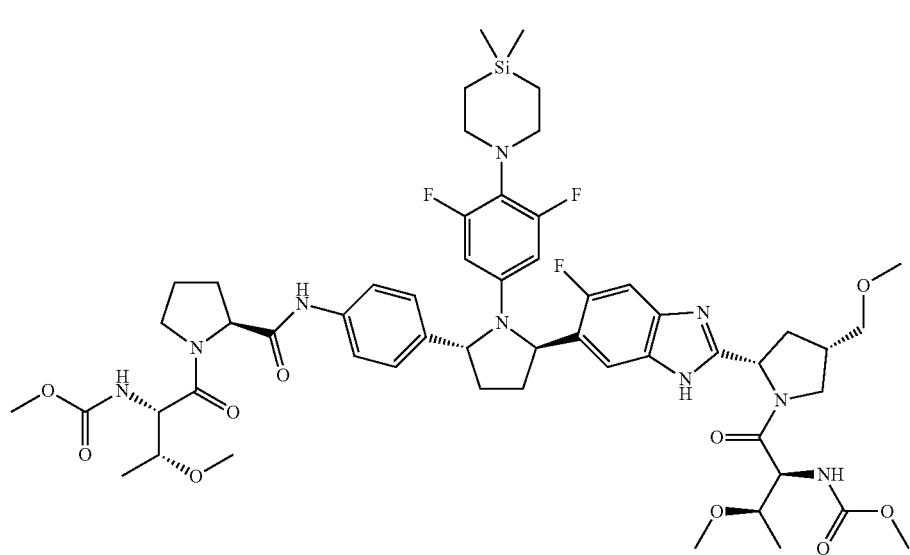
19b

-continued
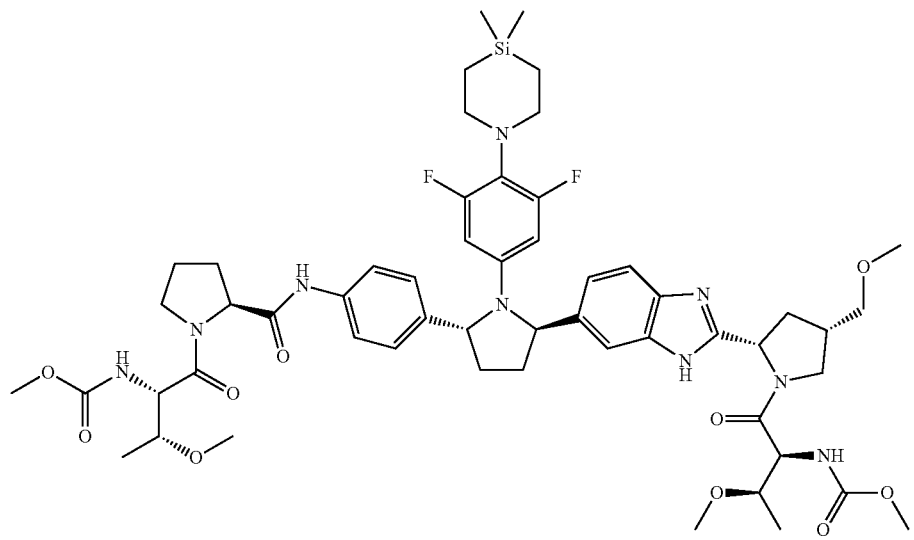
20b
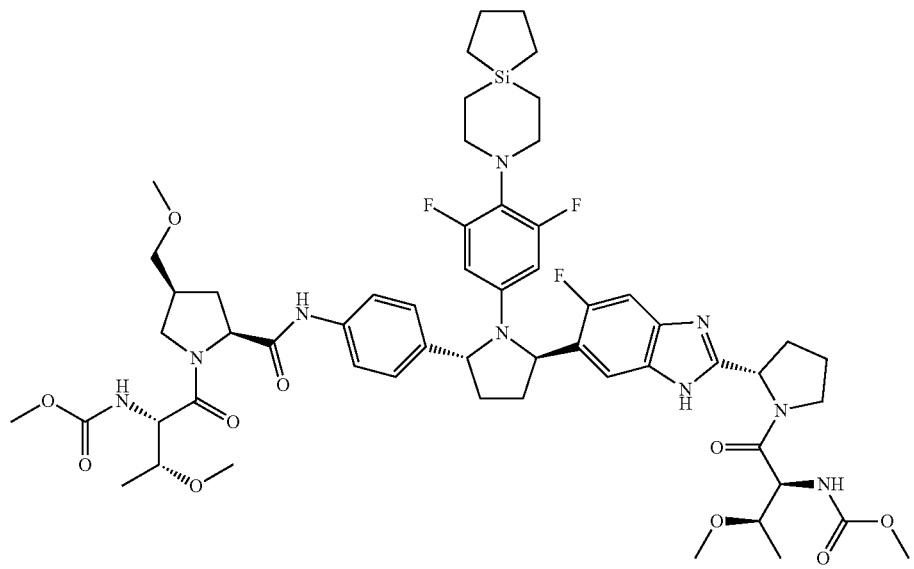
21b
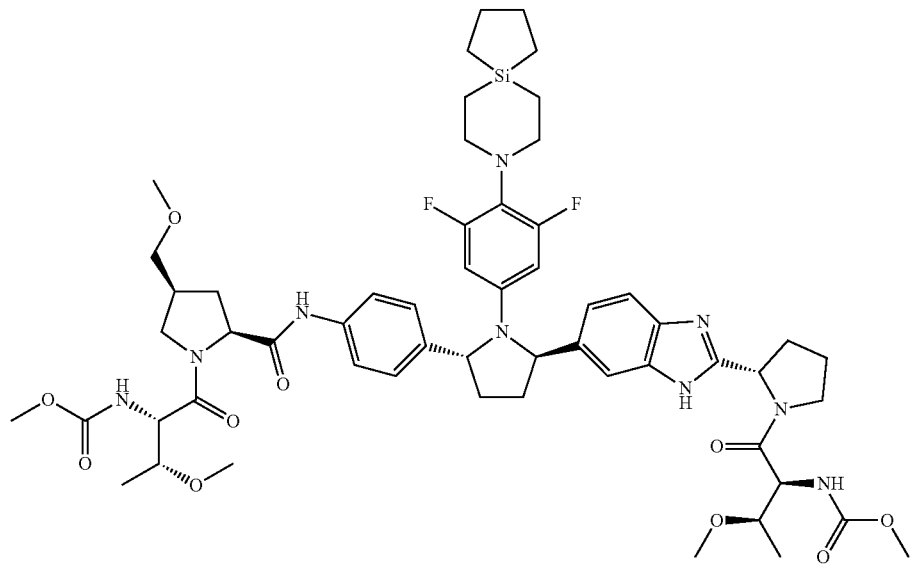
22b

-continued
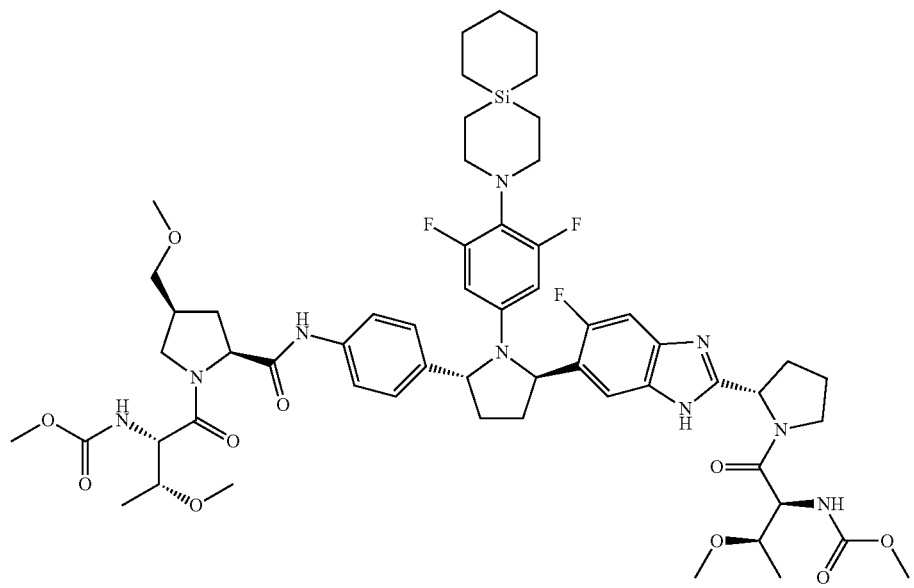
23b
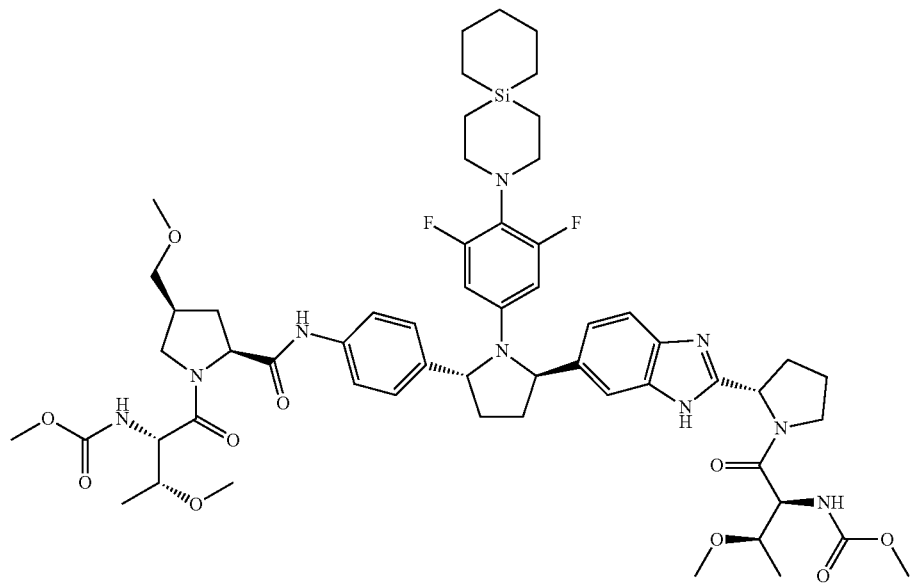
24b

-continued
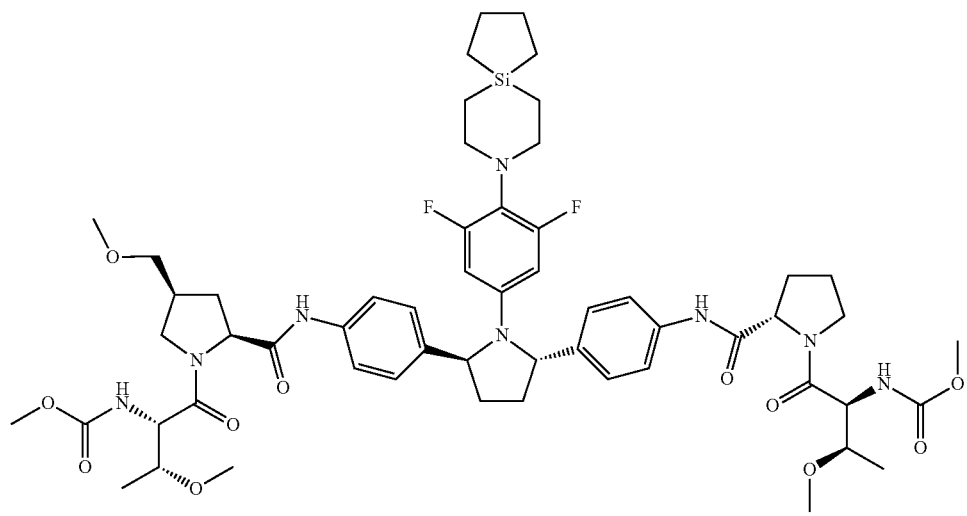
25a
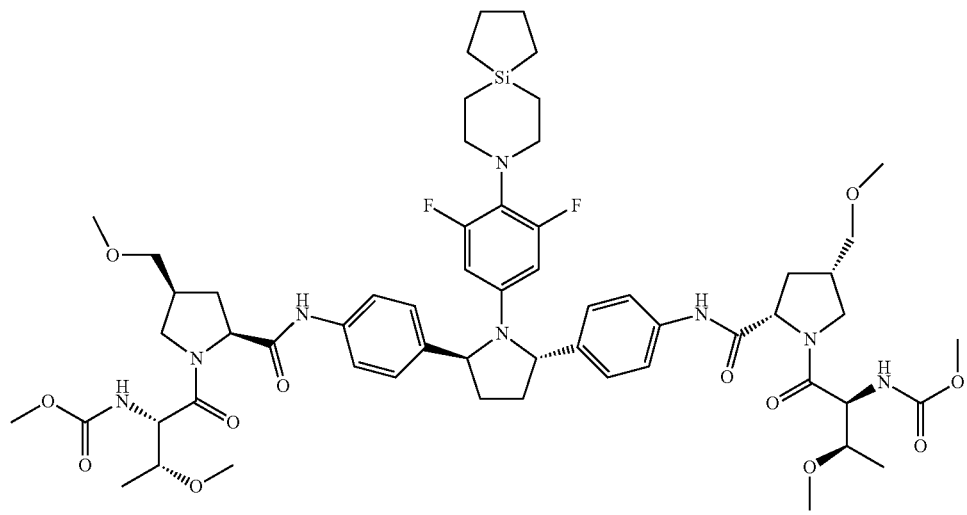
26a
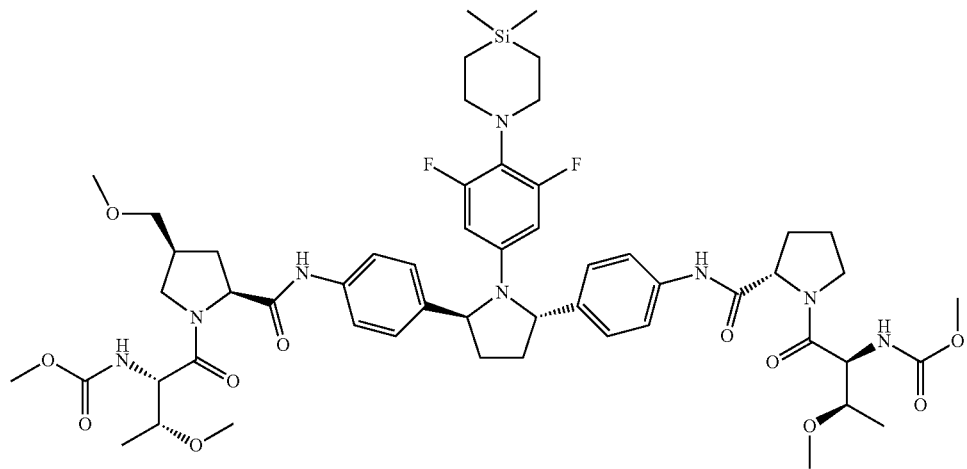
27a

-continued
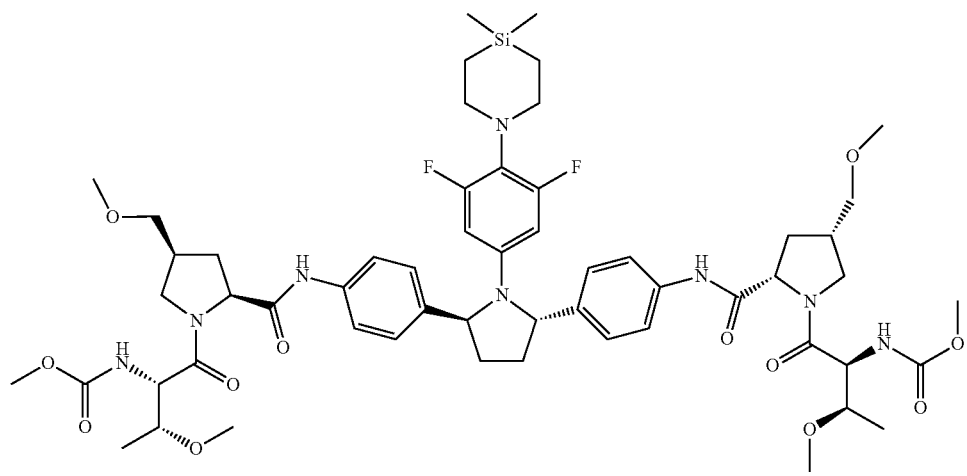
28a
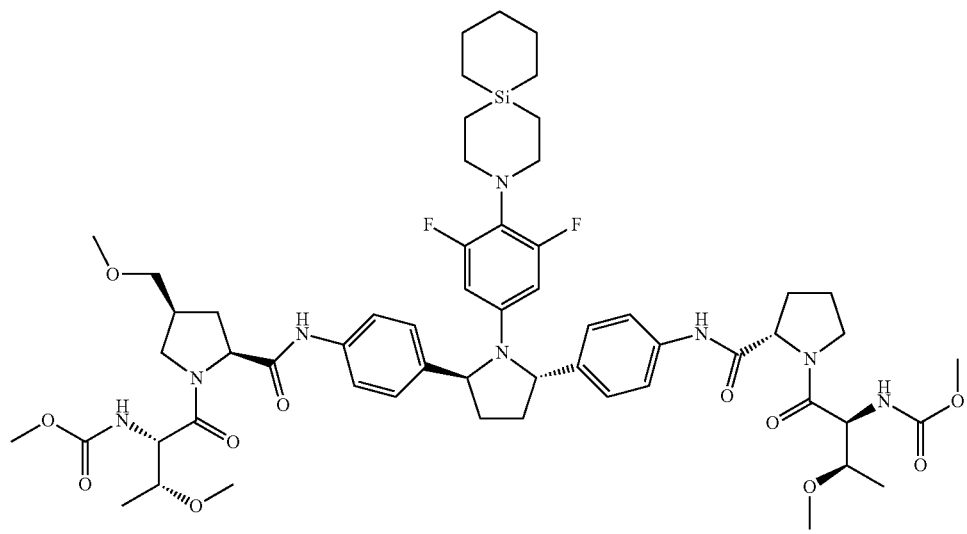
29a
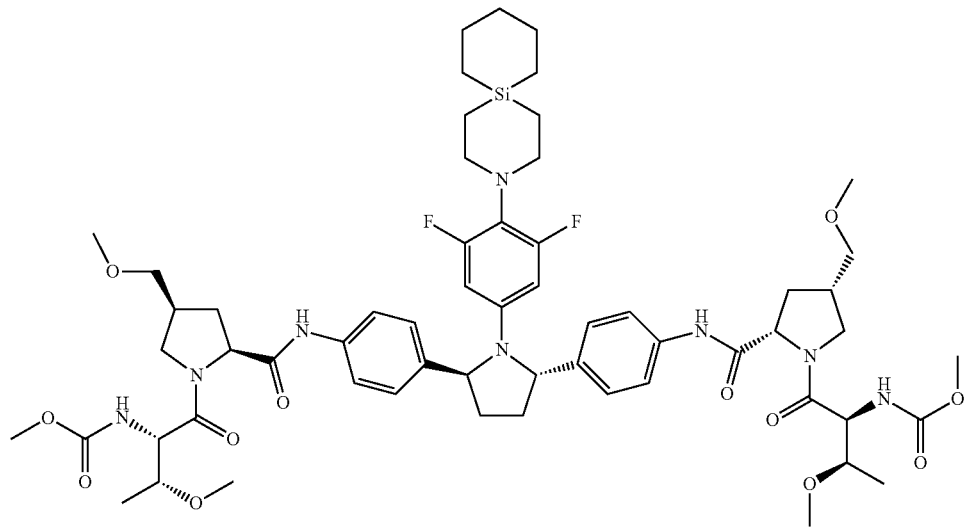
30a

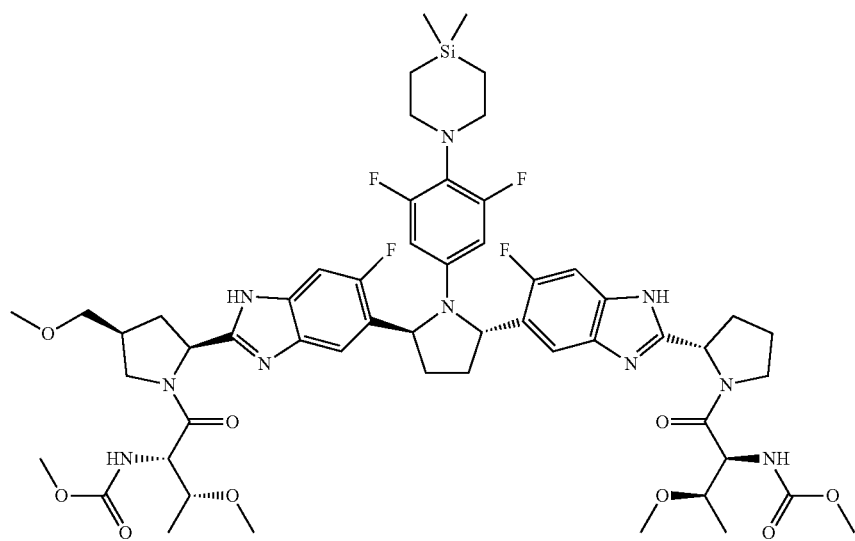
31a
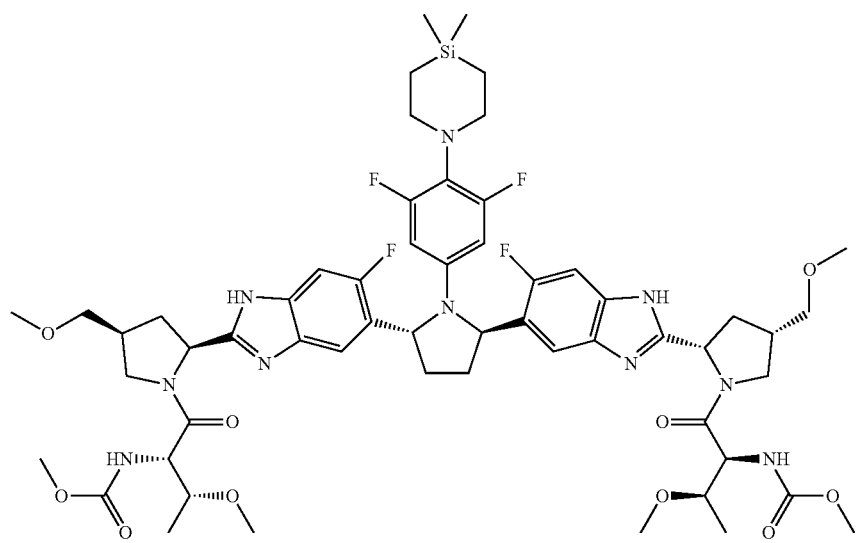
32b
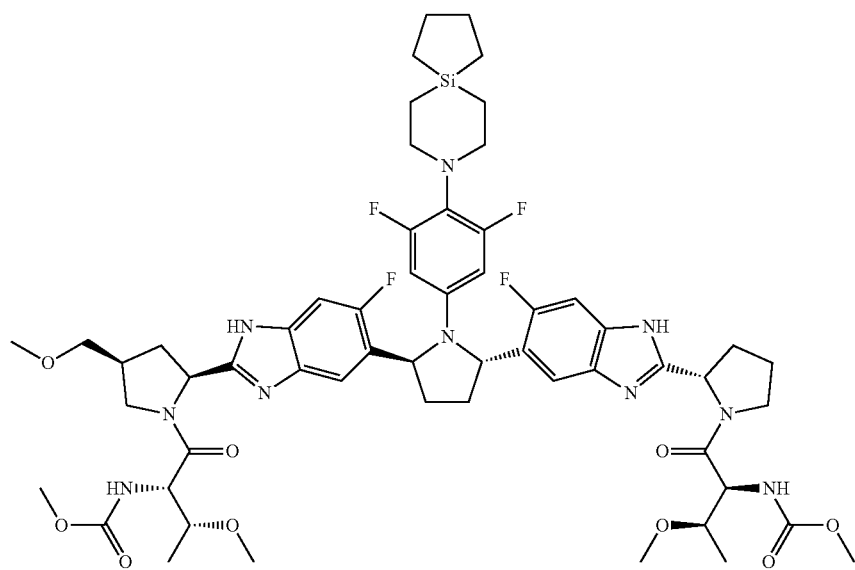
33a

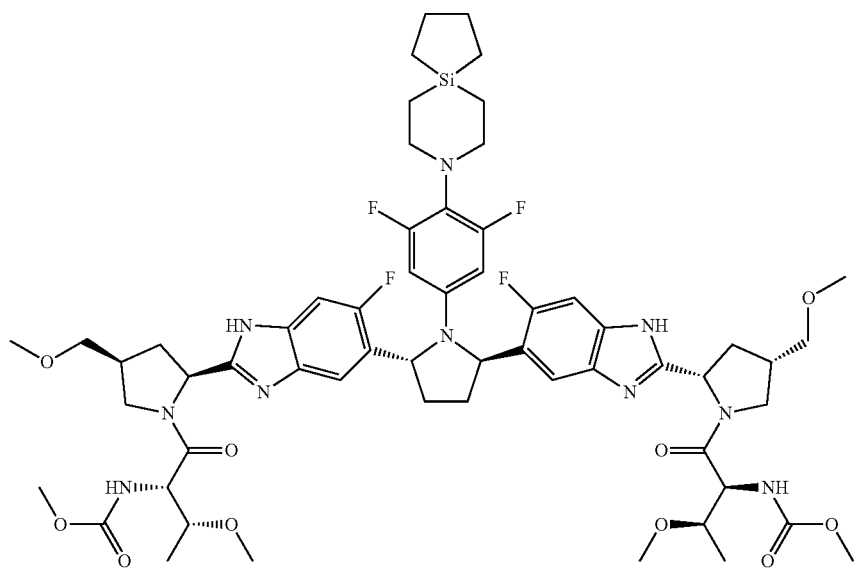
34b
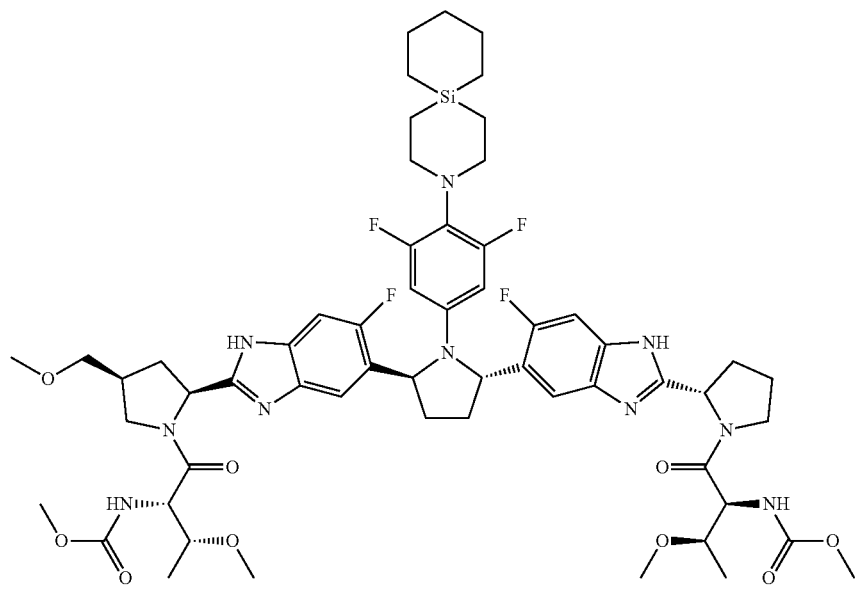
35a

-continued

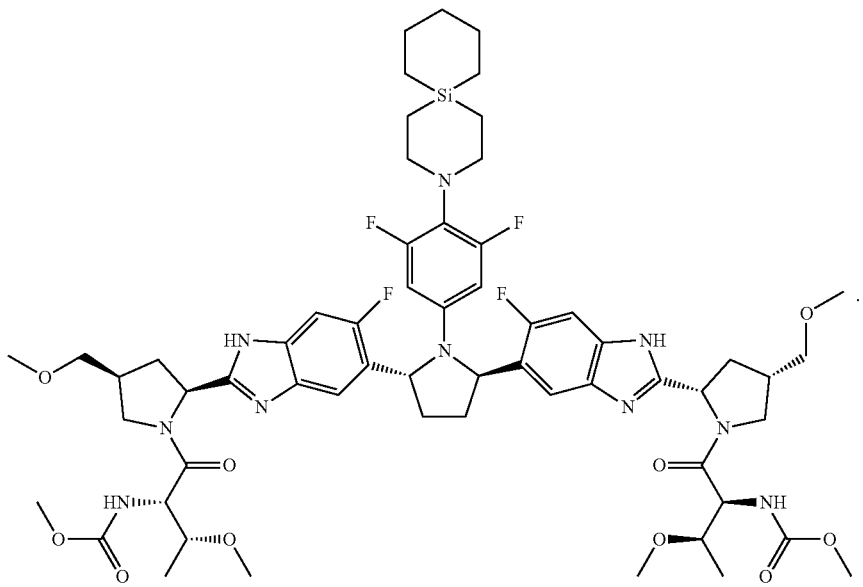

36b

14. A pharmaceutical composition, comprising a therapeutically effective amount of the compound according to claim 1, a pharmaceutically acceptable salt, a tautomer, a stereoisomer or a deuteride thereof, or a mixture thereof, and one or more pharmaceutically acceptable carriers.

15. A method for treating hepatitis C virus infection, comprising administering to a subject in need of such treatment a therapeutically effective amount of the compound according to claim 1, a pharmaceutically acceptable salt, a tautomer, a stereoisomer or a deuteride thereof, or a mixture thereof.

16. A method for treating hepatitis C virus infection, comprising administering to a subject in need of such treatment a therapeutically effective amount of the pharmaceutical composition according to claim 14.

17. The compound according to claim 1, wherein one of $R_3$ and $R_4$ is fluoro, and the other is hyrdogen, and $R_5$ and $R_6$ are selected from hydrogen.

18. The compound according to claim 1, wherein $R_3$ and $R_4$ are selected from fluoro, and $R_5$ and $R_6$ are selected from hydrogen.

19. The compound according to claim 1, wherein X is selected from

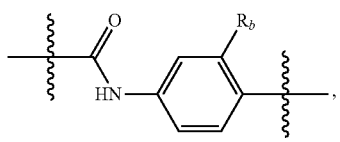

and Y is selected from

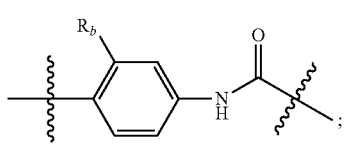

or X is selected from

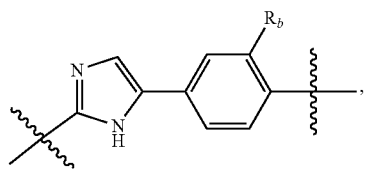

and Y is selected from

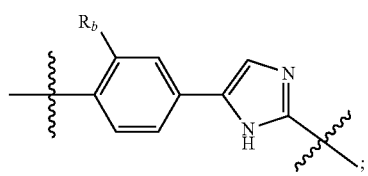

or X is selected from

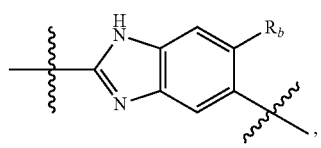

and Y is selected from

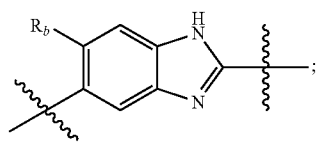

or X is selected from
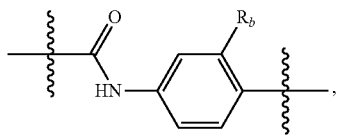
and Y is selected from
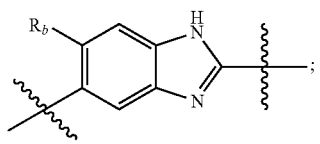
or X is selected from
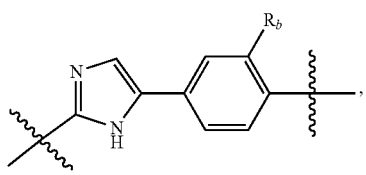
and Y is selected from the group consisting of
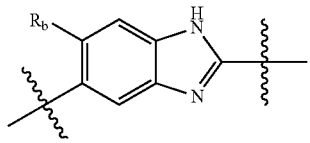
and
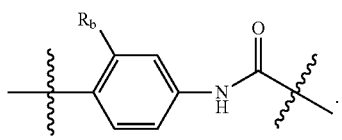
20. The compound according to claim 1, wherein X is selected from
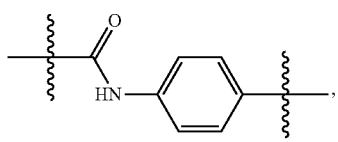
and Y is selected from
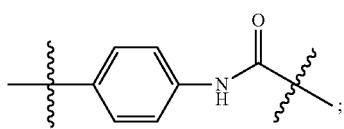 [SMILES: *C(=O)Nc1ccc(*)cc1]
or X is selected from
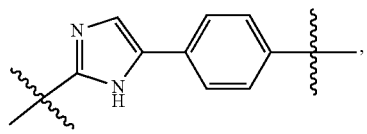 [SMILES: *c1ccc(-c2cnc(*)[nH]2)cc1]
and Y is selected from
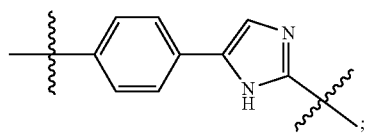 [SMILES: *c1ccc(-c2cnc(*)[nH]2)cc1]
or X is selected from
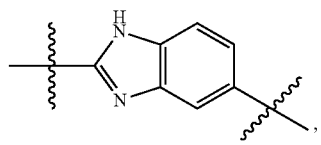 [SMILES: *c1ccc2[nH]c(*)nc2c1]
and Y is selected from
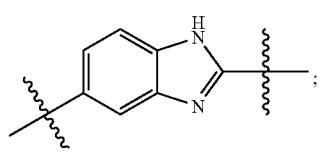 [SMILES: *c1ccc2[nH]c(*)nc2c1]
or X is selected from
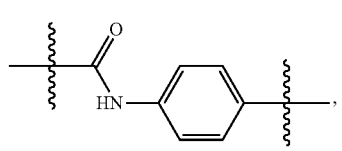 [SMILES: *C(=O)Nc1ccc(*)cc1]
and Y is selected from
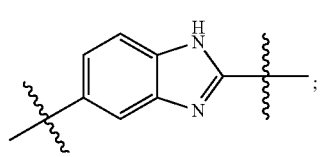 [SMILES: *c1ccc2[nH]c(*)nc2c1]
or X is selected from
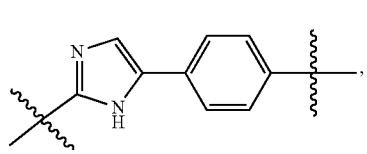 [SMILES: *c1ccc(-c2cnc(*)[nH]2)cc1]

and Y is selected fom the group consisting of
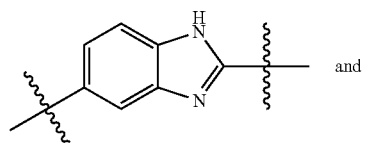
and
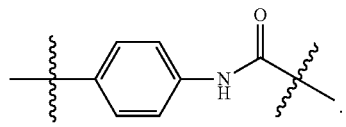
.
* * * * *